US009797916B2

(12) United States Patent
Connolly et al.

(10) Patent No.: US 9,797,916 B2
(45) Date of Patent: Oct. 24, 2017

(54) CHEMICAL ANALYZER

(71) Applicant: IDEXX Laboratories, Inc., Westbrook, ME (US)

(72) Inventors: David Lance Connolly, Eliot, ME (US); Mark Raymond Dumont, Saco, ME (US); Justin Jay Griffin, Scarborough, ME (US); John Harvey McGibbon, Old Orchard Beach, ME (US); Garland Christian Misener, Portland, ME (US); Jeffrey Eric Phelps, Freeport, ME (US); Carl Russell Rich, Gorham, ME (US); Kenneth Eugene Smith, Saco, ME (US); Dragan Vidacic, Exeter, NH (US)

(73) Assignee: IDEXX Laboratories, Inc., Westbrook, ME (US)

( * ) Notice: Subject to any disclaimer, the term of this patent is extended or adjusted under 35 U.S.C. 154(b) by 173 days.

(21) Appl. No.: 14/592,282

(22) Filed: Jan. 8, 2015

(65) Prior Publication Data
US 2015/0226759 A1  Aug. 13, 2015

Related U.S. Application Data

(60) Provisional application No. 61/925,950, filed on Jan. 10, 2014, provisional application No. 61/987,121, filed on May 1, 2014.

(51) Int. Cl.
*G01N 35/00* (2006.01)
*B25J 19/02* (2006.01)
(Continued)

(52) U.S. Cl.
CPC ........ *G01N 35/0099* (2013.01); *B25J 9/1697* (2013.01); *B25J 19/021* (2013.01);
(Continued)

(58) Field of Classification Search
None
See application file for complete search history.

(56) References Cited

U.S. PATENT DOCUMENTS

| 2,058,516 A | 10/1936 | Schaaff ........................... 141/24 |
| 2,204,471 A | 6/1940 | Campbell, Jr. et al. ........ 141/29 |

(Continued)

FOREIGN PATENT DOCUMENTS

| EP | 0042337 | 12/1981 |
| EP | 0042340 | 12/1981 |

(Continued)

OTHER PUBLICATIONS

The Notification of Transmittal of the International Search Report and Written Opinion of the International Searching Authority, or Declaration, in English, dated Mar. 25, 2015; the International Search Report, in English, dated Mar. 25, 2015; and the Written Opinion of the International Searching Authority, in English, dated Mar. 25, 2015, each of which was issued by the International Bureau of WIPO for Applicant's corresponding PCT Application No. PCT/US15/10671, filed on Jan. 8, 2015.

*Primary Examiner* — Jill Warden
*Assistant Examiner* — Benjamin R Whatley
(74) *Attorney, Agent, or Firm* — Bodner & O'Rourke, LLP; Gerald T. Bodner; Christian P. Bodner

(57) ABSTRACT

A medical apparatus for analyzing fluid samples includes an outer casing, a slide loading mechanism disposed within the outer casing for loading fluid analysis slides, a slide ejecting mechanism disposed within the outer casing for ejecting fluid analysis slides, an evaporation cap opening mechanism disposed within the outer casing for opening an evaporation cap, an evaporation cap closing mechanism disposed within the outer casing for closing an evaporation cap, a drawer locking mechanism disposed within the outer casing for locking a drawer associated with the outer casing, a camera (Continued)

disposed within the outer casing, and a robot disposed within the outer casing. The robot is movable in three dimensions and has means for conducting three or more of the following operations: slide loading; slide ejecting; evaporation cap opening; evaporation cap closing; drawer locking; and camera manipulation.

26 Claims, 83 Drawing Sheets

(51) Int. Cl.
    *B25J 9/16*         (2006.01)
    *G01N 35/10*      (2006.01)
    *G01N 35/02*      (2006.01)
    *G01N 35/04*      (2006.01)
    *G01N 1/31*       (2006.01)

(52) U.S. Cl.
    CPC ........ *G01N 1/312* (2013.01); *G01N 35/00029* (2013.01); *G01N 35/00732* (2013.01); *G01N 35/025* (2013.01); *G01N 35/04* (2013.01); *G01N 35/109* (2013.01); *G01N 2035/00039* (2013.01); *G01N 2035/00079* (2013.01); *G01N 2035/00138* (2013.01); *G01N 2035/00356* (2013.01); *G01N 2035/0405* (2013.01); *G01N 2035/0449* (2013.01); *G01N 2035/103* (2013.01); *Y10S 901/09* (2013.01); *Y10S 901/41* (2013.01)

(56) References Cited

U.S. PATENT DOCUMENTS

| | | | |
|---|---|---|---|
| 2,363,474 A | 11/1944 | Schlesinger | 222/179.5 |
| 2,586,513 A | 2/1952 | Butler | 210/94 |
| 2,598,869 A | 6/1952 | White | 141/113 |
| 2,665,825 A | 1/1954 | Poitras et al. | 222/209 |
| 2,692,820 A | 10/1954 | Alway et al. | 210/659 |
| 2,721,008 A | 10/1955 | Morgan, Jr. | 222/334 |
| 2,797,149 A | 6/1957 | Skeggs | 436/53 |
| 2,802,605 A | 8/1957 | Parker | 222/215 |
| 3,036,893 A | 5/1962 | Natelson | 436/170 |
| 3,106,845 A | 10/1963 | Dimmick | 73/864.11 |
| 3,164,304 A | 1/1965 | Jager et al. | 222/192 |
| 3,190,731 A | 6/1965 | Weiskopf | 422/557 |
| 3,300,099 A | 1/1967 | Marona | 222/207 |
| 3,323,689 A | 6/1967 | Elmore | 222/385 |
| 3,341,087 A | 9/1967 | Rosin et al. | 222/422 |
| 3,367,746 A | 2/1968 | Maurukas | 422/510 |
| 3,449,081 A | 6/1969 | Hughes | 422/430 |
| 3,460,529 A | 8/1969 | Leucci | 600/580 |
| 3,526,480 A | 9/1970 | Findl et al. | 422/66 |
| 3,533,744 A | 10/1970 | Unger | 436/63 |
| 3,572,400 A | 3/1971 | Casner et al. | 141/1 |
| 3,574,064 A | 4/1971 | Binnings et al. | 435/286.4 |
| 3,615,240 A | 10/1971 | Sanz | 73/864.13 |
| 3,616,264 A | 10/1971 | Ray et al. | 435/287.3 |
| 3,618,829 A | 11/1971 | Elmore et al. | 222/209 |
| 3,645,423 A | 2/1972 | DeGraw | 222/207 |
| 3,650,437 A | 3/1972 | Binnings et al. | 222/136 |
| 3,659,934 A | 5/1972 | Costanza et al. | 353/103 |
| 3,675,488 A | 7/1972 | Viktora et al. | 73/863.12 |
| 3,748,044 A | 7/1973 | Liston | 356/404 |
| 3,754,866 A | 8/1973 | Ritchie et al. | 422/73 |
| 3,756,920 A | 9/1973 | Kelbaugh et al. | 435/287.3 |
| 3,758,274 A | 9/1973 | Ritchie et al. | 422/50 |
| 3,788,816 A | 1/1974 | Rohrbaugh et al. | 422/64 |
| 3,790,346 A | 2/1974 | Ritchie | 422/64 |
| 3,810,779 A | 5/1974 | Pickett et al. | 427/256 |
| 3,832,135 A | 8/1974 | Drozdowski et al. | 436/47 |
| 3,855,867 A | 12/1974 | Roach | 73/864.18 |
| 3,856,470 A | 12/1974 | Cullis et al. | 422/64 |
| 3,873,273 A | 3/1975 | Moran et al. | 422/64 |
| 3,883,308 A | 5/1975 | Matte | 422/64 |
| 3,904,372 A | 9/1975 | Lightner | 422/63 |
| 3,915,651 A | 10/1975 | Nishi | 73/864.16 |
| 3,918,913 A | 11/1975 | Stevenson et al. | 73/863.72 |
| 3,926,514 A | 12/1975 | Costanza et al. | 353/113 |
| 3,942,952 A | 3/1976 | Atwood | 73/864.91 |
| 4,041,995 A | 8/1977 | Columbus | 141/275 |
| 4,043,756 A | 8/1977 | Sommervold | 436/43 |
| 4,052,161 A | 10/1977 | Atwood et al. | 436/34 |
| 4,059,405 A | 11/1977 | Sodickson et al. | 436/44 |
| 4,061,469 A | 12/1977 | DuBose | 422/64 |
| 4,067,694 A | 1/1978 | Blakely et al. | 422/63 |
| 4,090,791 A | 5/1978 | Siddiqi et al. | 356/414 |
| 4,118,280 A | 10/1978 | Charles et al. | 435/287.3 |
| 4,119,381 A | 10/1978 | Muka et al. | 356/244 |
| 4,142,656 A | 3/1979 | Smith et al. | 222/325 |
| 4,152,390 A | 5/1979 | Nosco et al. | 422/63 |
| 4,160,646 A | 7/1979 | Furutani et al. | 436/169 |
| 4,161,508 A | 7/1979 | Janchen | 422/519 |
| 4,198,483 A | 4/1980 | Sogi et al. | 435/309.1 |
| 4,198,485 A | 4/1980 | Stark, Jr. | 521/55 |
| 4,210,724 A | 7/1980 | Sogi et al. | 435/309.2 |
| 4,219,529 A | 8/1980 | Tersteeg et al. | 422/65 |
| 4,224,032 A | 9/1980 | Glover et al. | 436/46 |
| 4,234,538 A | 11/1980 | Ginsberg et al. | 422/64 |
| 4,234,539 A | 11/1980 | Ginsberg et al. | 422/64 |
| 4,236,894 A | 12/1980 | Sommervold | 436/43 |
| 4,264,560 A | 4/1981 | Natelson | 422/417 |
| 4,271,123 A | 6/1981 | Curry et al. | 422/64 |
| 4,272,482 A | 6/1981 | Jessop et al. | 422/65 |
| 4,277,440 A | 7/1981 | Jessop et al. | 422/509 |
| 4,287,155 A | 9/1981 | Tersteeg et al. | 422/64 |
| 4,296,069 A | 10/1981 | Smith et al. | 422/64 |
| 4,296,070 A | 10/1981 | Montalto et al. | 422/65 |
| 4,298,571 A | 11/1981 | DiFulvio et al. | 422/65 |
| 4,298,575 A | 11/1981 | Berglund | 73/864.13 |
| 4,302,420 A | 11/1981 | Jakubowicz et al. | 422/63 |
| 4,303,611 A | 12/1981 | Jessop | 422/65 |
| 4,308,231 A | 12/1981 | Kolber et al. | 422/64 |
| 4,321,122 A | 3/1982 | Whitcomb et al. | 204/400 |
| 4,325,909 A | 4/1982 | Coulter et al. | 422/63 |
| 4,335,620 A | 6/1982 | Adams | 73/863.11 |
| 4,340,390 A | 7/1982 | Collins et al. | 436/54 |
| 4,347,750 A | 9/1982 | Tersteeg et al. | 73/864.31 |
| 4,351,799 A | 9/1982 | Gross et al. | 422/63 |
| 4,359,447 A | 11/1982 | Welch | 422/63 |
| RE31,150 E | 2/1983 | Ginsberg et al. | 422/64 |
| 4,387,990 A | 6/1983 | Yazawa et al. | 356/244 |
| 4,392,195 A | 7/1983 | Inoue | 700/162 |
| 4,399,711 A | 8/1983 | Klein | 73/864.16 |
| 4,420,566 A | 12/1983 | Jessop et al. | 436/46 |
| 4,424,191 A | 1/1984 | Jakubowicz | 422/65 |
| 4,429,373 A | 1/1984 | Fletcher et al. | 422/403 |
| 4,430,299 A | 2/1984 | Horne | 422/64 |
| 4,441,532 A | 4/1984 | Hrubesh | 141/1 |
| 4,451,433 A | 5/1984 | Yamashita et al. | 422/63 |
| 4,452,899 A | 6/1984 | Alston | 436/46 |
| 4,455,280 A | 6/1984 | Shinohara et al. | 422/63 |
| 4,475,666 A | 10/1984 | Bilbrey et al. | 222/14 |
| 4,488,810 A | 12/1984 | Hatanaka et al. | 356/244 |
| 4,503,011 A | 3/1985 | Hubeau | 422/73 |
| 4,512,952 A | 4/1985 | Blanding et al. | 422/63 |
| 4,522,921 A | 6/1985 | Ogawa | 436/47 |
| 4,539,855 A | 9/1985 | Jacobs | 73/864.25 |
| 4,540,549 A | 9/1985 | Manabe | 422/64 |
| 4,549,809 A | 10/1985 | Minekane et al. | 356/436 |
| D282,203 S | 1/1986 | Leonard et al. | D10/81 |
| 4,568,519 A | 2/1986 | Hamilton et al. | 422/64 |
| 4,584,275 A | 4/1986 | Okano et al. | 435/287.3 |
| 4,599,219 A | 7/1986 | Cooper et al. | 422/430 |
| 4,615,360 A | 10/1986 | Jacobs | 141/18 |
| 4,627,014 A | 12/1986 | Lo et al. | 702/25 |
| 4,629,703 A | 12/1986 | Uffenheimer | 436/45 |
| 4,644,807 A | 2/1987 | Mar | 73/864.62 |
| 4,647,431 A | 3/1987 | Sekine et al. | 422/63 |
| 4,656,006 A | 4/1987 | Assmann et al. | 422/63 |
| 4,656,007 A | 4/1987 | Douchy et al. | 422/64 |
| 4,670,219 A | 6/1987 | Nelson et al. | 422/63 |
| 4,675,301 A | 6/1987 | Charneski et al. | 436/180 |

(56) References Cited

U.S. PATENT DOCUMENTS

| | | | |
|---|---|---|---|
| 4,678,755 A | 7/1987 | Shinohara et al. | 436/43 |
| 4,680,164 A | 7/1987 | Kelln | 422/72 |
| 4,681,741 A | 7/1987 | Hanaway | 422/509 |
| 4,695,430 A | 9/1987 | Coville et al. | 422/65 |
| 4,706,207 A | 11/1987 | Hennessy et al. | 702/21 |
| 4,710,352 A | 12/1987 | Slater et al. | 422/63 |
| 4,713,974 A | 12/1987 | Stone | 73/864.23 |
| 4,719,085 A | 1/1988 | Jacobs | 422/401 |
| 4,731,058 A | 3/1988 | Doan | 604/155 |
| 4,737,344 A | 4/1988 | Koizumi et al. | 422/501 |
| 4,738,826 A | 4/1988 | Harris | 422/516 |
| 4,752,449 A | 6/1988 | Jackson et al. | 422/73 |
| 4,761,268 A | 8/1988 | Andersen et al. | 422/72 |
| 4,769,009 A | 9/1988 | Dykstra | 604/155 |
| 4,770,053 A | 9/1988 | Broderick et al. | 73/866.5 |
| 4,774,055 A | 9/1988 | Wakatake et al. | 422/64 |
| 4,785,407 A | 11/1988 | Sakagami | 702/22 |
| 4,794,085 A | 12/1988 | Jessop et al. | 436/54 |
| 4,798,705 A | 1/1989 | Jakubowicz et al. | 422/63 |
| 4,808,380 A | 2/1989 | Minekane | 422/64 |
| 4,814,279 A | 3/1989 | Sugaya | 435/303.1 |
| 4,821,586 A | 4/1989 | Scordato et al. | 73/864.18 |
| 4,823,992 A | 4/1989 | Fiorentini | 222/333 |
| 4,826,659 A | 5/1989 | Akisada | 422/63 |
| 4,837,159 A | 6/1989 | Yamada | 436/45 |
| 4,841,208 A | 6/1989 | Itoh | 318/561 |
| 4,855,109 A | 8/1989 | Muraishi et al. | 422/63 |
| 4,863,695 A | 9/1989 | Fullemann | 422/501 |
| 4,928,540 A | 5/1990 | Kido et al. | 73/864.11 |
| 4,931,257 A | 6/1990 | Quenin et al. | 422/501 |
| 4,935,374 A | 6/1990 | Jacobs et al. | 436/103 |
| 4,943,415 A | 7/1990 | Przybylowicz et al. | 422/404 |
| 4,963,333 A | 10/1990 | Shaw et al. | 422/568 |
| 5,034,191 A | 7/1991 | Porte | 422/64 |
| 5,037,613 A | 8/1991 | Shaw et al. | 422/64 |
| 5,039,615 A | 8/1991 | Takahata | 436/44 |
| 5,049,359 A | 9/1991 | Azuma et al. | 422/67 |
| 5,049,487 A | 9/1991 | Phillips et al. | 435/4 |
| 5,075,079 A | 12/1991 | Kerr et al. | 422/64 |
| 5,089,229 A | 2/1992 | Heidt et al. | 422/64 |
| 5,102,624 A | 4/1992 | Muraishi | 422/64 |
| 5,126,952 A | 6/1992 | Kildal-Brandt et al. | 702/91 |
| 5,141,871 A | 8/1992 | Kureshy et al. | 436/47 |
| 5,149,501 A | 9/1992 | Babson et al. | 422/404 |
| 5,174,960 A | 12/1992 | Shaw et al. | 422/63 |
| 5,174,963 A | 12/1992 | Fuller et al. | 422/82.05 |
| 5,182,083 A | 1/1993 | Barker et al. | 422/63 |
| 5,213,764 A | 5/1993 | Kerr et al. | 422/511 |
| 5,250,262 A | 10/1993 | Heidt et al. | 422/64 |
| 5,257,212 A | 10/1993 | Kildal-Brandt et al. | 702/25 |
| 5,283,195 A | 2/1994 | Muszak et al. | 436/48 |
| 5,304,350 A | 4/1994 | Meserol | 422/501 |
| 5,314,825 A | 5/1994 | Weyrauch et al. | 436/43 |
| 5,336,467 A | 8/1994 | Heidt et al. | 422/64 |
| 5,340,540 A | 8/1994 | Miller | 422/64 |
| 5,425,918 A | 6/1995 | Healey et al. | 422/64 |
| 5,455,008 A | 10/1995 | Earley et al. | 422/511 |
| 5,474,910 A | 12/1995 | Alfano | 435/34 |
| 5,478,750 A | 12/1995 | Bernstein et al. | 436/164 |
| 5,483,843 A | 1/1996 | Miller et al. | 73/864.23 |
| 5,525,514 A | 6/1996 | Jacobs et al. | 436/46 |
| 5,525,551 A | 6/1996 | Ohta | 438/789 |
| 5,645,798 A | 7/1997 | Schreiber et al. | 422/410 |
| 5,653,942 A | 8/1997 | Terashima et al. | 422/63 |
| 5,654,200 A | 8/1997 | Copeland et al. | 436/46 |
| 5,658,532 A | 8/1997 | Kurosaki et al. | 422/64 |
| 5,730,939 A | 3/1998 | Kurumada et al. | 422/67 |
| 5,753,512 A | 5/1998 | Riall et al. | 436/50 |
| 5,772,962 A | 6/1998 | Uchida et al. | 422/67 |
| 5,811,306 A | 9/1998 | Komatsu | 436/54 |
| 5,837,546 A | 11/1998 | Allen et al. | 436/169 |
| 5,879,944 A | 3/1999 | Komatsu | 436/50 |
| 5,897,837 A | 4/1999 | Mizuno | 422/510 |
| 6,013,528 A | 1/2000 | Jacobs et al. | 436/54 |
| 6,136,270 A | 10/2000 | Maes et al. | 422/64 |
| 6,183,693 B1 | 2/2001 | Bogen et al. | 422/64 |
| 6,268,162 B1 | 7/2001 | Phillips et al. | 435/14 |
| 6,296,809 B1 | 10/2001 | Richards et al. | 422/64 |
| 6,326,160 B1 | 12/2001 | Dunn et al. | 435/14 |
| 6,352,861 B1 | 3/2002 | Copeland et al. | 436/46 |
| 6,372,485 B1 | 4/2002 | Clark et al. | 435/288.7 |
| 6,387,326 B1 | 5/2002 | Edwards et al. | 422/63 |
| 6,458,324 B1 | 10/2002 | Schinzel | 422/65 |
| 6,531,094 B2 | 3/2003 | Seto et al. | 422/64 |
| 6,531,095 B2 | 3/2003 | Hammer et al. | 422/64 |
| 6,663,832 B2 | 12/2003 | Lebl et al. | 422/64 |
| 6,783,733 B2 | 8/2004 | Bogen et al. | 422/64 |
| 6,797,518 B1 | 9/2004 | Jacobs et al. | 436/46 |
| 6,830,731 B1 | 12/2004 | Buechler et al. | 422/82.08 |
| 6,890,761 B2 | 5/2005 | Ishizawa et al. | 436/180 |
| 6,913,933 B2 | 7/2005 | Jacobs et al. | 436/180 |
| 6,919,044 B1 | 7/2005 | Shibata et al. | 422/63 |
| 6,937,955 B2 | 8/2005 | Barnes | 702/94 |
| 6,984,527 B2 | 1/2006 | Miller | 436/180 |
| 7,198,956 B2 | 4/2007 | Uffenheimer et al. | 436/180 |
| 7,256,045 B2 | 8/2007 | Jacobs et al. | 436/43 |
| 7,270,785 B1 | 9/2007 | Lemme et al. | 422/64 |
| 7,616,317 B2 | 11/2009 | Misener et al. | 356/446 |
| 7,632,468 B2 | 12/2009 | Barski et al. | 422/561 |
| 8,287,823 B2 | 10/2012 | Sellers et al. | 422/563 |
| 8,585,989 B2 | 11/2013 | Rich et al. | 422/563 |
| 2001/0019826 A1 | 9/2001 | Ammann | 435/6.11 |
| 2002/0054830 A1 | 5/2002 | Bogen et al. | 422/64 |
| 2002/0182108 A1 | 12/2002 | Ishihara et al. | 422/62 |
| 2003/0022380 A1 | 1/2003 | Jakubowicz et al. | 436/54 |
| 2003/0027206 A1 | 2/2003 | Ammann et al. | 435/6.11 |
| 2003/0104634 A1 | 6/2003 | Jacobs et al. | 436/180 |
| 2004/0072363 A1 | 4/2004 | Schembri | 436/174 |
| 2004/0191923 A1 | 9/2004 | Tomasso et al. | 436/180 |
| 2005/0036911 A1 | 2/2005 | Sellers et al. | 422/65 |
| 2005/0286265 A1* | 12/2005 | Zampini | F21S 9/022 362/612 |
| 2006/0148063 A1 | 7/2006 | Fauzzi et al. | 435/286.4 |
| 2006/0211253 A1 | 9/2006 | Chen et al. | 438/714 |
| 2007/0166194 A1 | 7/2007 | Wakatake | 422/64 |
| 2010/0254854 A1 | 10/2010 | Rich et al. | 422/64 |
| 2011/0093207 A1 | 4/2011 | Ingber et al. | 702/19 |
| 2011/0304722 A1 | 12/2011 | Nilsson et al. | 348/79 |
| 2013/0065797 A1* | 3/2013 | Silbert | G01F 23/265 506/39 |
| 2013/0132006 A1 | 5/2013 | Gwynn et al. | 702/55 |

FOREIGN PATENT DOCUMENTS

| | | |
|---|---|---|
| EP | 0353592 | 2/1990 |
| WO | WO9108463 | 6/1991 |
| WO | WO9605488 | 2/1996 |
| WO | WO2008140742 | 11/2008 |
| WO | WO2013106269 | 7/2013 |

* cited by examiner

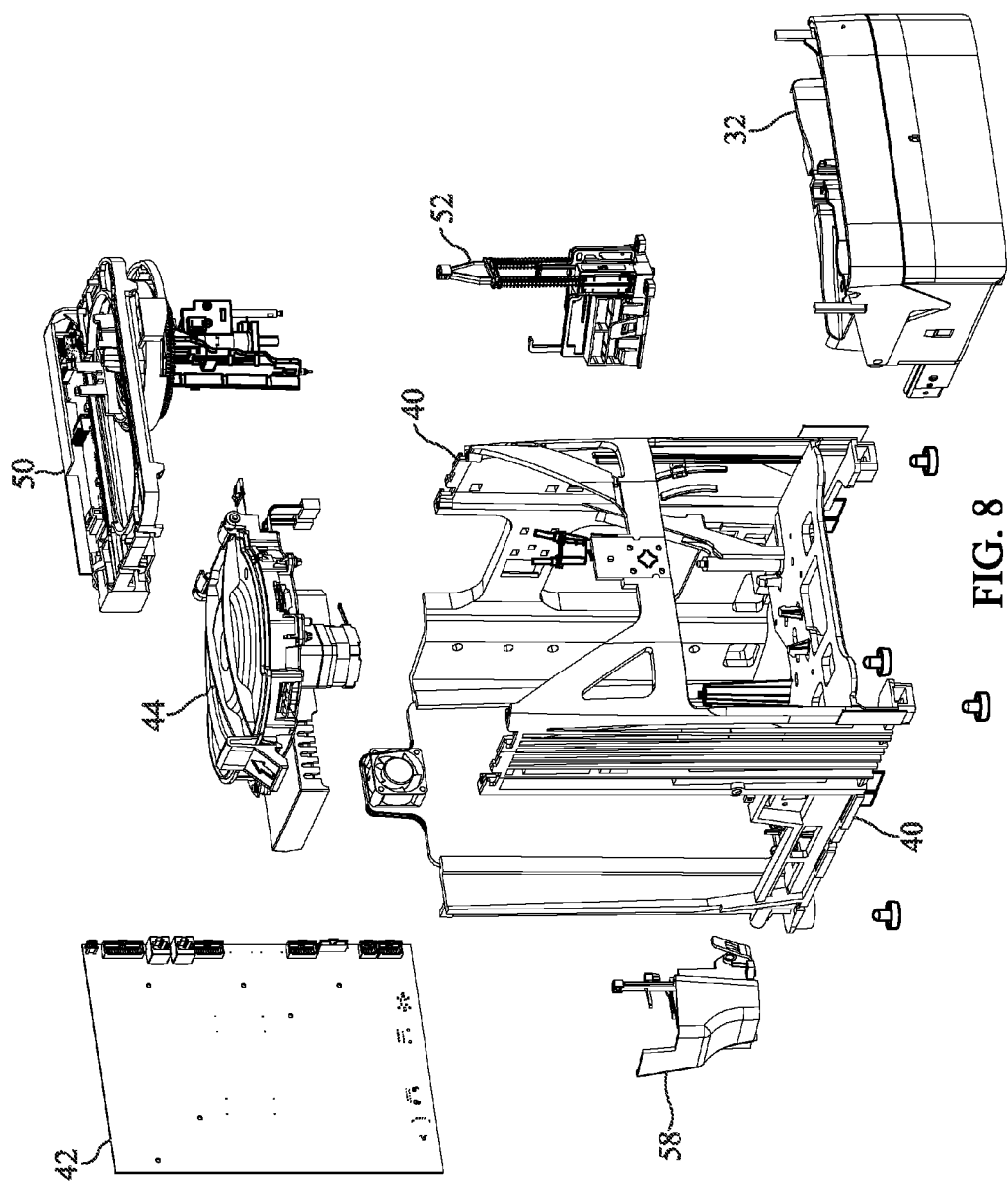

CHEMICAL ANALYZER

CROSS-REFERENCE TO RELATED APPLICATIONS

This application is related to U.S. Provisional Application Ser. No. 61/925,950, filed on Jan. 10, 2014, and entitled "Chemical Analyzer", and U.S. Provisional Application Ser. No. 61/987,121, filed on May 1, 2014, and also entitled "Chemical Analyzer", the disclosure of each of which is incorporated herein by reference and on which priority is hereby claimed.

BACKGROUND OF THE INVENTION

Field of the Invention

This invention relates to chemical analyzers which automatically analyze fluids, and more particularly relates to "dry chemistry" analyzers. Even more specifically, this invention relates to chemical analyzers that are particularly adapted for biological fluid testing purposes wherein a change in an optical characteristic of a sample is sensed and analyzed automatically by the analyzer. The analyzer of the present invention has particular utility for human and veterinary applications.

Description of the Prior Art

Automated systems have been developed for carrying out quantitative chemical analysis of fluid samples using essentially dry, analytical elements, which elements offer substantial storage and handling conveniences. The "dry" analytical elements are preferably in the form of test slides. These test slides are formed as a multi-layer element containing the necessary free agents for reaction with components of a biological fluid, such as a blood serum, deposited thereon. Certain reactions colorimetrically produce a change in optical density, or fluoresce, which is sensed by a reflectormeter or fluorometer, the amount of light reflected from or fluoresced by the test element varying in accordance with the reaction and being indicative of the amount of a particular component present in the fluid. Such test slides containing a dry analyte are well known in the art and are described in U.S. Pat. No. 4,647,431, which issued to Takasi Sekine, et al., and an improved version of the conventional test slide described in the Sekine, et al. patent is disclosed in U.S. Pat. No. 8,287,823, which issued to James M. Sellers, et al., and U.S. Pat. No. 8,585,989, which issued to Carl Russell Rich, the disclosure of each of which is incorporated herein by reference. Automated chemical analyzers and instruments which conduct test procedures utilizing dry chemical reagent test slides are also known, such as the VETTEST® analyzer and the CATALYST DX® analyzer available from IDEXX Laboratories, Inc. of Westbrook, Me.

A very capable "dry chemistry" analyzer is described in U.S. Pat. No. 5,089,229, which issued to Thomas Heidt, et al., the disclosure of which is incorporated herein by reference. The chemical analyzer described in the aforementioned '229 Heidt, et al. patent includes a rotatable turntable which is adapted to hold a plurality of reagent test slides, a sample metering device, an incubator or temperature controller, a reflectometer, a slide inserter mechanism, a slide ejector mechanism and associated electronics, computer or microprocessor, and software. The rotatable turntable preferably holds up to twelve slides about its circumference. The dry analytical test slides come individually pre-packaged, and are inserted by the operator onto the rotatable turntable one at a time by using the inserter mechanism. The turntable positions the reagent test slides under the metering device, which device deposits a predetermined amount of sample onto each slide. The turntable also carries the slides above a reflectometer. After testing has been completed, the ejector mechanism automatically removes the reagent test slides from the turntable.

An improved automated analyzer which utilizes reagent test slides is described in U.S. Patent Application Publication No. 2010/0254854, filed on Nov. 5, 2009, and naming Carl Russell Rich, et al. as the inventors, the disclosure of which is incorporated herein by reference. The Rich, et al. published application discloses a chemical analyzer which includes a slide transport mechanism, a slide inserter mechanism which inserts a plurality of chemical reagent test slides onto the slide transport mechanism, a reflectometer/fluorometer which is positioned in proximity to the slide transport mechanism and the chemical reagent test slides situated thereon, a sample metering device that aspirates a sample fluid from a vial or centrifuge rotor and deposits a predetermined volume of the sample fluid onto the chemical reagent test slides, an incubator for maintaining the reagent test slides situated on the slide transport mechanism at a predetermined temperature, and a slide ejector mechanism which removes the reagent test slides from the slide transport mechanism.

OBJECTS AND SUMMARY OF THE INVENTION

It is an object of the present invention to provide a chemical analyzer in the form of a small, desktop unit.

It is another object of the present invention to provide a chemical analyzer which can run a series of tests simultaneously in a relatively short period of time.

It is still another object of the present invention to provide a chemical analyzer which is relatively inexpensive to manufacture and has a relatively low operating cost.

It is yet a further object of the present invention to provide a chemical analyzer which has a reduced number of components than that of conventional analyzers without sacrificing accuracy in the test results it provides.

It is still another object of the present invention to provide an automated analyzer which can run tests on not only reagent test slides but also slide-based immunoassays, such as disclosed in PCT Patent Application Publication No. WO2013/106,269, filed on Jan. 7, 2013, and having Eugene Chan, et al. as the named inventors, the disclosure of which is incorporated herein by reference.

It is another object of the present invention to provide a chemical analyzer which accepts consumables, that is, reagent test slides, pipette tips, reagent packs, whole blood separator cups (i.e., centrifuge rotors) or pre-spun sample, mixing and diluent cups, in a simple user interface and queues run commands based on information received from an external computer or system electronically interfacing therewith.

It is a further object of the present invention to provide a chemical analyzer which carefully manages the light conditions and temperature of the analyzer's interior environment to provide a stable environment for slide development and slide reading.

It is yet another object of the present invention to provide an instrument for the analysis of dry analytical slides which is highly automated to reduce the amount of user hands-on time.

It is yet a further object of the present invention to provide a chemical analyzer which requires fewer motors for operation and includes a fluid handler in the form of a three-axis robot which is used to actuate the loading of slides onto a slide transport mechanism, the ejection of slides therefrom, and the selective opening and closing of evaporation caps 54 on the slide transport mechanism, among other functions.

It is still another object of the present invention to provide a chemical analyzer having two heating zones, one of which can quickly compensate for colder slides without also affecting the temperature of slides that have already been warmed.

It is yet another object of the present invention to provide a chemical analyzer which conducts tests on chemical reagent test slides and which provides for the radial alignment of the reflectometer/fluorometer (i.e., the "optics module") used therein.

It is still another object of the present invention to provide an optics module for use in a chemical analyzer which conducts tests on chemical reagent test slides, in which one or more light emitting diodes (LEDs) are used to illuminate the reagent test slides, and one or more photodiodes simultaneously measure the intensity of the slide illuminating LEDs and provide reference measurements to normalize the measurement taken by a photodiode forming part of the optics module.

It is yet another object of the present invention to provide a slide transport mechanism for a chemical analyzer which conducts tests on a plurality of chemical reagent test slides situated in a side-by-side radial arrangement, wherein the slide transport mechanism controls the evaporation of a liquid sample metered onto the slides and limits slide-to-slide chemistry cross-talk to ensure good assay development.

It is yet a further object of the present invention to provide a chemical analyzer for conducting colorimetric, or reflectance and/or fluorescence, tests on a plurality of chemical reagent test slides using an optics module, wherein the chemical analyzer determines precisely not only where each slide is located on a slide transport mechanism and within an incubator housing of the chemical analyzer but also where each slide is situated in relation to the optics module.

It is a further object of the present invention to provide a chemical analyzer for conducting reflectance and fluorescence tests on a plurality of chemical reagent test slides, which provides accurate thermal control of the slides as they are being cycled through the chemical analyzer and which quickly warms cold slides and precisely maintains the temperature of already warmed slides.

It is still another object of the present invention to provide a chemical analyzer for conducting tests on a plurality of chemical reagent test slides, which analyzer includes a carousel for effecting the movement of the test slides in a circular path, wherein the slide carousel 48 is removable from the analyzer for cleaning and easily replaceably mountable on a driving hub, the analyzer including carousel load assist guides to provide means for locating the carousel on the driving hub.

It is yet another object of the present invention to provide a chemical analyzer for conducting tests on a plurality of chemical reagent test slides, which includes a slide carousel 48 having a plurality of radially extending spokes, the carousel effecting movement of the chemical reagent test slides in a circular direction, each spoke of the slide carousel 48 having a movable evaporation cap, the slide carousel 48 evenly distributing a predetermined amount of pressure on the spokes thereof to retain each slide in a particular position relative to the slide carousel 48 and to maintain pressure on the slide caps to aid in the prevention of evaporation of a liquid sample metered onto the chemical reagent test slides.

It is an object of the present invention to provide a chemical analyzer for conducting tests on a plurality of chemical reagent test slides and which includes an optics module having a combined reflectometer/fluorometer and in which an autonomous heater is provided to effect the relative rapid warm up of the optics module and to maintain the internal components of the optics module at a predetermined temperature.

It is another object of the present invention to provide a chemical analyzer for conducting tests on a plurality of chemical reagent test slides, which includes a slide transport mechanism having a window formed therein, and an optics module situated in alignment with the window, and wherein the chemical analyzer may conduct a self-test to detect whether the viewing window of the slide transport mechanism needs to be cleaned to maintain accurate measurements.

It is yet a further object of the present invention to provide a chemical analyzer for conducting tests on a plurality of chemical reagent test slides, which includes a camera that identifies what consumables, such as disposable pipette tips, sample cups, a separator cup (i.e., centrifuge rotor), diluent cups, and reagent packs are loaded on the analyzer.

It is still another object of the present invention to provide a chemical analyzer which internally includes a vision system having one or more cameras which function to read a bar code on each slide of a plurality of reagent test slides on which tests are conducted by the chemical analyzer, and which can detect the presence or absence of reagent test slides in a slide loading mechanism of the analyzer, pipette tips, a diluent cup, a sample cup, a centrifuge rotor and other components of the analyzer.

It is a further object of the present invention to provide a chemical analyzer having a fluid handler which includes a liquid sample metering pipette or probosis on which may be mounted a disposable pipette tip, and further includes a tip shucker mechanism which removes the disposable tip from the liquid sample metering pipette without spillage or splashing of any liquid contained within or on the tip to prevent sample splatter inside the analyzer.

It is an object of the present invention to provide a chemical analyzer for conducting tests on a plurality of chemical reagent test slides, which analyzer includes a disposable slide drawer and a sloped shelf beneath a slide ejector mechanism that encourages a randomized landing pattern of used slides within the drawer.

It is yet another object of the present invention to provide a chemical analyzer for conducting tests on a plurality of chemical reagent tests, which includes a slide drawer for receiving used slides and which can determine whether the slide disposal drawer needs to be emptied.

In accordance with one form of the present invention, a chemical analyzer for conducting colorimetric (reflectance and fluorescence) tests on a plurality of chemical reagent test slides is a highly automated instrument that reduces the amount of user hands-on time. Automated tasks completed by the analyzer includes slide handling, sample processing, and slide reading. The chemical analyzer minimizes data entry by identifying loaded consumables, such as slides and reagent packs. Consequently, the user does not need to double check the identity of these consumables or worry about inaccurate test results due to, for example, the wrong reagent being added, since the chemical analyzer will double check the identity of the consumables before drawing or mixing any fluids.

The chemical analyzer of the present invention not only identifies the user-added components, such as slides, diluent cups, a centrifuge rotor containing a liquid sample, and the like, but also determines if there are any missing items in order to conduct tests on a liquid sample to be deposited on one or more of the chemical reagent test slides. More specifically, the chemical analyzer is equipped to identity the presence of slides in a slide load area, individual slide type and lot, the presence or absence of a liquid sample, and whether the sample is in a cup or in a whole blood separator cup (i.e., a centrifuge rotor), the number of disposable pipette tips that are present in the analyzer for use in a sample metering operation, and what types of reagent consumables are present, if any.

The chemical analyzer of the present invention has one or more cameras that use machine vision algorithms to meet all of the detection needs listed above. The camera or cameras can identify the reagent consumable type and lot by reading identifying information from a printed bar code on the reagent test slides. A two-camera system is preferably incorporated in the chemical analyzer, in which one camera is dedicated to identifying the type and lot of the slides, while the second camera is tasked with other identification needs.

The chemical analyzer employs a slide carousel 48 to transport the reagent test slides in a circular path above an optics module. The slide carousel 48 permits the chemical analyzer to parallel process multiple slides, bringing the slides to various stations of the analyzer that read the slides, dispense samples onto the slides, and provides a slide entry and exit. Additionally, the slide carousel 48 of the analyzer transports the slides above a fixed heating plate so that the slides are incubated and maintained at a constant temperature.

As mentioned previously, the optics module combines the functions of a fluorometer and a reflectometer to read different types of slides. Combining these functions in a single optics module permits the individual placement of each slide in only one critical location to conduct such reflectance and fluorescence measurements.

Liquid sample handling within the chemical analyzer of the present invention involves moving a liquid sample between fluid wells for dilution or for immunoassay runs. The liquid sample also needs to be deposited on these slides. The chemical analyzer employs a three-axis fluid handling system to access all of the necessary locations required for dilution, centrifugation, mixing, aspirating and dispensing on reagent test slides a liquid sample.

The sample handling station includes a fluid handler having a pump portion which aspirates, dispenses and mixes sample and diluent fluids, and is very compact to meet space considerations, which results in a chemical analyzer having a relatively overall small, tabletop or bench top compact shape and relatively low weight.

In the chemical analyzer of the present invention, reagent test slides need to be moved in and out of the slide transport mechanism for each run cycle. Furthermore, the reagent test slides must stay covered to minimize evaporation except in the moment of fluid/sample dispense. The chemical analyzer of the present invention accomplishes the automated loading of the test slides by the interaction between a slide loading mechanism and an actuating arm on the fluid handler forming part of the fluid metering mechanism. The slide carousel, which covers the reagent test slides and which effects the movement of the test slides in a circular path over a heated plate, includes evaporation caps. These evaporation caps are moved aside at a particular location where fluid is dispensed or metered onto a chemical reagent test slide situated at that location. After a fluid sample is dispensed onto the reagent test slide, the evaporation cap of the slide carousel is quickly repositioned over the film of the reagent test slide to prevent evaporation.

Once the run cycle is completed for the plurality of chemical reagent test slides, the slides are ejected, one by one, from the slide transport mechanism and are directed in a random pattern into a slide and pipette tip waste drawer. To accomplish each of these motions, the chemical analyzer of the present invention makes use of the fluid handler's ability to move along three axes, specifically in an X-direction (that is, left and right, when viewing the chemical analyzer from the front thereof), a Z-direction (that is, up and down, when viewing the chemical analyzer from the front thereof) and in a theta ($\theta$) direction (that is, a radial direction within an X-Y plane). Force is applied in the Z-direction by movement of the fluid handler having one or more extending actuating arms, the actuating arms cooperating with a slide insertion mechanism, a slide ejector mechanism, and the slide carousel to effect movement of the evaporation caps on the slide carousel.

As stated previously, the chemical analyzer of the present invention has the capability to quickly identify components, such as a sample cup, a diluent cup, a mixing cup, disposable pipette tips and a sample centrifuge rotor, placed in the analyzer by the user. Consequently, the analyzer can also quickly alert the user should the wrong components be placed in the analyzer or components that are required for conducting a test are missing.

The chemical analyzer includes a side door which the user can access for maintenance purposes. During maintenance, the optics module preferably remains powered, and selected light emitting diodes (LEDs) of the optics module are energized to illuminate a window in the slide transport mechanism above the optics module so that the user can easily see if the window needs to be cleaned.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 8 is an exploded view of the primary assemblies of the chemical analyzer of the present invention.

DETAILED DESCRIPTION OF THE PREFERRED EMBODIMENTS

Figure 1:
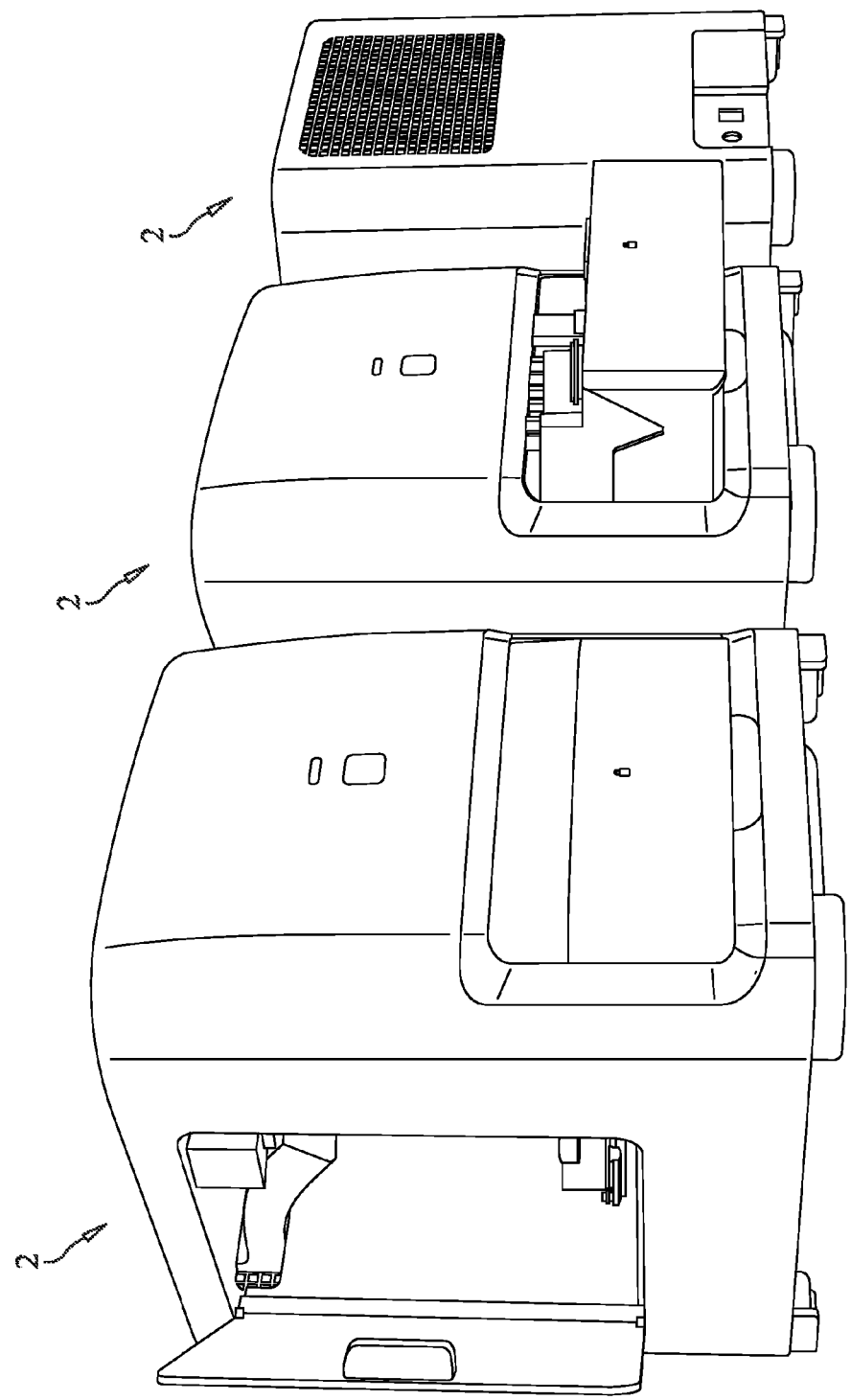
FIG. 1 is a perspective view of three chemical analyzers formed in accordance with the present invention, the analyzers being in different arrangements and configurations.
Figure 1A:
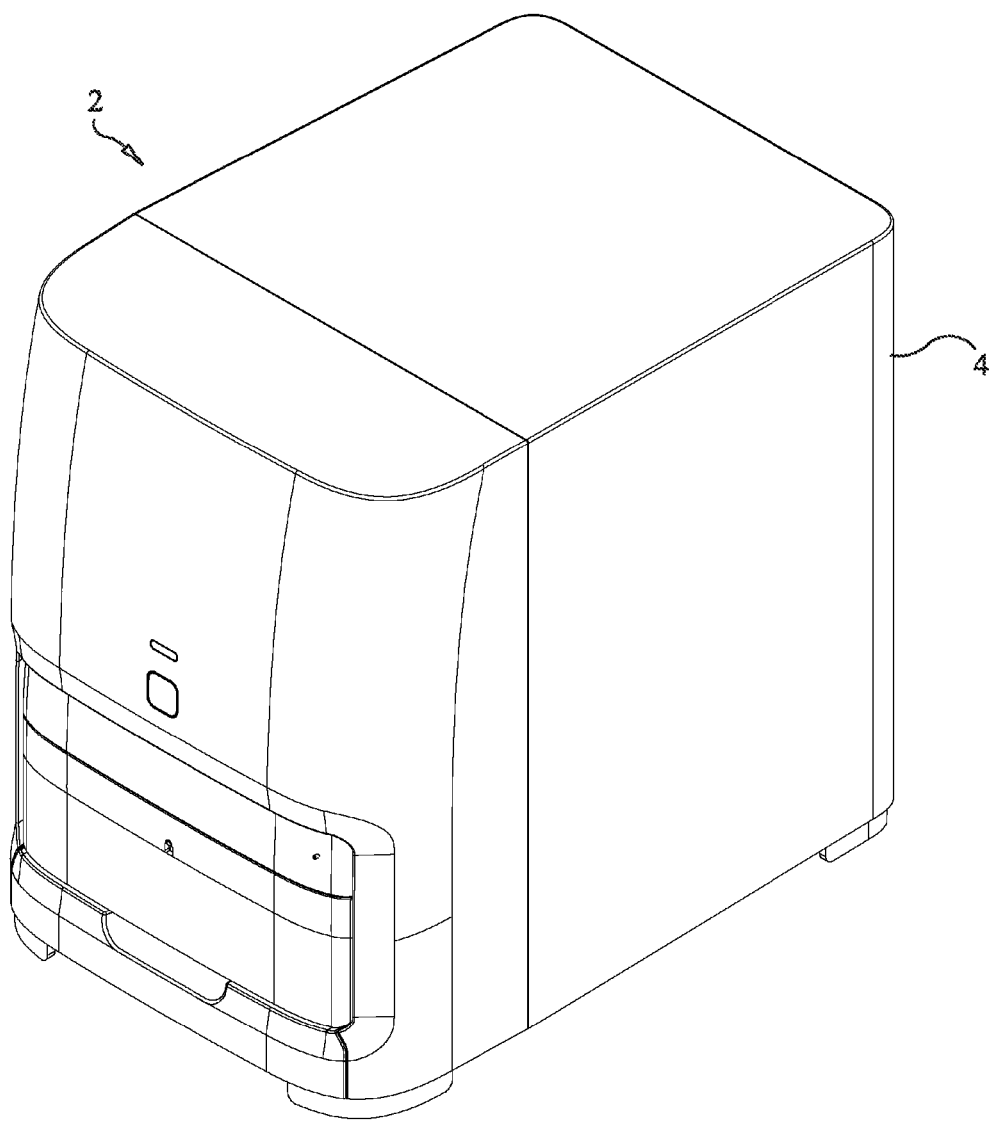
FIG. 1A is a front perspective view of a chemical analyzer formed in accordance with the present invention.
Figure 2:
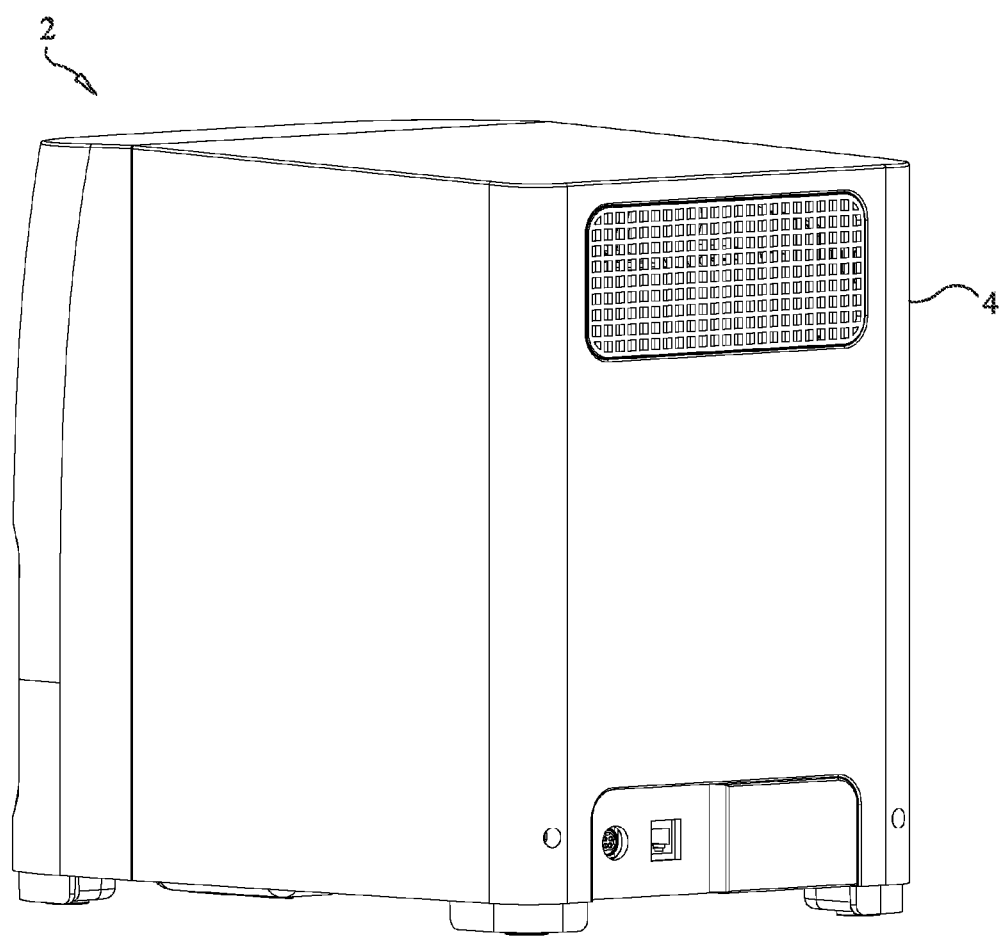
FIG. 2 is a rear perspective view of a chemical analyzer formed in accordance with the present invention.
Figure 2A:
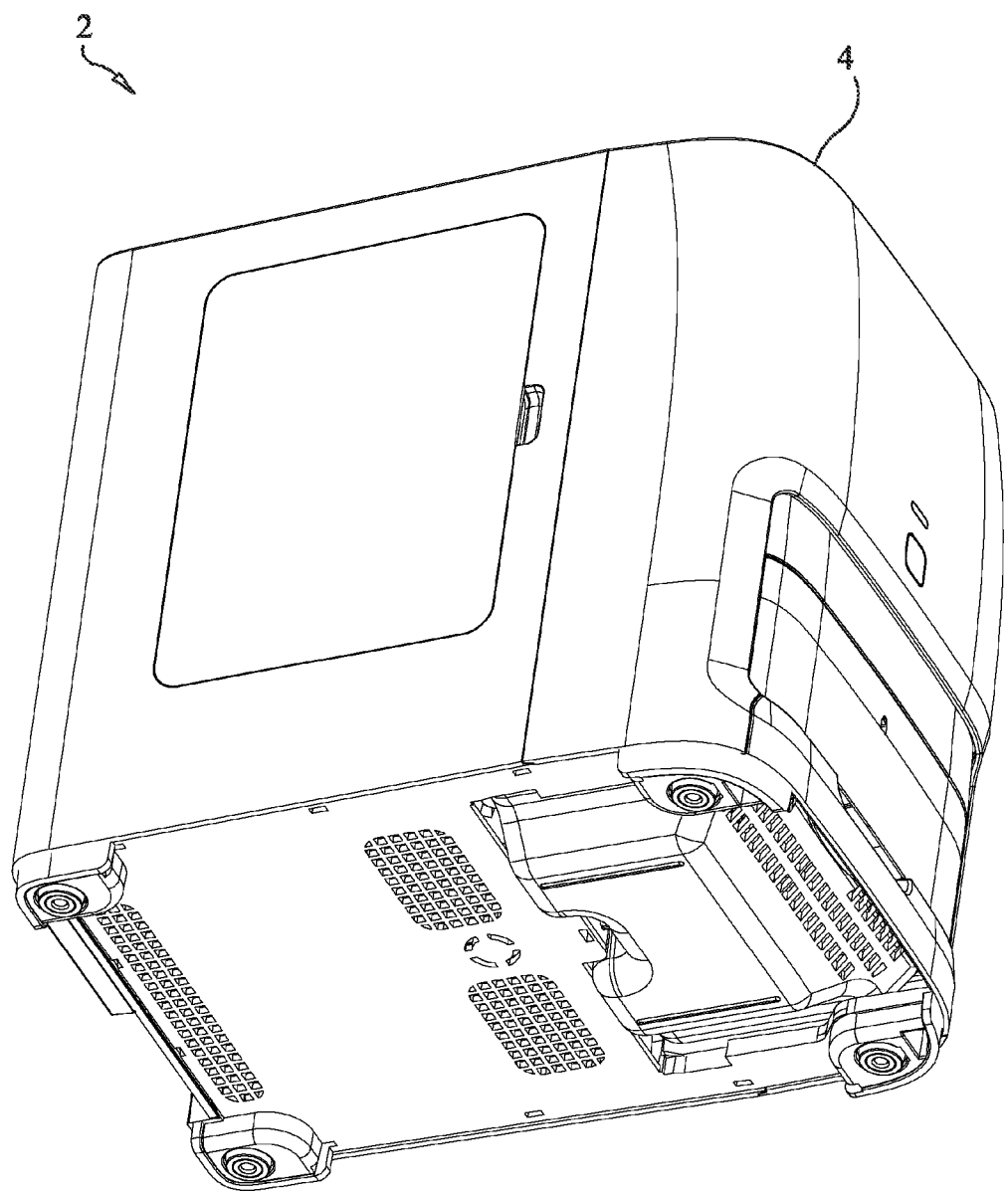
FIG. 2A is a bottom rear perspective view of a chemical analyzer formed in accordance with the present invention.
Figure 2B:
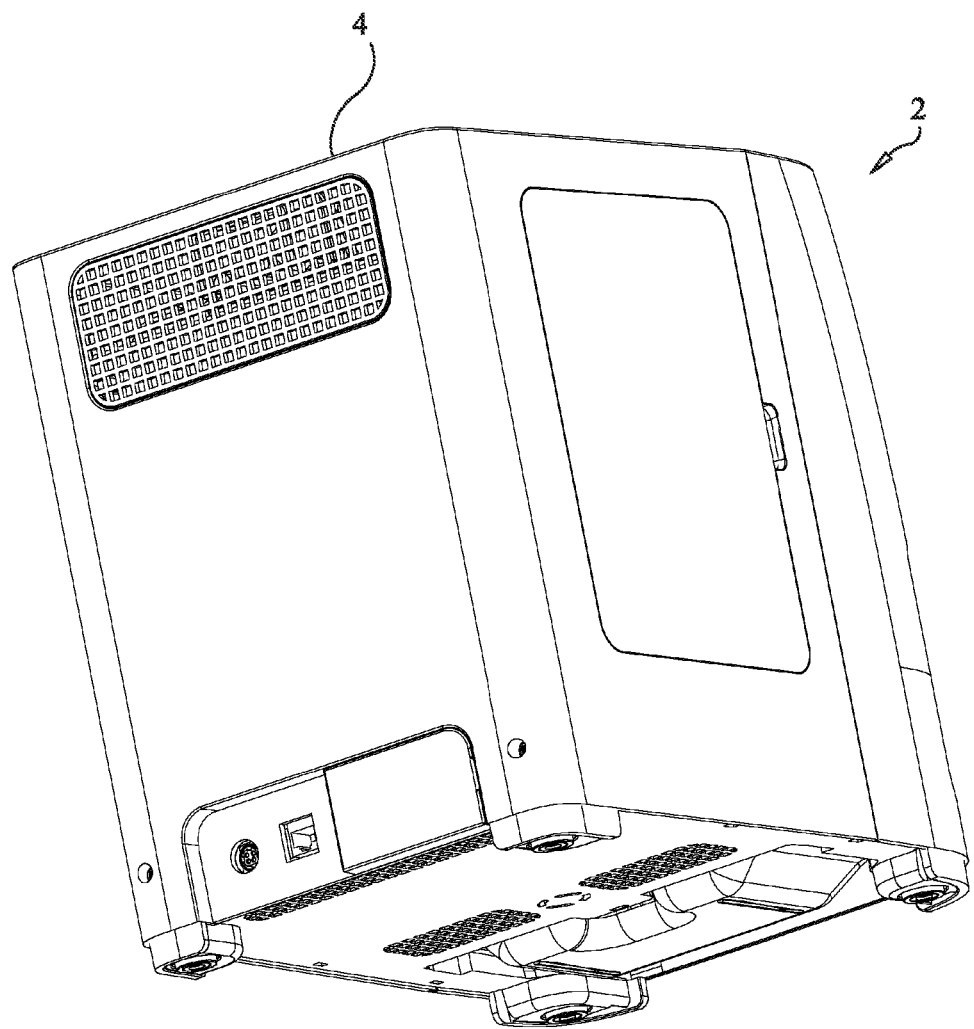
FIG. 2B is another bottom rear perspective view of a chemical analyzer formed in accordance with the present invention.
Figure 3:
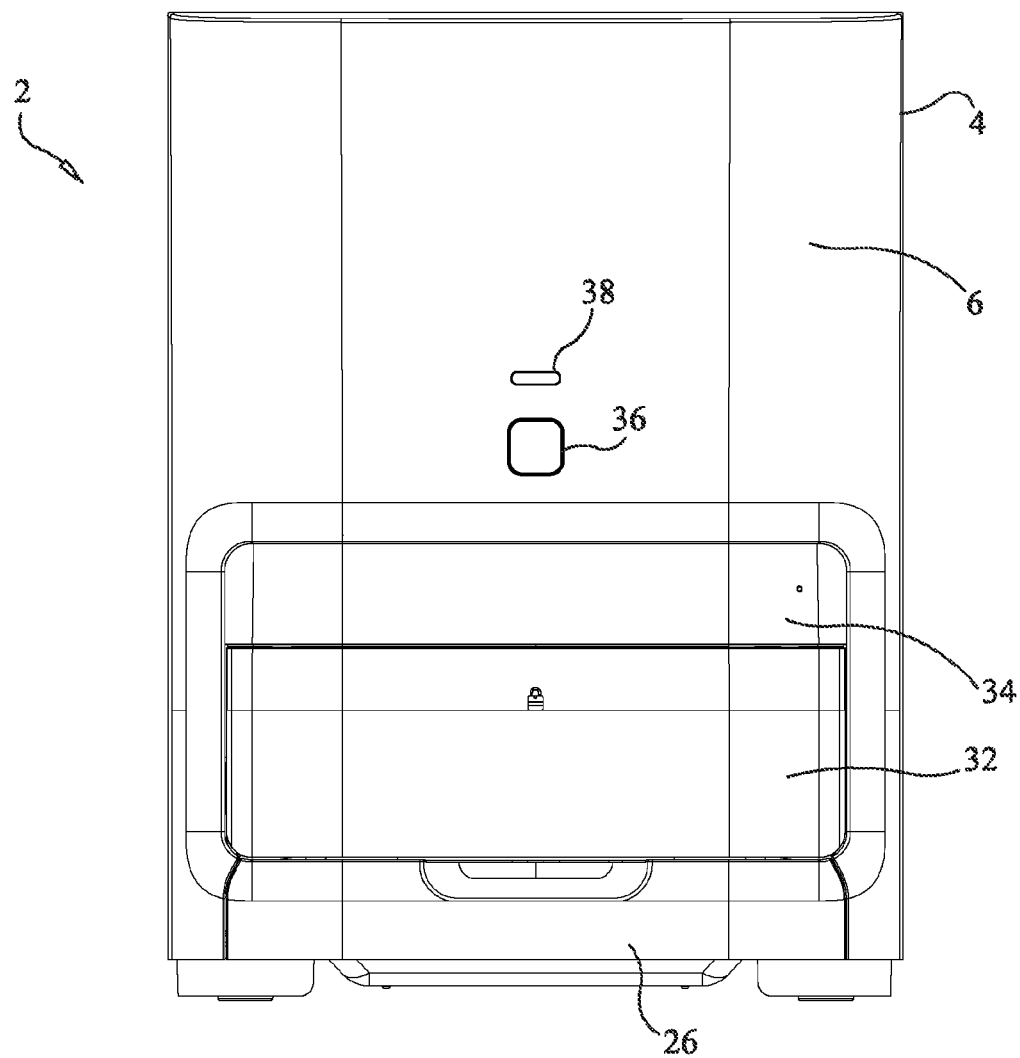
FIG. 3 is a front elevational view of a chemical analyzer formed in accordance with the present invention.
Figure 4:
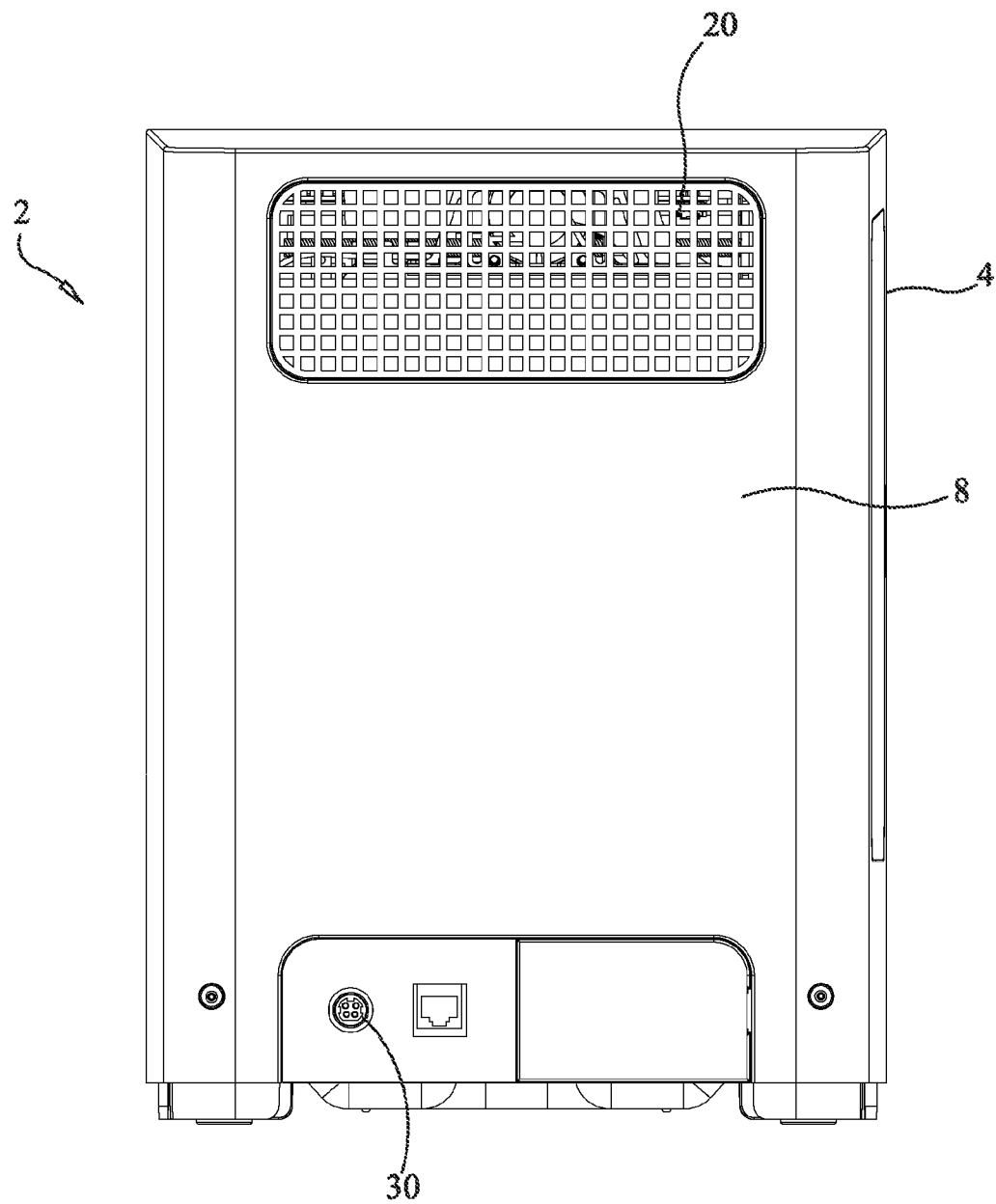
FIG. 4 is a rear elevational view of a chemical analyzer formed in accordance with the present invention.
Figure 5:
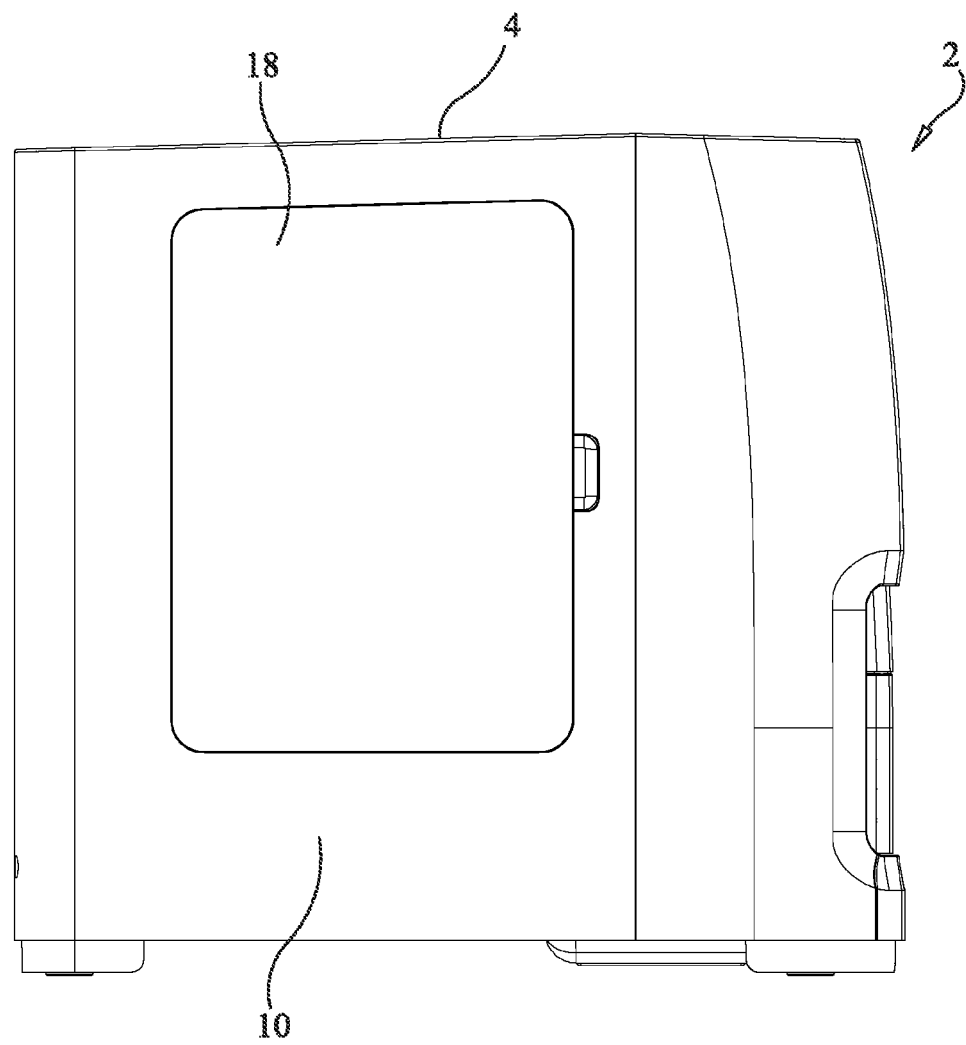
FIG. 5 is a left side elevational view of a chemical analyzer formed in accordance with the present invention.
Figure 6:
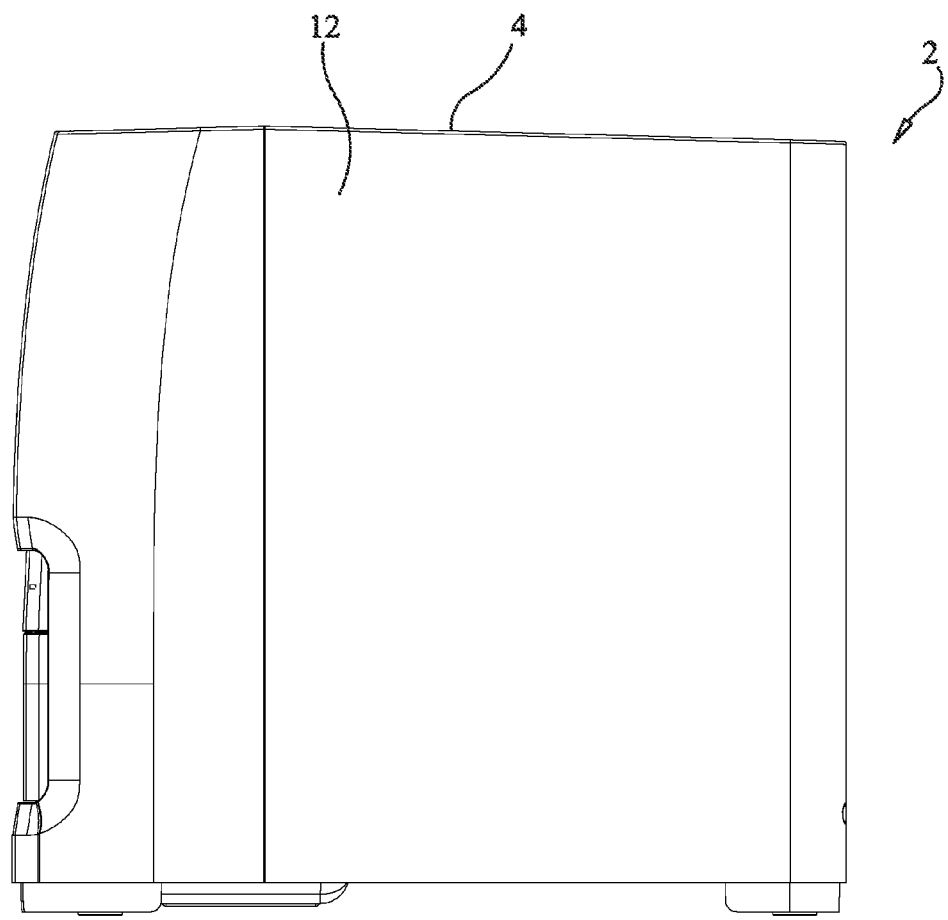
FIG. 6 is a right side elevational view of a chemical analyzer formed in accordance with the present invention.
Figure 7A:
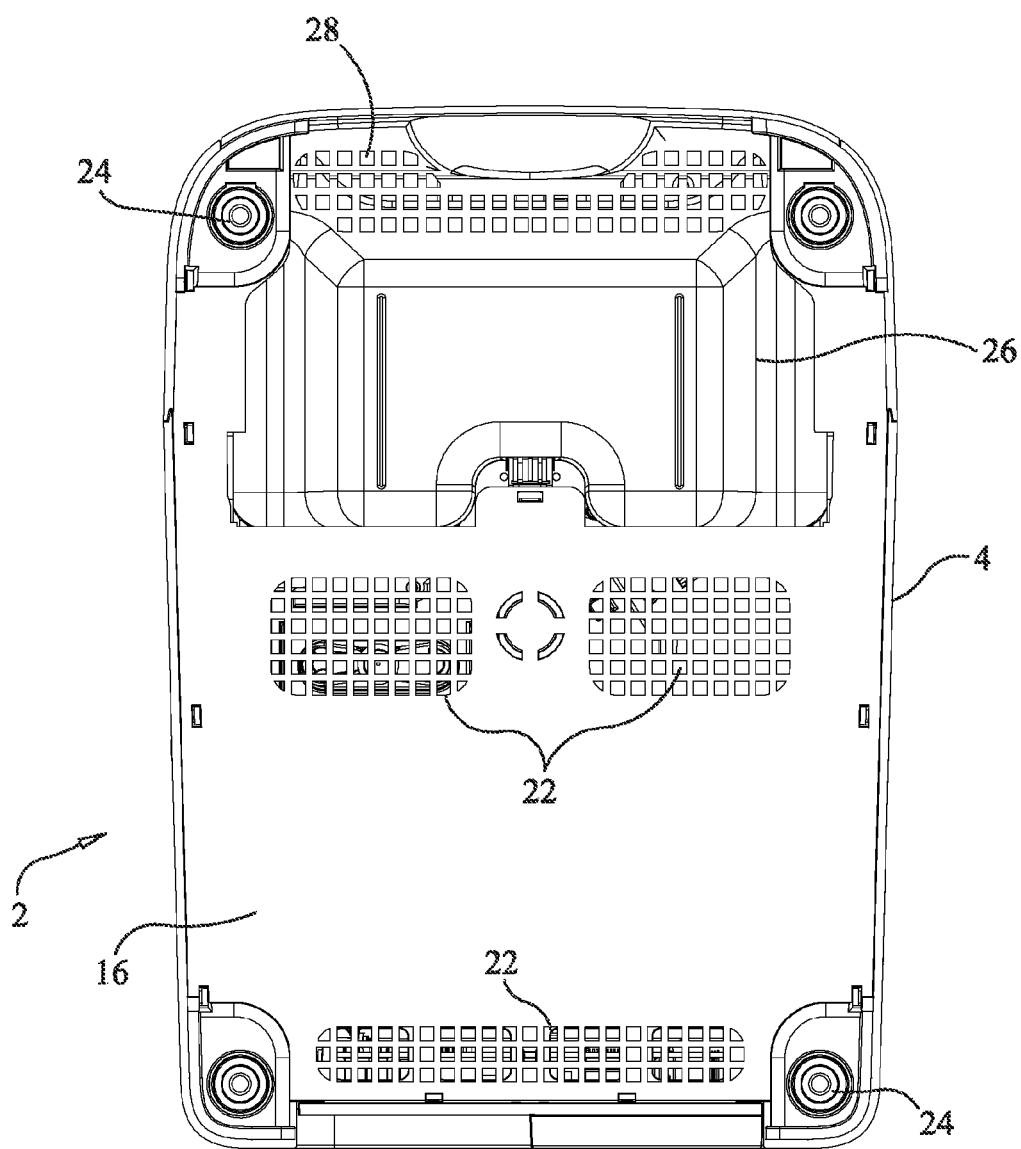
FIG. 7A is a bottom plan view of a chemical analyzer formed in accordance with the present invention.
Figure 7B:
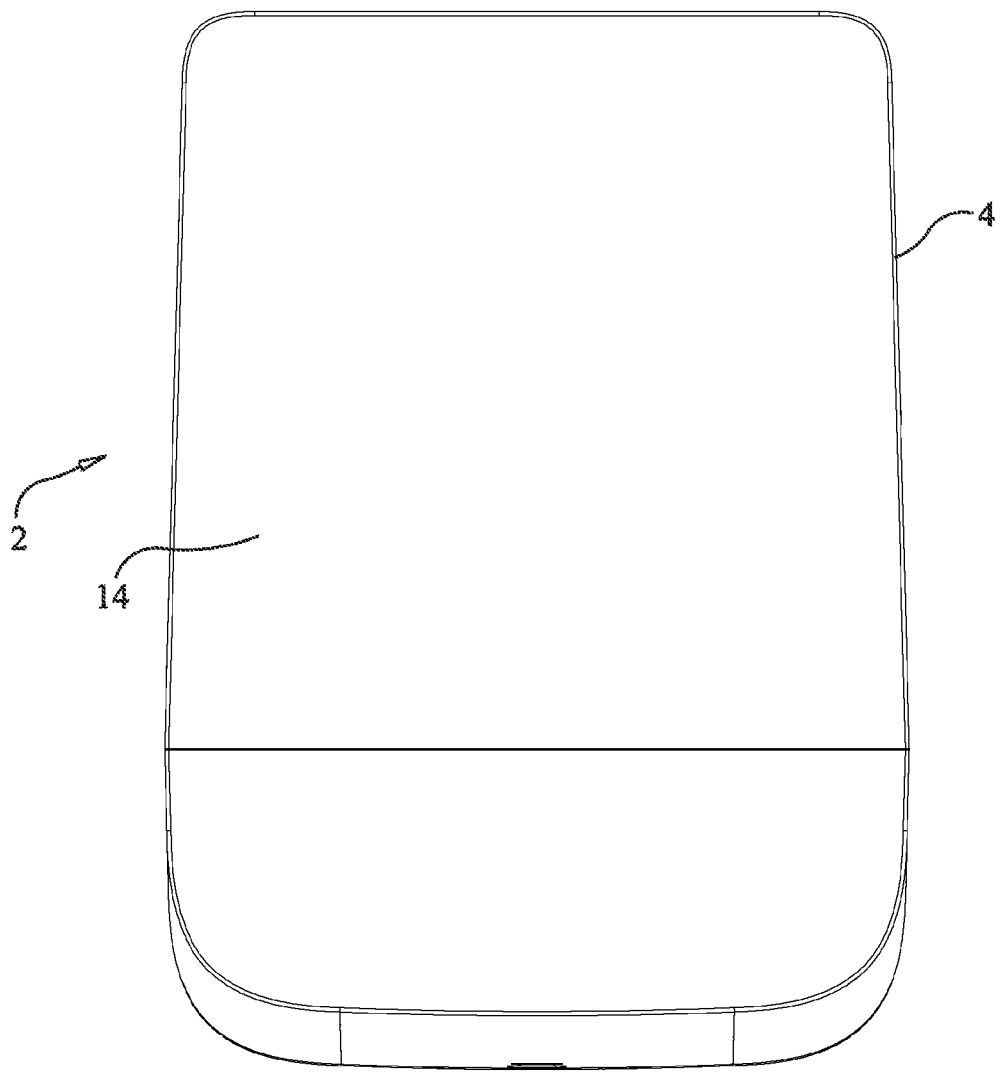
FIG. 7B is a top plan view of a chemical analyzer formed in accordance with the present invention.

Initially referring to FIGS. 1-7B of the drawings, it will be seen that a chemical analyzer 2 formed in accordance with one form of the present invention is a compact, desktop unit. Because the unit is relatively small and lightweight, it is quite portable and may be set up conveniently on a desk or table, requiring very little space. Furthermore, the chemical analyzer 2 has much fewer parts (less than 250 components) than many conventional chemical analyzers, the fewer parts increasing reliability and assembly time of the chemical analyzer 2, and requiring less alignment between the components.

As can be seen from FIGS. 1-7B of the drawings, the chemical analyzer 2 includes a housing 4 which defines an internal cavity, the housing having a front wall 6, an opposite rear wall 8, left and right opposite lateral side walls 10, 12, a top wall 14 and a bottom wall 16, all of which are interconnected.

The left lateral wall 10, when viewing the analyzer 2 from the front, includes a hinged access panel 18 which may be opened by the user of the analyzer 2 to gain access to the interior cavity of the housing for maintenance and inspection, and for cleaning certain components of the chemical analyzer 2. The rear wall 8 of the housing has formed in it a multiplicity of openings to define a vent 20 through which heated air is discharged. An internal fan draws ambient air through an intake vent 22 located on the bottom wall 16 of the analyzer 2. The analyzer 2 is raised above a supporting surface on which the analyzer 2 rests by a plurality of feet 24 mounted near the corners of the bottom wall so as to allow air flow into the intake vents situated on the bottom wall of the housing. As will be described below, a pull out drawer 26 for receiving waste pipette tips and used chemical reagent test slides also includes air intake vents 28 for additional air flow through the analyzer 2.

The rear wall of the housing further includes a number of connectors. One is a power connector 30 to provide power for the electronic circuitry of the analyzer 2, and one or more other connectors are provided for exchanging data between the analyzer 2 and a remote user interface (RUI), which may also be referred to herein as the IDEXX VetLab Station (IVLS). The IVLS provides an integrated, in-house diagnostic instrumentation laboratory in which user information is input through the IVLS and transferred to the chemical analyzer 2. The chemical analyzer 2 conducts reflectance and fluorescence measurements on chemical reagent test slides, analyzes these measurements and provides analytical data via the rear-mounted connectors to the IVLS through interconnecting cables, where the IVLS will show the analytical data on a display thereon.

The front wall of the housing of the chemical analyzer 2 includes an opening formed through the thickness thereof in which is mounted a pull out drawer (also referred to herein as the "consumables manager drawer") 32 for the user to place thereon a plurality of reagent test slides to be loaded into the analyzer components, cups of liquid sample, diluent cups, mixing cups, a centrifuge rotor and one or more disposable pipette tips, all of which are referred to as "consumables" because they will be discarded after an analysis run has been completed. There is a vertical wall 34 disposed over the drawer 32 and which rises into the interior cavity defined by the housing when the consumables drawer 32 is pulled outwardly from the front wall of the housing. When the consumables manager drawer 32 is returned to its original position within the housing by the user pushing thereon, the vertical wall 34 will lower so that it meets the top edge of the front face of the consumables manager drawer 32.

Mounted above the consumables drawer 32 and the sliding vertical wall 34 is a push button switch 36 for starting an analysis, as well as an indicator light 38, which illuminates when the analyzer 2 is conducting a test on a plurality of reagent test slides loaded into the analyzer 2.

As may be seen from FIG. 8 of the drawings, the chemical analyzer 2 of the present invention is comprised of several assemblies and sub-assemblies mounted within the interior cavity defined by the housing. There is a chassis or frame 40 which supports the various components and assemblies of the analyzer 2, and further adds support to the outer housing.

A controller 42, which is essentially a printed circuit board containing electrical circuitry, controls the operation of the chemical analyzer 2. This printed circuit board, i.e., the controller 42, is mounted within the interior cavity adjacent the rear wall of the housing.

A slide processing unit 44, which includes a slide transport mechanism within an incubator housing 278 and having a slide carousel 48 which transports a plurality of chemical reagent test slides loaded in the analyzer 2 in a circular path over a heated plate, is supported by the chassis 40 and mounted in the lower portion of the interior cavity of the analyzer 2 and behind and approximately at the same height as the consumables manager drawer 32 described previously.

Figure 9:
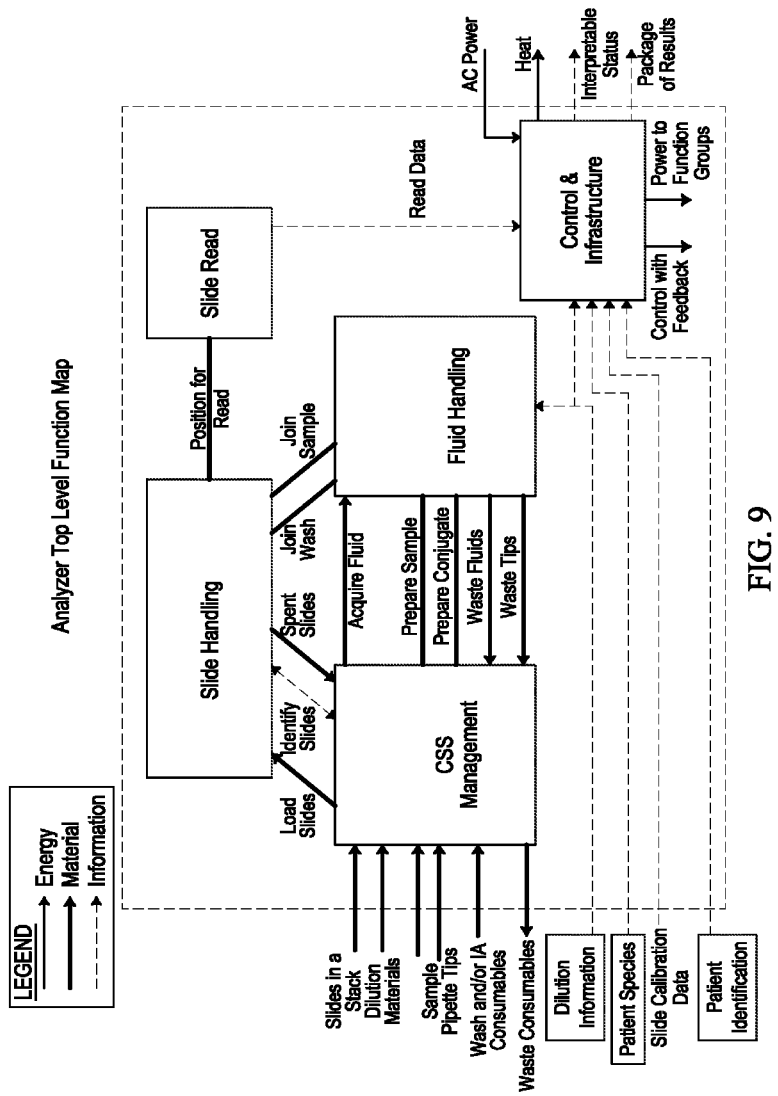
FIG. 9 is a top level function map of the chemical analyzer of the present invention.

The analyzer 2 also includes a fluid handler 50, sometimes referred to herein as a robot, which performs several functions, including metering a precise volume of liquid sample onto each chemical reagent test slide loaded into the slide processing unit 44, which is accomplished by a slide inserter mechanism 51. There is also a cap open and close assembly 52 which, as will be described in greater detail, selectively opens and closes a plurality of evaporation caps 54 located on the slide carousel 48 of the slide processing unit 44. The slide processing unit 44 also includes an optics module 56, which takes reflectance and fluorescence measurements on the plurality of reagent test slides on which a liquid sample is deposited, and provides these measurements in the form of electrical signals to the controller 42, which will process and analyze these colorimetric measurement signals. Finally, the chemical analyzer 2 includes a slide eject assembly 58, which removes used slides from the slide processing unit and directs the slides into a waste drawer 26. A top level function mapping diagram, illustrating the flow of information, material and energy within the analyzer in performing its functions, is shown in FIG. 9. Certain of these assemblies, and their sub-assemblies, of the analyzer will now be described in greater detail.

Figure 18:
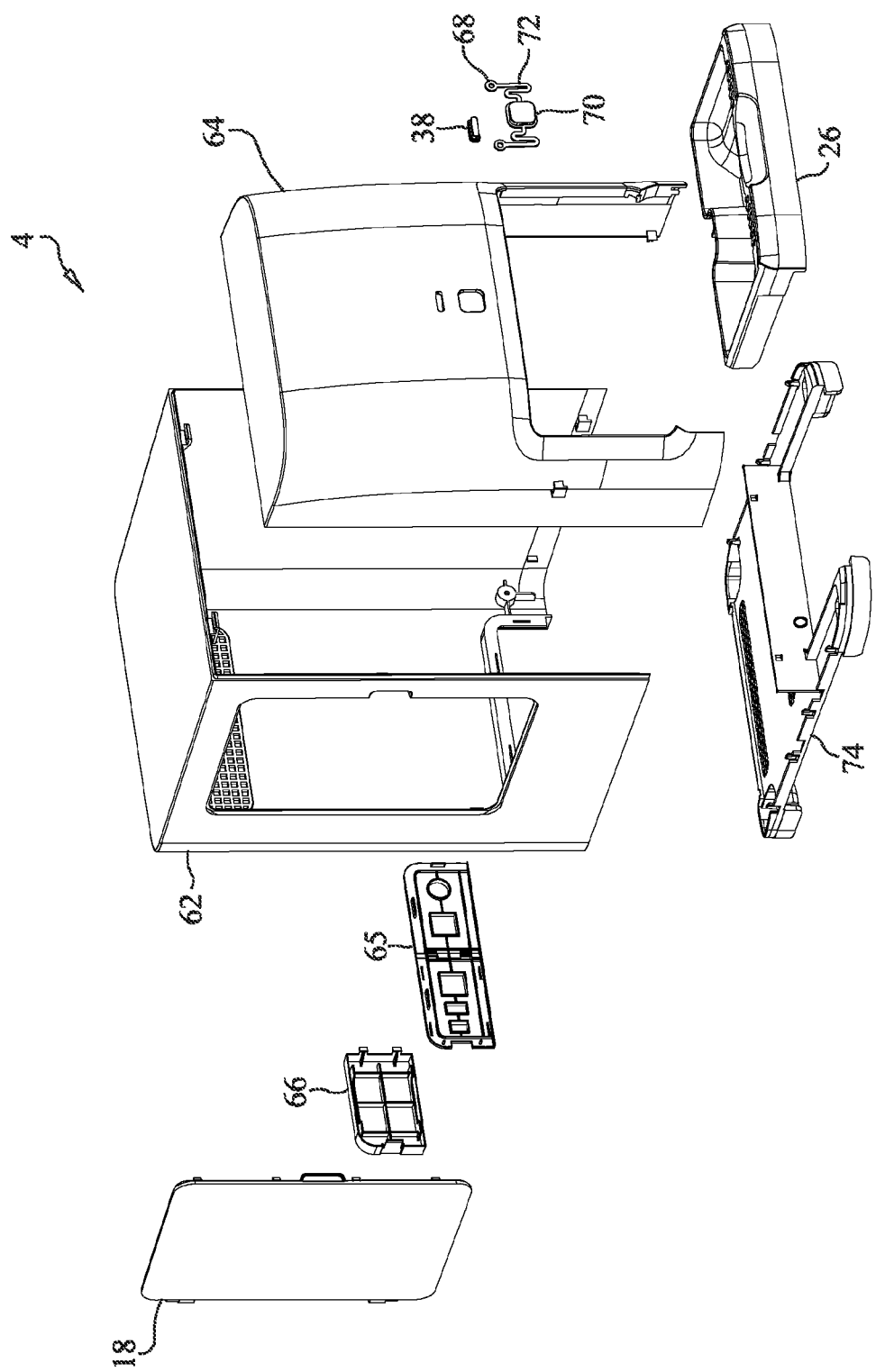
FIG. 18 is an exploded view of the housing of the chemical analyzer of the present invention.
Figure 19:
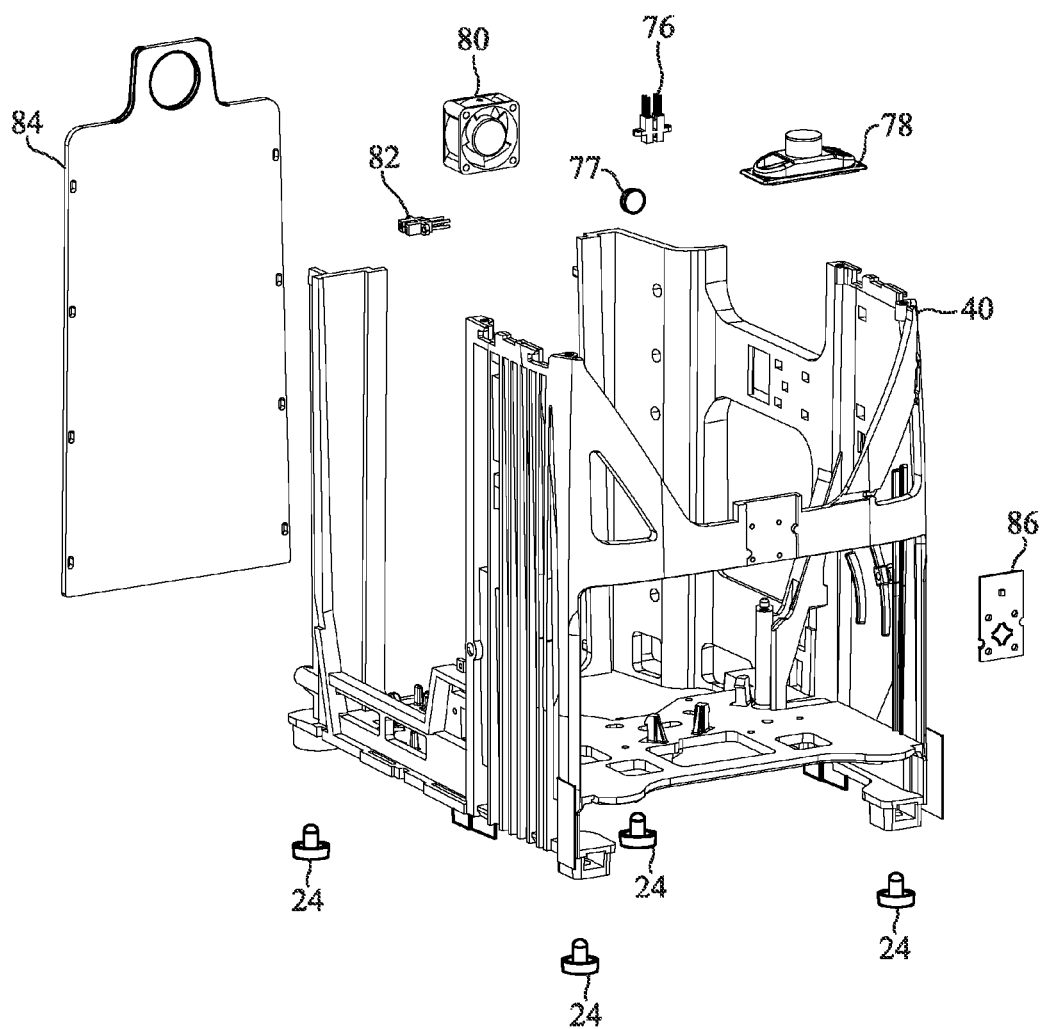
FIG. 19 is an exploded view of the internal chassis of the chemical analyzer of the present invention.

Turning now to FIGS. 18 and 19, the chassis 40 and housing (also referred to herein as the enclosure) of the chemical analyzer 2 will now be described in greater detail. An exploded view of the housing, or enclosure, is shown in FIG. 18. The enclosure is preferably formed from two main components, that is, a rear enclosure section 62 and a front enclosure section 64 which mates with the rear enclosure section. On the left side wall of the rear enclosure section 62 is a maintenance access door 18, which may be opened by the user to gain access to the assemblies, sub-assemblies and other components of the chemical analyzer 2 within the interior cavity defined by the enclosure. On the rear wall of the rear enclosure section is located an input/output (I/O) panel 65 having mounted thereon a number of various types of connectors for data transmission and reception and for power. The data connectors and power connector are mounted on the I/O panel which, in turn, is mounted on the rear wall of the enclosure, towards the bottom thereof. Various cables interconnect the data connectors to the remote RUI, or IVLS mentioned previously, which will be the data entry and display interface for the user with respect to the chemical analyzer 2. The IVLS includes a personal computer, a touch screen, an Ethernet network router and software. A hinged cover 66 mounted on the rear wall of the housing selectively covers certain of the connectors that are only used for diagnostic testing of the analyzer 2 by the manufacturer through a connection with the IVLS.

As mentioned previously, the front wall of the housing, which is preferably located on the front enclosure section, defines a large opening formed through the thickness thereof in which the consumables manager drawer 32 and vertical movable partition wall 34 is received. There is also a waste drawer 60 which is slidably received by the front enclosure section near the bottom thereof and under the consumables manager drawer 32. This waste drawer 26 receives discarded chemical reagent test slides and disposable pipette tips after a test has been completed on a plurality of reagent test slides.

Above the rather large opening formed in the front wall of the front enclosure section is situated what is referred to as a "button tree" 68, which is mounted in a small opening formed through the thickness of the front wall. The button tree 68 includes a depressible central main portion 70 having two opposite leaf spring portions 72 extending in opposite directions from the sides thereof, the leaf spring portions allowing the button tree to be mounted on the inside surface of the front wall, with the main central portion situated within the small opening in the front wall and movable therein when the user presses on the central portion. The central main portion will engage a pushbutton switch 36 disposed adjacent thereto to activate the chemical analyzer 2 to start an analysis procedure.

The rear enclosure section and front enclosure section are mounted on a base section 74. There is also an interruptible light sensor 76 situated in proximity to a wall or flange of the waste drawer. As will be described in greater detail, this "home" sensor 76 determines whether the waste drawer 26 is opened or closed. If the waste drawer 26 is opened, the sensor will prevent the chemical analyzer 2 from conducting an analysis run. Also, the sensor 76 is used to determine when the last time the waste drawer 26 has been opened to dispose of used pipette tips and chemical reagent test slides after a number of analysis runs have been performed. In this way, the chemical analyzer 2 can determine from how many analysis runs have been performed and when the last time the waste drawer 26 was opened, as detected by the waste drawer sensor, whether the waste drawer 26 is filled with used slides and pipette tips and whether the drawer should be emptied, and will convey this information to the user and instruct the user to open and empty the waste drawer.

Above the push button on the front wall is an LED 38 or, more preferably, a light pipe, optically connected to an LED, which illuminates to alert the user that the chemical analyzer 2 has been activated to conduct tests on a plurality of reagent test slides loaded into the analyzer 2.

An exploded view of the chassis 40, situated within the outer housing or enclosure of the chemical analyzer 2, is shown in FIG. 19 of the drawings. The chassis 40 is an open framework which is used to support not only the outer housing but also the various assemblies, sub-assemblies and components of the chemical analyzer 2. Mounted on the chassis 40 is a speaker 78, connected to the electronic circuitry of the chemical analyzer 2, to provide information to the user concerning the status and use of the chemical analyzer 2. Furthermore, and as mentioned previously, there is a waste drawer home sensor 76 which is mounted on the chassis 40 in proximity to the waste drawer 26 and which is used to detect whether the waste drawer 26 is in an open or closed position. There is also a waste drawer lock magnet 77.

A DC (direct current) fan 80 is mounted on the chassis 40 to draw air from the bottom of the outer enclosure and through air intake vents formed in the waste drawer, through the interior cavity thereof and out a discharge vent situated on the rear wall of the rear enclosure section. Furthermore, the chemical analyzer 2 includes a maintenance access door home sensor 82, to determine if the access door is opened or closed. If the access door is opened, this is sensed by the maintenance access door home sensor 82, and the chemical analyzer 2 will not operate when the door is opened.

The chemical analyzer 2 also includes a thermal barrier 84, mounted on and situated near the rear portion of the chassis 40. The thermal barrier 84 is disposed between the controller printed circuit board, mounted at the rear of the chassis 40, and the other sub-assemblies of the chemical analyzer 2 so that any heat generated by the electronic circuitry on the printed circuit board of the controller 42 will not affect the controlled temperature within the rest of the interior cavity of the housing where the main assemblies and sub-assemblies, and other components, of the chemical analyzer 2 are located.

The chassis 40 also includes four feet 24 pop riveted to and situated in the four corners of the chassis 40, in order to raise the chassis 40 and bottom wall of the housing above the top surface of the laboratory bench or other supporting surface on which the chemical analyzer 2 is placed. Also, as shown in this figure, a printed circuit board 86, on which the "smart button" activation switch is located, is shown.

The chassis 40 is, primarily, a structural component: it positions and provides support for all other sub-systems of the chemical analyzer 2. The chassis 40 also supports the outer housing, which is preferably a polycarbonate/ABS barrier between the inner workings of the analyzer 2 and its clinical environment, and provides a structural foam molding within the enclosure. Besides providing structural stability, the chassis 40, and the outer housing, help maintain a relatively stable internal temperature conducive to the more precise thermal control of other sub-systems of the chemical analyzer 2.

The inner chassis element fits snuggly inside the outer housing. Along with the outer housing, the two components provides a stiff, strong support system to stabilize the various stations, assemblies and sub-assemblies within the chemical analyzer 2 and to protect those stations from light, dust and from the weight (within reason) of objects placed on the enclosure's top wall. The chassis 40 organizes the interior cavity of the chemical analyzer 2 so that each sub-system not only has the space to function properly but also so that each sub-system can access necessary components of other systems. For example, the fluid handler 50, mentioned previously, can access the consumables manager drawer 32, open and close the evaporation caps 54 on the slide carousel 48 of the slide processing unit 44, and engage the tip shucker 88, which is used to remove disposable tips on the pipette or proboscis of the fluid metering sub-assembly. Also, the chassis 40 ensures that the slide processing unit's slide entrance is level with the slide inserter and eject mechanism, and so that the slide eject mechanism 58 is positioned over the slide waste pathway leading to the waste drawer. Furthermore, the chassis 40 ensures that the controller 42, with its printed circuit board, is both separated from other sub-systems by the thermal barrier board (the heat generated by the electrical circuitry on the printed circuit board of the control could adversely affect proper analyzer function) and connected via cables that are themselves wrapped around hubs and wound under cable clips in the chassis 40 itself.

Besides promoting correct functioning (and, consequently, accurate slide readings) of the chemical analyzer 2 by organizing its sub-systems into three-dimensional space, the chassis 40 promotes correct functioning by regulating temperature and levels of light inside the chemical analyzer 2. This regulation is made possible by near total enclosure of the analyzer 2, with exceptions for air vents and power/communication cable access. The ventilation system, coupled with a fan, allows for cooling the interior of the analyzer 2, while the insulation provided by the outer housing slows the dissipation of heat. These design considerations take into account the variety of clinical environments in which the chemical analyzer 2 might be used—in cool or warm environments, under strong clinical lights or near windows, and next to walls or other instruments.

The chassis 40 also provides easy methods for signals to and from the user. As mentioned previously, a "smart button" activation switch located at the center of the front wall of the outer housing provides a way for the user to signal that he or she has placed all added components in the consumables manager drawer 32 and has closed the drawer. The chassis 40, with its outer housing, also provides indications to the user concerning the operation of the analyzer 2. For example, an LED light situated above the "smart button" activation switch located on the front wall of the outer housing indicates the mode in which the analyzer 2 is in, for example, wait/sleep and busy/ready. The audio speaker mounted near the bottom of the chassis 40 beeps to indicate error messages. In the event that the chemical analyzer 2 needs service or cleaning, a generously-sized door on the left side wall of the outer housing swings open to provide easy access to the slide processing unit 44 and other sub-assemblies within the interior cavity of the chemical analyzer 2.

There are additional features of the chassis 40 and housing of the chemical analyzer 2 which are described below. The top portion of the inner chassis 40 is preferably completely open, allowing for easy vertical access to the inner sub-systems of the chemical analyzer 2 during assembly. The thermal board is heat-staked to the rear of the chassis 40 during assembly.

The chassis 40 also provides snap-into-place features. For example, on the chassis floor, snap features allow the evaporation cap open and close mechanism 52 and the slide eject mechanism 58 to be easily attached thereto.

The consumables manager drawer 32 slides into and out of the chassis 40 on runners mounted on the inner surface of the chassis 40. The height of these runners facilitates the even plane of the slide inserter mechanism and the entrance slot formed on the slide processing unit 44. Furthermore, the structure on the chassis 40 for mounting the slide eject mechanism 58 is designed to line up with the slide eject slot on the slide processing unit 44. The mounting of the evaporation cap open and close mechanism is consistent with the total vertical height needed for that mechanism to contact the evaporation caps 54 on the slide carousel 48 of the slide processing unit 44.

The chassis 40 and housing of the chemical analyzer 2 also maintains a thermal equilibrium within the interior cavity of the housing where the assemblies and sub-assemblies for processing the slides are located. The housing and chassis 40 provide a central thermal zone and a rear thermal zone. The central thermal zone, which is the larger of the two, is located towards the front of the analyzer 2 and contains the slide processing unit 44, the fluid handler (which includes the fluid metering mechanism) and the consumables manager drawer 32. As will further be described below, the chassis 40 and housing also provide a means of reliable, consistent ventilation, which makes the process of maintaining appropriate temperatures for the sub-systems, especially the slide processing unit 44, more predictable.

A rear thermal zone, provided by the chassis 40 and housing, is separated from the central thermal zone by the thermal barrier board. This thermal barrier board is composed of the same structural foam as the rest of the chassis 40. The designation of the rear thermal zone is, essentially, to insulate the controller 42, and its printed circuit board, from the other sub-systems of the analyzer 2, as the controller board will generate a fair amount of heat when in use.

As mentioned previously, the housing and chassis 40 provide a ventilation system, which pulls air into the interior cavity of the housing and analyzer 2 from beneath the analyzer 2. There are preferably three ventilation openings situated on the bottom wall of the housing, and a ventilation pattern on the bottom front wall of the waste drawer. The air drawn into the analyzer 2 is discharged through a top vent formed in the rear wall of the housing, the air flow being effected principally by natural convection, although a small fan, as mentioned previously, is mounted in proximity to the discharge vent at the top portion of the rear wall of the housing and may be used especially in hot environments.

The positioning of the ventilation system, especially the inflow of cool air, toward the front of the analyzer 2 takes into account the likelihood that the analyzer 2 will be placed next to another lab instrument or a wall. Ventilation of the rear thermal zone occurs as air flow, from natural convection or from the fan, moves over the top portion of this zone, cycling air out the back and carrying fresh air up through the bottom of the analyzer housing. The housing also minimizes the dispersal of analyzer heat if the clinical environment is cool.

As mentioned previously, there is a hinged door mounted on the left side wall of the housing, and which is selectively maintained in a closed position using a magnetic latch. A window defined by the interior chassis 40 in alignment with the hinged door is sized to match the dimensions of the door. This simple means of accessing the interior of the analyzer 2, and especially the slide processing unit 44, allows for easy service and cleaning. Furthermore, the side access door is slightly wider than the diameter of the slide carousel 48 of the slide processing unit 44, so that the slide carousel 48 can be easily removed without tedious repositioning. The same side door offers access to the whole blood separator (i.e., centrifuge) for cleaning.

Preferably, the bottom wall of the housing is raised above the surface on which the analyzer 2 rests by about 15 millimeters, which allows human fingers to lift or move the analyzer 2 from the bottom thereof.

The weight of a notebook, lunch box, small pet or other object accidentally placed on the top wall of the housing can be safely supported by the chassis 40 and housing. The polycarbonate/ABS blend of the housing is quite stiff. Furthermore, a cross beam runs over the fluid handling station of the analyzer 2 to prevent excess bowing of the top wall of the housing.

Low levels of interior light are essential to accurate optics module readings. While the chassis 40 and housing do permit the entrance of a small amount of light, via, for example, the vents in the waste drawer, the front and rear enclosure sections mate with one another in an overlapping seam which limits the entrance of stray light.

Also, portions of the chassis 40 may be provided with a coating, such as of copper, that would minimize any electromagnetic interference (EMI).

Figure 68:
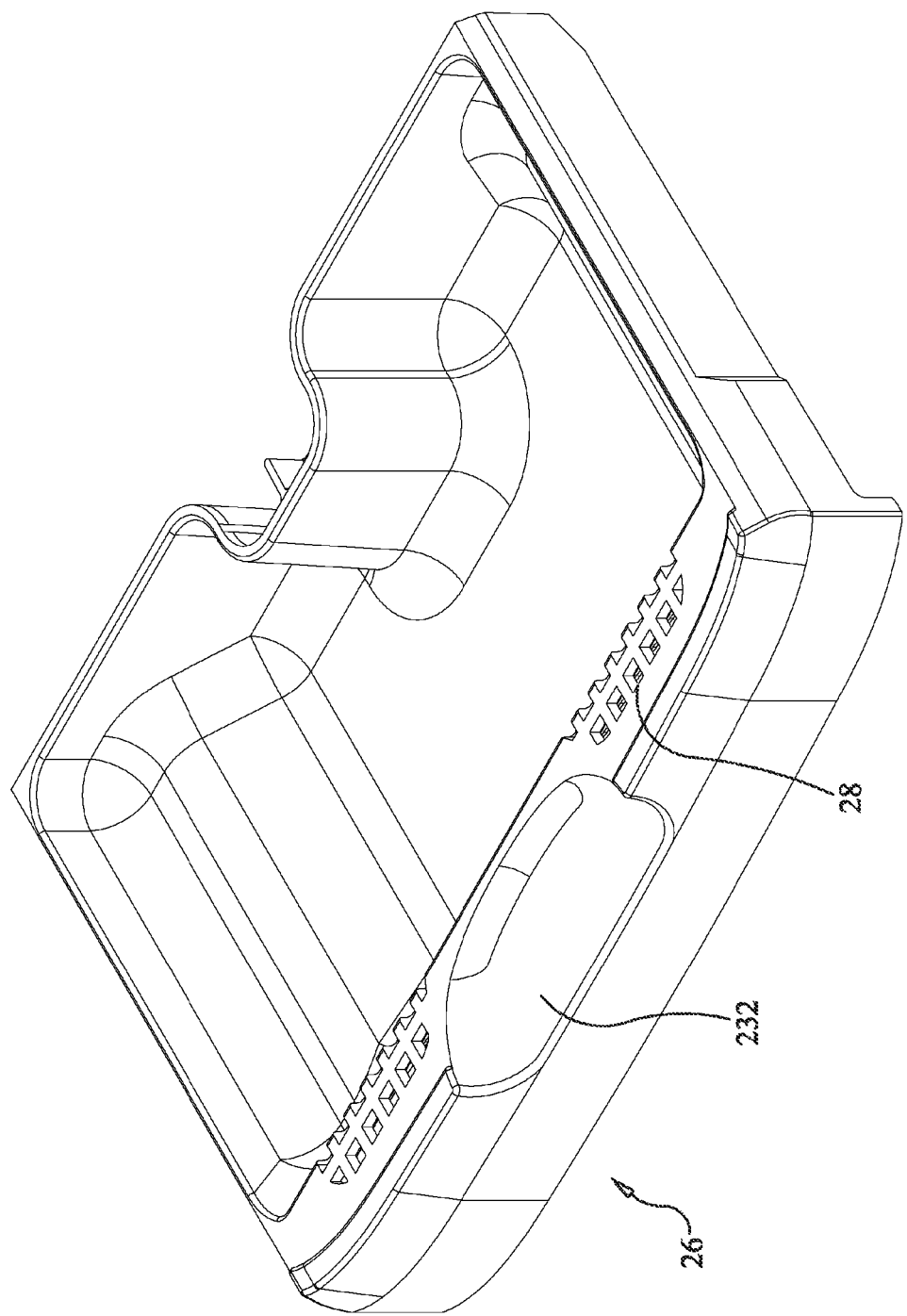
FIG. 68 is front perspective view of a waste drawer of the chemical analyzer of the present invention.
Figure 69:
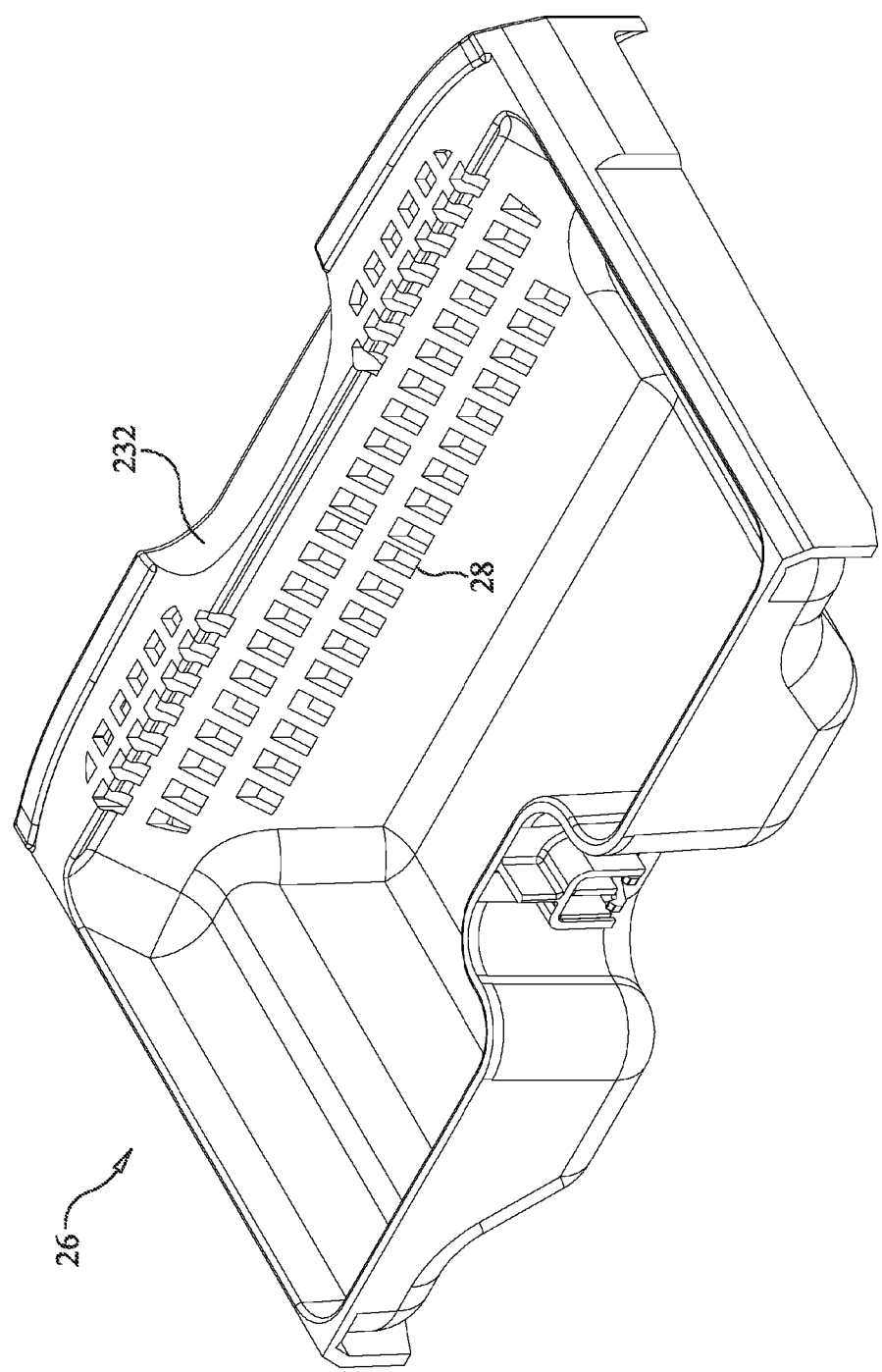
FIG. 69 is rear perspective view of a waste drawer of the chemical analyzer of the present invention.
Figure 70:
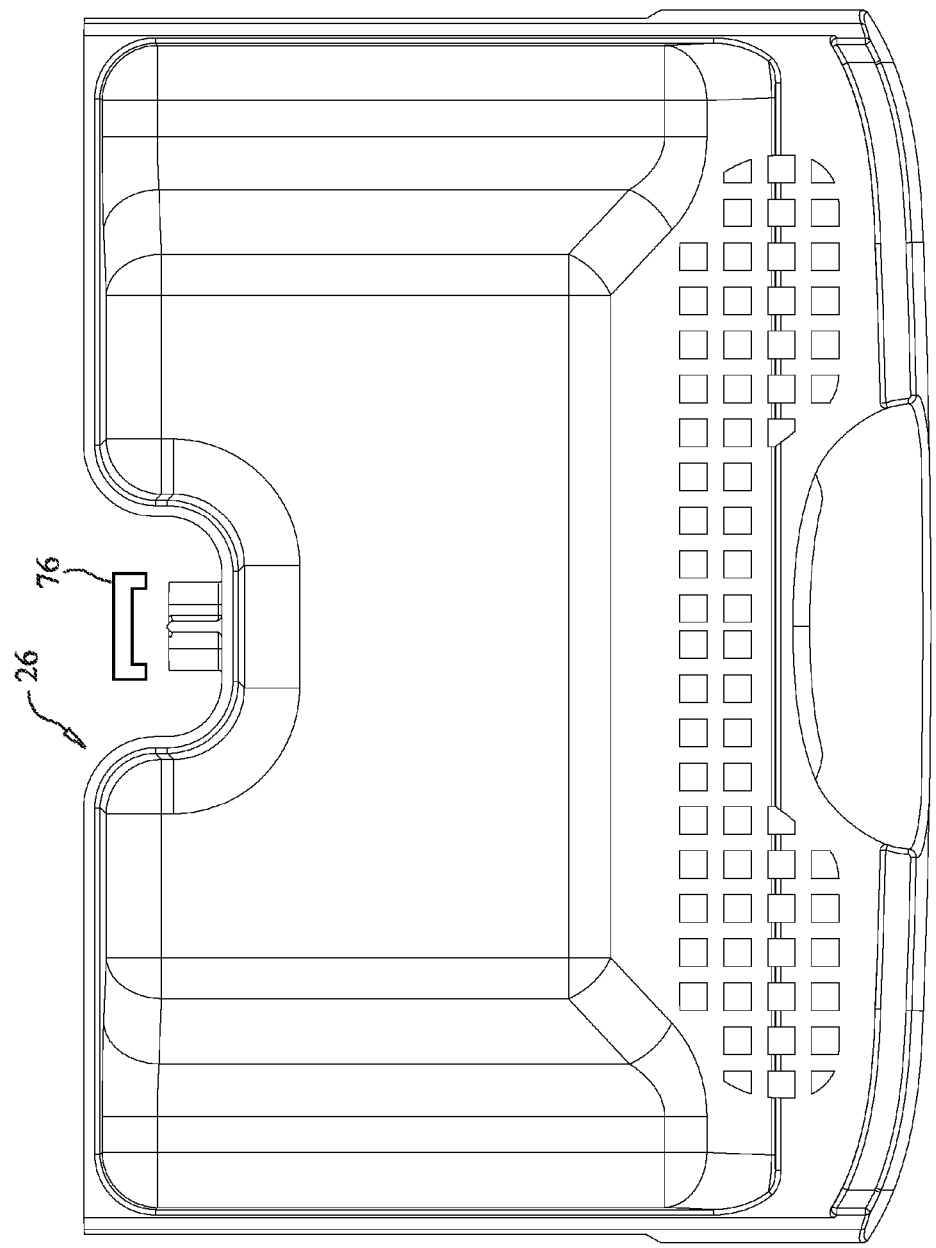
FIG. 70 is top plan view of a waste drawer of the chemical analyzer of the present invention.
Figure 71:
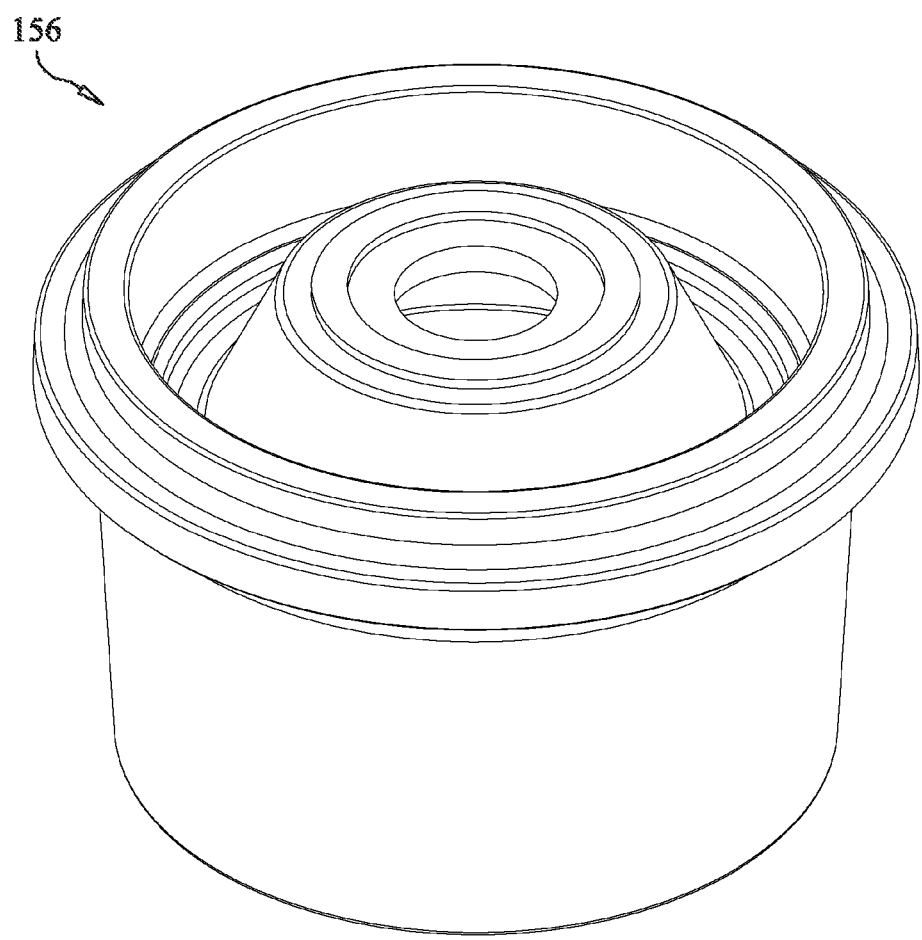
FIG. 71 is top perspective view of a centrifuge rotor forming part of the centrifuge of the chemical analyzer of the present invention.
Figure 72:
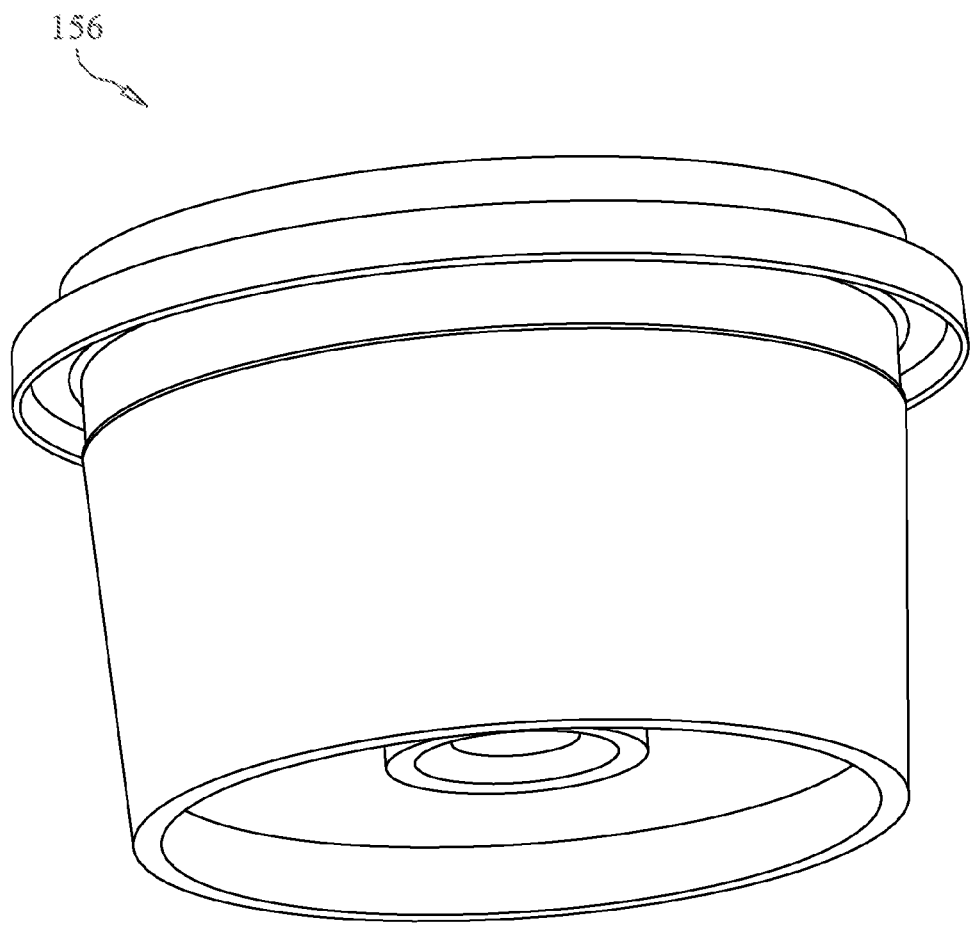
FIG. 72 is bottom perspective view of a centrifuge rotor forming part of the centrifuge of the chemical analyzer of the present invention.
Figure 73:
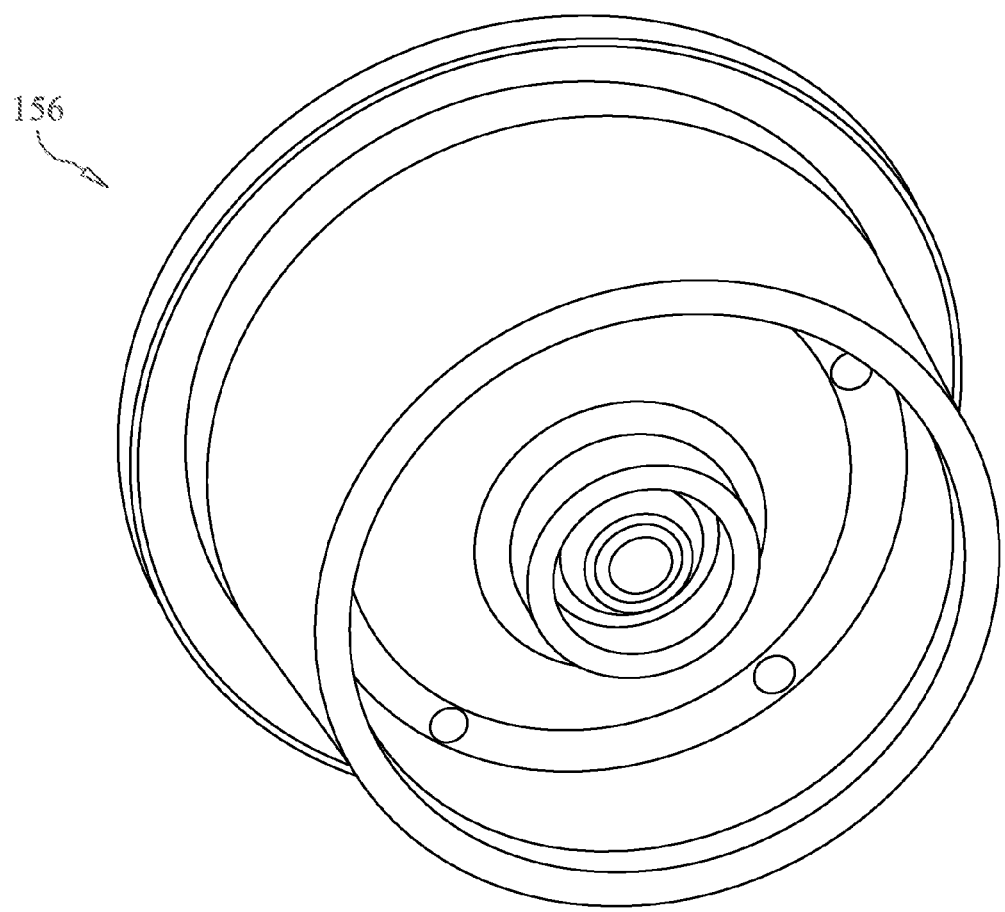
FIG. 73 is another bottom perspective view of a centrifuge rotor forming part of the centrifuge of the chemical analyzer of the present invention.

The waste drawer 26, which is shown in FIGS. 68-70, is preferably formed of the same material (i.e., polycarbonate/ABS blend) as the housing, which provides a consistent exterior look and feel to the analyzer 2. There are at least three design features relating to the structure of the waste drawer. They are 1) the venting pattern at the front of the drawer to help control a thermal equilibrium within the analyzer 2; 2) a sloped shelf beneath the slide/pipette eject pathway, as will be described in greater detail, that encourages a randomized landing pattern for used slides and pipette tips so that they do not pile in one place within the drawer; and 3) an optical sensor at the rear wall of the waste drawer. This sensor indicates whether or not the waste drawer 26 is closed. Furthermore, movement (or lack of movement) of the waste drawer 26 detected by this sensor can help indicate if the waste drawer 26 needs to be emptied.

The LED indicator situated above the depressible "smart button" activation switch located on the front wall of the housing is preferably illuminatable in three different colors (green, red and amber) to provide visual feedback to the user of the analyzer 2. The status of the light, which also blinks at preferably two different frequencies, is controlled by the controller 42 and its associated electrical circuitry. Furthermore, audio feedback of the status and operation of the analyzer 2 is provided to the user via a speaker mounted to the bottom wall of the housing.

As mentioned previously, there is a depressible button piece, forming part of the "smart button", located on the front wall of the analyzer housing. This piece, when pressed, engages a circuit board mounted, momentary pushbutton switch supported by the inner chassis 40.

As will be described in greater detail, there is a "tip shucker" which protrudes from the inner chassis 40 and which is situated thereon within range of the robot arm forming part of the fluid handler. The tip shucker is a small static feature designed to loosen a disposable pipette tip from the end of the proboscis on the robot arm before the pipette tip is dispensed into the waste drawer. The tip shucker is especially designed to minimize or prevent any liquid sample splatter inside the analyzer 2 when the tip is removed from the end of the proboscis.

There are preferably three data connectors situated on the rear wall of the housing. They are an RJ45 connector, a USB connector and a mini-USB connector. Preferably, these connectors are provided for field service and operations, and are hidden from the user behind a small access panel situated on the rear wall of the housing. There is also another data connector which may be connected to the remote RUI, or IVLS, as described previously.

Figure 20:
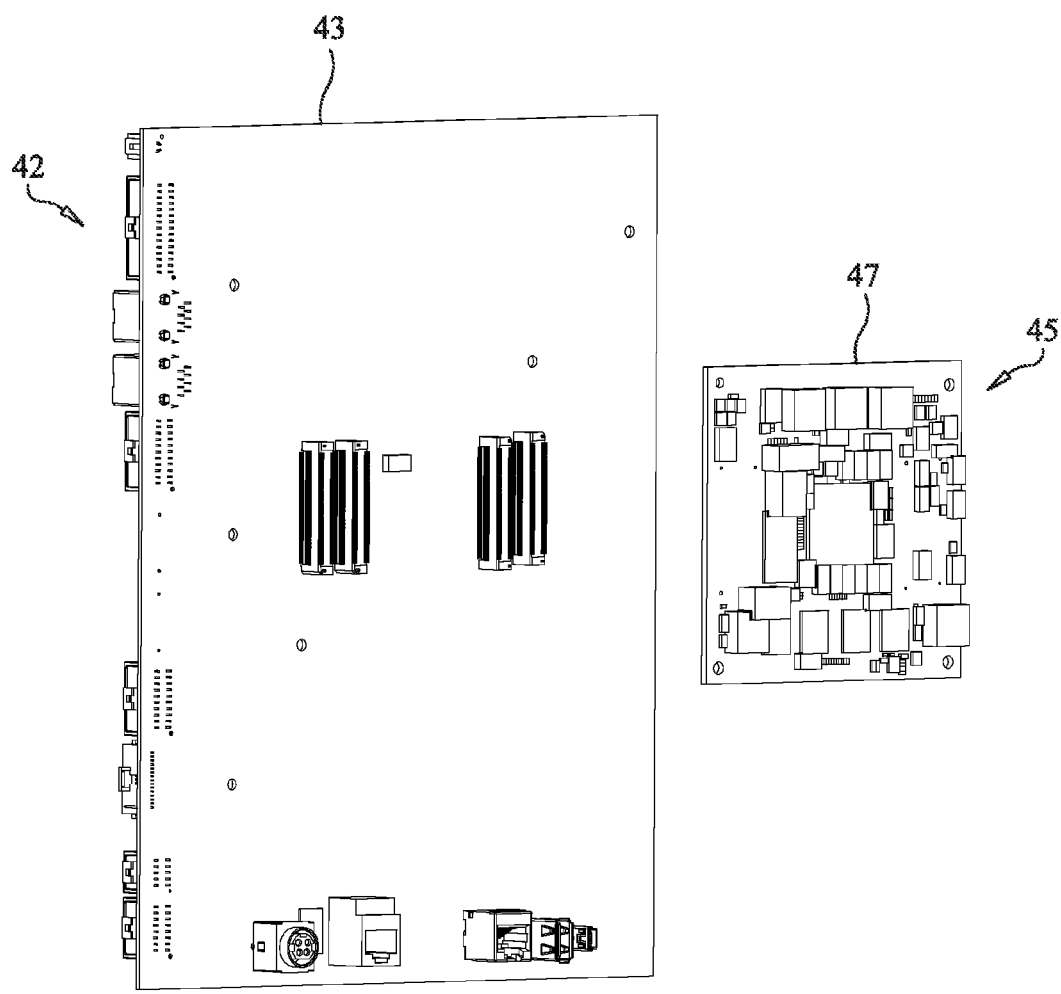
FIG. 20 is an exploded view of the controller of the chemical analyzer of the present invention.

The controller 42 of the analyzer 2 is shown in FIG. 20 of the drawings. The controller 42 includes a printed circuit board (a "mother board") 43 having electrical circuitry thereon, and a control module 45 in the form of a smaller printed circuit board (a "daughter board") 47 which is mounted on and electrically connected to the mother board 43. The control module 45 manages memory for analyzer operation as well as all of the power supplies required to support the microprocessor operation on the control module 45. Preferably, the control module 45 holds a ZYNQ™ integrated circuit manufactured by Xilinx, Inc. of San Jose, Calif.

The controller board 43 provides the signal conditioning to convert the sequences of control signals generated by the control module 45 into appropriate drive signals for the various motors, heaters and sensors used in the analyzer 2. Preferably, high speed signals are kept to the control module 45, rather than the mother board 43, because high speed circuitry may affect other local circuitry on the controller board.

All of the analyzer's "decisions" are made by the microprocessor on the control module 45. These decisions range from timing the LEDs that illuminate a slide to making the calculations concerning a concentration, and to determine the amount of force exerted by any of the motors used in the analyzer 2.

The controller board 43 provides plug-in connections for the slide carousel 48, the optics module 56, the consumables manager drawer sensor, the bar code reader, the cameras, heaters, fluid handler and the chassis 40 of the analyzer 2. The electrical circuitry on the controller board 43 either transmits signals on the cables connected to each of the assemblies and sub-assemblies of the analyzer 2 to control the operation thereof or receive signals from these assemblies and sub-assemblies.

The control module 45, including the ZYNQ™ processor, controls the management of the power supplies, motors, and feedback from the various sensors of the analyzer 2, and controls the communication of signals between the analyzer 2 and the IVLS through the USB connector or by WiFi communications. The control module 45 also relies heavily on closed-loop sensing at the locations where motions of the various components and sub-assemblies are being driven. For example, the movement of the fluid handler is sensed and controlled by the controller 42 on a continuous basis. As will be explained in greater detailed, there are potentiometers on the fluid handler which constantly provide feedback signals that are digitized and monitored by the controller 42. These potentiometers are fixed to the fluid handler's three axes of movement, that is, the X-direction, the theta ($\theta$) direction and the Z-direction. Decisions based on the data provided to the controller 42 are determined by software programmed into the controller 42. The fluid handler follows a "subway map" of taught positions, such as its position for dispensing fluid or picking up a pipette tip.

The controller 42 is also provided with information, and makes decisions based thereon, from home sensors on the slide carousel portion of the slide processing unit 44, the liquid sample pump on the fluid handler, the consumables manager drawer 32, the maintenance panel and the rear flip door that covers certain connectors on the rear wall of the housing. For the slide carousel 48 and the pump on the fluid handler, the home sensor provides feedback to the controller 42 for control module-driven movement of these components, while the sensors on the consumables manager drawer 32, the maintenance panel and the waste drawer 26 provide signals to the controller 42 to determine whether or not these components are in their "home" position. Preferably, none of the access panel, the consumables manager drawer 32 and the waste drawer 26 is directly moved by the controller 42, but knowledge of their position is important for directing the safe movement of the fluid handler or, in the case of consumables manager drawer 32, making sure that the drawer is fully closed before the centrifuge motor is activated.

There is also a pressure sensor on the pump of the fluid handler which provides feedback signals to the controller 42. This pressure sensor uses a respiratory process (literally "inhaling" and "exhaling" air) to perform clot detection and to evaluate the nearness of a surface. The feedback signal from the pressure sensor, and the fact that the sensor allows for minute adjustments to be made in individual analyzers, mean that minor manufacturing irregularities need not impact analyzer performance at least in terms of the fluid handler movement or its location.

AC power from a conventional wall outlet is converted to 24 volts DC power and supplied to the controller 42 and its associated mother board 43. The controller 42 also measures how much power is coming in and how much is being used. The 24 volts DC power is then converted to lower voltages for use by various integrated circuits forming part of the electrical circuitry of the controller 42.

Preferably, the chemical analyzer 2 of the present invention has no power switch. It cannot be turned off, only sent to sleep. During sleep mode, the processor on the control module 45 runs at a reduced clock rate to save power. Major sections of the analyzer 2 will be powered off to save power. The important functionality given this power set up is the ability of the analyzer 2 to "wake up", which means that, when the analyzer 2 is in a sleep mode, the processor stands ready to be woken by a signal from the RUI, or IVLS, or if the "smart button" activation switch is depressed by the user.

The controller 42 also receives feedback signals from the vision system incorporated in the analyzer 2. There is a camera 228 on the fluid handler, and another nearly identical camera 230 mounted on the chassis 40 which is used to read bar codes on the reagent test slides. A primary difference between the two cameras is focal length. The camera 228 on the fluid handler is programmed to respond to prompt signals from the controller 42. The prompt signals represent a prediction of what the analyzer's contents, such as the presence of added consumables, should be in a certain situation, for example, when a specific test is queued on the RUI or IVLS.

The controller 42, with its mother board 43 and control module 45 situated thereon, is located near the rear wall of the housing of the analyzer 2. This location allows the printed circuit board 43 to have a larger dimension, and with more space between integrated circuits situated thereon, helps keep the integrated circuits at a lower temperature.

The control module 45 functions to provide precise directions, accurate modifications and reliable, safe operations of all of the various assemblies and sub-assemblies and mechanisms within the analyzer 2. This reliability, which depends on the ability of the control module 45 to anticipate and avoid instrument damage, as well as its ability to compensate for normal wear and tear, provides the chemical analyzer 2 of the present invention with dependability, a long useable life and low cost for manufacture and repair.

Figure 16:
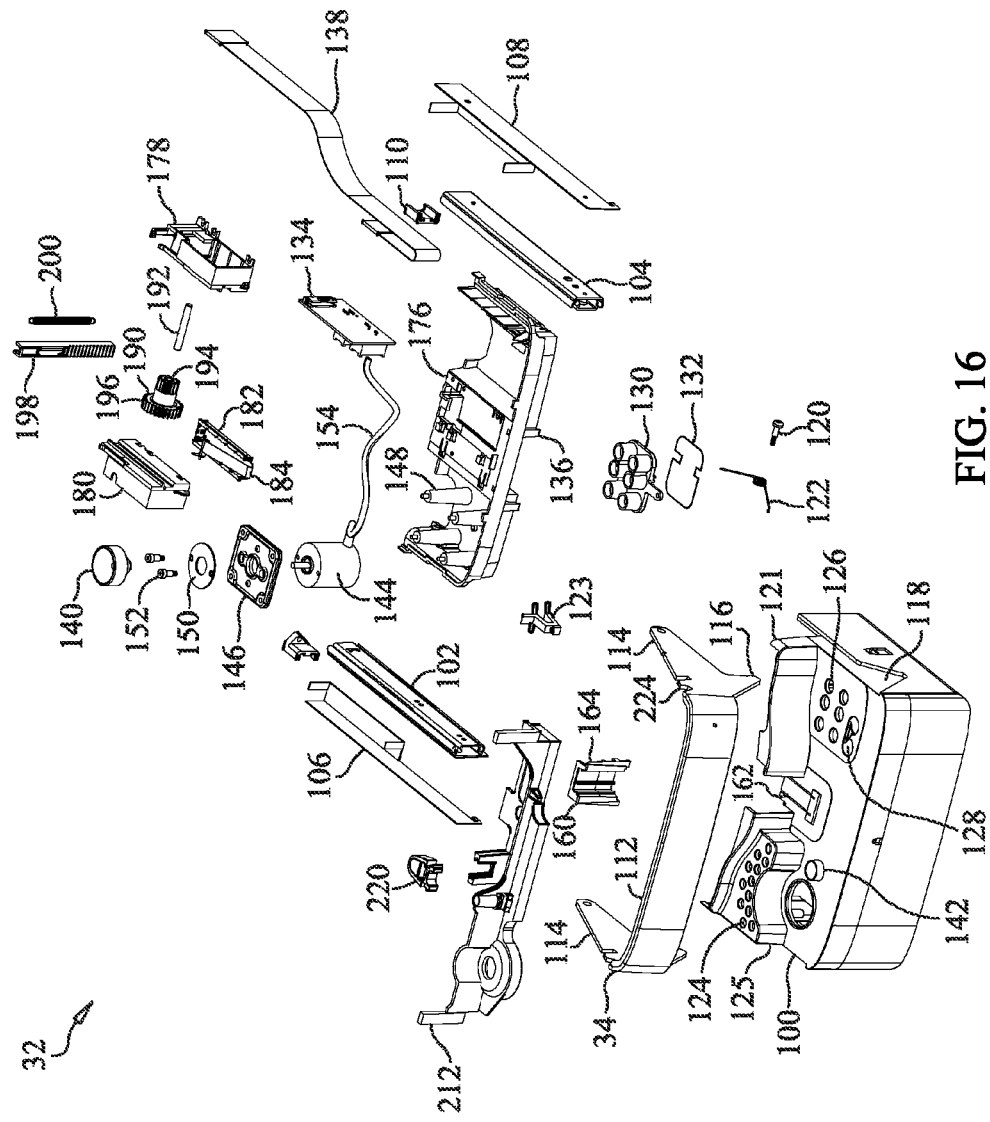
FIG. 16 is an exploded view of the consumables manager drawer of the chemical analyzer of the present invention, which includes the slide loader, the slide inserter mechanism and the lifting door of the chemical analyzer of the present invention.

The consumable slides and sample drawer assembly (i.e., the consumables manager drawer 32) provides the user with a straightforward means of adding single-use components, such as pipette tips, reagent test slides, a blood centrifuge rotor and reagents to the analyzer 2. The drawer assembly also makes these added components (or "consumables") assessible to the fluid handler, so that the consumables can be identified and slides can be prepared. Furthermore, the consumable slides and sample drawer assembly includes mechanisms for feeding slides into the slide processing unit 44 and for locking the drawer in a closed position while slides are being prepared and analyses run. An exploded view of the consumable slides and sample drawer assembly is shown in FIG. 16.

The consumable slides and sample drawer (i.e., the consumables manager drawer 32) assembly will first be described in general, and then will be described in greater detail.

The consumable slides and sample drawer assembly includes a pull out drawer 100 and other sub-assemblies, including mechanisms for allowing the user to load a plurality of chemical reagent test slides in the analyzer 2 and a mechanism for inserting the slides into the slide processing unit 44, as well as a whole blood separator or centrifuge.

The drawer 100 itself may be pulled out by a user from the front of the analyzer 2. There are left and right drawer slides 102, 104 which attach to the left and right lateral sides of the drawer 100 to allow the drawer 100 to be withdrawn from and pushed into the opening formed in the front wall of the analyzer housing. The left and right drawer slides 102, 104 are respectively attached to left and right mounting brackets 106, 108 which are attached to the chassis 40 of the analyzer 2. A drawer stop 110 mounted on the right drawer slide (or both slides) prevents the drawer from being pulled outwardly from the front wall of the analyzer 2 beyond a predetermined distance.

As also mentioned previously, there is a lifting door, or wall 34, which normally resides over the drawer and which rises when the drawer is pulled outwardly from the front wall of the analyzer 2. The lifting door or wall 34 is preferably U-shaped in structure, with a front wall portion 112 that normally resides flush with the front wall portion of the drawer when the drawer is retracted to its full extent into the front wall of the housing, and two parallel side legs 114 which are joined to the opposite lateral sides of the front wall portion 112 of the lift door 34. As can be seen from the drawings, the side legs 114 include downwardly extending protrusions, or followers 116. The followers 116 rest on respective top edges of a camming shoulder 118 which extends slightly outwardly from each side wall portion of the drawer. The free end of each side leg of the lift door 34 includes an opening to receive a shoulder bolt 120 or other fastener so that the side legs are pivotably mounted to support members on opposite lateral sides of the chassis 40. There is preferably also a torsion spring 122 mounted on each shoulder bolt 120 and engaging the lift door 34 to bias the lift door downwardly such that the protrusions 116 on the side legs thereof engage the cam edges of the shoulders 118 on the side walls of the drawer. A lock light and lens 123 is also shown in FIG. 16.

When the drawer 100 is pulled outwardly from the front wall of the housing by a user, the protrusions 116 on the side edges of the lift door 34 travel along sloped portions of the top edges of the camming shoulders 118, causing the lift door to pivot on the shoulder bolts 120 and rise into the interior cavity of the housing, such that the lift door 34 is hidden behind the upper portion of the front wall of the analyzer housing. When the drawer 100 is pushed back into the opening in the front wall of the housing by the user, the protrusions 116 on the side legs of the lift door 34 will travel down the sloping camming edges on the shoulders 118 of the drawer, due to the bias of the torsion springs 122 on the lift door, causing the lift door 34 to lower against the upper surface of the top wall of the drawer 100. The lift door 34 and the drawer 100 will meet and, together, provide not only a more aesthetically pleasing appearance to the front of the analyzer 2, but will also prevent a user from accessing the interior of the analyzer 2, especially when a sample run is being performed. The drawer also includes an anti-splash backwall 121.

The drawer 100 of the consumables manager drawer assembly includes a plurality of wells 124 (there are preferably 12) formed in a raised surface 125 of the top wall of the drawer, located on the left side of the drawer when the analyzer 2 is viewed from the front. These wells 124 are provided for receiving disposable pipette tips, which the user may place therein when the drawer is open. On the right side of the top wall of the drawer 100 is found one or more sets of spaced apart wells 126 for receiving reagent "packs". These packs are, essentially, a set of cups containing various chemical reagents, each cup being sealed with a foil cover, which is pierced by disposable tip fitted onto the end of a proboscis of the fluid handler, as will be described in greater detail. Each reagent pack preferably includes three pierceable cups, joined together in a particular spaced apart relationship by a common supporting substrate, such as plastic or cardboard. The spaced apart cups containing the chemical reagents are received in the spaced apart wells 126 situated on the top wall of the drawer 100. As can be seen from FIG. 16, there are preferably three wells 126 forming each set, and there are preferably two sets of wells formed in the top wall of the drawer.

It should be noted that the reagent pack wells 126 have a particular spacing between them, as mentioned previously. More specifically, one well of each set is offset from its next adjacent well by a greater distance than the distance between which the middle and third well are spaced. The reagent pack has a similar spacing. This particular arrangement of the wells 126, and the cups of each reagent pack, is designed so that the reagent packs may only be received by a set of reagent wells 126 in a particular orientation. In this way, the analyzer 2 will be able to associate, based on pre-programmed information, a particular chemical reagent of a reagent pack with a well of the set of wells 126 in which the reagent pack is received. There is also a bar code on each reagent pack, which is read by a camera in the analyzer 2. The bar code identifies the type of reagents contained in the cups, and this information is conveyed to the controller 42 by the camera reading the bar code on the reagent pack.

There are also two or more receptacles 128 or wells formed in the upper surface of the drawer 100 for receiving diluent cups and/or a mixing cup. The receptacles 128 are preferably located on the right side of the top surface of the drawer 100 when the analyzer 2 is viewed from the front. These receptacles 128 may have different sizes and/or shapes, and similarly the diluent cup and mixing cup may be formed with different sizes and/or shapes so that the diluent cup may only be received by the diluent cup receptacle, and the mixing cup may only be received by the mixing cup receptacle. In this way, the user of the analyzer 2 is prevented from inadvertently placing the diluent cup filled with a diluent in the mixing cup receptacle, and the mixing cup in the diluent cup receptacle.

Alternatively, the diluent cup and the mixing cup may be of the same size and shape but joined together on their outer surfaces by an elongated connection member. The connection member is preferably joined to the diluent cup and mixing cup tangentially to their outer surfaces or at least off-center from their respective diameters. A slot formed in the upper surface of the drawer interconnects the diluent cup receptacle with the mixing cup receptacle, and this slot is also positioned either tangentially to the outer circumference of the receptacle or off-center from their respective diameters in the same fashion as the connection member is positioned with respect to the diluent and mixing cups. Accordingly, the diluent cup and mixing cup, rigidly tethered together by the offset connection member, are placed together on the drawer in their respective receptacles, with the offset connection member being received by the offset interconnecting slot. If the mixing cup were positioned inadvertently by the clinician or user of the analyzer 2 over the diluent cup receptacle, and the diluent cup positioned over the mixing cup receptacle, the connection member would not be in alignment with and would not be receivable by the offset interconnecting slot so that the diluent cup and mixing cup could not be received by the wrong receptacles. Thus, this structure prevents the diluent cup and mixing cup from being incorrectly placed in the mixing cup receptacle and the diluent cup receptacle, respectively.

In the chemical analyzer 2 of the present invention, it is preferred if the reagents in the cups of the reagent packs are maintained at a particular temperature (preferably, 37° Celsius). Accordingly, a heater block 130 is mounted on the underside of the top wall of the drawer 100 in alignment with each set of wells 126 that receives a respective reagent pack. The heater block 130 is formed from a thermally conductive material, such an aluminum, and includes a plurality of receptacles. The recessed portions of the top wall of the drawer 100, which defines the wells 126 for receiving the chemical reagent cups of the reagent packs, are closely received by the receptacles formed in the heater block 130 so as to be in thermal communication with the heater block. Situated underneath and against the bottom surface of the heater block 130 and in thermal communication therewith is an electrical heater pad 132 having electrical wires situated therein. The wires are electrically connected to a printed circuit board 134 mounted on a sub-base 136 of the drawer 100, and energization of the heater pad 132 is controlled by the controller 42 of the analyzer 2 through this printed circuit board 134. A thermistor, thermocouple or other temperature sensing device is mounted on the heater block 130 and senses the temperature thereof, and output signals from the sensor are communicated to the controller 42. The heater pad 132 controls the temperature of the heater block 130 which, in turn, controls the temperature of the wells 126 and the cups of chemical reagents of a reagent pack placed therein. The printed circuit board 134 is connected via a flexible ribbon cable 138 to a connector mounted on the chassis 40, which connects to the electrical circuitry on the controller 42.

As also can be seen from FIG. 16, the drawer 100, preferably on its left side when the analyzer 2 is viewed from the front thereof, includes a blood sample separator, or centrifuge, which includes a cup-shaped "chuck" 140 for receiving a centrifuge rotor, the chuck 140 being exposed on the top surface of the drawer 100. Adjacent the rotor receiving chuck 140 is a sample well 142 for receiving a cup containing a blood sample, serum or other liquid for testing.

Figure 16A:
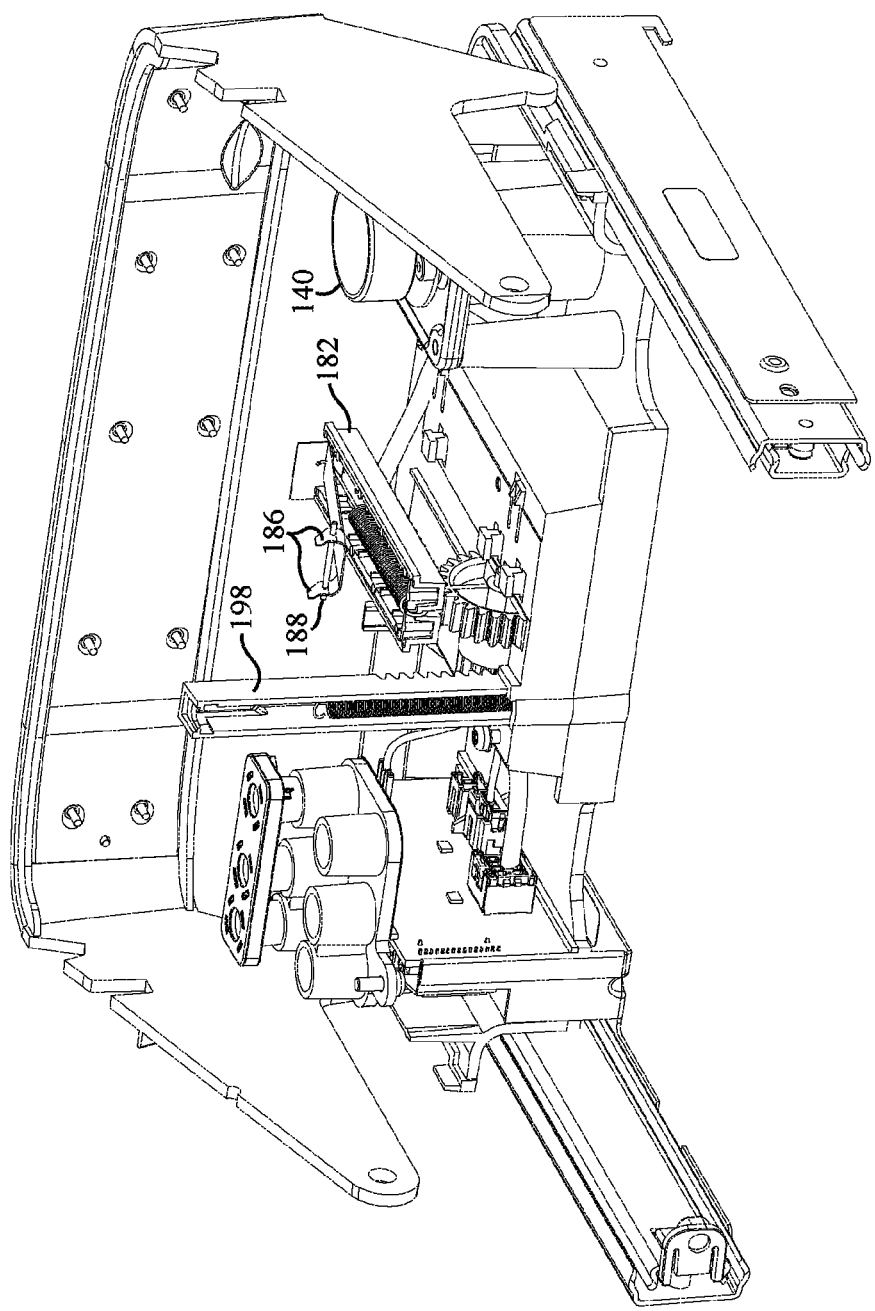
FIG. 16A is a perspective view of the consumables manager drawer of the chemical analyzer of the present invention, with certain components thereof having been removed to facilitate an understanding thereof.
Figure 16B:
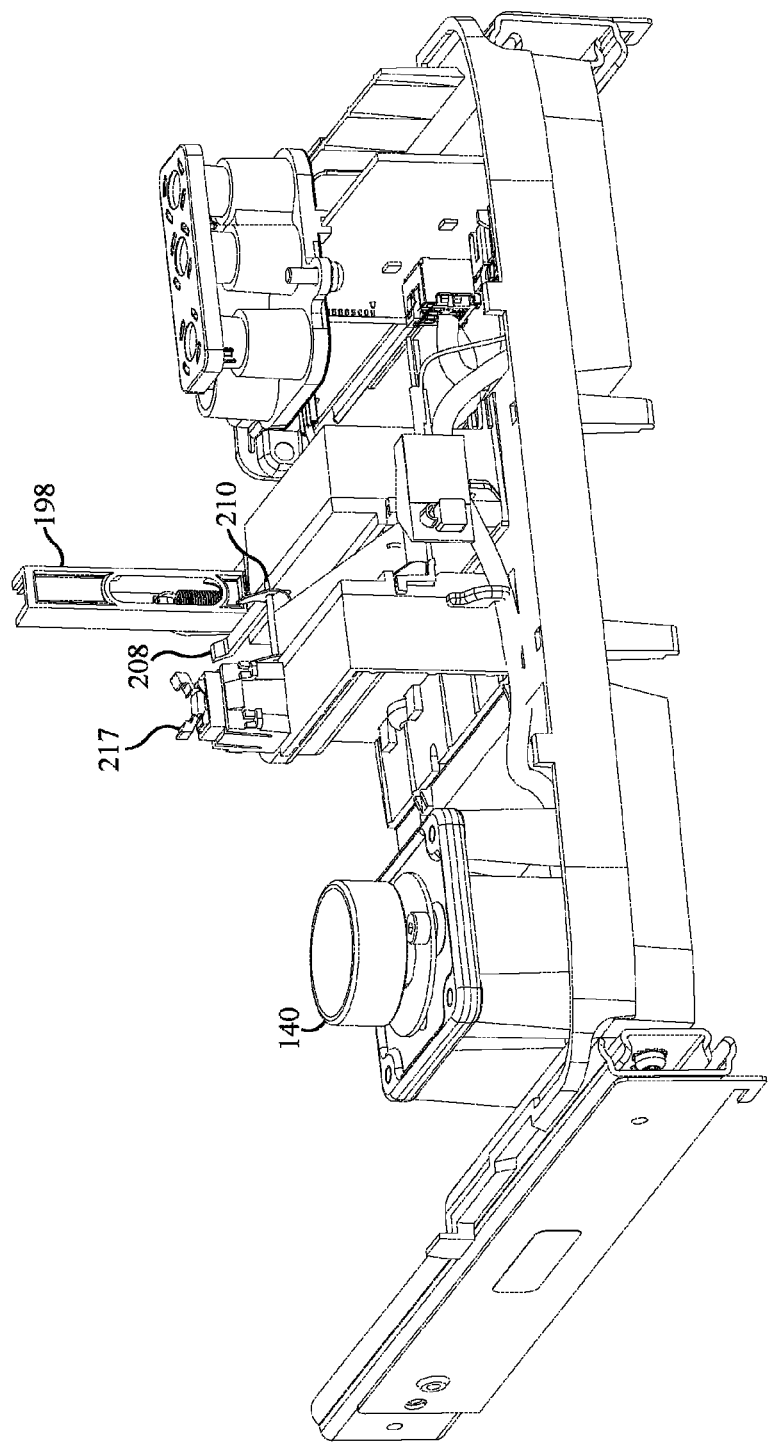
FIG. 16B is another perspective view of the consumables manager drawer of the chemical analyzer of the present invention, with certain components thereof having been removed to facilitate an understanding thereof.

The blood separator, or centrifuge, includes a high revolution motor 144, which is mounted to a plate-like vibration isolator 146, the vibration isolator 146 being in turn mounted to four upstanding spaced apart posts 148 extending upwardly from the inside top surface of the sub-base 136 of the drawer 100, with the motor 144 being suspended by the vibration isolator 146 and residing between the four upwardly extending posts 148 (see FIGS. 16 and 16B). There is a disk 150, forming part of the centrifuge motor mount, situated on the top surface of the vibration isolator 146, the shaft of the centrifuge motor 144 extending through the center aperture formed in each of the vibration isolator 146 and the disk 150, and two shoulder bolts 152 which are received through corresponding openings in the disk and vibration isolator and which screw into the top, axial surface of the centrifuge motor 144 to hold the motor in place on the vibration isolator 146. The cup, or chuck 140, on which is placed a centrifuge rotor, is mounted on the centrifuge motor shaft and is exposed on the top surface of the drawer 100. The centrifuge motor 144 is connected via an electrical wire 154 to the printed circuit board 134 of the drawer, the printed circuit board 134 being connected to the controller 42 through the ribbon cable 138 mentioned earlier. The controller 42 of the analyzer 2 will energize and de-energize the centrifuge motor 144, if necessary, when a blood sample needs to be centrifuged during a sample run.

By suspending the centrifuge motor 144 in the manner described, transmission of vibrations emanating from the centrifuge motor, when running, to the drawer 100 and other components of the analyzer 2, and in particular, to the centrifuge rotor placed in the chuck, are kept to a minimum or prevented.

FIGS. 71-75 are various views of the centrifuge rotor 156 and the chuck 140 of the blood centrifuge. There is a close, but non-friction, fit between the chuck 140 and the rotor 156, and this fit is designed to allow the user to easily place the rotor on and remove it from the chuck, without causing any spillage of the rotor contents. This close fit also minimizes the generation and transmission of vibrations during centrifugation, as the rotor 156 essentially "floats" on, but is retained by, the chuck 140.

Figure 74:
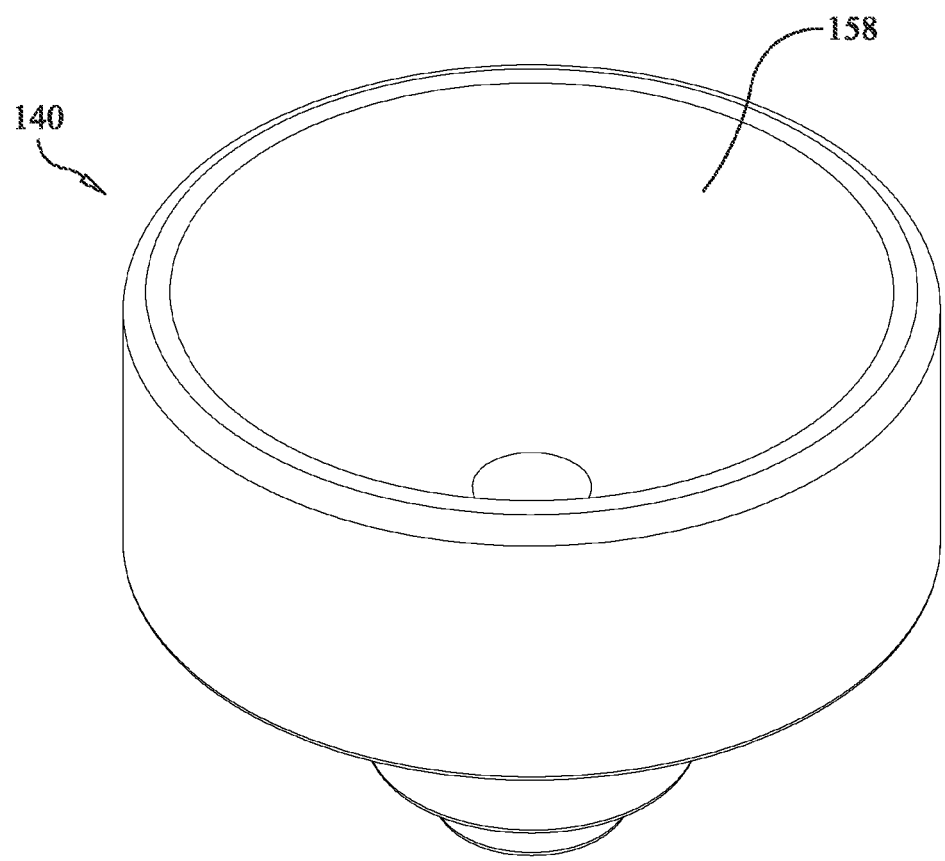
FIG. 74 is top perspective view of a chuck for mounting a centrifuge rotor forming part of the centrifuge of the chemical analyzer of the present invention.
Figure 75:
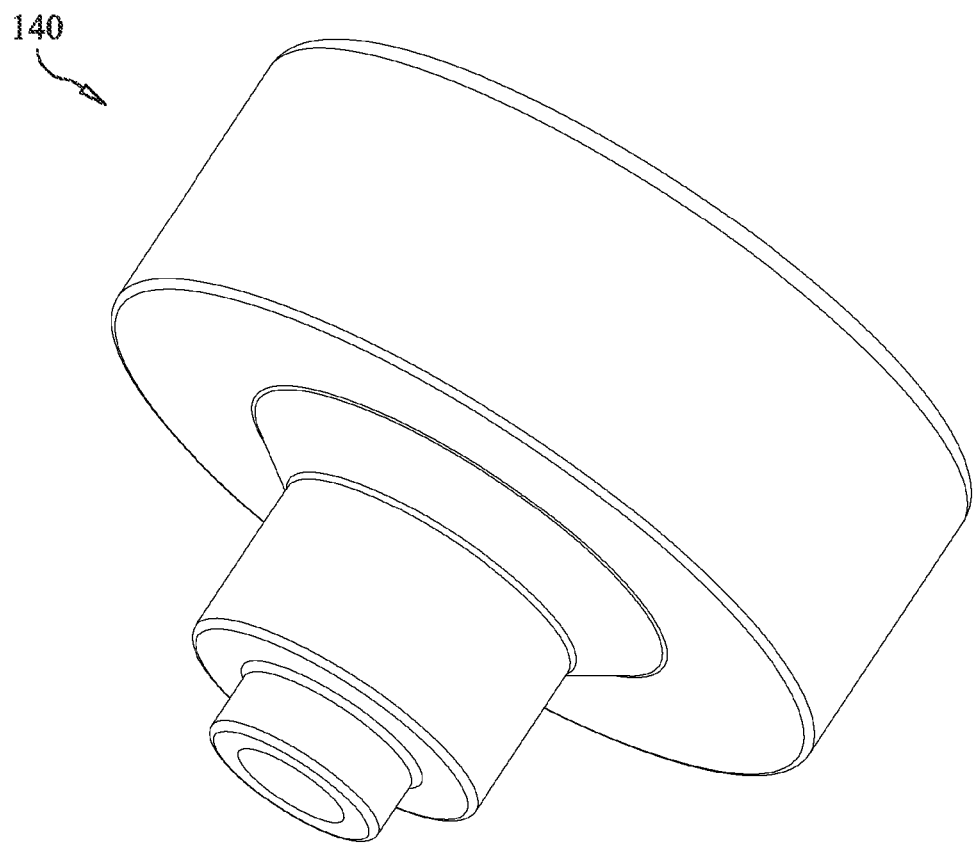
FIG. 75 is bottom perspective view of a chuck for mounting a centrifuge rotor forming part of the centrifuge of the chemical analyzer of the present invention.

As can be seen from FIGS. 74 and 75, the chuck 140 is a cylindrically-shaped body having a concave, cup-shaped receptacle 158 formed on its upper axial end, i.e., the end opposite to where the chuck attaches to the shaft of the centrifuge motor 144. The outer side wall of the chuck 140 is preferably slightly tapered downwardly and radially inwardly, away from the rotor-receiving axial end, with a continuously varying reduced diameter, to allow air to escape between the rotor 156 and chuck 140 when the rotor is placed thereon. The rotor 156 has a lower cylindrical side wall, and a convex bottom wall which is closely received by the cup-shaped receptacle 158 of the centrifuge chuck 140. The chuck 140 preferably does not include fingers to grasp the underside of the rotor, unlike the structure of the centrifuge and rotor disclosed in the aforementioned U.S. Patent Application Publication No. 2010/0254854; rather, the close fit between the rotor 156 and chuck 140 maintains these two components together, even in high speed rotation during centrifugation. It is believed that either a vacuum is created between the rotor 156 and the chuck 140, or a thin layer of air resides between these two components, that keeps the rotor and chuck together during centrifugation and imparts a rotational force on the rotor 156, yet allows the rotor to be easily removed from or placed on the chuck 140 by the user.

As mentioned previously, the analyzer 2 includes a drawer sub-base 136 on which the drawer 100 is mounted. The sub-base 136 supports not only the centrifuge motor 144, but also the mechanism for inserting slides from the slide loader into the slide processing unit 44.

More specifically, there is a slide loader 160 that is mounted on the top surface of the drawer 100 and which is accessible to the user when the drawer is pulled outwardly from the front wall of the analyzer 2.

The slide loader 160 preferably snaps onto the upper surface of the top wall of the drawer 100, in alignment with two parallel extending slots 162 formed through the thickness of the top wall, which are used by the slide inserter mechanism 51 that interfaces with the slide loader 160. The slide loader 160 may be referred to herein as having a "waterfall" shape, as it preferably includes a cascading, curved surface which interfaces with a plurality of reagent test slides in a stacked arrangement. The slide loader 160 includes a pair of spaced apart, upstanding, vertically disposed guide blocks 164, which define the curved interface surface, between which a stack of reagent test slides is placed. The upstanding guide blocks 164 are situated perpendicularly on the upper surface of the top wall of the drawer 100, adjacent to the pair of parallelly disposed slots 162.

The slide loader 160, preferably having a waterfall appearance, is described in detail in U.S. Pat. No. 7,632,468, which issued to Stanislaw Barski, et al., the disclosure of which is incorporated herein by reference. Preferably, the user places a plurality of chemical reagent test slides held in a stacked arrangement by a slide retaining clip, such is disclosed in the aforementioned U.S. Pat. Nos. 7,632,468 and 8,585,989, the disclosure of each of which is also incorporated herein by reference, onto the slide loader 160, and withdraws the retaining clip, the stack of reagent test slides being retained by the loader between the two upstanding guide blocks 164, ready to be delivered to the slide processing unit 44 by the slide inserter mechanism 51. Preferably, each chemical reagent test slide 166 has a trapezoidally-shaped frame 168 surrounding a film portion 170 on which a dry analyte has been previously applied. Such a trapezoidally-shaped reagent test slide 166 is shown in U.S. Pat. Nos. 8,287,823 and 8,585,989, the disclosure of each of which is incorporated herein by reference. Each slide includes an orientation notch 172, formed in a front edge of the slide frame, which is offset from the center thereof so as to ensure that the slides may only be placed on the loader 160 in a particular orientation, a pair of cutouts 174 formed in the lateral side edges, which receive ribs protruding from the guide blocks 164 of the loader so that the plurality of reagent test slides will be retained in a stacked arrangement on the loader when removed from the retaining clip, and a bar code situated on the upper surface of the frame 168 which identifies the chemistry or analyte on the slide, which bar code is read by one of the cameras of the analyzer 2.

The center portion 176 of the sub-base 136 of the drawer 100 is raised and provides a mounting surface for mounting the slide inserter mechanism 51. More specifically, the slide inserter mechanism 51 includes a right slide glide block 178 and a left slide glide block 180, separated from each other by a predetermined distance. Each of the right and left slide glide blocks 178, 180 includes a slot extending longitudinally therein, the opposite slots of the slide glide blocks 178, 180 receiving between them a horizontal gear rack loader piece 182.

The gear rack loader piece 182 is an elongated member having a generally U-shape in cross-section. Formed on its lower surface is a gear rack with teeth, and mounted on its upper surface is an elongated leaf spring 184.

Figure 76:
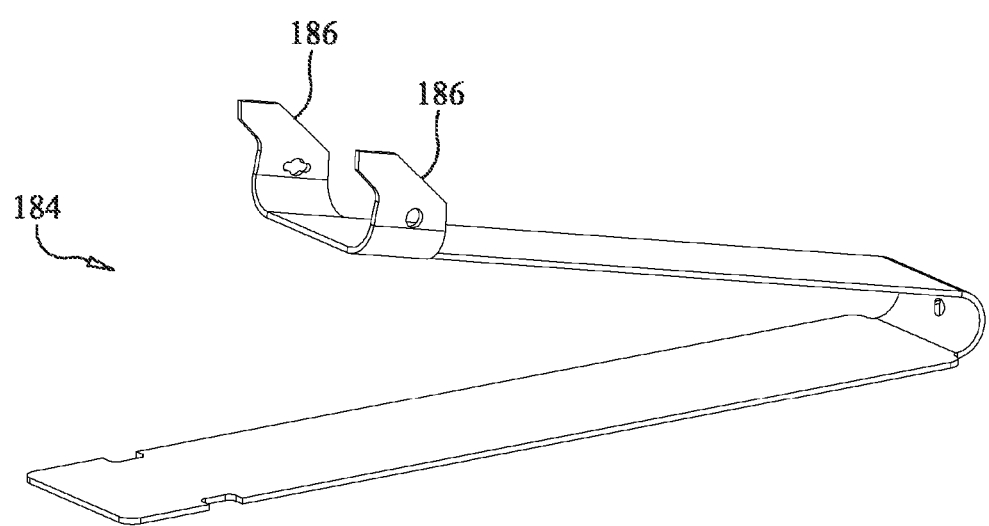
FIG. 76 is perspective view of a leaf spring forming part of the slide inserter mechanism of the chemical analyzer of the present invention.

The leaf spring 184 includes a free end opposite to the axial end on which the spring is mounted on the gear rack loader piece 182 (see FIGS. 16, 16A and 76). The free end is formed with two spaced apart, upwardly protruding fins 186, each fin 186 being received in a corresponding slot 162 formed through the thickness of the top wall of the drawer 100. The free end of the leaf spring also has mounted thereon a transverse bar 188.

A step gear wheel 190 is mounted to the sub-base 136 of the drawer beneath the right and left slide glide blocks 178, 180. More specifically, the step gear wheel 190 is rotatably mounted on a pin 192 which is preferably secured to the sub-base 136 of the drawer 100. The wheel 190 includes on one axial end thereof a first pinion gear 194 and on the opposite axial end thereof a second pinion gear 196. The first pinion gear 194 has a smaller diameter than the second pinion gear 196. The second pinion gear 196 engages the toothed rack situated on the bottom surface of the gear rack loader piece 182 and, when rotated in opposite directions, imparts reciprocating movement to the gear rack loader piece 182 in a horizontal direction within the slots between the right and left slide glide blocks 178, 180.

The slide inserter mechanism 51 also includes a vertically disposed, elongated actuator 198. The actuator 198 is mounted on the sub-base 136 of the drawer 100 and held in place in a vertical disposition, but is reciprocatingly movable thereon. A coiled return spring 200, whose opposite axial ends are secured to the actuator 198 and the sub-base 136 of the drawer 100, biases the actuator 198 upwardly away from the sub-base 136 and outwardly from the upper inside surface of the sub-base 136.

The top axial end of the actuator 198 is selectively contacted by an elongated member 202 extending downwardly from the fluid handler and, more precisely, the robot thereof. As mentioned earlier, the fluid handler can move in the X-direction (between the left and right, when the analyzer 2 is viewed from the front), the Z-direction (the vertical direction, up and down, when the analyzer 2 is viewed from the front) and in a radial Y-direction (through an angle θ, in the X-Y plane). When the extended arm 202 of the fluid handler is moved in the Z-direction, the arm 202 can engage the top axial end portion of the actuator 198 of the loader, causing the actuator to move downwardly against the bias of the actuator spring 200.

In a preferred form of the invention, the upward free end of the actuator 198 includes an end wall having a U-shaped opening formed therein. The extended arm 202 of the fluid handler, or more particularly, the robot thereof, includes a free end formed with an end plate 204 which is selectively receivable by the U-shaped opening formed in the end wall of the actuator 198. The fluid handler, and robot thereof, may be moved in the θ direction (X-Y plane) so that the end plate 204 of the fluid handler arm 202 may be received by the U-shaped opening of the actuator 198. This positive engagement between the actuator 198 of the slide inserter mechanism 51 and the extended arm 202 of the fluid handler robot will insure that the two components are mechanically linked together so that the robot arm 202 will force the actuator 198 of the slide inserter mechanism 51 to move reciprocatingly upwardly and downwardly with movement of the fluid handler robot arm until the fluid handler is rotated in an opposite θ direction to disengage the robot arm 202 from the actuator 198.

The actuator 198 also includes a rack with teeth. This toothed rack on the actuator 198 engages the smaller diameter pinion gear 194 on the step gear wheel 190. When the actuator 198 is forced downwardly by movement of the fluid handler in the Z-direction, it causes the step gear wheel 190 to rotate on the mounting pin 192 in a first rotational direction. The larger pinion gear 196 on the step gear wheel 190 engages the toothed rack on the bottom side of the horizontal gear rack loader piece 182, causing the loader piece to move in an axial direction through the slots of the right and left slide glide blocks 178, 180 in a direction inwardly towards the slide processing unit 44 of the analyzer 2. The fins 186 of the leaf spring 184 mounted to the horizontal gear rack loader piece 182 move through their respective slots 162 formed through the thickness of the top wall of the drawer 100, also in the direction of the slide processing unit 44.

The fins 186, which extend through the slots 162 above the upper surface of the top wall of the drawer 100, engage the rear edge of the lowest reagent test slide in the stack of slides held in place between the guide blocks 164 of the slide loader 160. When the gear rack loader piece 182 moves inwardly, towards the slide processing unit 44, the fins 186 of the leaf spring 184 will push the lowermost slide from the loader 160 along the upper surface of the top wall of the drawer and through a slide entrance slot 206 on the slide processing unit 44.

There are a pair of parallelly disposed, spaced apart, elongated members, resembling "skis" 208, mounted on the upper surface of the right and left slide glide blocks 178, 180, below the bottom surface of the top wall of the drawer 100 and above the gear rack loader piece 182. The free ends of the "ski" members 208 are upwardly turned to engage the bottom surface of the drawer top wall.

When the gear rack loader piece 182 moves in a direction towards the slide processing unit 44, the transverse bar 188 situated on the free end of the leaf spring 184 rides on the upper surfaces of the "ski" members 208, that is, between the "ski" members and the bottom surface of the drawer top wall, until it passes the upturned free ends of the "ski" members. The upturned free ends define ramps on which the transverse bar 188 will travel when the gear rack loader piece 182 is moved in an opposite direction.

When the fluid handler retracts towards its upper position, the vertically disposed actuator 198 of the slide inserter mechanism 51, biased by the spring 200, will move upwardly (or will be pulled upwardly by the fluid handler), away from the sub-base 136. The engagement of the toothed rack on the actuator 198 with the step gear wheel 190 will cause the step gear wheel to rotate in an opposite direction. The engagement of the larger pinion gear 196 with the toothed rack of the gear rack loader piece 182 will cause the loader piece to slide in an opposite direction, away from the slide processing unit 44, through the slots of the right and left slide glide blocks 178, 180. The transverse bar 188 on the leaf spring 184, attached to the gear rack loader piece 182, will be forced to ride over the upturned free ends of the "ski" members 208 and along the length thereof on the lower surfaces of the members 208. By this action, the fins 186 on the leaf spring 184, which are generally triangular in shape, will be forced downwardly in their respective slots 162 in which they travel so that they do not engage, and pass under, the bottom frame surface of the next reagent test slide in the stack, which is now the lowest slide in the stack. Thus, the leaf spring 184 is forced downwardly by the "skis" members 208 to allow the fins 186 to pass beneath the lowest test slide, until the fins 186 pass beyond the rear edge of the lowest test slide.

At the end of its rearward travel, in a direction away from the slide processing unit 44, the upward bias of the leaf spring 184 on the gear rack loader piece 182 will force the transverse bar 188 on its free end to enter and be received by a transverse slot 210, formed in the upper surface of the right and left slide glide blocks 178, 180 and positioned past the axial ends of the "ski" members 208 that are opposite the upturned ends. The slot 210 positions the transverse bar 188 to ride on the upper surfaces of the "ski" members 208 again when the gear rack loader piece 182 is forced to move toward the slide processing unit 44. The fins 186 will be forced upwardly, to extend higher through the slots 162, by the bias of the leaf spring 184. The forward edge of each fin 186 will now be able to engage the lowest test slide in the stack of slides situated within the loader 160, the lowest test slide resting on the upper surface of the top wall of the drawer 100. The slide insertion process described above is now repeated until all of the slides in the loader 160 have been loaded into the slide processing unit 44 through the entrance slot 206 thereof.

In summary, downward movement of the fluid handler, which is actuated by the electrical circuitry of the controller 42, results in a reciprocating, horizontal movement of the fins 186 exposed through the slots 162 of the top wall of the drawer 100 to move the slides, one by one, from the loader 160 into the slide processing unit 44.

The consumable slides and sample drawer assembly also includes an engager 212. The engager 212 is an elongated, generally planar cover piece that is lowered onto the top wall of the drawer 100 and raised therefrom by an arm 202 extending from the fluid handler. The engager 212 includes a curved dome 214 which is used to selectively cover a centrifuge rotor resting in the chuck 140 or cup of the sample separator. The curved dome 214 is provided to minimize any inadvertent splashing, and to prevent damage to the other components of the analyzer 2, should for some reason the centrifuge rotor become disengaged from the chuck 140 on which it is secured. The curved backsplash 216 is also provided to minimize any splashing that may possibly occur during operation of the blood separator.

The engager 212 further includes two upstanding, spaced apart posts 218, each defining open, U-shaped channels facing each other on which a movable slide weight piece 220 is mounted and moves reciprocatingly therebetween. When the drawer 100 is in a retracted position within the opening in the front wall of the analyzer 2, the engager 212 is lowered by the fluid handler to reside over the top wall of the drawer 100. The slide weight piece 220, movable upwardly and downwardly on the posts of the engager 212, rests on the uppermost test slide in the stack of slides mounted on the loader 160.

The slide weight piece 220 serves at least two functions. First, the slide weight piece 220 exerts a force on the top slide in the stack of slides placed on the slide loader 160 and helps force the slides in the stack to move downwardly through the loader as the slide inserter mechanism 51 removes each lowermost slide from the loader. Furthermore, the slide weight piece 220 has a planar lower surface which is dimensioned in width and length to completely cover the film portion of the uppermost slide to minimize any evaporation of the analyte on the film portion of the slide, since it is the top slide in the stack that is primarily exposed to the atmosphere, and respective middle and bottom slides in the stack of slides mounted on the slide loader 160 are protected from deleterious environmental effects by the slide directly resting above it.

Figure 16C:
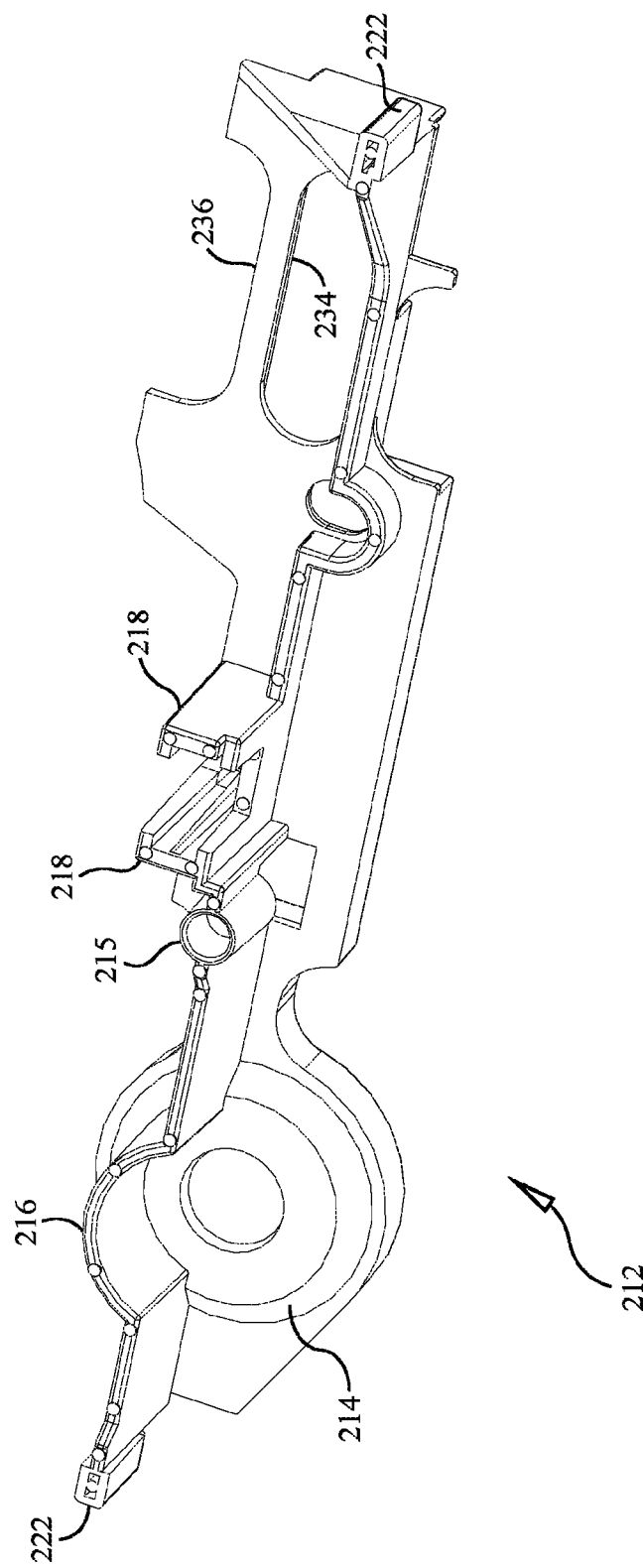
FIG. 16C is a perspective view of an engager forming part of the consumables manager drawer of the chemical analyzer of the present invention.

As can be seen from FIG. 16C, the engager 212 also includes a pair of oppositely disposed, planar projections, or stops 222, which protrude outwardly from the lateral sides of the engager. As also can be seen from FIG. 16, the upper edge of the lift door 34, and in particular, the upper edge of each side leg 114 thereof, has formed therein respective slots or notches 224. When the engager 212 is lowered toward the drawer 100 by the fluid handler robot arm 202, the projections, or stops 222, are received by the notches 224 formed in the side legs 114 of the lift door 34. The engagement of the stops 222 and the notches 224 in the lift door 34 retains the lift door in its lowered position and prevents the lift door from being raised.

Thus, since the lower projections 116 on the lift door 34 engage the camming edges of the shoulders 118 of the consumables manager drawer 32, the drawer 100 may not be pulled outwardly by the clinician or user of the analyzer 2 when the engager 212 is lowered by the fluid handler and the stops 222 thereof are received in the notches 224 of the lift door. This is a safety feature provided on the analyzer 2 to prevent the drawer from being opened inadvertently by a user when the slides are being prepared or analyses are being run.

A further description of the consumable slides and sample drawer assembly (i.e., the consumables manager drawer 32) will now be provided.

The consumable slides and sample drawer assembly functions like a drawer. To be opened, the drawer 100 is pulled straight out from the front of the analyzer 2. It opens via a pair of metal drawer rails 102, 104 on either side of the drawer. When the drawer 100 is pulled opened, a separate but adjacent lift door 34—which, when the drawer is in a closed position lies flush with the front of the drawer to conceal the contents of the drawer—rises into the interior cavity of the analyzer 2. The lift door's rising action relies on the interaction of the sides of the door 34 with curved camming edges or runners 118 situated along the lateral sides of the drawer itself, which guide the lift door 34 upwardly when the drawer 100 is pulled opened. This paired action—an opened drawer translates to a lifted door—makes the interface of the drawer 100 easy for human hands to access when the drawer is opened, and conceals the contents of the consumable slides and sample drawer assembly when the drawer is closed.

The consumable slides and sample drawer assembly accepts disposable pipette tips, reagent test slides and reagents. All of the wells provided for holding the pipette tips and reagents have been placed so that they can be accessed by the range of movement of the robot arm 202 of the fluid handler. The consumable slides and sample drawer assembly manages the organization and presentation of these consumables, and provides a centrifuging action of blood samples and heating of reagents to approximately 37° Celsius. The actual aspiration, mixing or dispensing of fluids is performed by the fluid handler, which will be described in greater detail.

In addition to the aforementioned wells 124, 126 provided for disposable pipette tips and reagents, the consumable slides and sample drawer 32 also includes two wells 128 for holding either a single diluent cup and an interconnected mixing cup, as described previously, or two diluent cups interconnected with one another. A well is also provided for holding a sample cup.

Once the user has added the appropriate consumables to the consumable slides and sample drawer assembly, and closed the drawer, the lift door 34 falls back into place, and the engager 212 is lowered by the actuating arm 202 of the fluid handler. The drawer 32, and its corresponding lift door 34, cannot be opened except when the engager 212 has been lifted; conversely, when the engager 212 is in the lowered position, the drawer 32 cannot be pulled open.

The engager 212 preferably fits over some but not all of the consumables, and assists in slide loading and preparation functions. One of the engager's principal functions is to provide a cover, or weight, for the stack of slides aligned in the "waterfall" slide loader 160. The slide weight piece 220 is designed to be vertically pre-moving along its respective runners, or posts 218, in the engager 212. This weight piece 220, designed to protect the unprepared slides from any moisture in the lab environment, rests on the top slide and, due to gravity, drops down each time a slide from the bottom of the stack is removed from the loader 160 so that the slide in the top position of the stack remains covered until the last slide is pushed into the slide processing unit 44.

The mechanism by which slides are moved into the slide processing unit 44 involves translating the vertical motion of the downwardly extending arm 202 of the fluid handler robot to a horizontal motion, which guides each slide through an opening at the bottom of the waterfall-shaped loader and into the slide processing unit 44. A vertical gear rack actuator 198 in the slide inserter mechanism 51, when pressed downwardly by the extended arm 202 of the fluid handler robot, turns a circular pinion gear 194 on the pinion wheel 190. This gear 194 is attached to a pinion gear 196 of twice the diameter, thereby increasing the magnitude of the smaller gear's motion. The larger gear 196 moves a horizontal gear rack 182, which in turn moves the slide pusher leaf spring 184 on the horizontal gear rack forward. The pusher spring 184, whose two short prongs or fins 186 protrude through the horizontal top surface of the drawer, moves forward when the motion of the vertical gear rack actuator 198 has been translated to the horizontal gear rack 182. When the extended arm 202 of the fluid handler robot lifts away, a spring 200 returns the vertical gear rack actuator 198 to its original position, thereby reversing the movement of all gears up to this point.

There is preferably an LED "lock light" on the front wall of the drawer 32, and this lock light is energized to illuminate when the drawer is locked (that is, when the drawer 32 has been pushed shut, the engager 212 is lowered and the user presses the "smart button" switch on the front wall of the analyzer 2 to begin the run cycle).

To open the drawer 32, it is essential that the engager 212 be lifted away from its lowered position. When the engager 212 is lowered, it rests on or is in close proximity to the top surface of the drawer. The elongated arm 202 of the fluid handler, or robot, lifts the engager away.

The engager 212 includes a robot arm guide member 215. This is a tubular member extending outwardly from the top surface thereof. The tubular member 215 includes a bore extending axially therethrough. Within the bore is a pincer mechanism 217 which selectively grabs the edges of the end plate 204 of the free end of the fluid handler robot arm 202 when the robot arm is lowered into the bore of the engager tubular member 215, in order to secure the engager 212 to the robot arm 202 so that the engager will move upwardly and downwardly with movement of the fluid handler. The pincer mechanism will open, and release the extended arm 202 of the fluid handler robot when the arm is lowered again and further pressed against the pincer mechanism within the bore of the engager tubular member 215.

When the user pushes the drawer closed, the engager 212 is lowered, and the slide weight piece 220 rests on the top slide in the stack of slides on the loader 160. Power to the LED lock light causes the lock light to illuminate, and the engager 212 locks the drawer 32 closed.

The consumables are accessible through the openings in the engager 212 by the fluid handler. The engager 212 lowers over the consumables and causes the drawer 32 to lock. The drawer 32 is positioned within reach of the fluid handler's three planes of access so that the fluid handler can access all consumables (disposable pipette tips, slides, reagents and diluents) organized on the top surface of the drawer.

In order to centrifuge a blood sample, the centrifuge rotor's fit within the separator allows the rotor to spin but further provides room for the rotor to be easily removed by the user. The vision system, and in particular, one of the cameras thereof, identifies the presence of the whole blood centrifuge rotor.

In order to load slides into the analyzer 2, the slides are appropriately positioned on the loader 160, which is dimensioned to take into account the slide surface, geometry and height. The pusher spring 184 of the slide inserter mechanism 51, and in particular the fins 186 extending through the slots 162 formed through the top wall of the drawer, travel at a height that pushes only the bottom slide out from beneath the stack of slides and into the slide processing unit 44. The fluid handler's extended long arm 202 engages the slide inserter mechanism 51 by a vertical motion.

Preferably, the reagent consumables are properly incubated while resting in their identified wells formed in the top wall of the drawer 32. There is contact between the reagent pack and the heater block 130 situated under the reagent pack's wells 126. The user merely has to place the reagent packs in their respective wells 126. Electrical current is provided to a heating pad 132 in contact with the heater block 130 to incubate the reagent consumables.

As mentioned previously, when the engager 212 is lowered, the bottom surface of the slide weight piece 220 covers the film portion of the top slide in the stack on the loader 160 such that the top slide is not exposed to excess humidity in the surrounding environment of the analyzer 2.

The analyzer 2 of the present invention also can identify what consumables are placed by the user on the drawer 32. The analyzer 2 uses a vision system (see FIG. 17) having two similar cameras 228, 230, one 228 on the fluid handler and the other 230 mounted on the chassis 40, that are capable of identifying the types of reagent packs and slides. One of the cameras 230 can read the bar codes on each slide. The other camera 228, the one which is attached to the fluid handler robot, is also capable of identifying visual characteristics of consumables to identify, for example, whether a whole blood centrifuge rotor is positioned on the centrifuge chuck 140 or cup. One or more LEDs mounted on the chassis 40 within the interior cavity defined by the housing is selectively energized to provide illumination for the cameras 228, 230 to view the consumables and read the bar codes on the slides and reagent packs. The slide bar codes are read by one of the cameras 230 when each slide is positioned beneath a slide read window in the slide processing unit 44.

As mentioned previously, the consumable slides and sample drawer 32 is positioned above the waste drawer 26, which receives used slides and pipette tips. There is a curved indent 232 formed in the center of the front wall of the waste drawer 26, to allow the consumable slides and sample drawer 32 to be accessed by hand and opened manually, when not locked, by the user. The entire drawer 32 slides on a pair of metal drawer rails 226. At full extension, the drawer 32 displays all of its wells, but it does not slide out so much as to allow the user to access the interior of the analyzer 2 from the front thereof.

Along the sides of the drawer are thin shoulders 118 which define camming edges which guide the motion of the lift door 34. When the drawer 32 is pulled opened, two projections or prongs 116 on the lift door 34 ride up on these camming edges of the drawer, thereby raising the lift door and guiding it toward the interior of the analyzer 2. When the consumable slides and sample drawer 32 is pushed closed again, the projections 116 on the lift door 34 ride down the camming edges so that the front of the lift door comes to rest again in a position flush with the front of the drawer.

Figure 33:
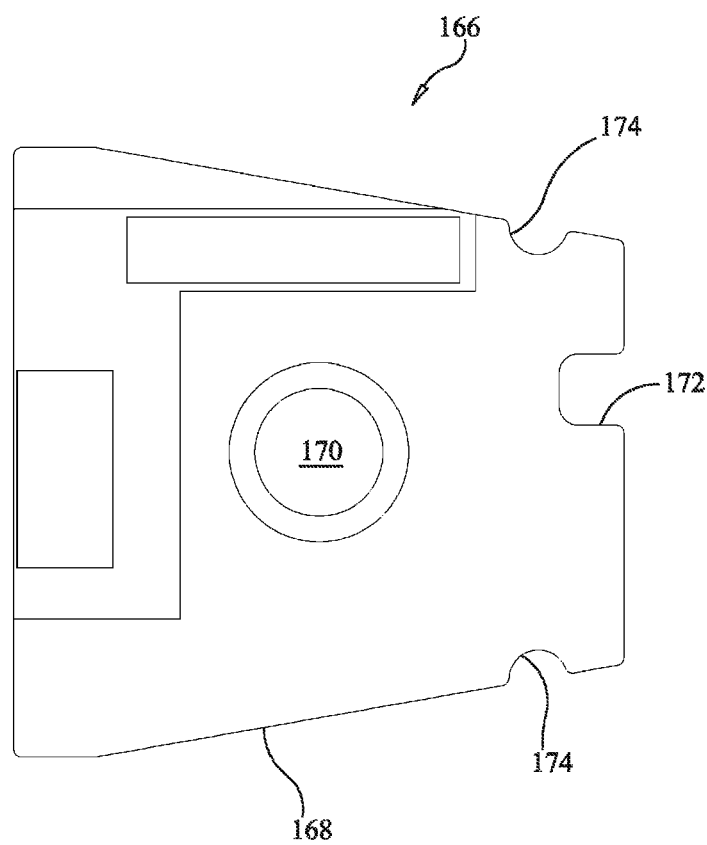
FIG. 33 is a top plan view of a chemical reagent test slide used by the chemical analyzer of the present invention.
Figure 34:
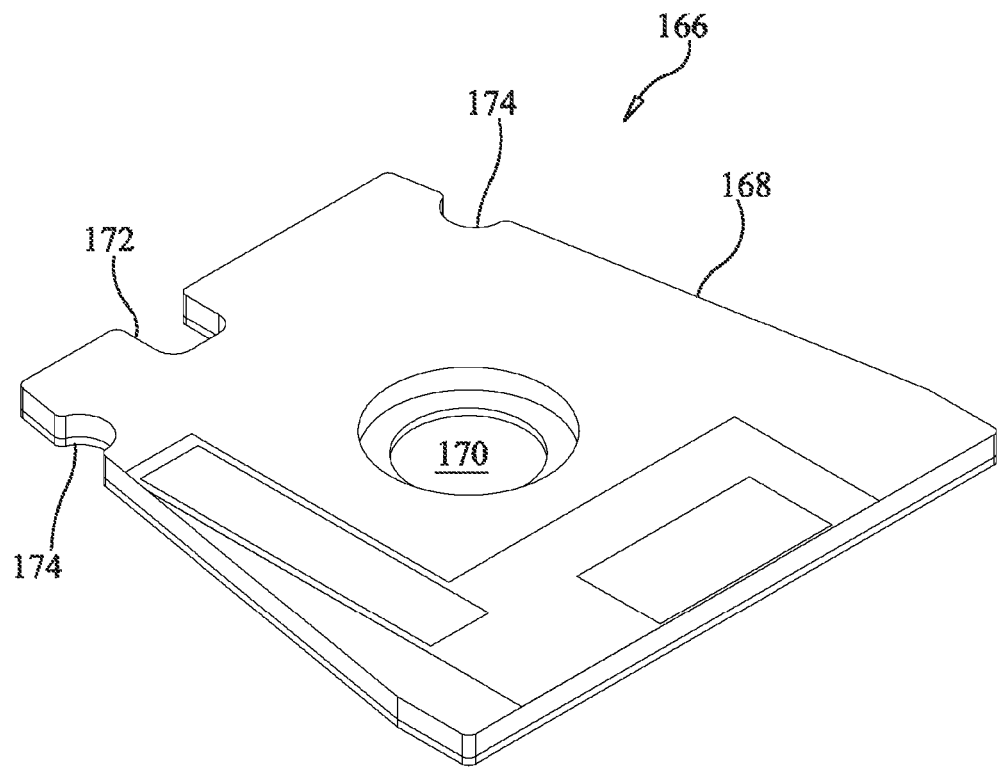
FIG. 34 is a perspective view of a chemical reagent test slide used by the chemical analyzer of the present invention.

The slide loader 160, in its preferred waterfall shape, is designed to accept trapezoidally-shaped chemical reagent test slides 166 (see FIGS. 33 and 34), as well as trapezoidally-shaped immunoassay slides, and the location and layout of the wells are designed to accept reagent packs. The consumable slides and sample drawer preferably includes twenty-two appropriately sized wells. On the left side of the drawer 32, when the analyzer 2 is viewed from the front, there are twelve wells 124 formed in the top surface of the drawer for receiving disposable pipette tips. Another cup (or chuck) 140 is provided for the centrifuge rotor of the whole blood separator, and another well 142 is provided for receiving a sample cup. On the right side of the top surface of the drawer are situated six wells 126 for reagents, which can hold up to two reagent packs, each having three cups of reagents, and two wells 128 for receiving diluting liquid cups or one diluting liquid cup and a mixing cup.

The six wells 126 which are provided for reagent packs are specifically spaced apart so that the reagent packs can only fit into the wells in a proper orientation. One of the wells of each of the two sets of three wells 126 is set slightly apart from the other two wells of each set, and the reagent packs have cups which are similarly spaced apart so that the packs can only fit into the wells 126 in one orientation.

Beneath the reagent wells 126 is an incubating heater comprising an aluminum block 130 having six hollow cones that match the hollows of the reagent wells 126. On the underside of the aluminum block 130 is a self-adhered heating pad or film 132, that maintains the incubator block 130 at a temperature within two degrees of 37° Celsius. Thus, the reagents placed in the drawer 32 will be maintained at an incubating temperature even before being accessed by the fluid handler.

As mentioned previously, the consumable slides and sample drawer assembly includes a whole blood separator, or centrifuge. This centrifuge is capable of spinning at 24,000 RPM. The centrifuge consists of a motor 144 and an aluminum chuck 140. The plastic centrifuge rotor sits over the centrifuge. When the centrifuge is on, cells are drawn into a silicone gel lining the equator of the centrifuge rotor. Once centrifuging is complete, the substance that slides back down to the deepest part of the centrifuge rotor is considered the sample. A butyl rubber isolation pad 146 on which the centrifuge motor 144 is mounted dampens the effects of any vibrations emanating from the centrifuge, when it is spinning.

As also described previously, the consumable slides and sample drawer assembly includes an engager 212, which moves when acted upon by the long arm 202 of the fluid handler, or robot. There is a collar-shaped guide member 214 on the engager 212, that accepts the notched end 204 of an elongated arm 202 extending from the fluid handler robot, and the engager 212 can be lifted up along guiding ribs mounted on the inside of the chassis 40 of the analyzer 2.

The collar-shaped guide member 214 on the engager 212 provides an especially stable connection with the fluid handler's elongated arm 202 for two reasons. First, the axially long collar 214 overcomes the fluid handler arm's off-centered placement within the engager 212 and the resistance that the ends of the engager may encounter from moving along the guides on the inside of the chassis 40. Second, the push-push function of the elongated arm 202 of the fluid handler robot, for slide loading purposes, requires a precise vertical motion. The long collar (i.e., arm guide member 214) on the engager which receives the robot arm 202 guides this motion and ensures that the robot arm properly contacts the axial end of the gear rack vertical loader piece.

The engager 212, when in a lowered position, hinders outward movement of the drawer 32 not only by the very fact that its resting position is in front of the raised portions 125 of the top wall of the drawer, but also because the engager 212 has lateral stops 222 which are received in the notches 224 of the lift door 34. When the engager 212 is in its lowered position, the drawer 32 is locked.

The engager 212 has formed through its thickness an opening for receiving the pipette tip attached to the proboscis of the fluid handler. Furthermore, the engager 212 has a pair of elongated slots 234, 236 (one slot 234 being fully encircled and the other slot 236 being partially opened at the inner edge of the enhancer) formed through its thickness, which slots 234, 236 are aligned with respective reagent packs resting in their corresponding receiving wells 126. The dimensions of the slots 234, 236 are chosen to be slightly smaller than the substrate that interconnects the reagent cups of each pack. Thus, the engager 212 is designed to overlap slightly with the corners and/or edges of the reagent packs so that the packs, whose foil covers have been punctured by the disposable tip mounted to the end of the proboscis of the fluid handler, are not lifted when the fluid handler pulls away from the reagent packs.

The drawer sub-base 136, located beneath the wells of the consumable slides and sample drawer 32, snaps into the drawer for ease of assembly. This structure serves as an attachment place for the slide inserter mechanism 51 and the printed circuit board 134 of the consumable slides and sample drawer assembly, and further has four upstanding posts 148 for securing the centrifuge.

Figure 17:
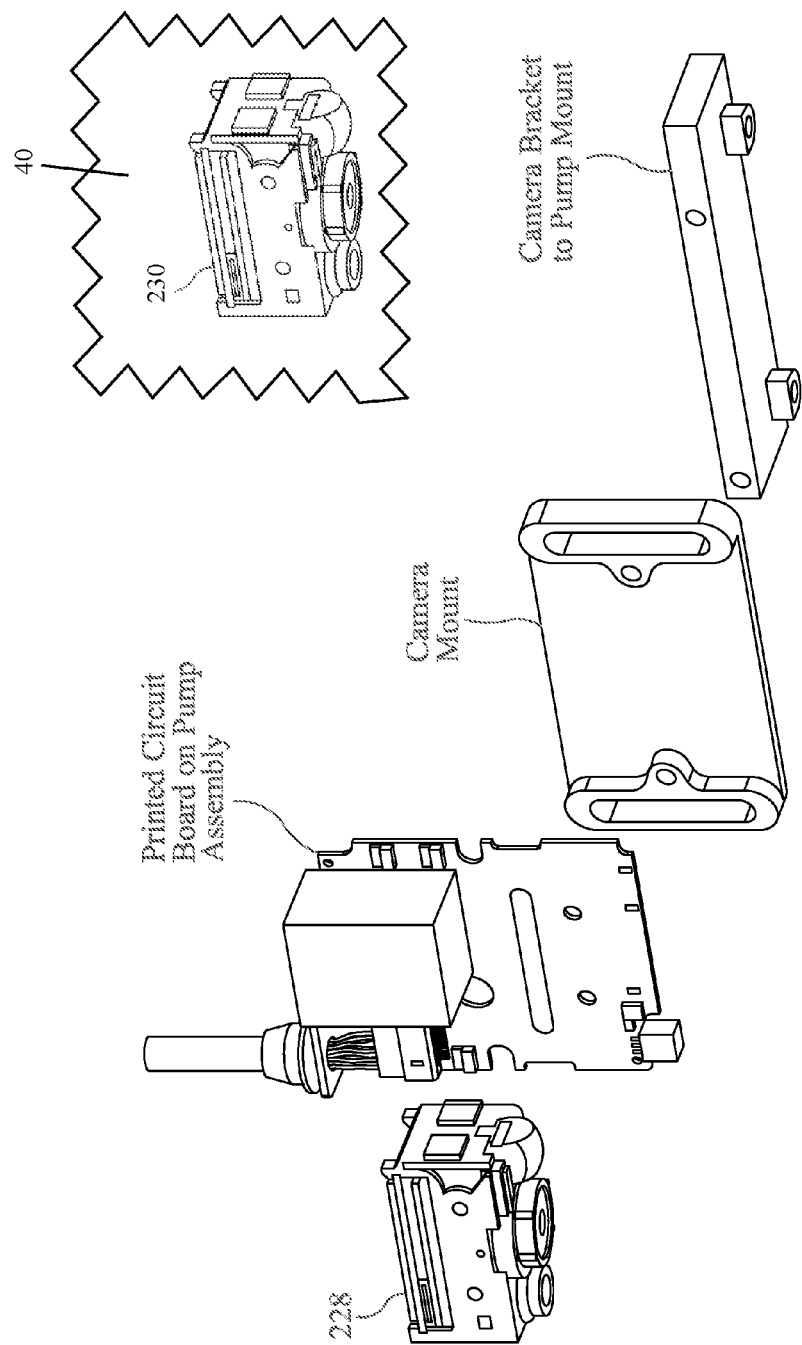
FIG. 17 is an exploded view of the vision system of the chemical analyzer of the present invention.

As mentioned previously, the analyzer 2 of the present invention includes a vision system comprising at least two cameras 228, 230 to read bar codes not only on the slides but also on reagent packs and to determine the presence or absence of various consumables loaded onto the consumable slides and sample drawer 32 by a user. An exploded view of the vision system is shown in FIG. 17 of the drawings.

More specifically, a first camera 228 is attached to the printed circuit board 238 mounted on the fluid handler. The second camera 230 is preferably mounted to a bracket on the chassis 40 of the analyzer 2. This second camera 230 is also preferably connected to its own printed circuit board. Each camera's printed circuit board is electrically connected to the electronic circuitry of the controller 42 through appropriate connectors and signal-carrying cables.

The camera 228 on the fluid handler serves several purposes. These purposes include identifying whether disposable pipette tips are situated in the wells 124 provided in the drawer for receiving such, detecting the presence or absence of reagent test slides in the slide loader mechanism 160, reading bar codes on the reagent packs, detecting the presence or absence of a dilution cup or cups in their respective wells 128, detecting the presence or absence of a sample cup in its respective well 142, detecting the position of the engager 212, and detecting the presence or absence of a centrifuge rotor on the cup or chuck 140 of the centrifuge. This camera 228 also has the ability to determine whether the covering plug on the fill hole of the centrifuge rotor has been removed.

The second camera 230, mounted to the chassis 40, serves the purpose of reading the bar codes on the reagent test slides that have been loaded into the slide processing unit 44.

During a run cycle, the control module 45 of the controller 42 controls the operation of the cameras 228, 230 and instructs the cameras to acquire the necessary images. The vision system executes the command, acquires the images and sends the images to the electrical circuitry of the analyzer 2 where the images are analyzed. The results of the image analysis are stored in the memory of the electrical circuitry associated with the vision system. The camera images may be compared with pre-stored images of the consumable slides and sample drawer 32, and differences, or similarities, between the camera images and the pre-stored images are used to determine the presence or absence of consumables, and to read the bar codes on the reagent packs (the read bar codes are compared with pre-stored bar codes).

Within each camera 228, 230 is a monochrome image sensor with a relatively large pixel size. The sensor's global shutter capability means that all pixels integrate at approximately the same time; that is, all pixels are both activated and deactivated simultaneously. This feature makes the cameras 228, 230 ideal for imaging while moving, especially for the camera 228 mounted on the fluid handler which is frequently moving.

Furthermore, the vision system of the analyzer 2 includes high-brightness amber LEDs mounted to the chassis 40 within the interior cavity of the housing. The exposure times of the LEDs are very brief, preferably between 2 and 3 milliseconds. Two additional red LEDs, also situated within the interior cavity of the analyzer 2, may provide auxiliary lighting and may be turned on and off, as needed. The exposure times of these red LEDs are longer than the high-brightness amber LEDs, the red LEDs being illuminated for preferably up to about 20 milliseconds.

Figure 14:
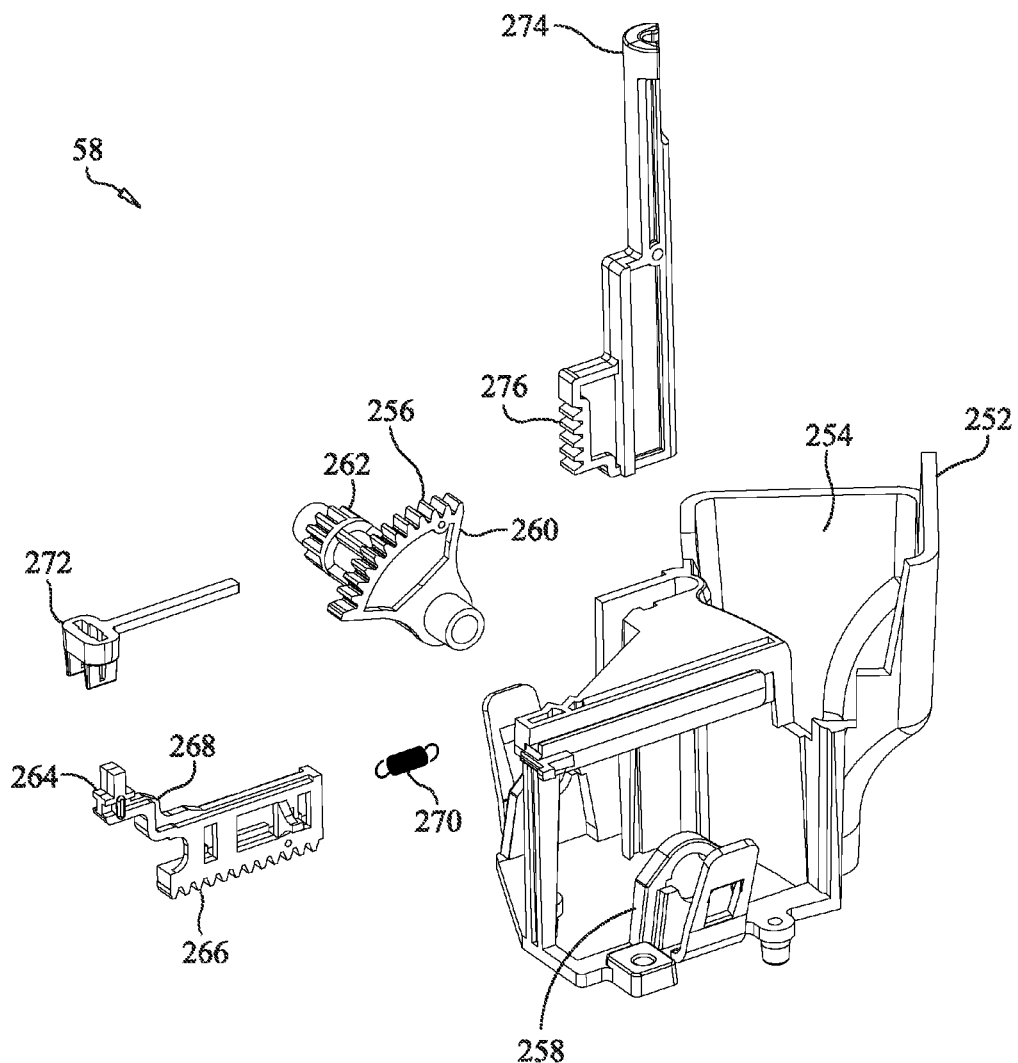
FIG. 14 is an exploded view of the slide eject mechanism of the chemical analyzer of the present invention.
Figure 15:
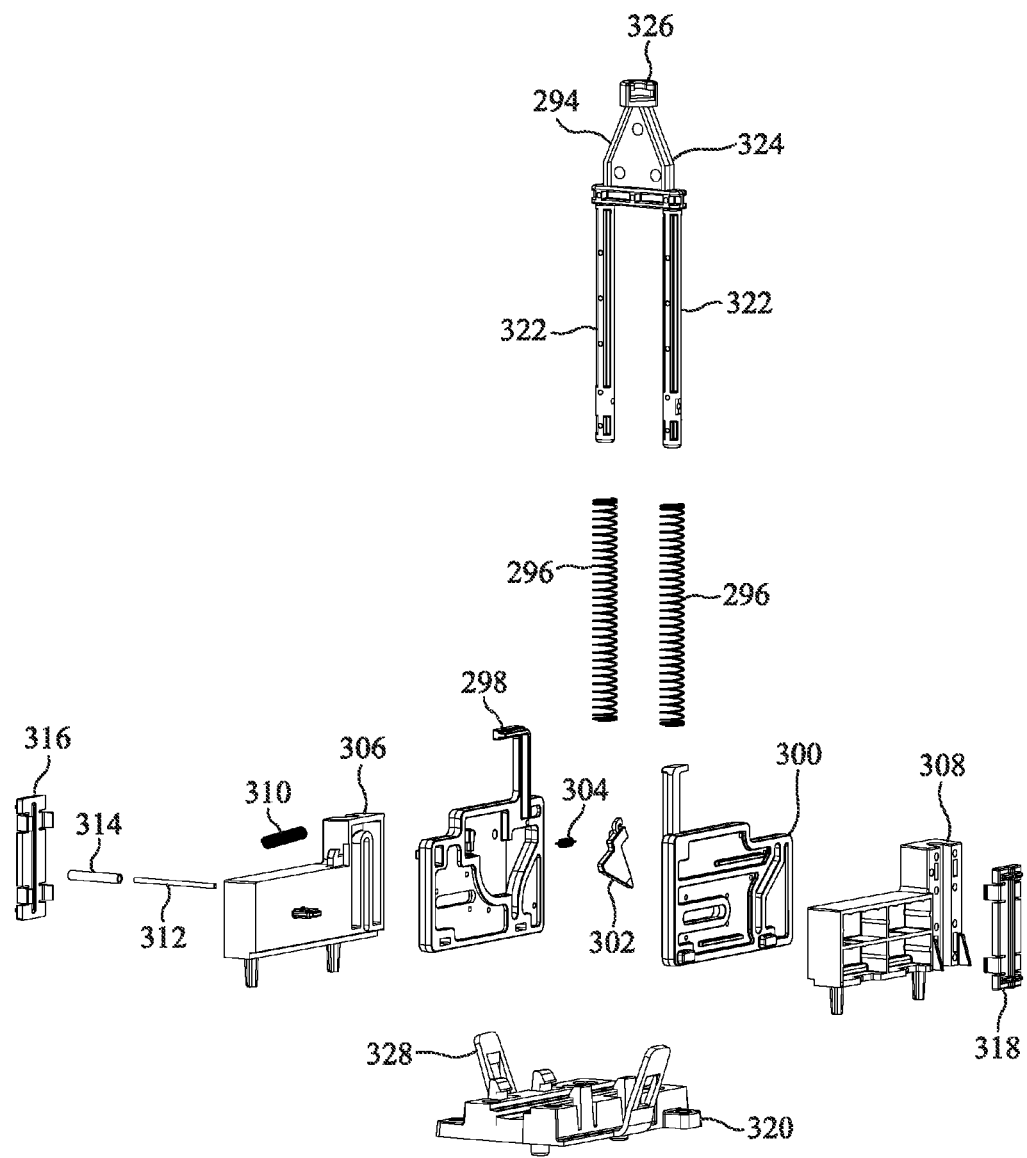
FIG. 15 is an exploded view of the evaporation cap open and close mechanism of the chemical analyzer of the present invention.

An exploded view of the slide ejector mechanism 58 is shown in FIG. 14 of the drawings. The ejector mechanism 58 preferably snaps into the base of the chassis 40 of the analyzer 2, and is situated adjacent to an ejector window or slot 250 formed in the slide processing unit 44, as will be described in great detail.

The slide ejector mechanism 58 includes a main body, or base 252, on which the various components of the mechanism are mounted. The base 252 is formed with an ejector chute 254 having a sloping ramp-like surface, which is used to direct slides removed from the slide processing unit 44 toward the waste drawer 26 through an opening in the base, the waste drawer 26 being situated below the consumable slides and sample drawer 32 on the front wall of the analyzer housing.

The slide ejector mechanism 58 includes a rotatable gear pin 256 held in place on the base 252 of the ejector mechanism by two inverted U-shaped brackets 258 situated at opposite axial ends of the gear pin 256. Situated on the gear pin 256, in proximity to one axial end thereof, is a partial pinion gear 260, i.e., the gear teeth only extending over a partial, arcuate angle of the gear pin. Nearer the other axial end of the gear pin 256 is situated a pinion gear 262 having a radius which is less than that of the partial pinion gear 260.

The base 252, or frame, of the ejector mechanism 58 has also mounted thereon above the gear pin 256 a pusher bracket 264. The pusher bracket 264 includes a main portion having a toothed rack 266 extending downwardly therefrom, and a pusher pin mounting leg 268 extending laterally from a side of the main portion.

The pusher bracket 264 is slidably mounted on the frame, or base 252, of the ejector mechanism 58 and positioned such that the toothed rack 266 is aligned with, and engages, the teeth of the partial gear 260 of the gear pin 256. There is a spring 270 which is fastened at one axial end to the base 252 of the ejector mechanism 58 and at the other axial end to the pusher bracket 264 so that the pusher bracket is biased inwardly of the base 252 on which it is mounted. The side extending leg 268 of the pusher bracket 264 has mounted thereon a pusher pin 272. The pusher pin 272 is received in a track formed in the base of the slide processing unit 44 on which the slides rest as they are moved in a circular path by the slide carousel 48 of the processing unit, as will be described in greater detail.

The slide ejector mechanism 58 also includes a vertically disposed, elongated actuator plunger 274, which is reciprocatingly movably mounted on the base 252 of the ejector mechanism. The actuator plunger 274 includes a toothed rack 276 on one of its sides, which rack 276 engages the smaller pinion gear 262 of the gear pin 256.

The slide ejector mechanism 58 operates in the following manner. The fluid handler is positioned over the actuator plunger 274 during a slide ejection procedure such that its elongated arm 202 is situated co-axially with the actuator plunger 274 of the ejector mechanism. The actuator plunger 274 is forced downwardly on the base 252 of the ejector mechanism 58 by the elongated arm 202 of the fluid handler robot. The upper axial end of the actuator plunger 274 is contacted by the arm 202 of the fluid handler and is forced downwardly thereby. The toothed rack 276 of the actuator plunger 274 engages the smaller pinion wheel gear 262 of the gear pin 256 and causes the gear pin 256 to rotate in one direction, as the actuator plunger 274 is forced downwardly on the base 252 of the ejector mechanism. The partial pinion wheel 260 of the gear pin 256 engages the toothed rack 266 of the pusher bracket 264 and causes a horizontal, sliding motion of the bracket on the base 252 of the ejector mechanism 58, in a direction towards the slide processing unit 44. The pusher pin 272 is forced into the slide processing unit 44, and the free end thereof engages the outer edge of a reagent test slide positioned in the slide processing unit 44 in alignment with the pusher pin 272, and forces the slide through a slide eject slot 250 of the slide processing unit 44. The slide eject slot 250 in the slide processing unit 44 is aligned with the ejector chute 254 of the ejector mechanism such that the ejected slide will fall into the chute and be directed by the chute towards the waste drawer 26.

When the fluid handler is raised such that its elongated arm 202 no longer presses downwardly against the axial end of the actuator plunger 274, the plunger bracket 264 slidably moves on the ejector base 252 in an opposite direction under the bias of the spring 270. Alternatively, the upper free end of the actuator plunger 274 may include a top wall having a U-shaped open slot formed therein, which slot receives the end plate 204 at the lower free end of the fluid handler robot arm 202, in much the same way as the robot arm engages the vertical actuator 198 of the slide inserter mechanism 51, so that upward and downward movement of the fluid handler robot arm 202 positively causes similar movement of the actuator plunger 274 of the slide ejector mechanism 58.

The pusher pin 272, attached to the pusher bracket 264, reverts back to its original position, in a direction outwardly from the slide processing unit 44. The engagement of the toothed rack 266 with the partial pinion gear 260 on the gear pin 256 causes the gear pin to rotate in an opposite direction. The engagement of the toothed rack 276 on the actuator plunger 274 and the smaller pinion gear 262 on the gear pin 256 causes the actuator plunger 274 to rise vertically to its original position (or, more preferably, is mechanically lifted by the elongated arm 202 of the fluid handler robot) prior to it being forced downwardly again by the elongated arm of the fluid handler robot.

The slide carousel 48 then moves the next slide into alignment with the pusher pin 272 and the slide eject slot 250, and the slide ejection process is repeated, with the fluid handler robot arm 202 moving downwardly to engage the actuator plunger 274 to push the pusher pin 272 into the slide processing unit 44 to force another slide out of the slide processing unit 44 and into the ejector chute 254 of the slide ejector mechanism.

The slide processing unit 44 is similar in structure in many respects to the slide transport mechanism described in U.S. Patent Application Publication No. 2010/0254854, the disclosure of which is incorporated herein by reference. The slide processing unit 44 of the chemical analyzer 2 of the present invention is shown in exploded form in FIG. 10. Generally, the slide processing unit 44 includes not only the mechanism for transporting the reagent test slides in a circular path, but also the structures for incubating the slides, that is, for maintaining the slides at a predetermined temperature, and the optics module 56, which includes a combined reflectometer/fluorometer.

Figure 10:
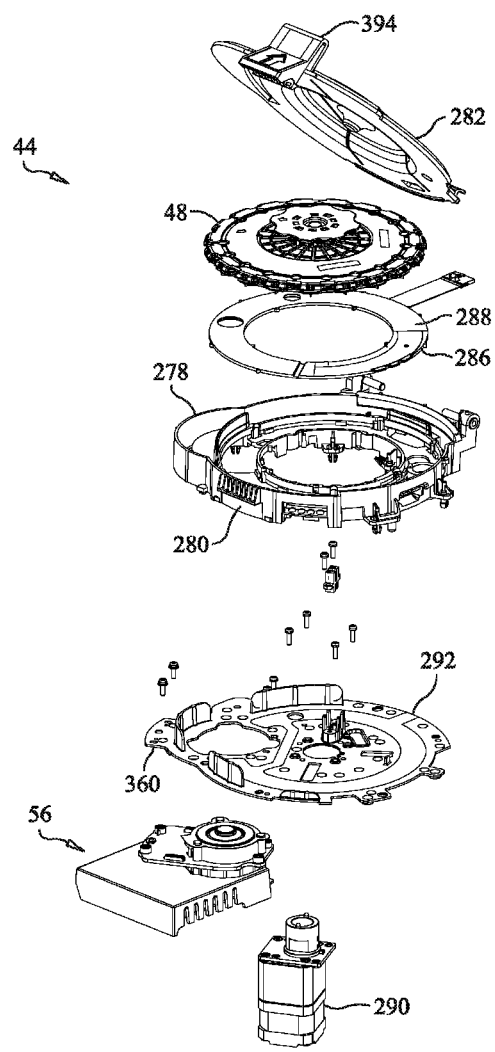
FIG. 10 is an exploded view of the slide processing unit of the chemical analyzer of the present invention.
Figure 35:
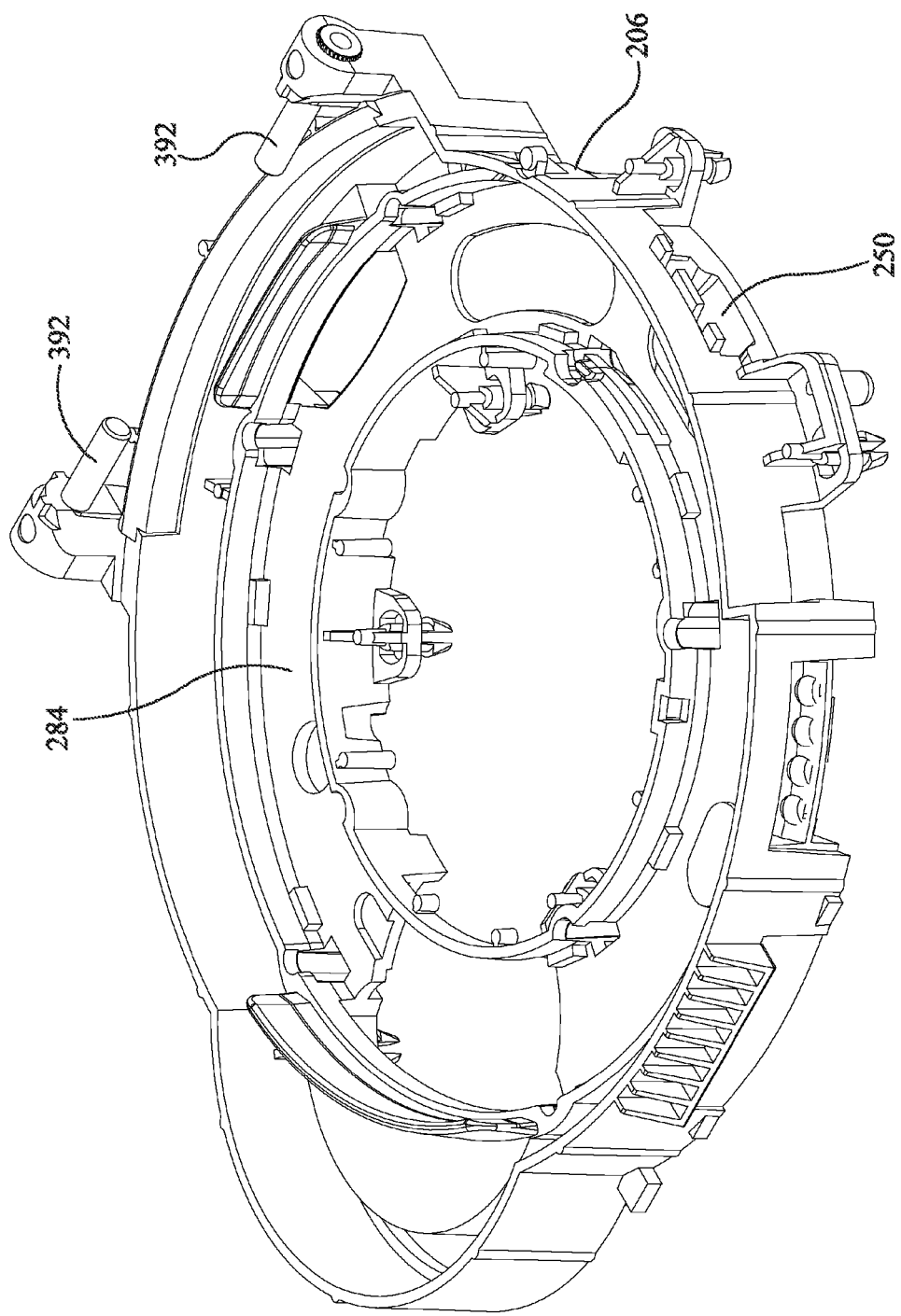
FIG. 35 is a perspective view of a portion of the slide processing unit of the chemical analyzer of the present invention.
Figure 36:
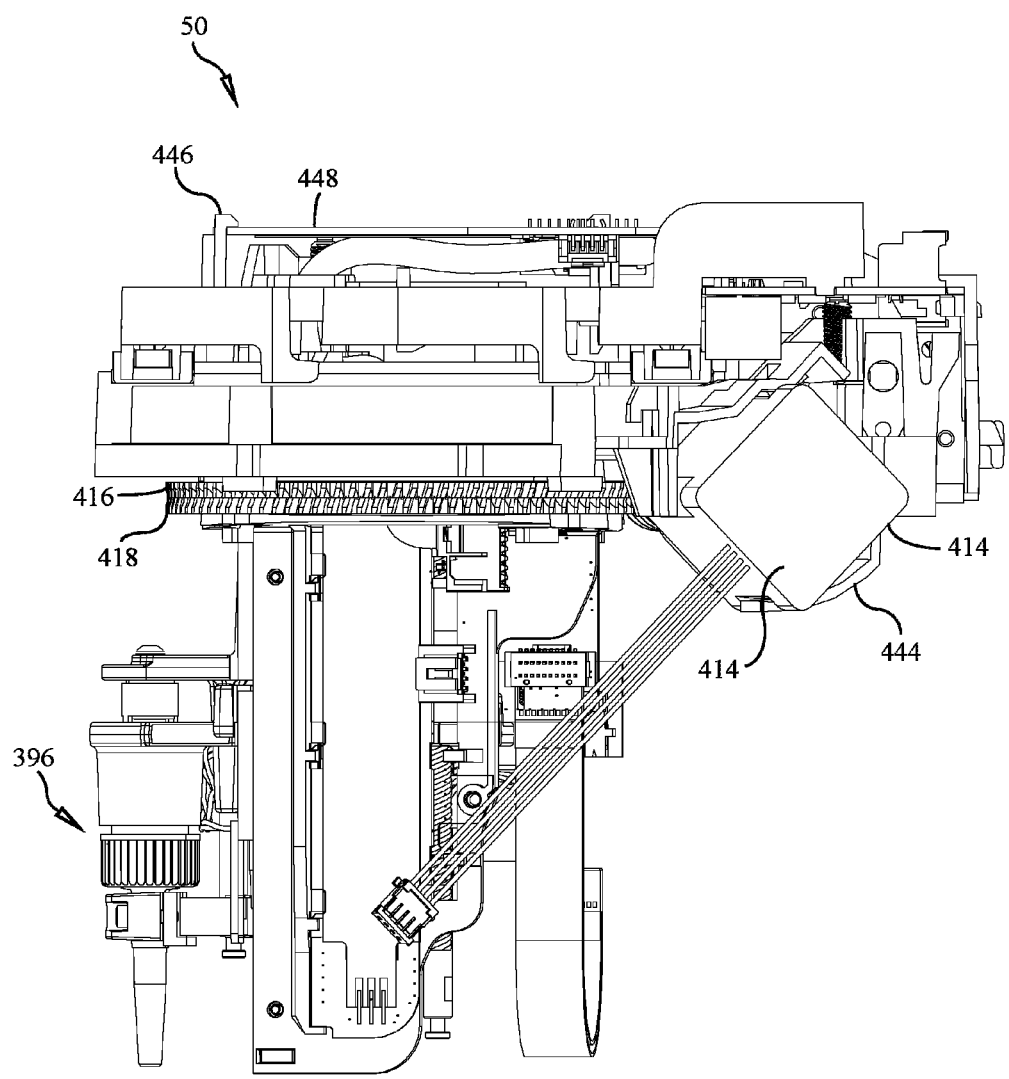
FIG. 36 is a perspective view of the fluid handler unit of the chemical analyzer of the present invention.
Figure 37:
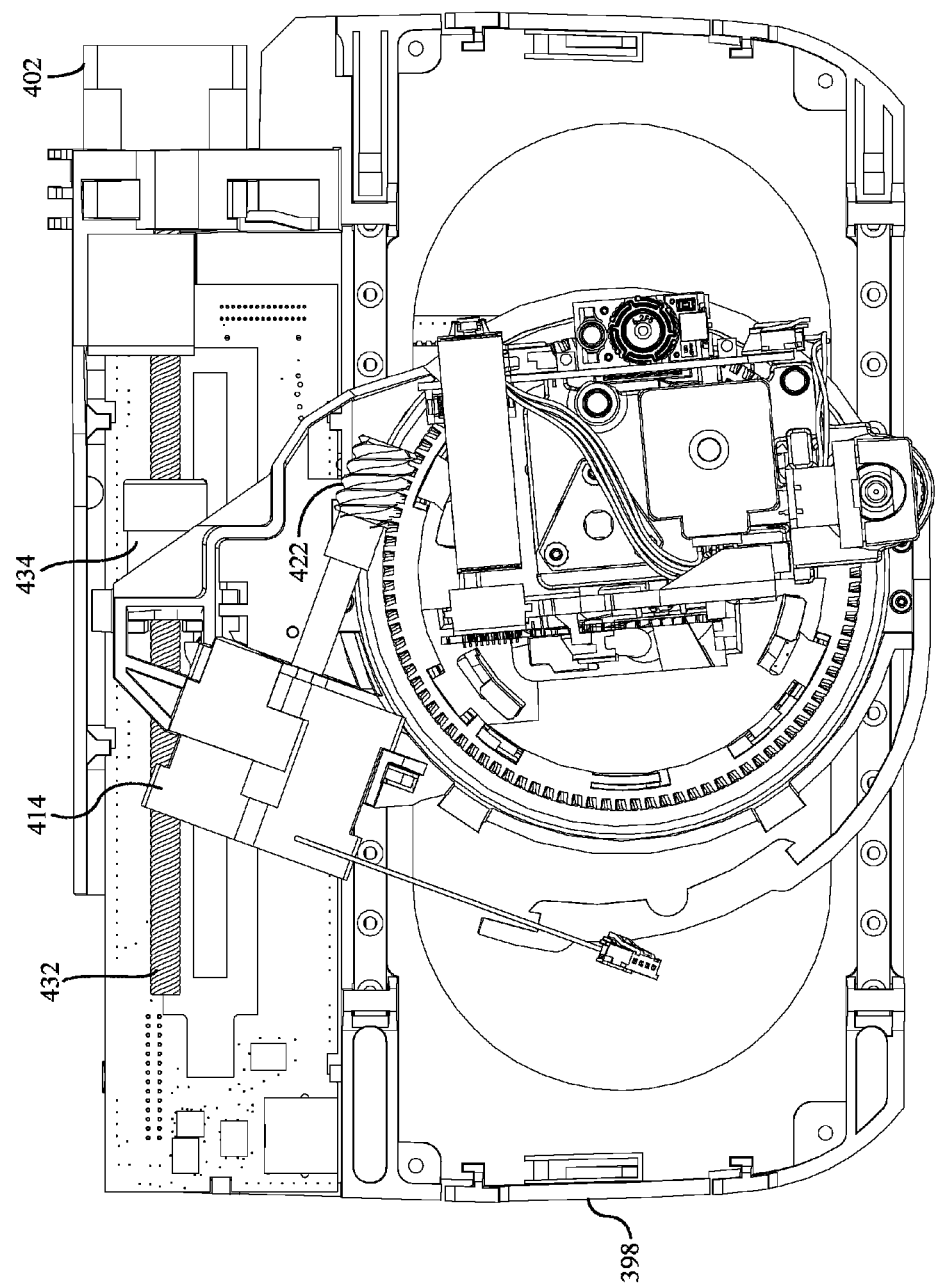
FIG. 37 is a bottom plan view of the fluid handler unit of the chemical analyzer of the present invention.
Figure 38:
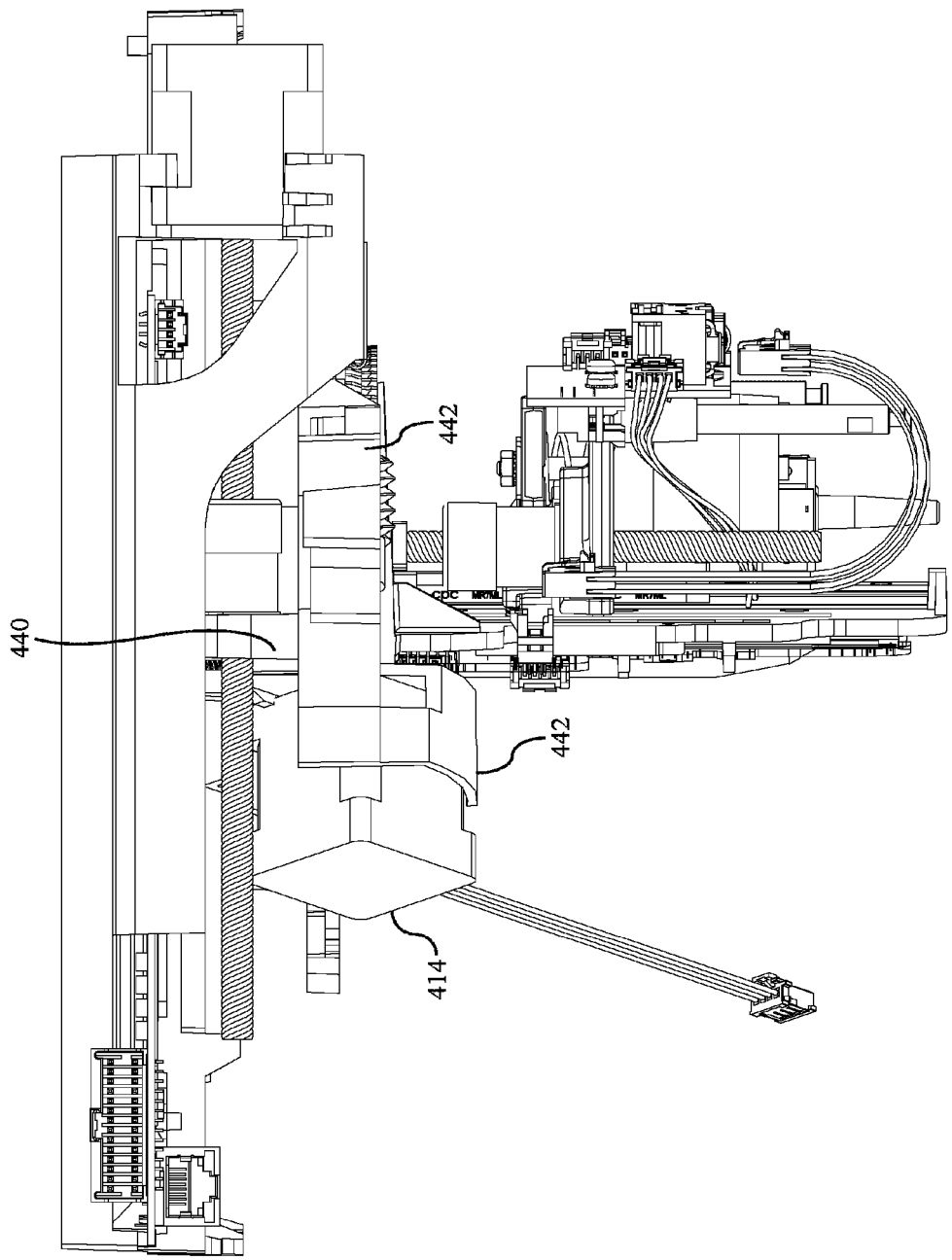
FIG. 38 is another perspective view of the fluid handler unit of the chemical analyzer of the present invention.
Figure 39:
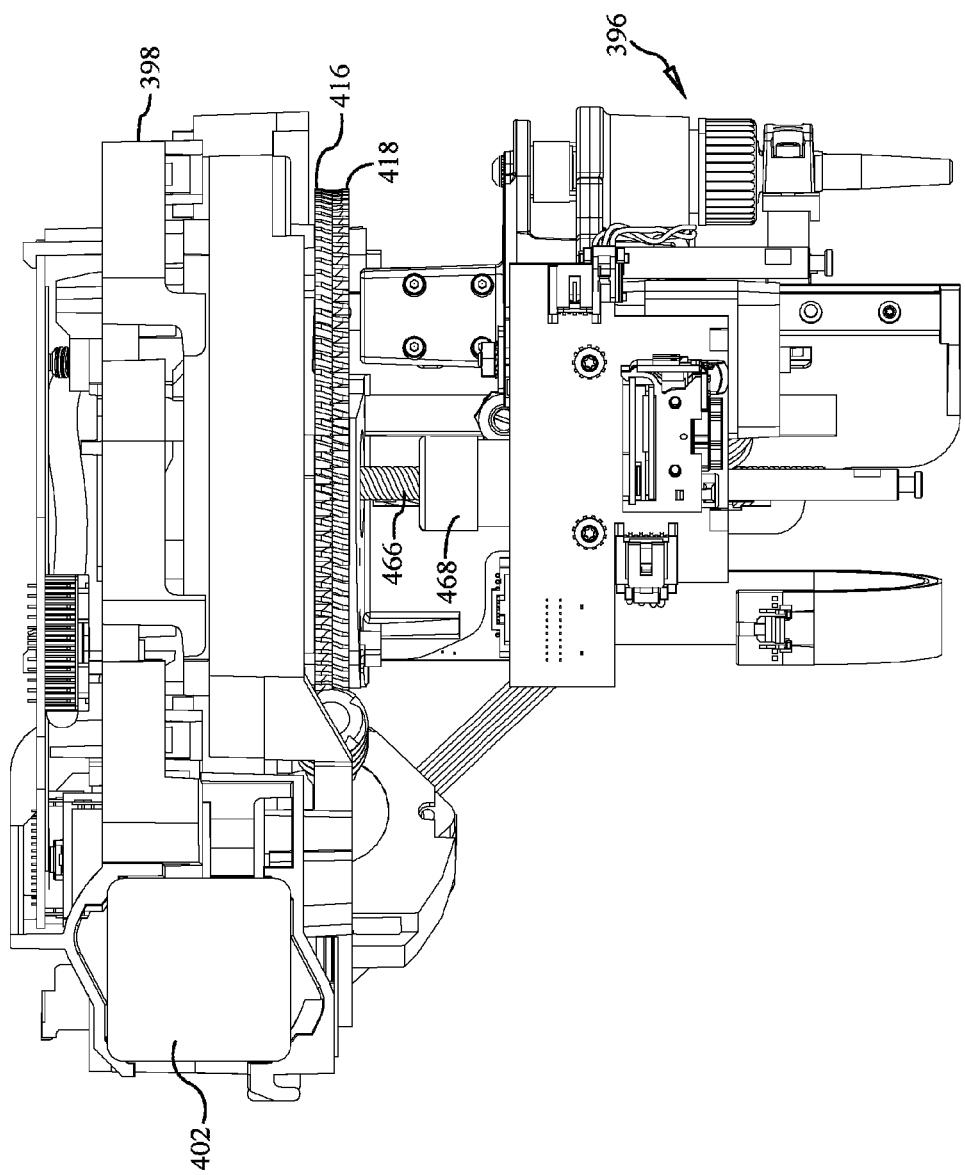
FIG. 39 is another perspective view of the fluid handler unit of the chemical analyzer of the present invention.
Figure 40:
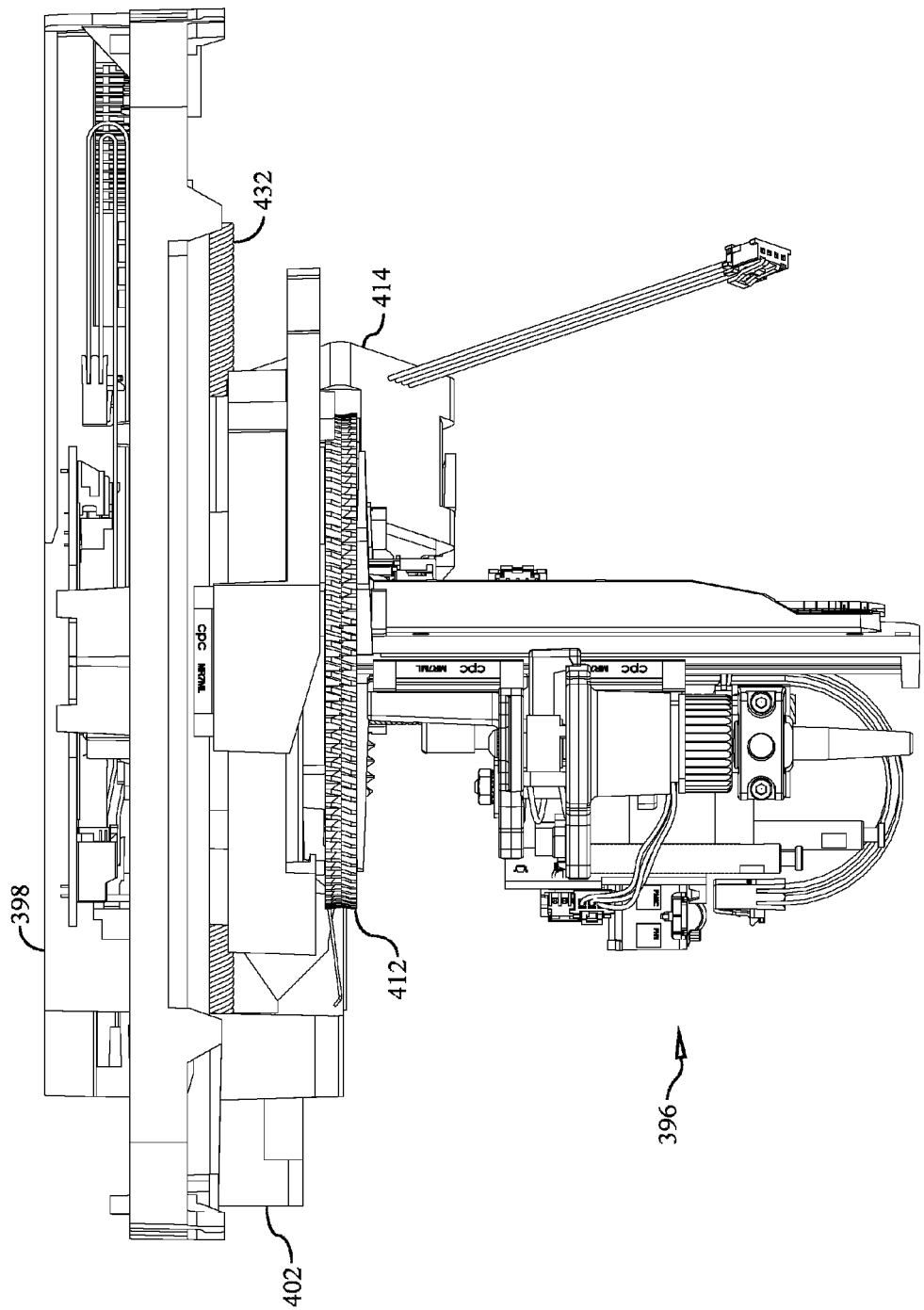
FIG. 40 is another perspective view of the fluid handler unit of the chemical analyzer of the present invention, with certain components thereof having been removed to facilitate an understanding thereof.
Figure 41:
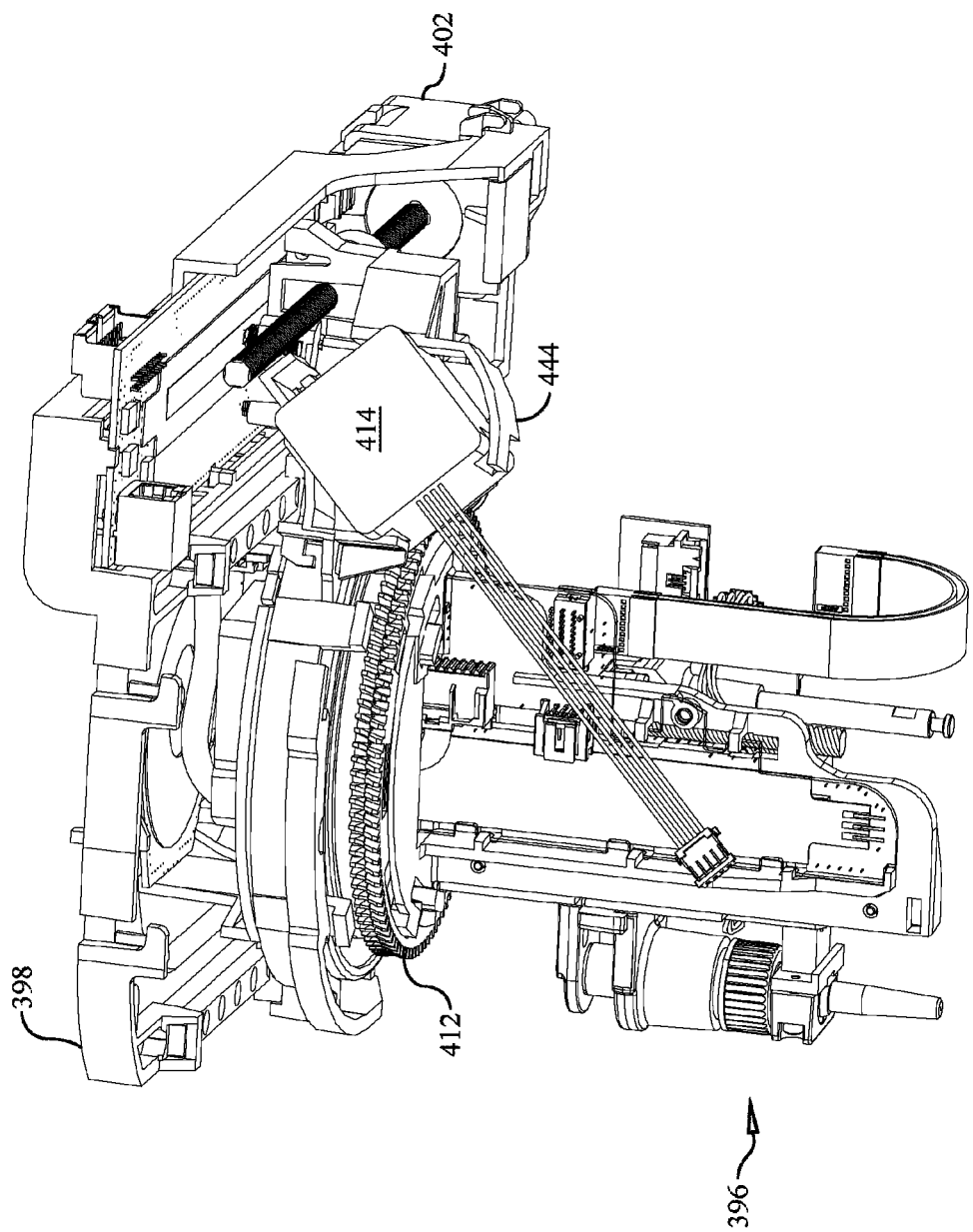
FIG. 41 is another perspective view of the fluid handler unit of the chemical analyzer of the present invention, with certain components thereof having been removed to facilitate an understanding thereof.
Figure 42:
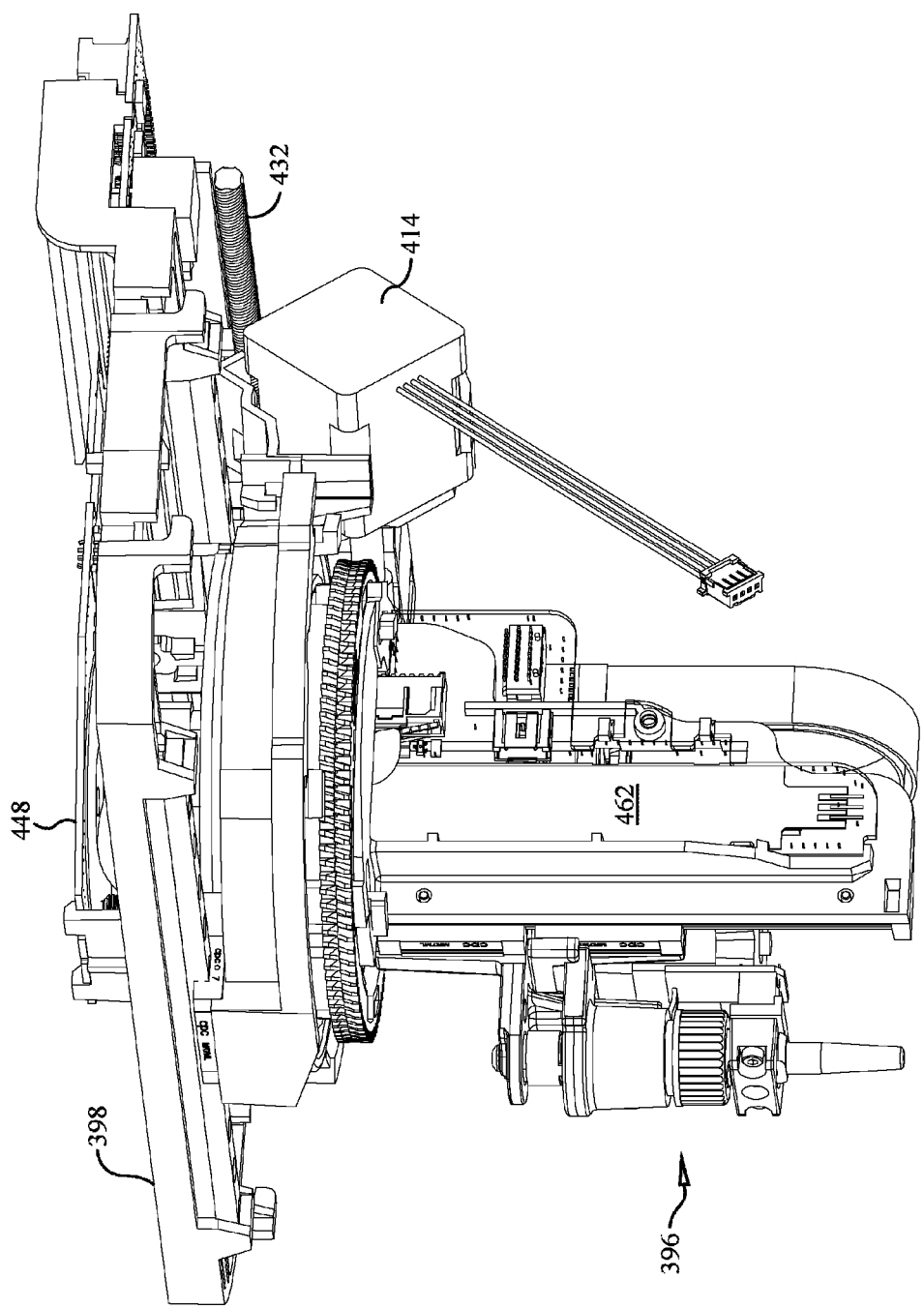
FIG. 42 is another perspective view of the fluid handler unit of the chemical analyzer of the present invention, with certain components thereof having been removed to facilitate an understanding thereof.
Figure 43:
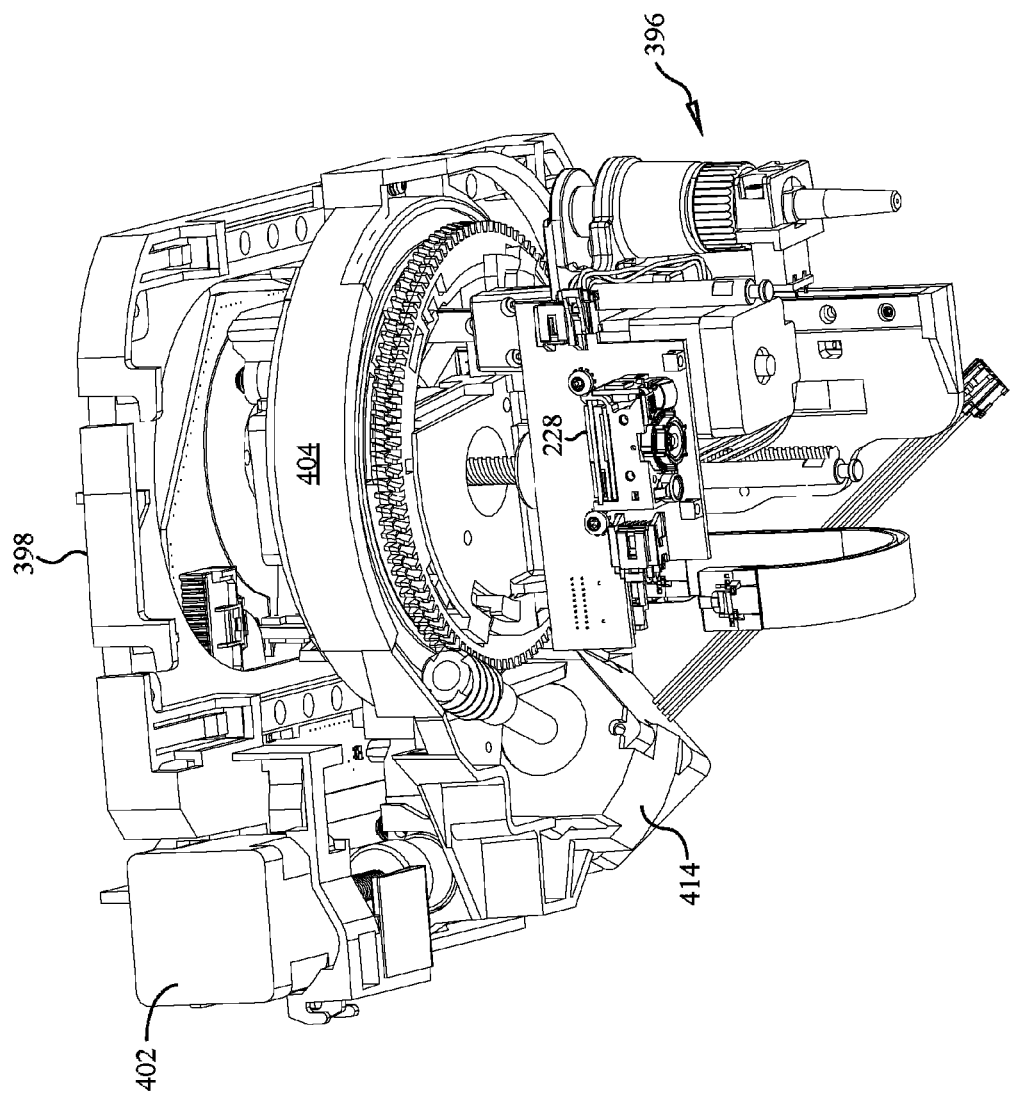
FIG. 43 is another perspective view of the fluid handler unit of the chemical analyzer of the present invention, with certain components thereof having been removed to facilitate an understanding thereof.
Figure 44:
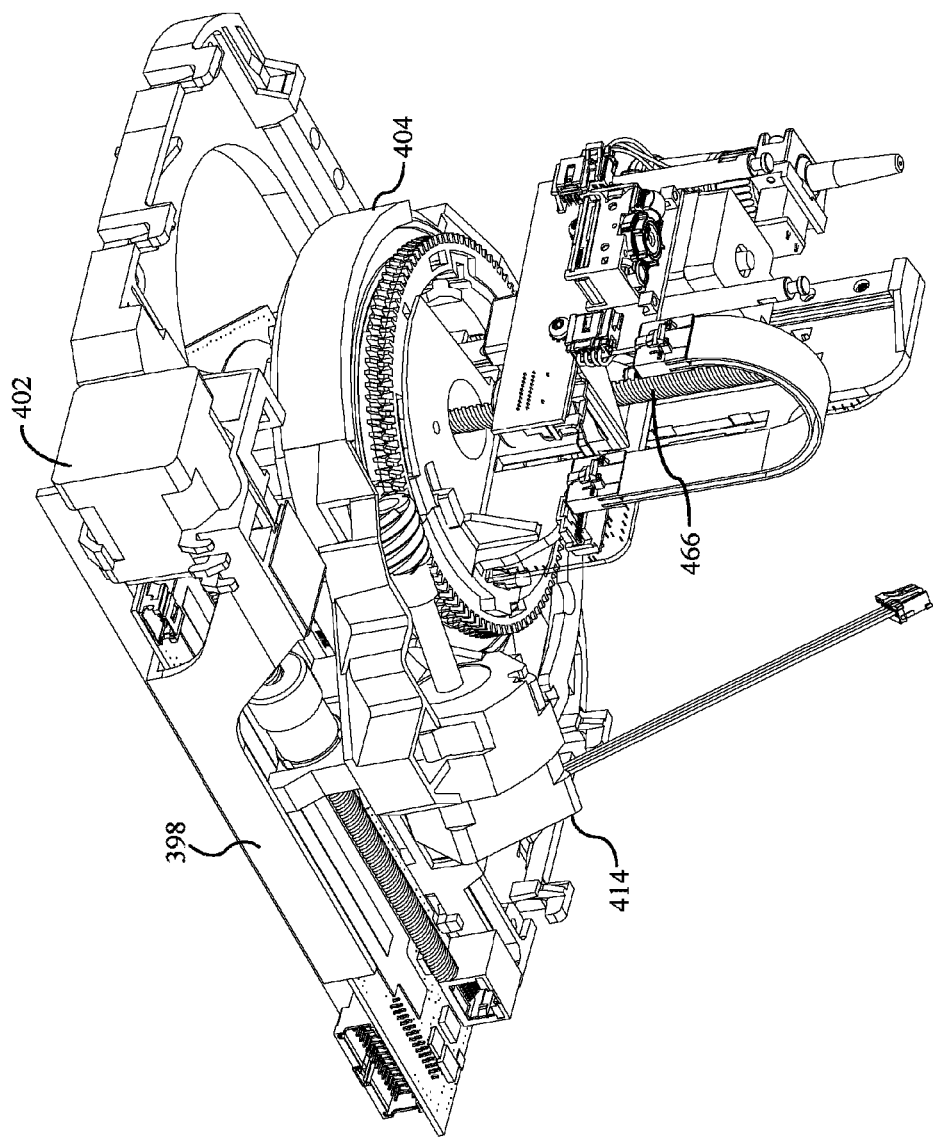
FIG. 44 is another perspective view of the fluid handler unit of the chemical analyzer of the present invention, with certain components thereof having been removed to facilitate an understanding thereof.
Figure 45:
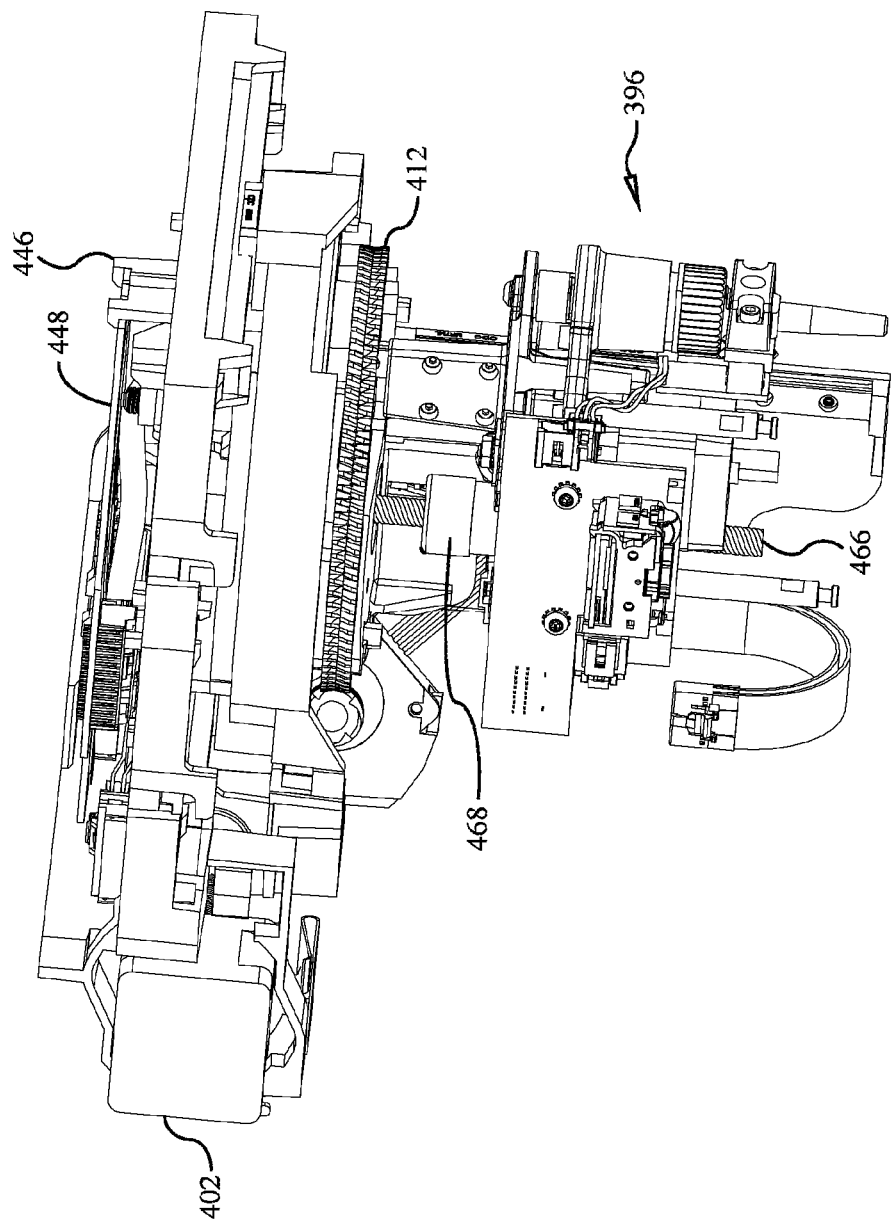
FIG. 45 is another perspective view of the fluid handler unit of the chemical analyzer of the present invention, with certain components thereof having been removed to facilitate an understanding thereof.
Figure 46:
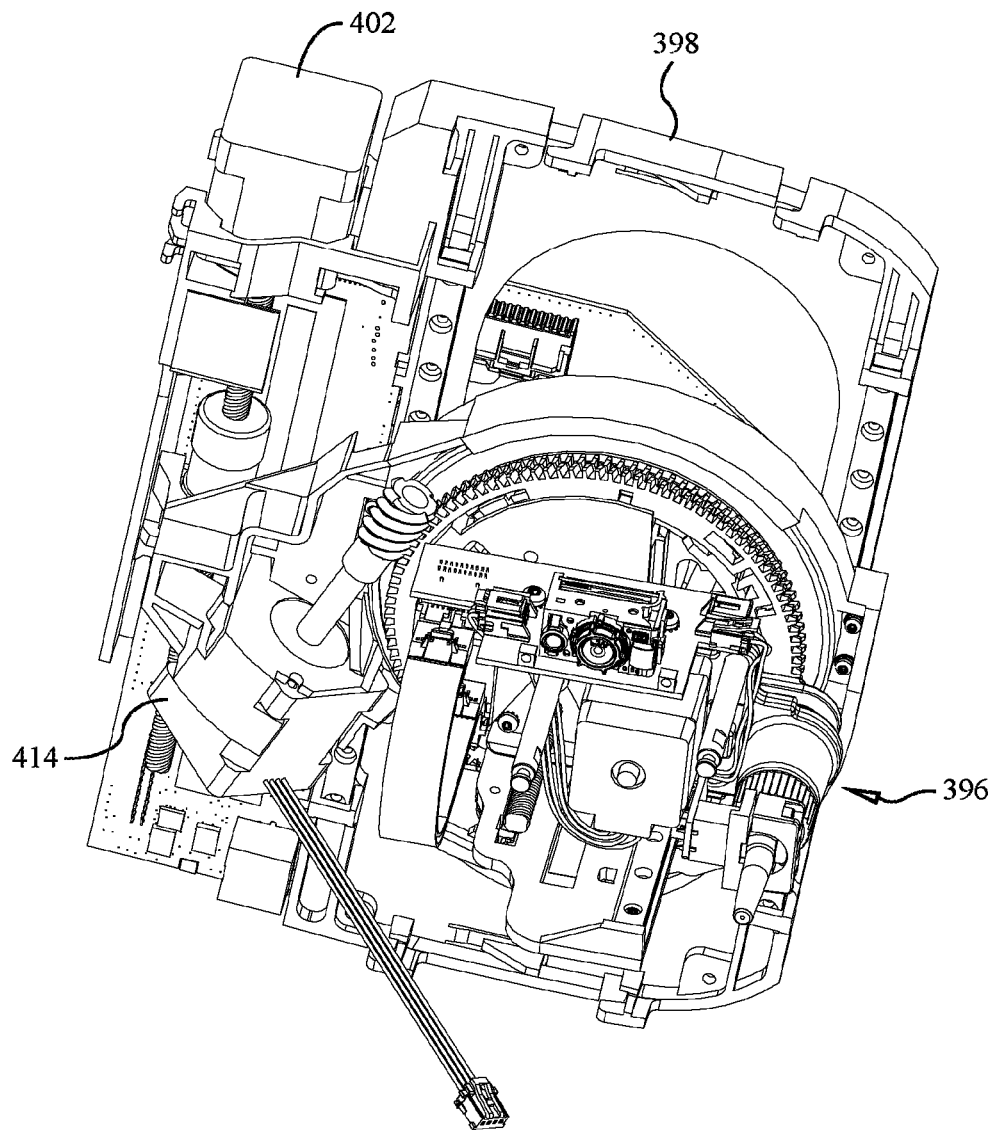
FIG. 46 is another perspective view of the fluid handler unit of the chemical analyzer of the present invention, with certain components thereof having been removed to facilitate an understanding thereof.
Figure 47:
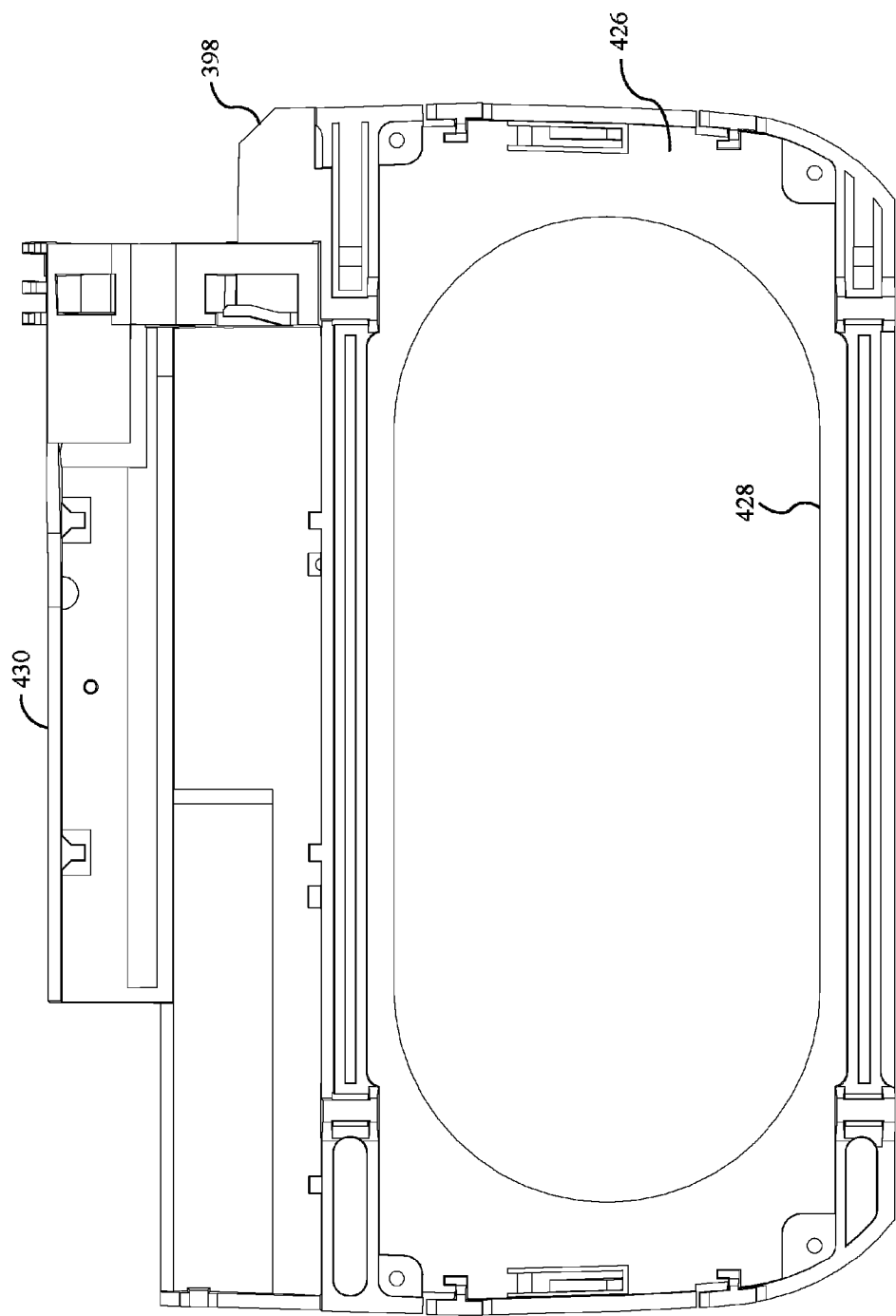
FIG. 47 is a bottom plan view of the base of the fluid handler unit of the chemical analyzer of the present invention.
Figure 48:
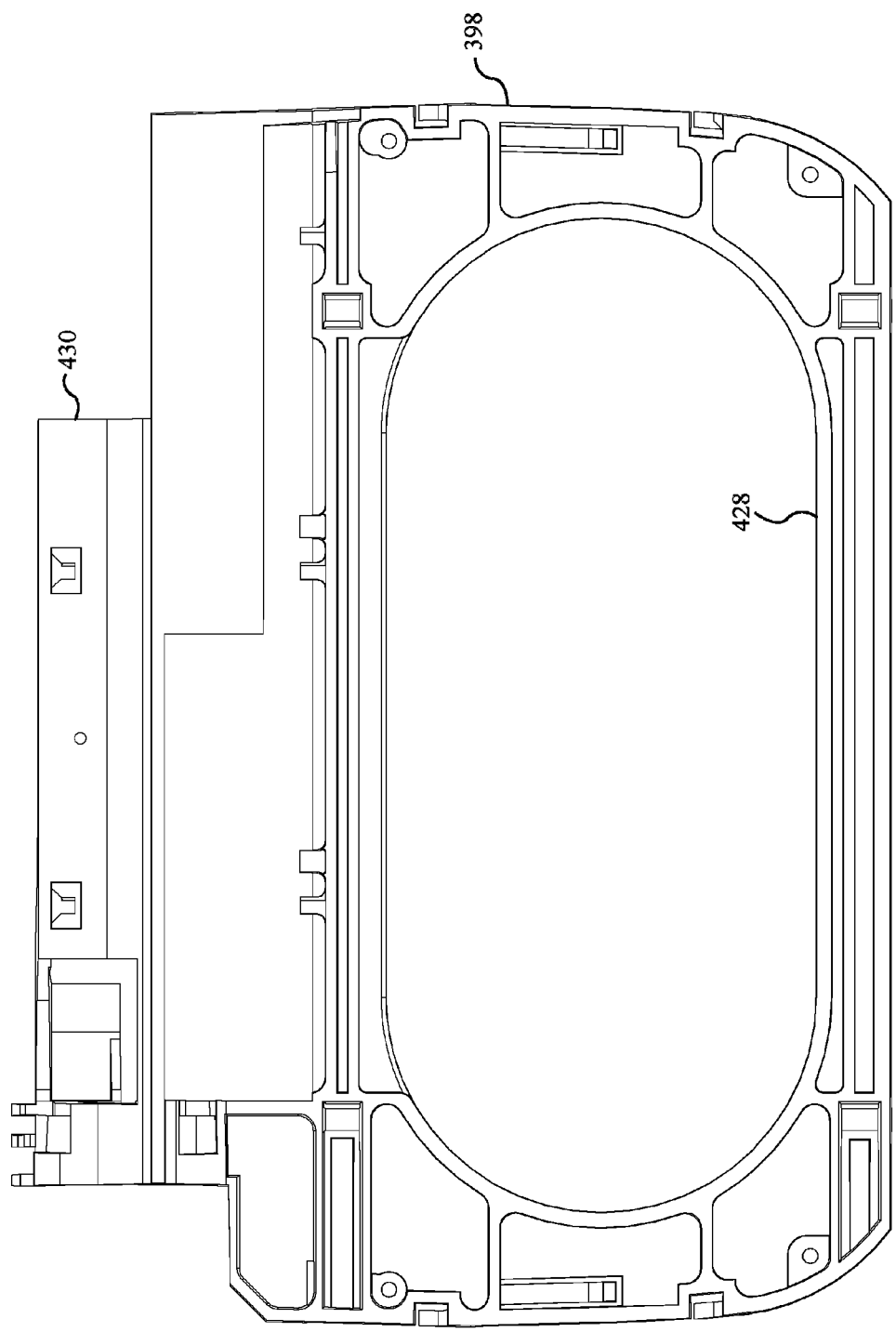
FIG. 48 is a top plan view of the base of the fluid handler unit of the chemical analyzer of the present invention.
Figure 49:
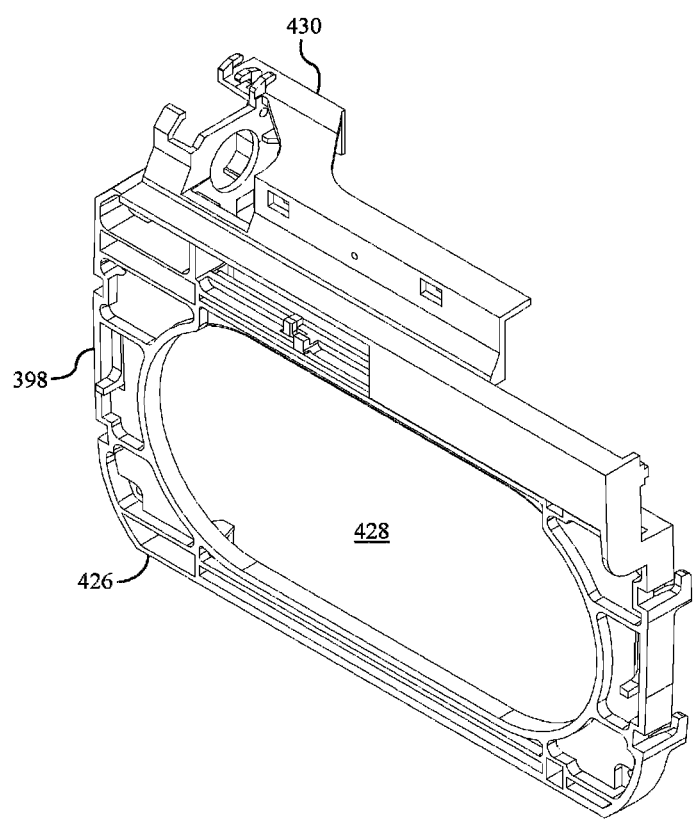
FIG. 49 is a perspective view of the base of the fluid handler unit of the chemical analyzer of the present invention.
Figure 50:
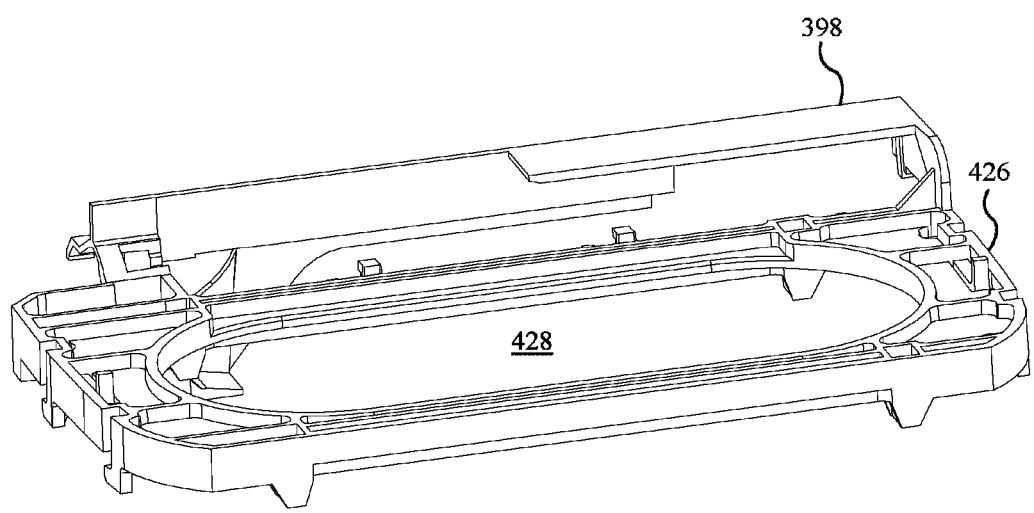
FIG. 50 is another perspective view of the base of the fluid handler unit of the chemical analyzer of the present invention.
Figure 51:
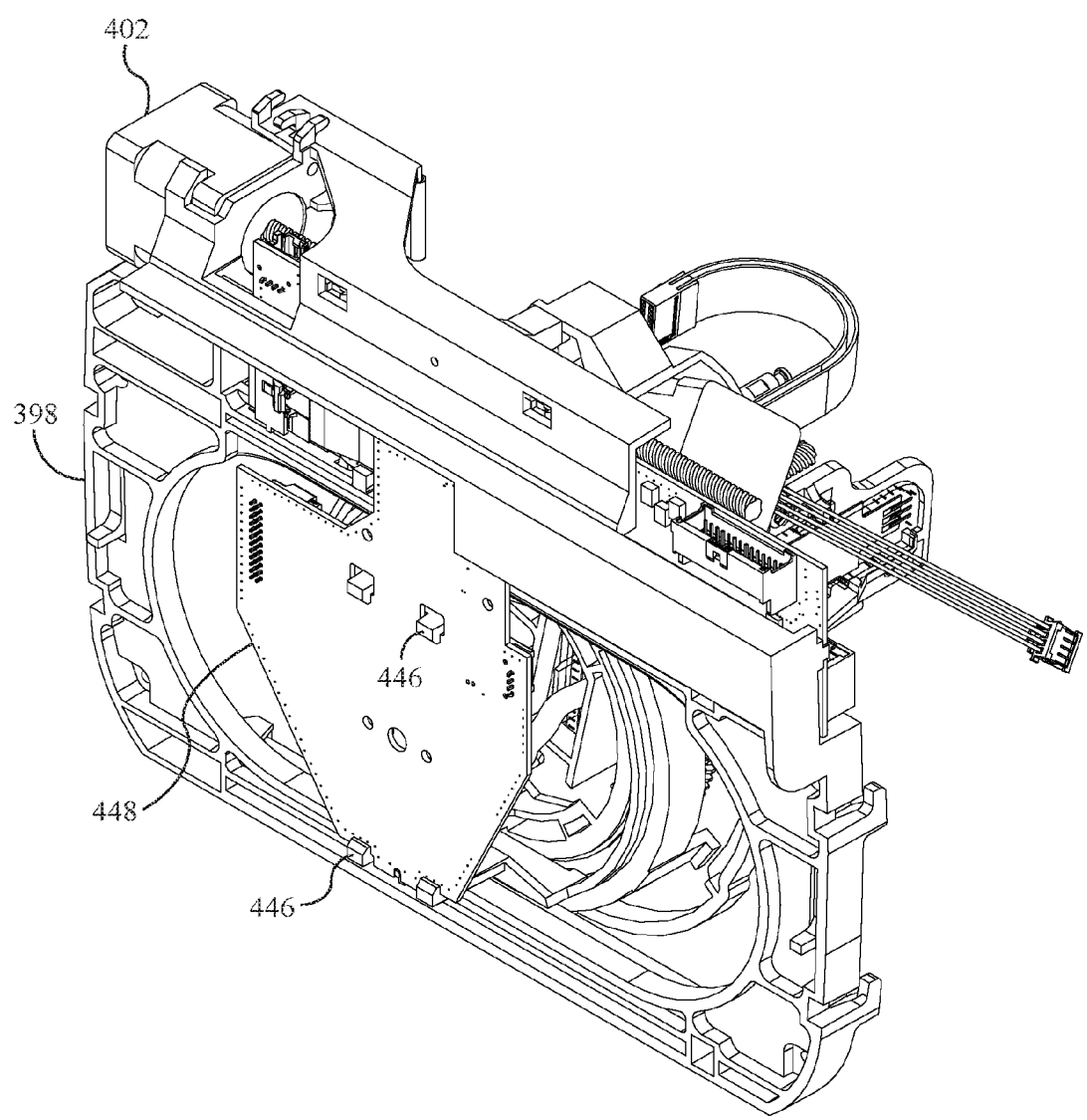
FIG. 51 is another perspective view of the fluid handler unit of the chemical analyzer of the present invention, with certain components thereof having been removed to facilitate an understanding thereof.
Figure 52:
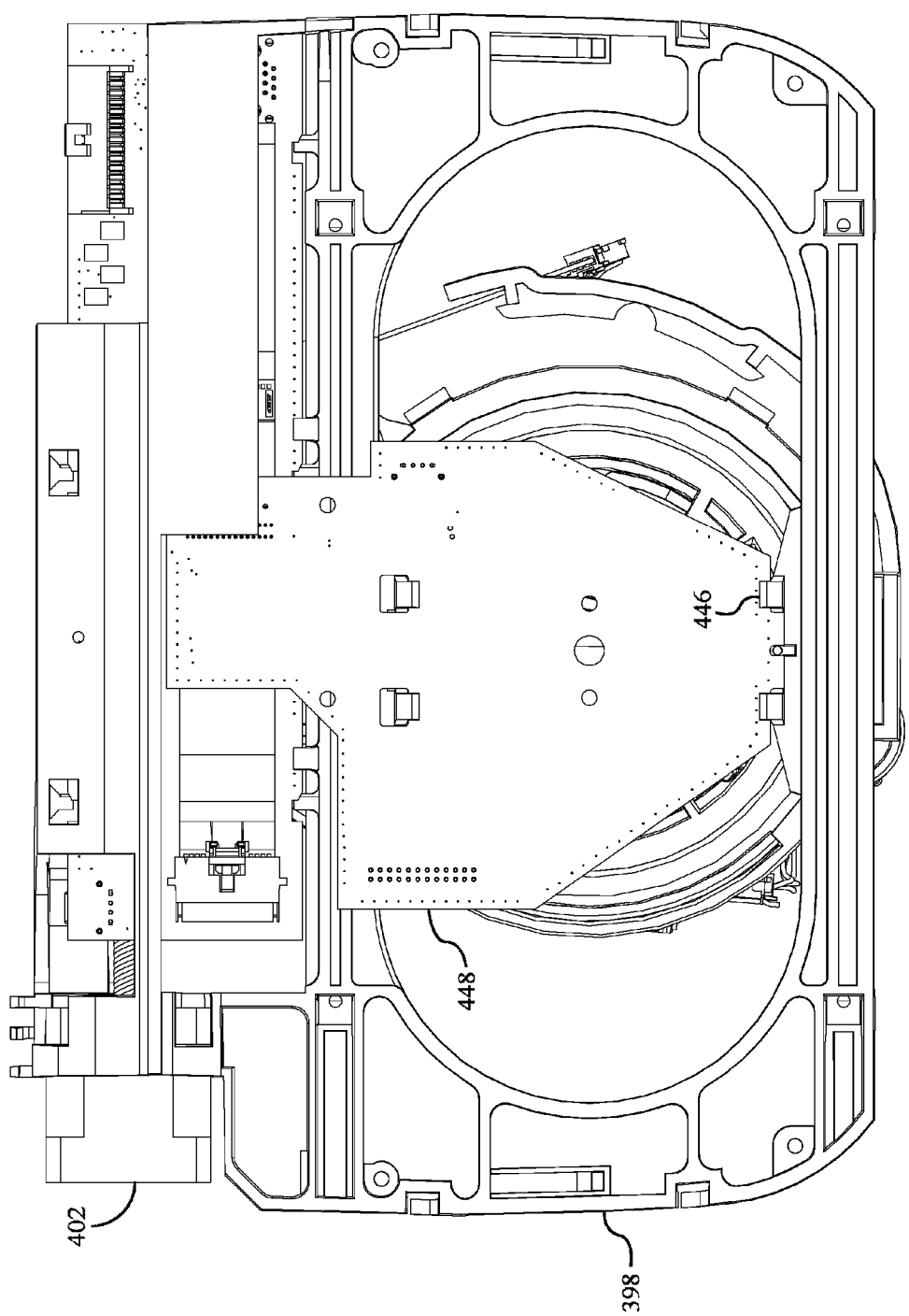
FIG. 52 is a top plan view of the fluid handler unit of the chemical analyzer of the present invention.
Figure 53:
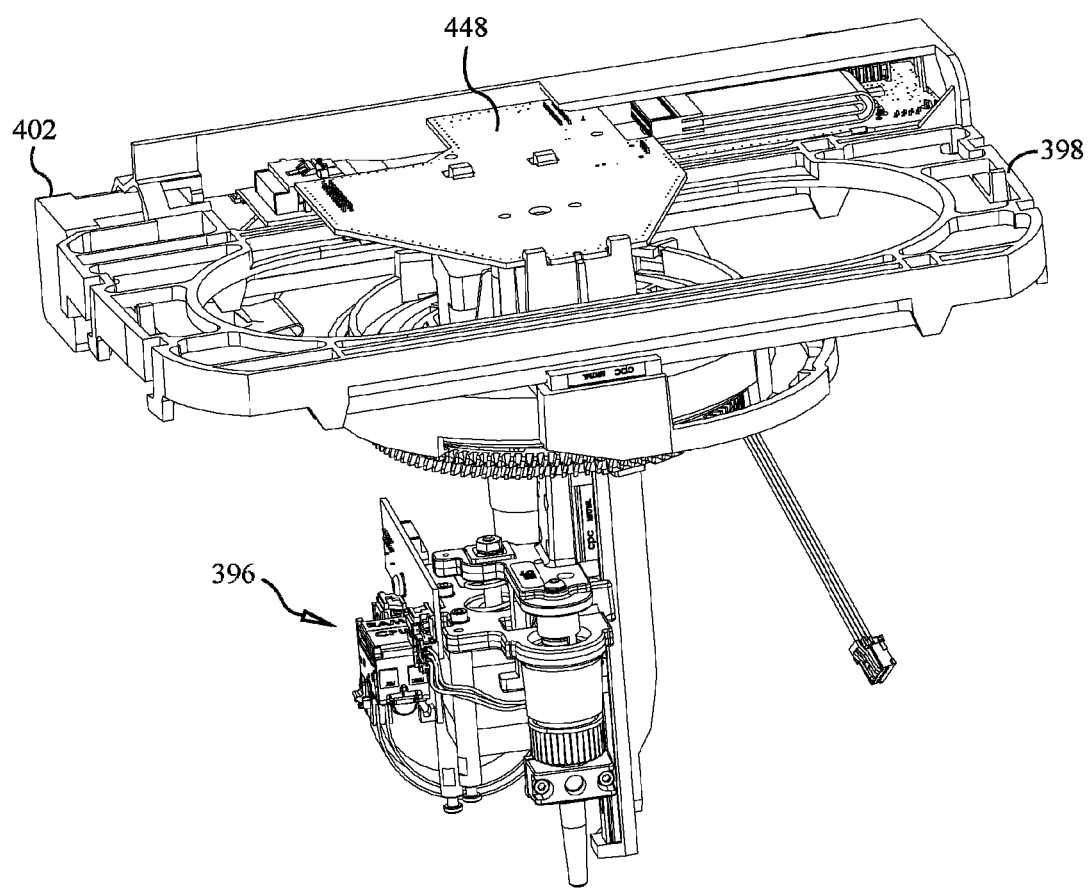
FIG. 53 is another perspective view of the fluid handler unit of the chemical analyzer of the present invention, with certain components thereof having been removed to facilitate an understanding thereof.
Figure 54:
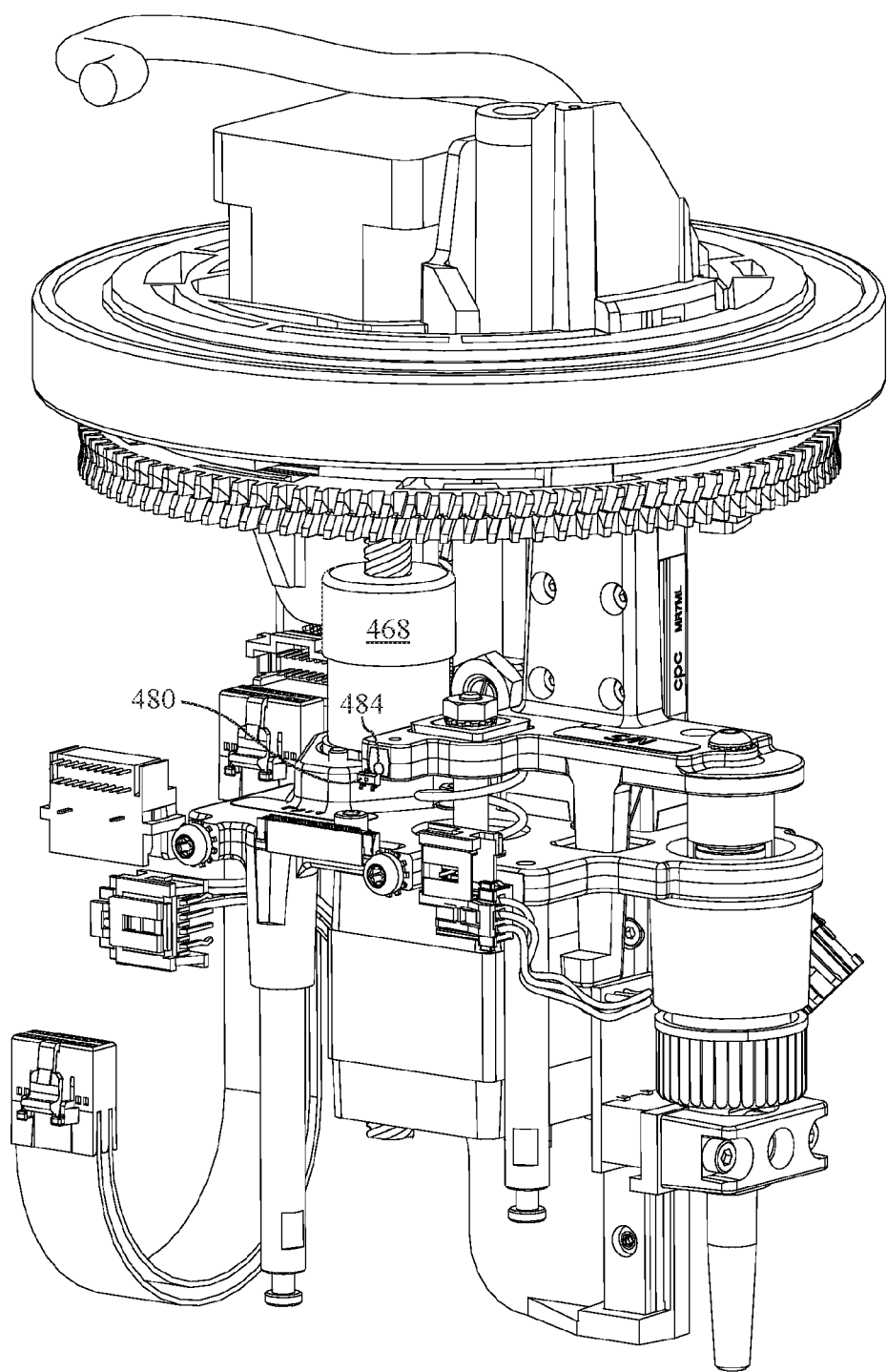
FIG. 54 is a perspective view of the pump assembly forming part of the fluid handler unit of the chemical analyzer of the present invention, with certain components thereof having been removed to facilitate an understanding thereof.
Figure 55:
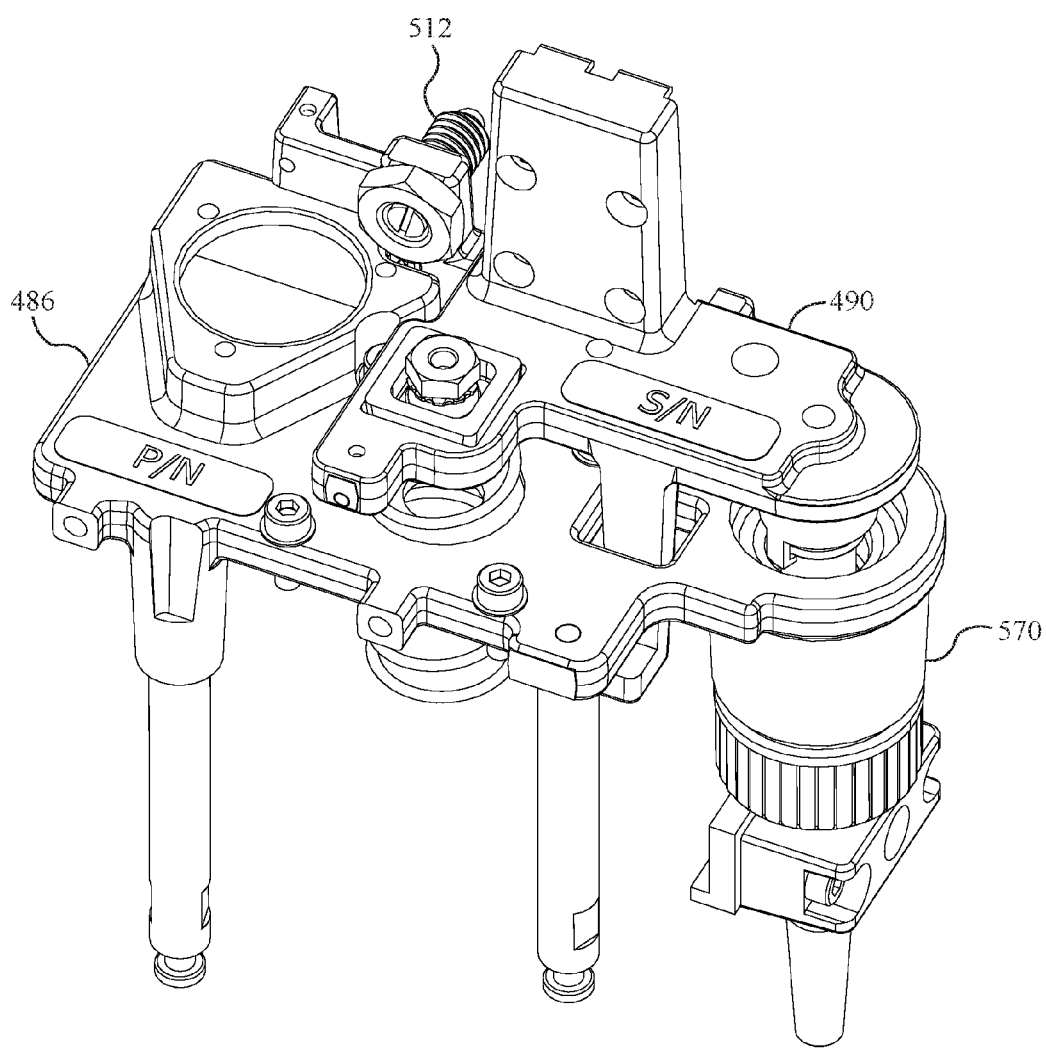
FIG. 55 is another perspective view of the pump assembly forming part of the fluid handler unit of the chemical analyzer of the present invention, with certain components thereof having been removed to facilitate an understanding thereof.
Figure 56:
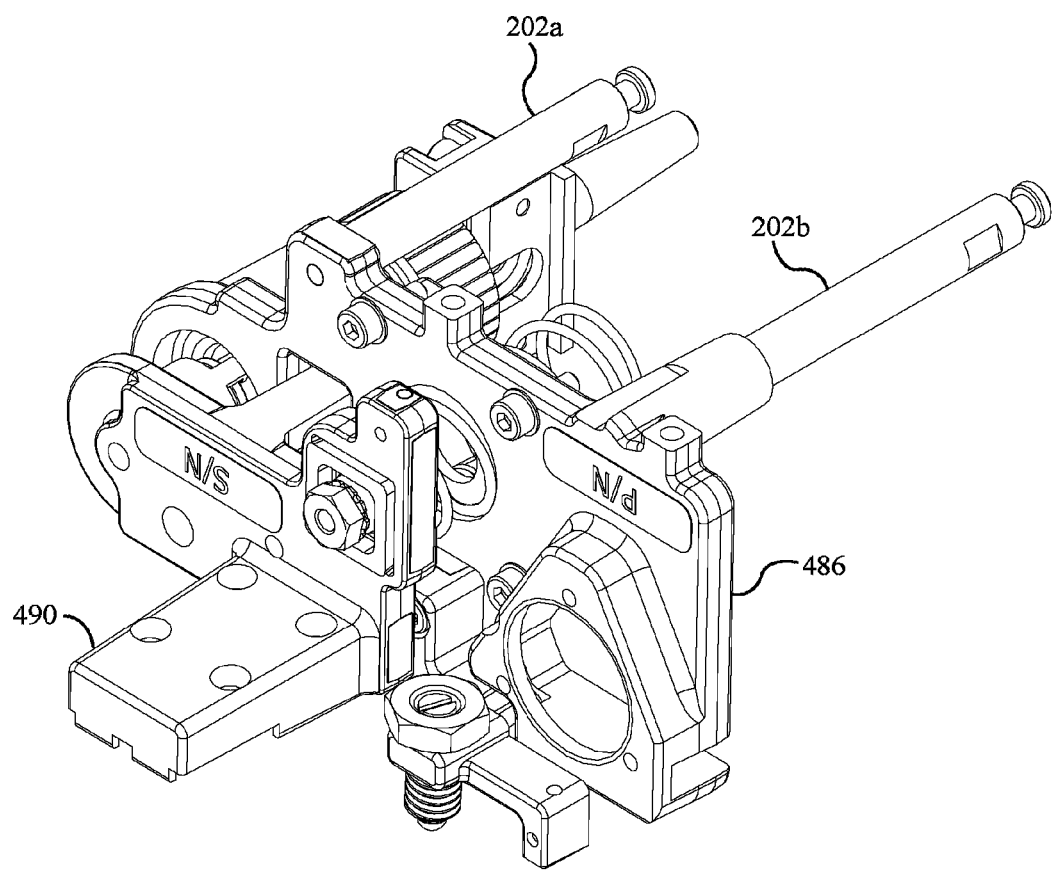
FIG. 56 is another perspective view of the pump assembly forming part of the fluid handler unit of the chemical analyzer of the present invention, with certain components thereof having been removed to facilitate an understanding thereof.
Figure 57:
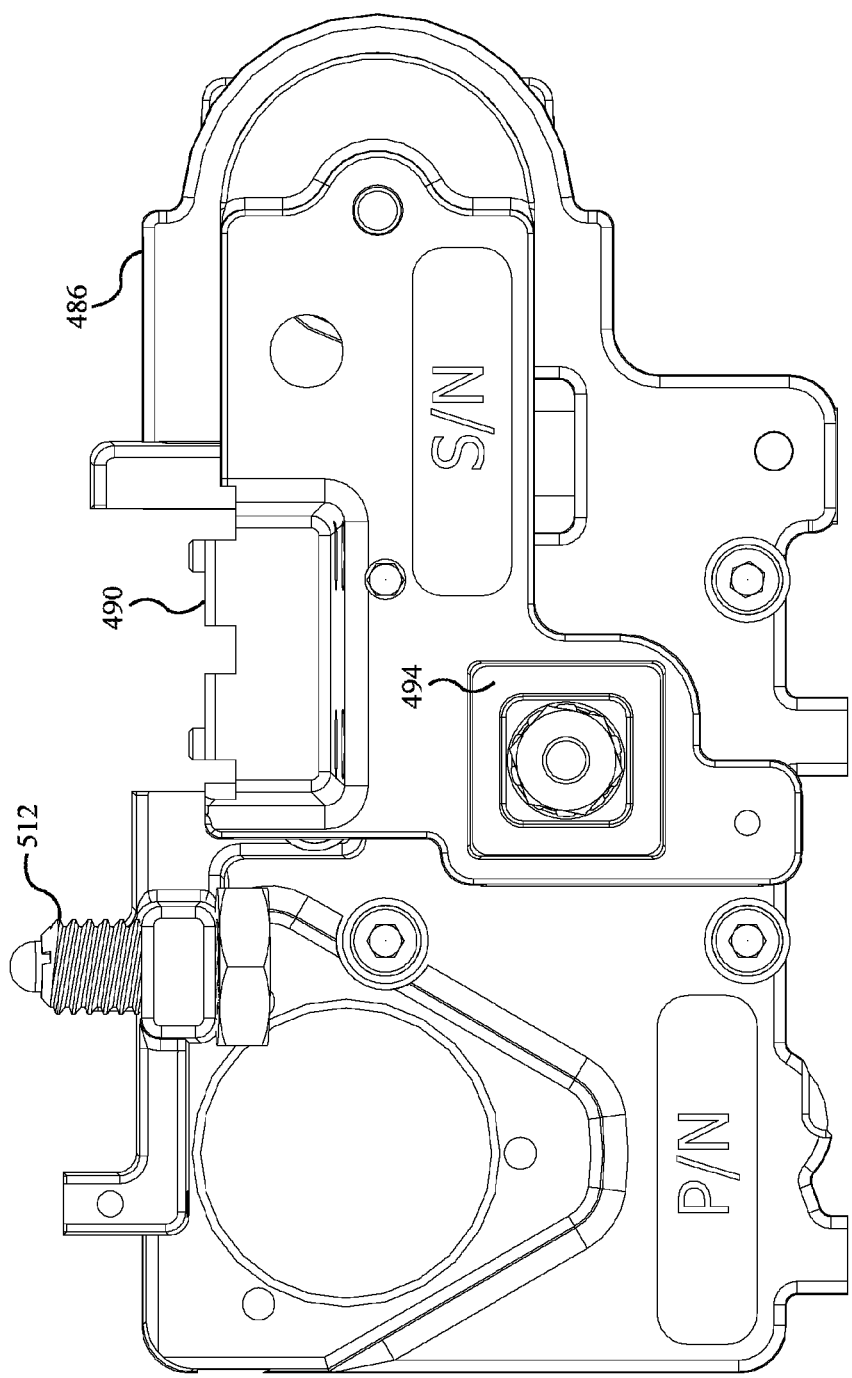
FIG. 57 is another perspective view of the pump assembly forming part of the fluid handler unit of the chemical analyzer of the present invention, with certain components thereof having been removed to facilitate an understanding thereof.
Figure 58:
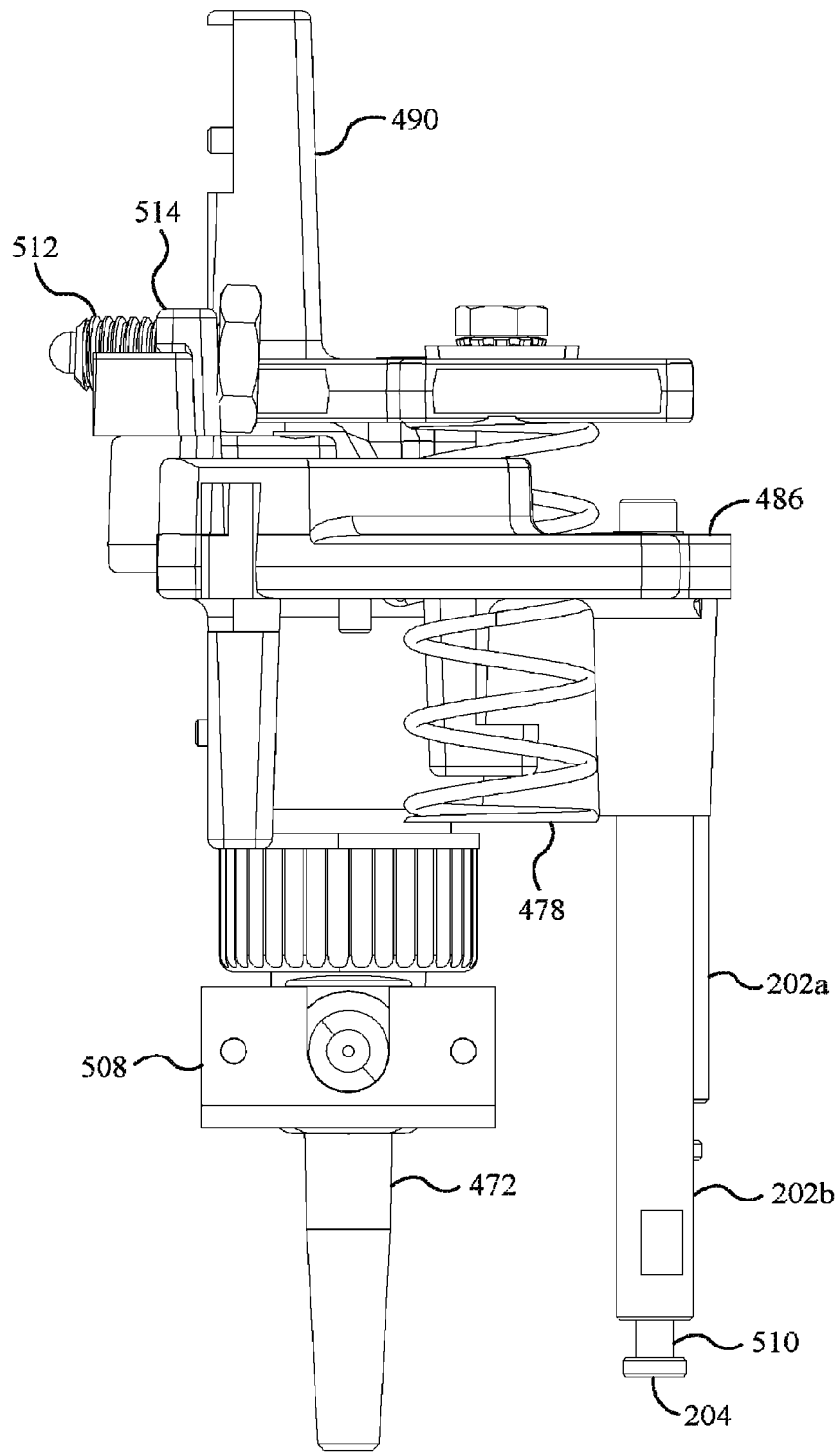
FIG. 58 is another perspective view of the pump assembly forming part of the fluid handler unit of the chemical analyzer of the present invention, with certain components thereof having been removed to facilitate an understanding thereof.
Figure 59:
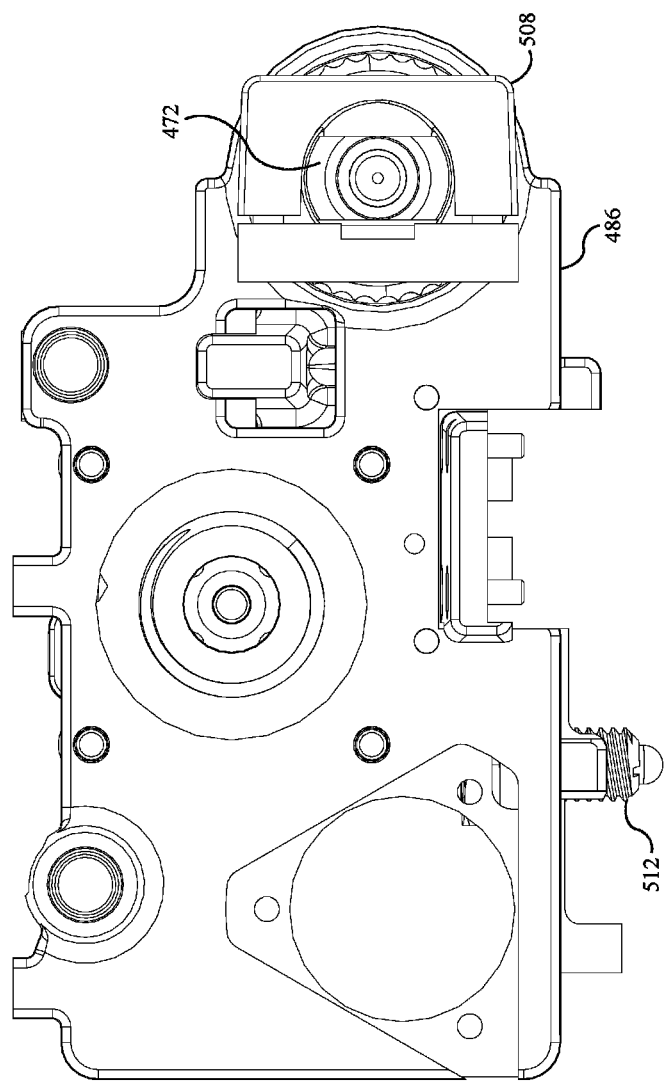
FIG. 59 is another perspective view of the pump assembly forming part of the fluid handler unit of the chemical analyzer of the present invention, with certain components thereof having been removed to facilitate an understanding thereof.
Figure 60:
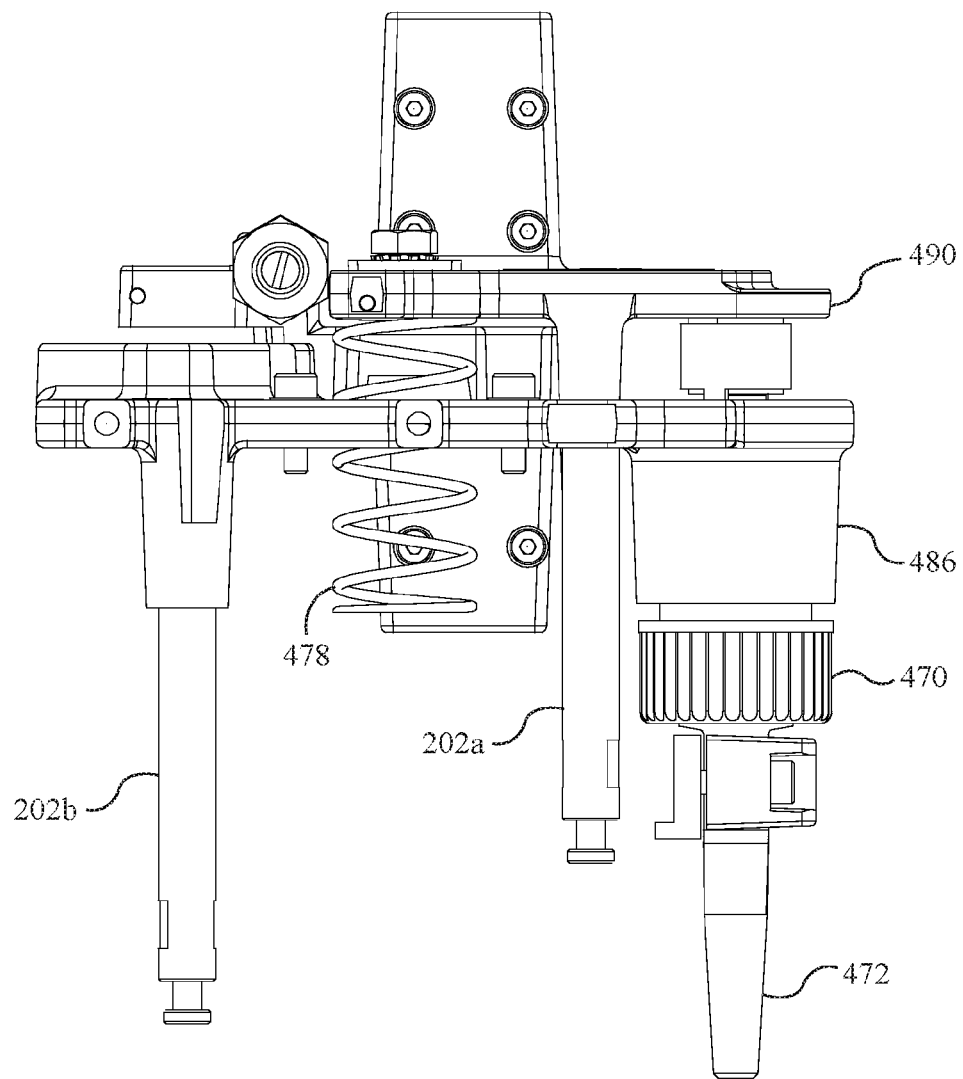
FIG. 60 is another perspective view of the pump assembly forming part of the fluid handler unit of the chemical analyzer of the present invention, with certain components thereof having been removed to facilitate an understanding thereof.
Figure 61:
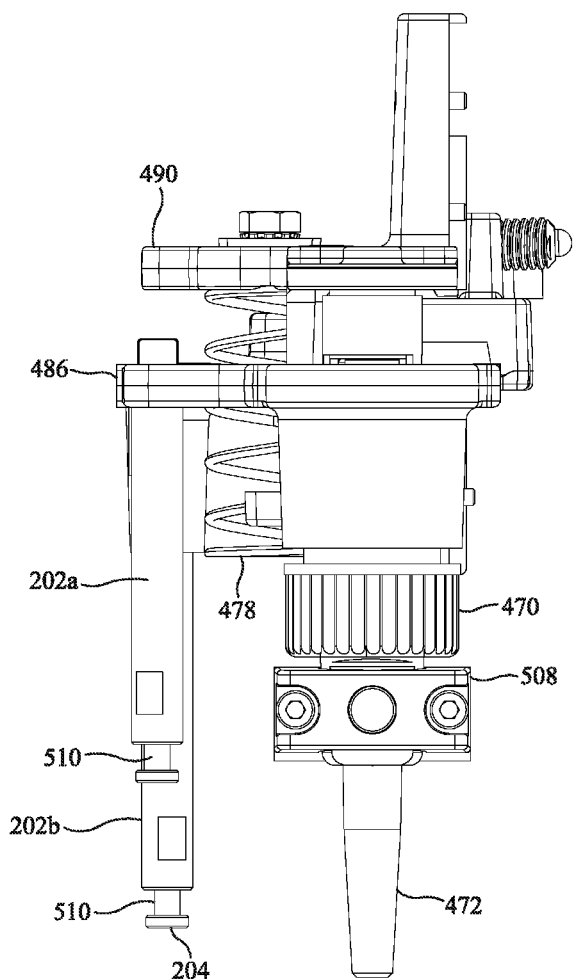
FIG. 61 is another perspective view of the pump assembly forming part of the fluid handler unit of the chemical analyzer of the present invention, with certain components thereof having been removed to facilitate an understanding thereof.
Figure 62:
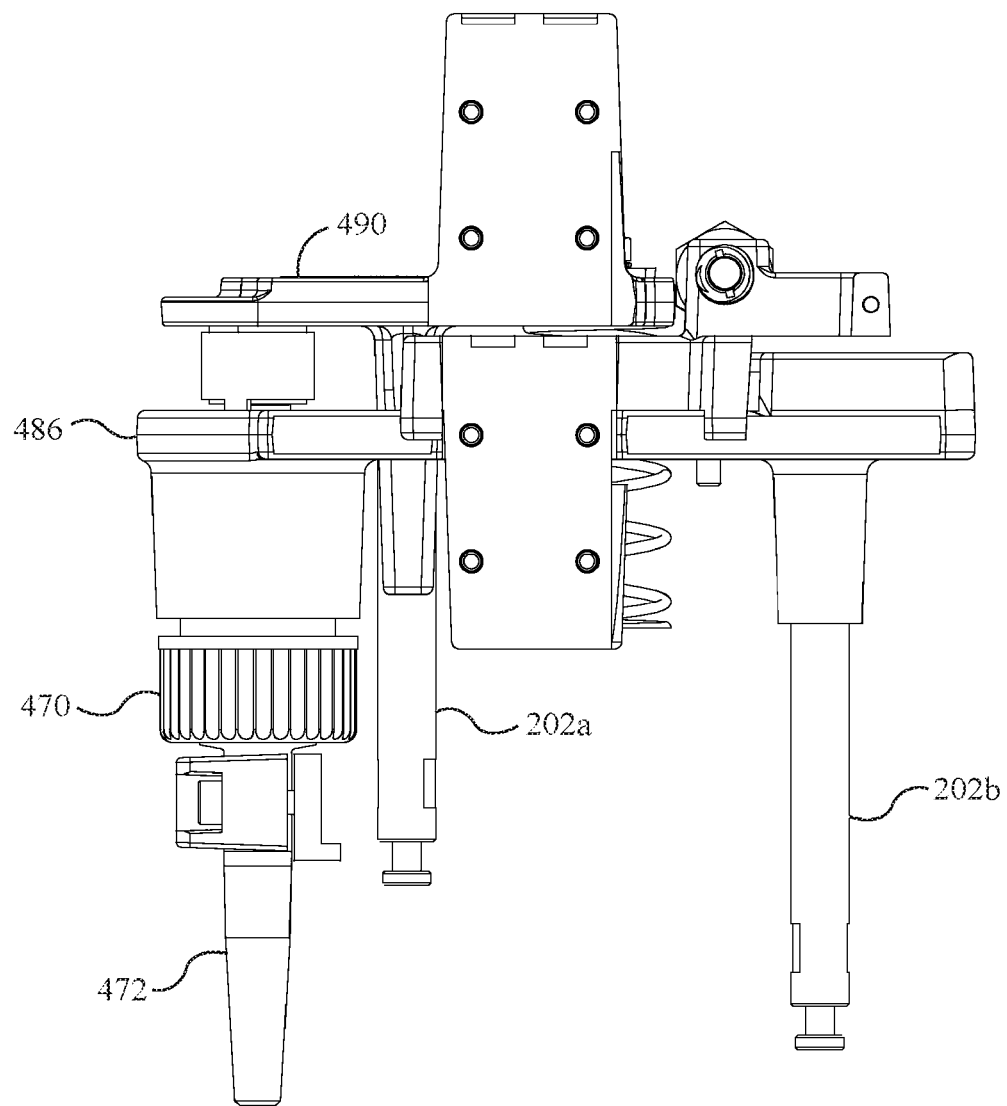
FIG. 62 is another perspective view of the pump assembly forming part of the fluid handler unit of the chemical analyzer of the present invention, with certain components thereof having been removed to facilitate an understanding thereof.
Figure 63:
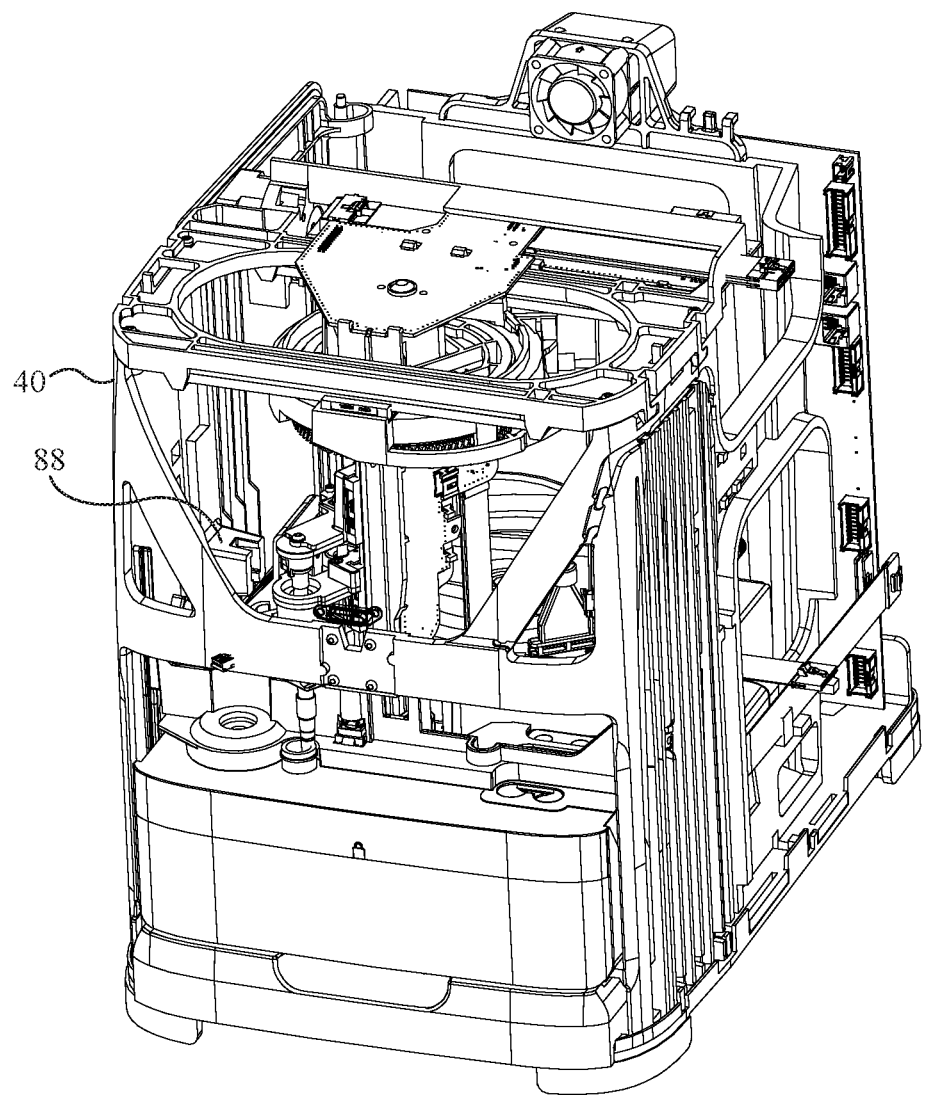
FIG. 63 is a front perspective view of the chemical analyzer of the present invention, with the enclosure thereof having been removed to facilitate an understanding of the placement of a disposable pipette tip removal member therein.
Figure 64:
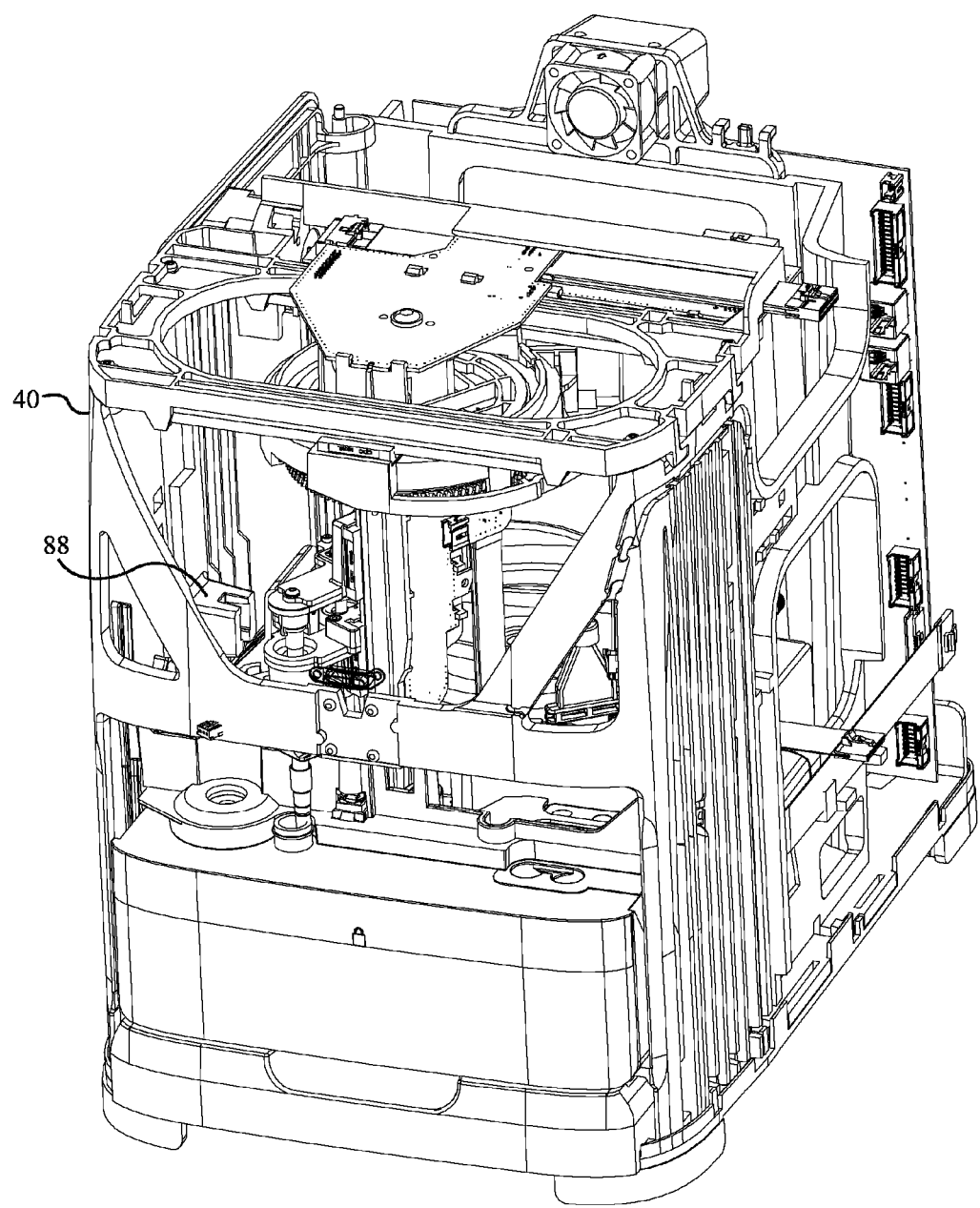
FIG. 64 is another front perspective view of the chemical analyzer of the present invention, with the enclosure thereof having been removed to facilitate an understanding of the placement of a disposable pipette tip removal member therein.
Figure 65:
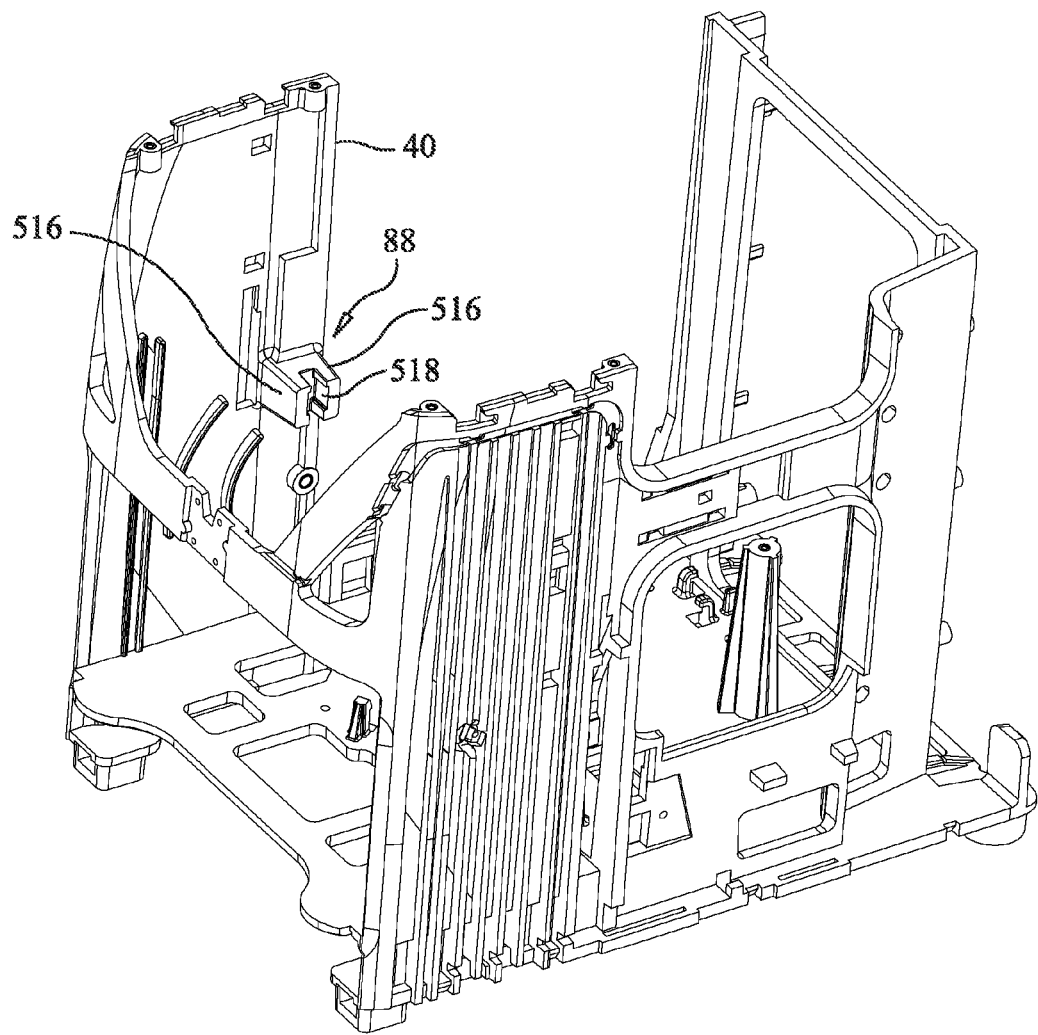
FIG. 65 is another perspective view of the chemical analyzer of the present invention, with the enclosure thereof having been removed to facilitate an understanding of the placement of a disposable pipette tip removal member therein.
Figure 66:
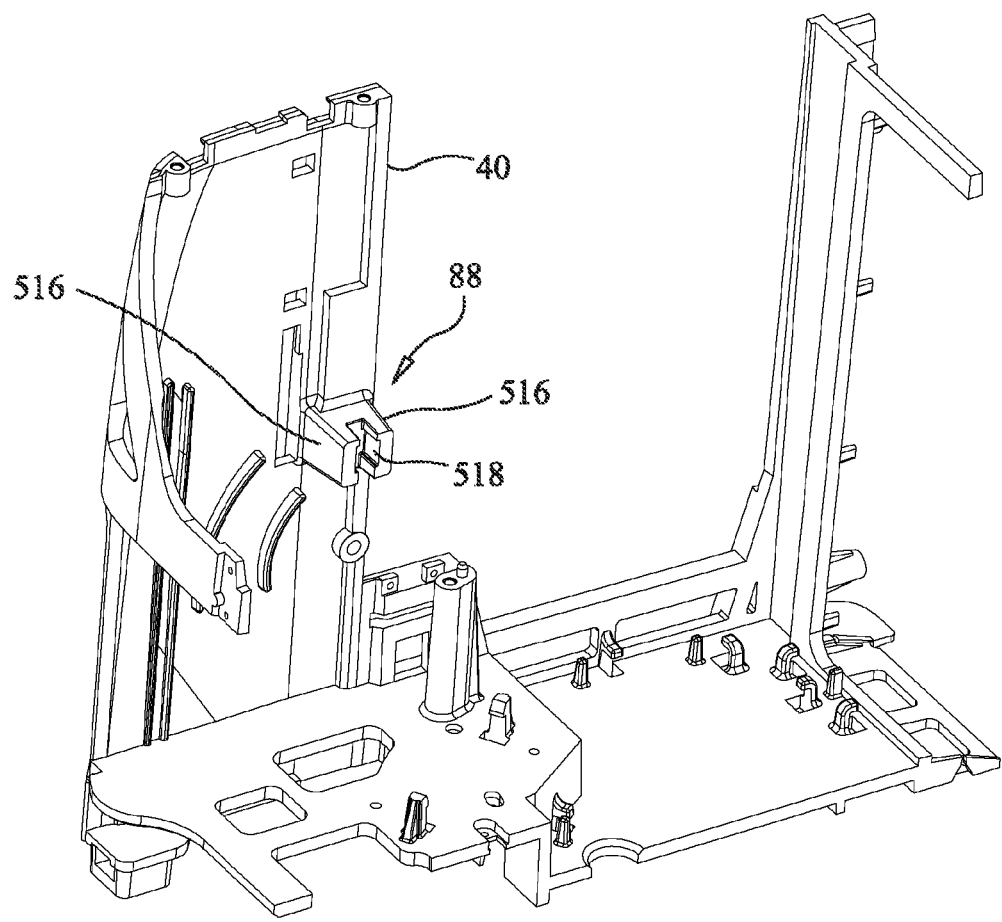
FIG. 66 is a perspective view of a section of the chemical analyzer of the present invention, with the enclosure thereof having been removed to facilitate an understanding of the placement of a disposable pipette tip removal member therein.
Figure 67:
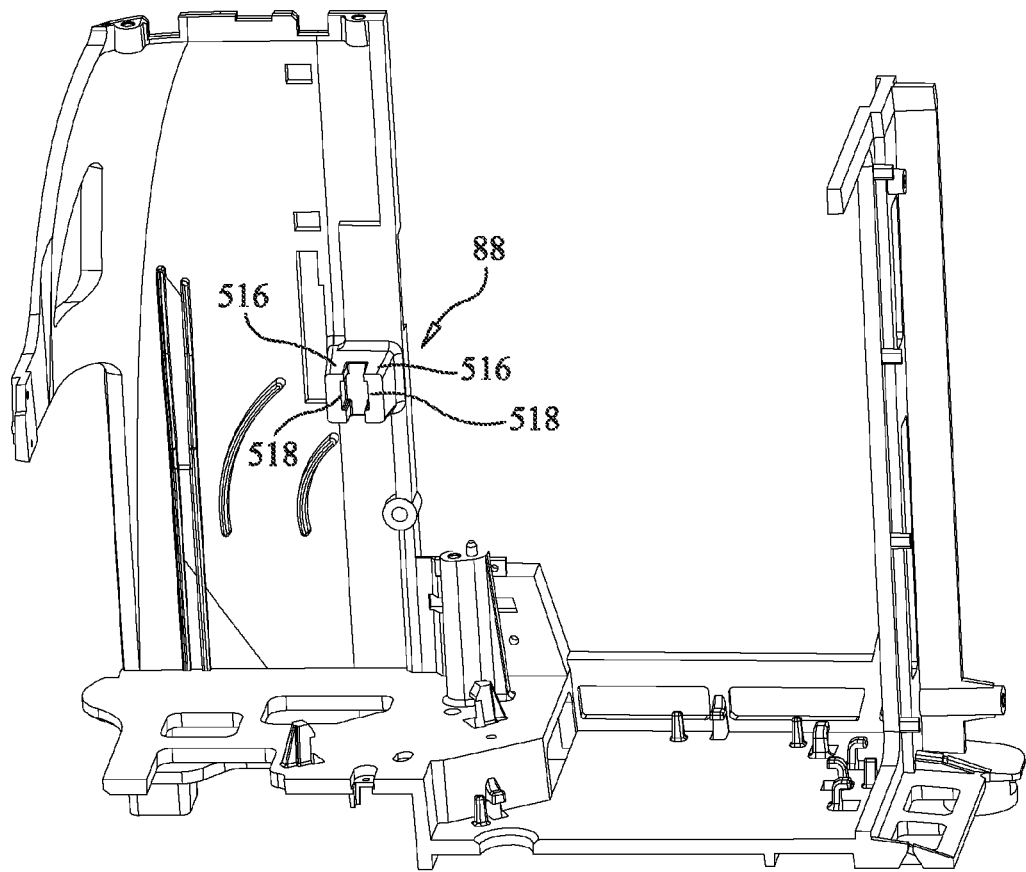
FIG. 67 is another perspective view of a section of the chemical analyzer of the present invention, with the enclosure thereof having been removed to facilitate an understanding of the placement of a disposable pipette tip removal member therein.

Basically, and as shown in FIGS. 10 and 35, the slide processing unit 44 includes a housing 278 having an external, generally circular side wall 280, which partially defines an incubator for maintaining the slides at a predetermined temperature, a slide carousel assembly 48 rotatable within the incubator housing 278 for moving the slides in a circular path along a slide track, a pivotable incubator cover 282 which is mounted over the slide carousel 48, a slide track 284 in which a plurality of reagent test slides are moved in a circular path by the slide carousel 48, a heater element 286 in thermal contact with the bottom plate 288 forming part of the slide track 284, an optics module 56, a motor 290 for rotating the slide carousel 48 and a supporting frame, preferably in the form of a normalizer casting plate 292, for mounting the optics module 56, the motor 290 and the slide track 284 thereon.

The evaporation cap open and close assembly 52 is shown in FIGS. 15 and 24-32 of the drawings. In some of these figures, the parts of the assembly have been removed to facilitate an understanding of the operation of the assembly and the movement of the components therein.

The evaporation cap open and close assembly 52 at least partially radially straddles the incubator housing 278 and the slide carousel 48 disposed therein in order to move radially outwardly and inwardly each evaporation cap 54 which is mounted to and movable on the slide carousel 48 which covers a chemical reagent test slide positioned below it.

Each evaporation cap 54 on the slide carousel 48, and there are preferably 18 such evaporation caps 54, is a generally elongated plate having an opening formed through the thickness thereof. The evaporation cap 54 may be moved radially on the slide carousel 48 so that the opening therein may be either in alignment with a corresponding opening of a plurality of openings formed in the top surface of the slide carousel 48, or moved radially out of alignment with the slide carousel openings. When the cap 54 is moved such that its opening is in alignment with the corresponding opening formed in the top surface of the slide carousel 48, the film portion 170 of a chemical reagent test slide 166 situated at that segment of the slide carousel 48 is exposed, and a liquid sample may be deposited thereon by the fluid handler. The cap open and close assembly 52 immediately thereafter pushes the evaporation cap 54 on the slide carousel 48 in the opposite radial direction such that the openings are no longer in alignment and the film portion 170 of the chemical reagent test slide 166 situated thereat is covered by the non-apertured portion of the evaporation cap 54.

The evaporation cap 54 is similar in many respects to that shown in FIG. 82b of the aforementioned U.S. Patent Application Publication No. 2010/0254854, and is shown in several of the figures herein to facilitate an understanding of how the cap open and close mechanism 52 effects movement of the evaporation cap 54.

The evaporation cap open and close assembly 52 includes several components. These components include a vertical actuator plunger 294, two compression springs 296, mounted on the plunger 294, a close cap shuttle 298, an open cap shuttle 300, a retract lever 302, a spring 304 which biases the retract lever 302 in a predetermined position, a right side portion 306 of the assembly housing, a left side portion 308 of the assembly housing which mates with the right side portion 306, a close cap shuttle return spring 310, a vertical actuator pin 312, a roller cover 314 which is mounted on the vertical actuator pin 312, a right shuttle cover 316 and a left shuttle cover 318, and a shuttle base 320.

More specifically, the vertical actuator plunger 294 appears as a forked unit having two spaced apart, downwardly extending legs 322 which are attached to a common joinder piece 324. At the top of the joinder piece 324, opposite to where the legs 322 are situated, is a pocket structure 326 which selectively receives the end plate 204 of one of two elongated arms 202 of the fluid handler robot. The fluid handler robot may be moved in the θ direction such that the end plate 204 of one of the elongated arms 202 may be received by and interlock with the pocket structure 326 on the vertical actuator plunger 294 and is captively received thereby so as to ensure a good mechanical link between the two. Movement of the fluid handler robot in the Z direction, up and down, will effect the same vertical movement of the actuator plunger 294. The fluid handler robot may be rotated in the opposite direction to release the vertical actuator plunger 294 from the end of its elongated arm 202 after the cap open and close function has been completed.

The vertical actuator compression springs 296 are mounted on the actuator plunger 294 to encircle each leg 322 thereof. The springs 296 will compress when the vertical actuator plunger 294 is moved downwardly by the fluid handler robot, and will expand to bias the vertical actuator plunger 294 to its original upward position, especially after completion of the cap open and close function and when released by the fluid handler robot arm 202.

At the free end of each leg 322 of the vertical actuator plunger 294 is an opening formed diametrically through the thickness thereof. The openings at the free ends receive an actuator pin 312, which extends transversely between the two legs 322. A cylindrical roller cover 314 is mounted on the actuator pin 312. As will be seen in greater detail, the actuator pin 312, with the roller cover 314 mounted thereon, is received within camming slots formed in two movable components of the cap open and close assembly 52.

The assembly 52 includes a right side housing piece 306 and a left side housing piece 308. These housing pieces 306, 308 are mounted on a shuttle base 320, which has structure, such as resilient flanges 328, to allow the entire assembly to be mounted on the chassis 40 of the analyzer 2 in a particular position with respect to the incubator housing 278 and the slide carousel 48 situated therein.

Interposed between the left side housing piece 308 and the right side housing piece 306 is a close cap shuttle 298 and an open cap shuttle 300. Each of the close cap shuttle 298 and the open cap shuttle 300 is generally a plate-like piece having extending from an upper surface thereof an L-shaped shuttle arm 330. The shuttle arm 330 of the close cap shuttle 298 and the shuttle arm 330 of the open cap shuttle 300 are disposed in opposite directions so that they face each other on opposite radial sides of the incubator housing 278. The shuttle arms 330 include horizontal legs 332 whose free ends are received in openings formed in the incubator housing radially inner and outer side walls so that they may contact the evaporation cap 54 on opposite longitudinal edges thereof to effect movement of the evaporation cap radially in a reciprocating fashion when the evaporation cap is moved into alignment with the cap open and close assembly 52 and, in particular, the shuttle arms 330 thereof.

Figure 24:
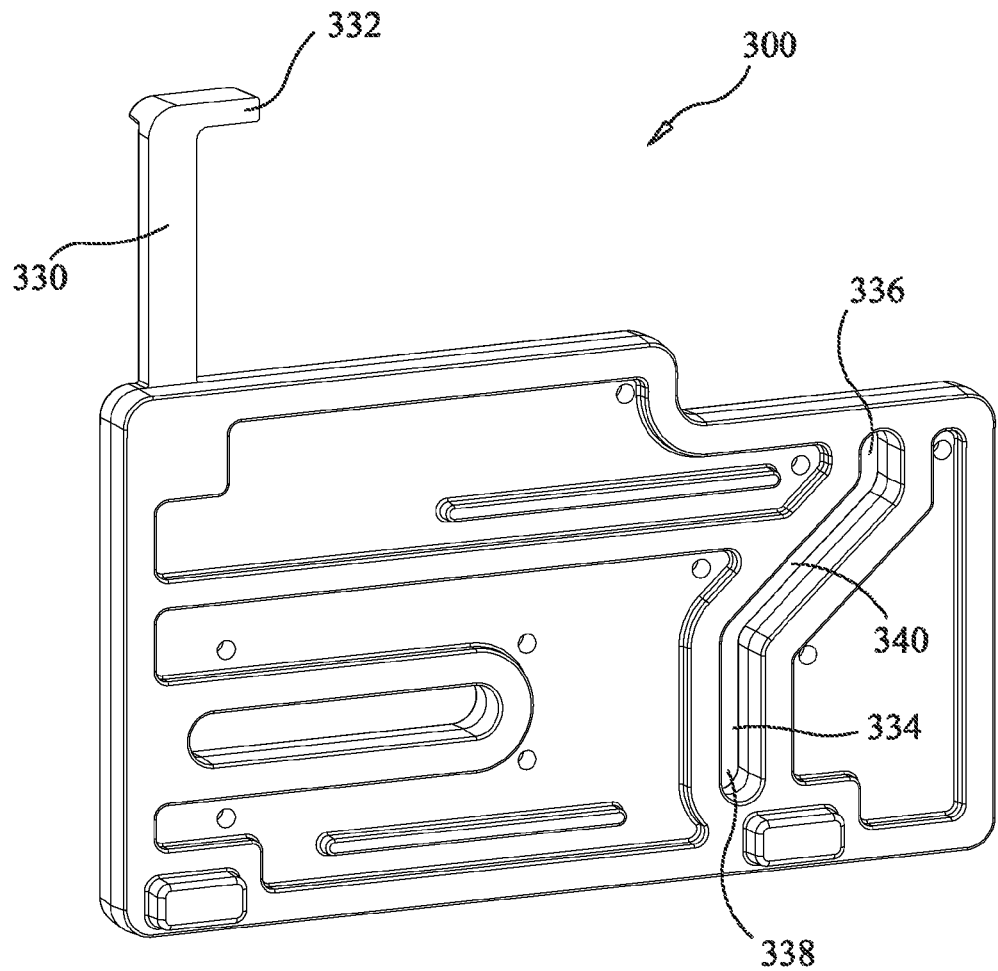
FIG. 24 is a perspective view of the open cap shuttle forming part of the evaporation cap open and close mechanism of the chemical analyzer of the present invention.
Figure 25:
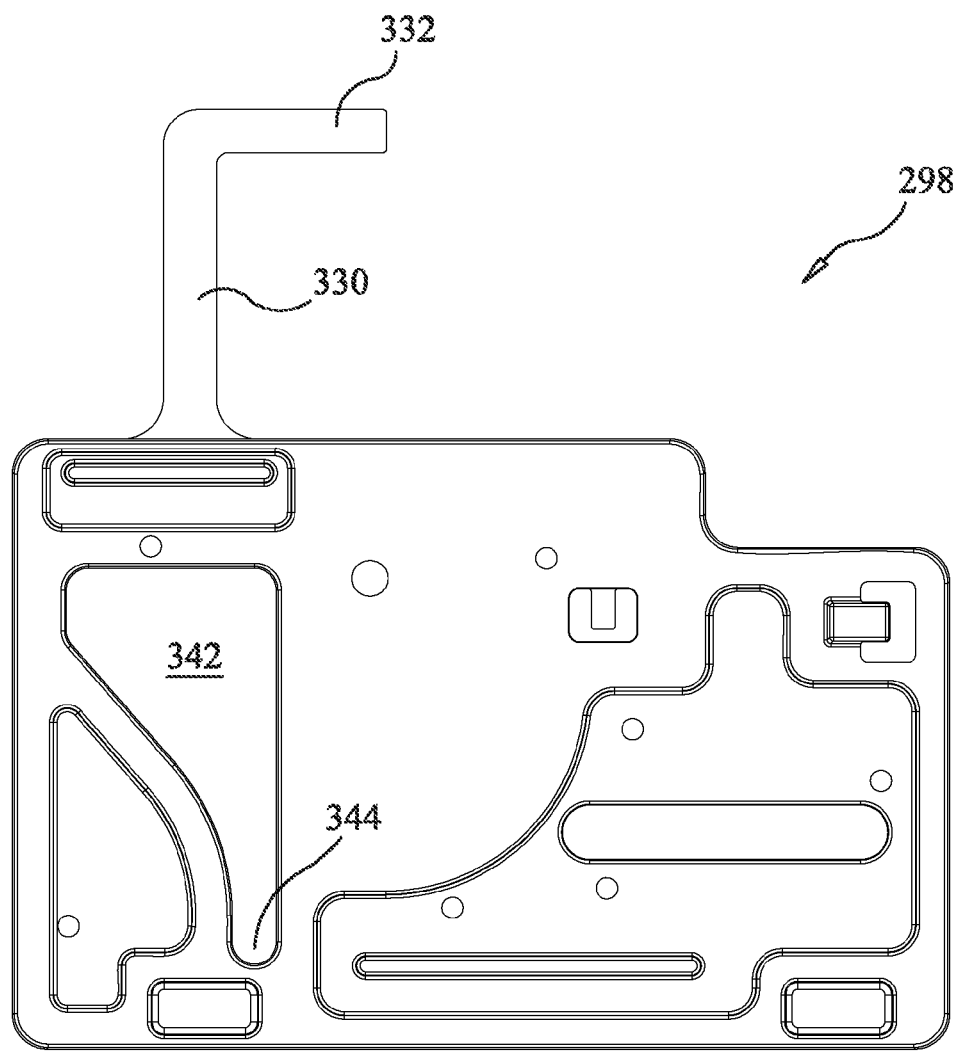
FIG. 25 is a front elevational view of the close cap shuttle forming part of the evaporation cap open and close mechanism of the chemical analyzer of the present invention.
Figure 26:
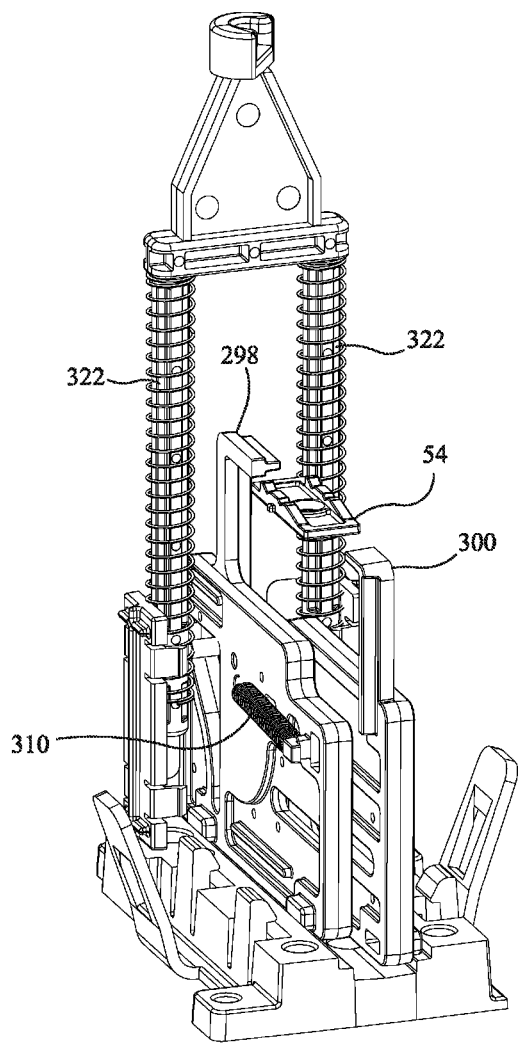
FIG. 26 is a perspective view of the evaporation cap open and close mechanism of the chemical analyzer of the present invention, and illustrating an evaporation cap situated in alignment therewith.
Figure 27:
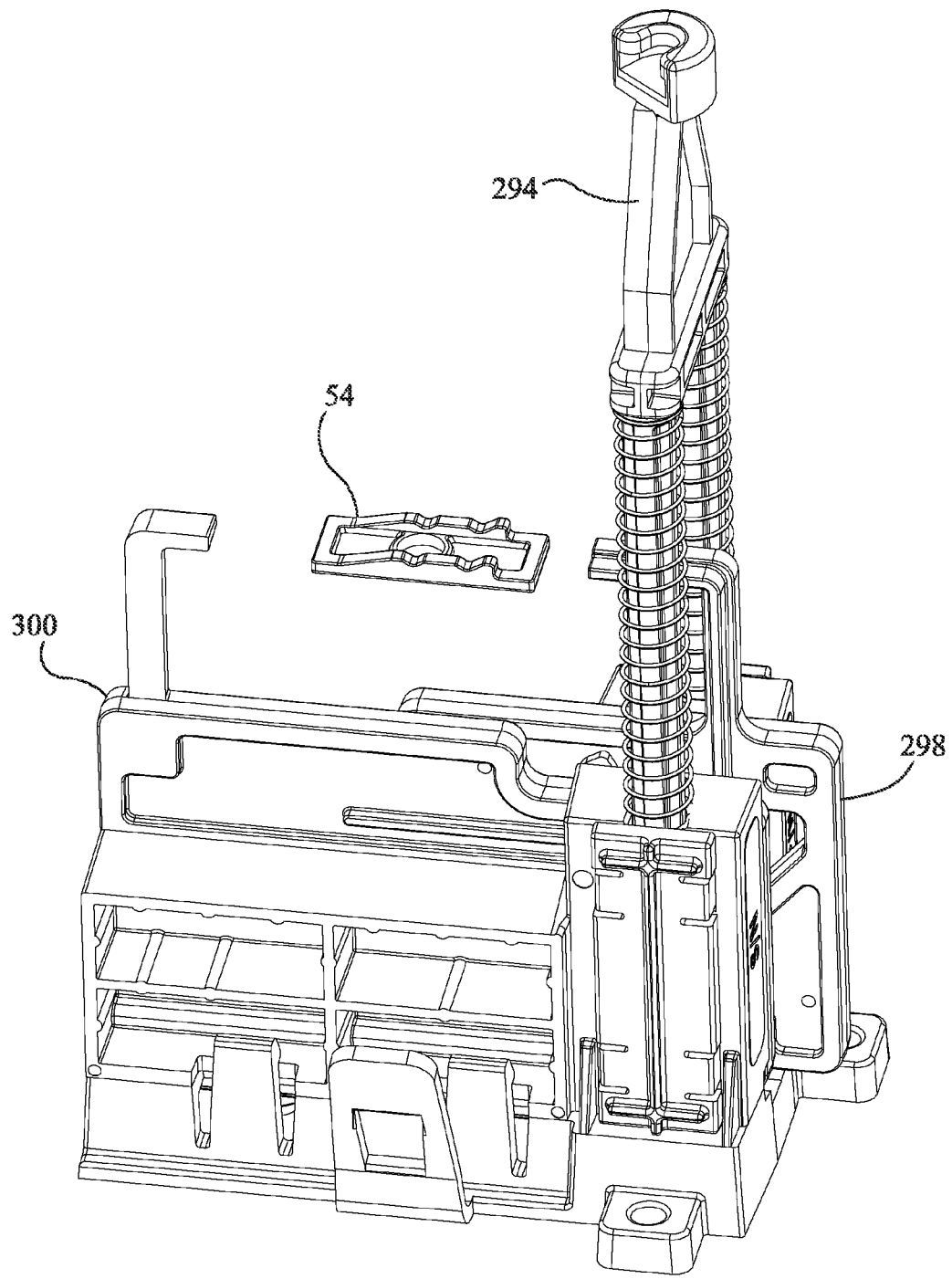
FIG. 27 is another perspective view of the evaporation cap open and close mechanism of the chemical analyzer of the present invention, and illustrating an evaporation cap situated in alignment therewith.
Figure 28:
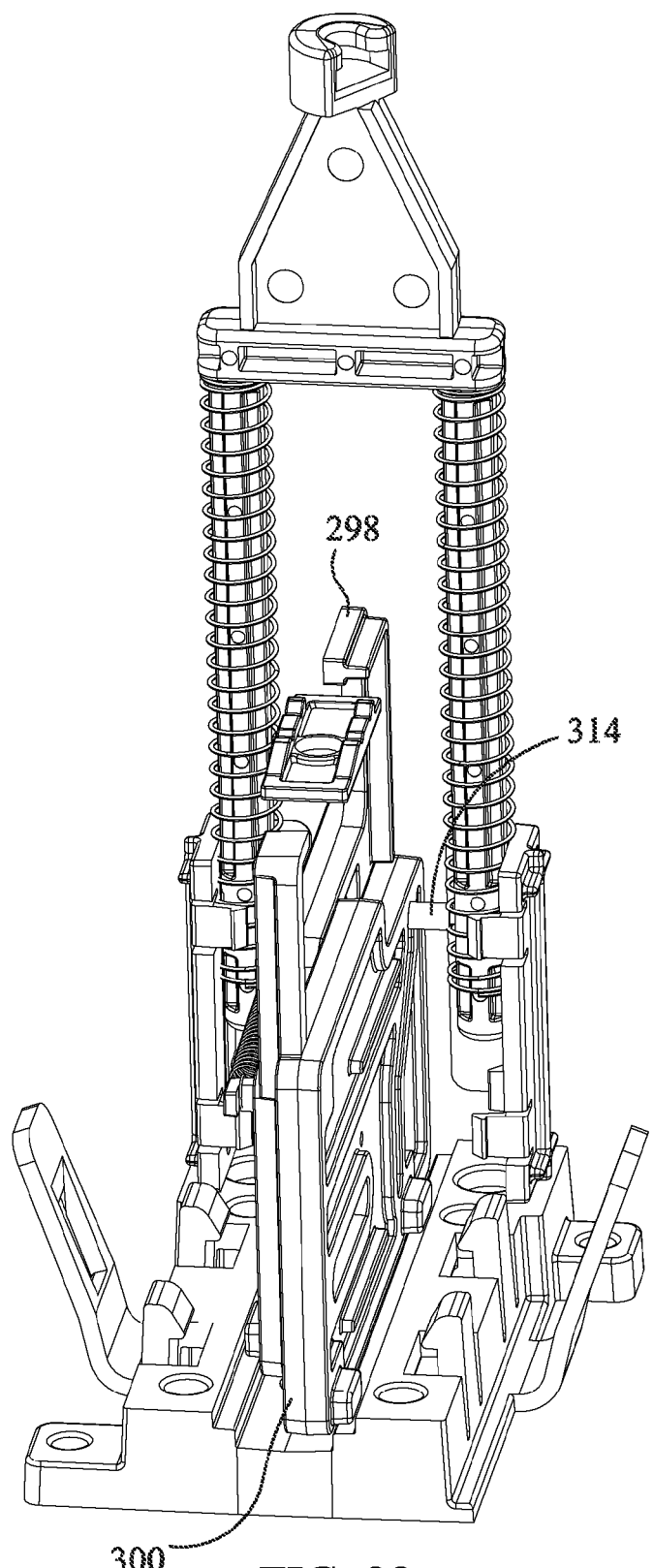
FIG. 28 is another perspective view of the evaporation cap open and close mechanism of the chemical analyzer of the present invention, with certain components thereof having been removed to facilitate an understanding thereof, and illustrating an evaporation cap situated in alignment therewith.
Figure 29:
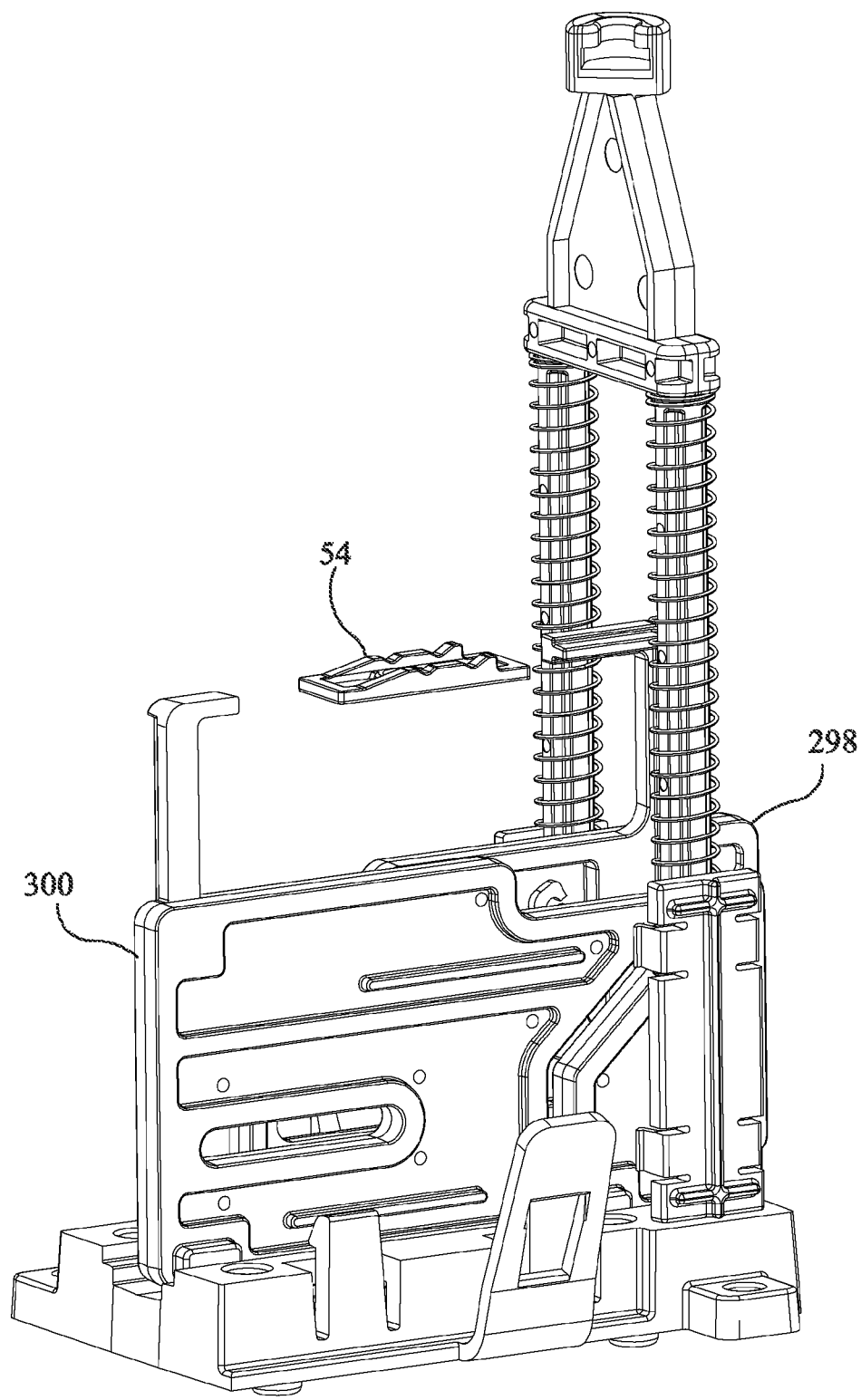
FIG. 29 is another perspective view of the evaporation cap open and close mechanism of the chemical analyzer of the present invention, with certain components thereof having been removed to facilitate an understanding thereof, and illustrating an evaporation cap situated in alignment therewith.
Figure 30:
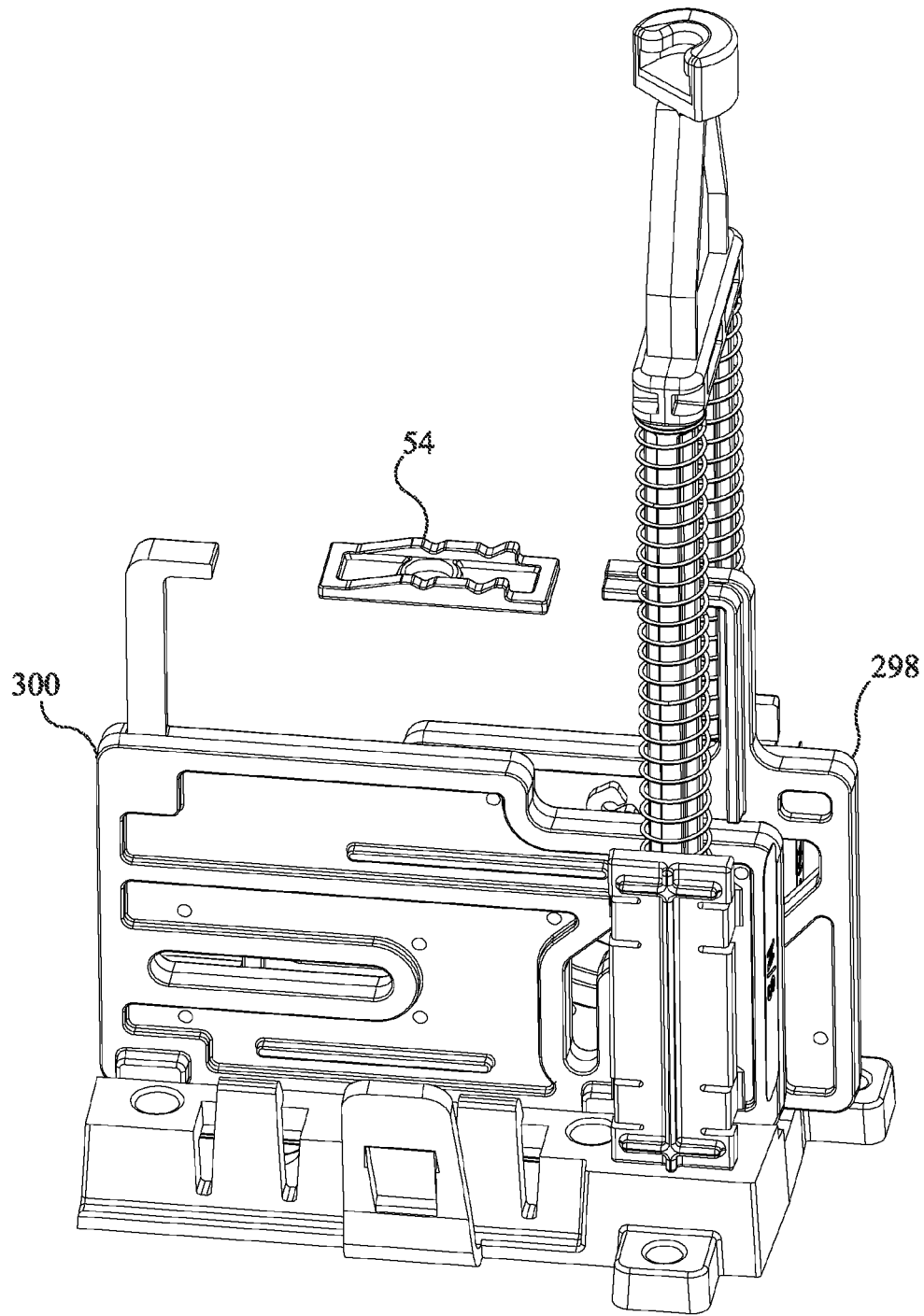
FIG. 30 is another perspective view of the evaporation cap open and close mechanism of the chemical analyzer of the present invention, with certain components thereof having been removed to facilitate an understanding thereof, and illustrating an evaporation cap situated in alignment therewith.

The open cap shuttle 300 is shown in FIG. 24. As can be seen from this figure, the open cap shuttle 300 includes a narrow slot 334 through which passes the actuator pin 312 and roller cover 314. The slot 334 includes three segments: an upper vertical segment 336, a lower vertical segment 338 displaced horizontally from the upper vertical segment 336, and a sloping center segment 340 interconnecting the upper vertical segment 336 with the lower vertical segment 338. The close cap shuttle 298, mounted adjacent to the open cap shuttle 300, includes an opening 342 having a generally inverted triangular configuration which at its lower apex terminates in a narrow slot 344, as shown in FIG. 25.

Figure 31:
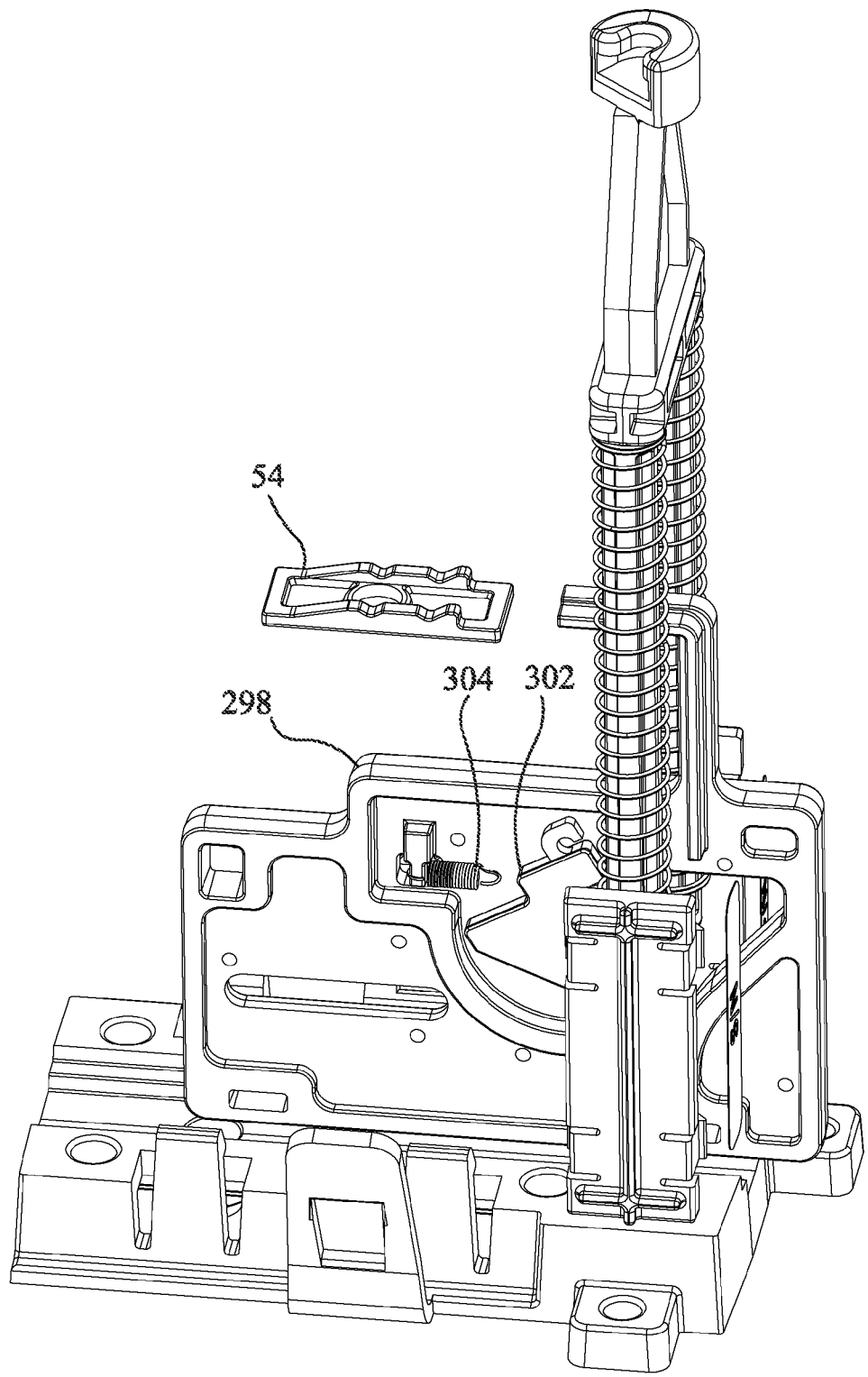
FIG. 31 is another perspective view of the evaporation cap open and close mechanism of the chemical analyzer of the present invention, with certain components thereof having been removed to facilitate an understanding thereof, and illustrating an evaporation cap situated in alignment therewith.
Figure 32:
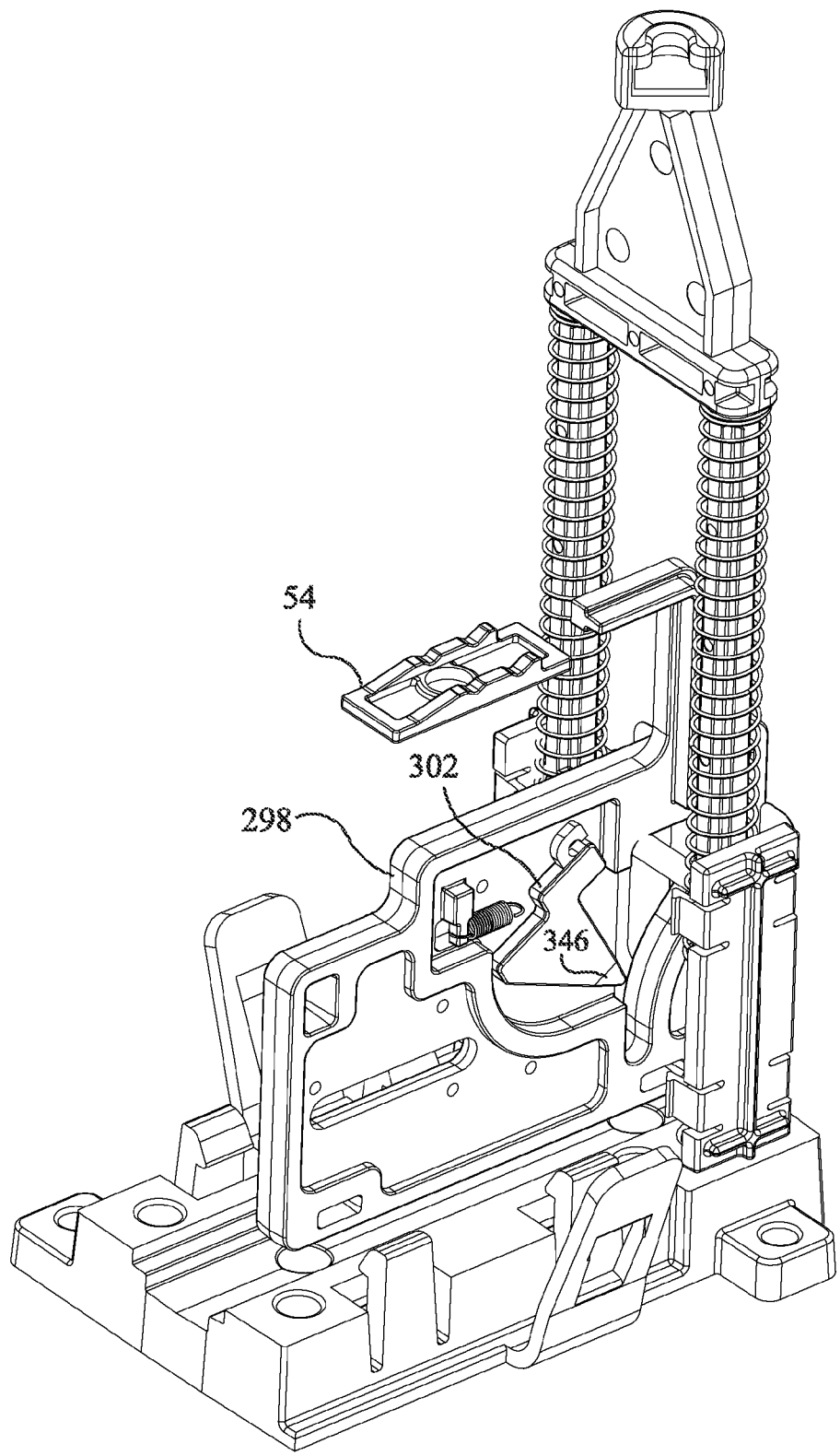
FIG. 32 is another perspective view of the evaporation cap open and close mechanism of the chemical analyzer of the present invention, with certain components thereof having been removed to facilitate an understanding thereof, and illustrating an evaporation cap situated in alignment therewith.

As can be seen from FIGS. 31 and 32, there is a retract lever 302 hingedly mounted on the close cap shuttle 298. The retract lever 302 includes a triangular nose 346 which at least partially extends into the opening 342 formed through the thickness of the close cap shuttle 298. The retract lever 302 is biased by a spring 304 connected thereto and to the close cap shuttle 298 such that the triangular nose 346 is forced upwardly on the closed cap shuttle 298 and extends into the opening 342 formed therein. The actuator pin 312 mounted on the actuator plunger 294, and the roller cover 314 thereon, is also received through the opening 342 formed in the close cap shuttle 298.

There is also a lever return spring (i.e., the close cap shuttle return spring 310) which is connected between the right side housing piece 306 and the close cap shuttle 298.

The downwardly extending legs 322 of the vertical actuator plunger 294 are received in corresponding channels formed in the right side housing piece 306 and the left side housing piece 308. The legs 322 of the actuator plunger 294 are retained within these channels by a right shuttle cover 316 and a left shuttle cover 318 which are respectively mounted on the right side housing piece 306 and the left side housing piece 308 to close the channels formed therein.

The cap open and close assembly 52 works in the following manner. When the vertical actuator plunger 294 is forced downwardly by the fluid handler robot arm 202, the purpose of which is to open an evaporation cap 54 in the slide carousel 48 which is positioned in alignment with the cap open and close assembly 52, the actuator pin 312 and roller cover 314 thereon are forced downwardly through the narrow slot 344 and the larger opening 342 formed through the thicknesses in the open cap shuttle 300 and the close cap shuttle 298, respectively. The travel of the actuator pin 312 through the narrow slot 344 of the open cap shuttle 300 forces the open cap shuttle to slide between the two housing pieces 306, 308 in a first direction, so that the horizontal free end 332 of the shuttle arm 330 affixed thereto enters the incubator housing 278 and pushes on an evaporation cap 54 aligned with it by the slide carousel 48. This action causes the opening in the evaporation cap 54 to become aligned with the opening in the top surface of the slide carousel 48 so that the fluid handler may deposit a liquid sample on the film portion of a reagent test slide positioned under the openings.

The actuator pin 312 also engages the nose 346 of the retract lever 302 mounted on the close cap shuttle 298 as the pin 312 moves downwardly through the opening 342 formed through the close cap shuttle 298. Since the opening 342 in the close cap shuttle 298 is relatively large, the close cap shuttle 298 does not move as the actuator pin 312 progresses downwardly therethrough.

At some point in its downward movement, the actuator pin 312 enters the bottom slot 344 of the opening 342 formed in the close cap shuttle 298 and passes the nose 346 of the retract lever 302. The nose 346 of the retract lever 302 is then free to move upwardly again under the bias of the spring 304 connected thereto.

When the vertical actuator plunger 294 is moved upwardly by the fluid handler robot arm 202, the movement of the actuator pin 312 in the close cap shuttle 298 and the open cap shuttle 300 is reversed. The pin 312 follows the path of the narrow slot 334 in the open cap shuttle 300 to move the open cap shuttle in an opposite direction and retract the shuttle arm 330 mounted thereon away from the evaporation cap 54. Now, the actuator pin 312, being beneath the pivoted retract lever 302 on the close cap shuttle 298, engages the underside of the retract lever 302, which essentially narrows the opening 342 formed in the close cap shuttle 298 so that the horizontal free end 332 of the L-shaped shuttle arm 330 of the close cap shuttle 298 enters the incubator housing 278 from the opposite radial side and engages the evaporation cap 54 on its opposite lateral side to push the cap 54 in an opposite direction such that the opening formed therein is no longer in alignment with the opening formed in the top surface of the slide carousel 48. The non-apertured portion of the evaporation cap 54 now covers the film portion 170 of the slide positioned below it to minimize any evaporation of the analyte and liquid sample deposited thereon. Thus, the cap open and close assembly 52, when actuated by the fluid handler robot, opens (uncovers) each evaporation cap 54 on the slide carousel 48 and immediately closes the cap after a liquid sample is deposited thereon by the fluid handler, and this operation is performed sequentially as the slide carousel 48 is rotated under the pipette (i.e., probosis) of the fluid handler.

The cap open and close assembly 52 also has the capability of opening all of the evaporation caps 54 on the slide carousel 48 and maintaining the caps in an open position. This operation is performed when the controller 42 of the analyzer 2 runs a test to determine if the window of the optics module 56 and slide track 284 requires cleaning. In order to accomplish this, the fluid handler robot arm 202 is only moved partially in a downward motion, that is, less than the full downward movement required to open and close the caps 54. Under these circumstances, the actuator pin 312 moves through the circuitous slot 334 formed in the open cap shuttle 300 to move the shuttle arm 330 into the incubator housing 278 to push the evaporation cap 54 to its open position. However, the partial downward movement of the actuator pin 312 through the opening 342 of the close cap shuttle 298 is not so much that it passes below the nose 346 of the retract lever 302. The retract lever 302 thus stays below the actuator pin 312 such that the close cap shuttle 298 is not moved when the actuator plunger 294 is pulled upwardly by the fluid handler robot arm 202. Thus, the shuttle arm 330 on the close cap shuttle 298 does not engage the evaporation cap 54 positioned in alignment with it, and the evaporation cap remains in the open position. By this action, all of the evaporation caps 54 on the slide carousel 48 may be moved to their open position so that the analyzer 2 may determine whether the optics module window needs to be cleaned.

The slide processing unit 44 accepts chemistry and electrolyte slides from the consumable slides and sample drawer 32, presents them to the fluid handler for sample application, and then positions them above a combined reflectometer/fluorometer optics module 56 for reading (i.e., colorometric measurements). In order to facilitate accurate reading by the optics module 56, the slide processing unit 44 manages the placement, movement, temperature, and moisture level of the slides. Using the slide carousel 48 as a method of delivering slides to the optics module 56 allows the development of multiple slides to be monitored (i.e., allows a slide to be read multiple times), which consequently allows for a range of analyses to be run.

The slide processing unit 44 is situated precisely in relationship to the slide inserter mechanism 51 to accept each slide into a separate carousel segment. While loaded slides are moved by the slide carousel 48 in a slide track 284 toward the fluid dispense location and the optics module 56 (preferably, a counter-clockwise direction from the user's elevated point of view), the carousel continues presenting empty slots to the slide inserter mechanism 51. Slides are loaded every second slot on the carousel, the slots being located at the ends of eighteen of the nineteen fingers or segments extending radially from the central mounting hub of the carousel. The nineteenth carousel segment contains the optics module's white test tile: this segment never receives a slide. The position of this segment is communicated to the controller 42 via a home flag/home flag sensor and step counting feature on the slide processing unit 44.

The slide carousel 48 does not actually carry the slides; rather, the carousel segments include ribs on either side of each slide which at least partially define the slide receiving slots and help to maintain the slides in position as the carousel is moved by a motor to push the slides situated below it in a circular path along the slide track 284. For a more detailed explanation of the operation and structure of the slide carousel 48 and track, reference should be had to the aforementioned U.S. Patent Application Publication No. 2010/0254854.

The slide carousel 48 includes evaporation caps 54 which cover the sample location of each slide. The evaporation caps 54 are individually opened and closed when a sample fluid is deposited by the fluid handler on the slides, as will described in greater detail. As the slides are sequentially pushed forward toward the slide processing unit 44 through the entrance slot 206 by the slide inserter mechanism 51, the carousel 48 is timed to rotate to present an empty slot to the slide inserter mechanism 51 until all of the slides—preferably up to eighteen of them—are loaded into the slide processing unit 44.

Rather than rest on a surface of, or be carried by, the slide carousel 48, the slides lie and slide directly on an aluminum ring 288 forming the bottom surface of the slide track 284. A heating element 286 is bonded directly to the underside of this aluminum ring 288. The function of this heating element 286 is to keep each slide and its respective sample deposited on it at, or nearly at, the optimized operational temperature of the slides. With this function in mind, the heating element 286 is highly specific, and can maintain temperatures to within 0.15 degree Celsius of the target slide temperature (37 degrees Celsius). The entire heating element 286 is designed to warm up quickly (within five to seven minutes of instrument startup), and is controlled by the electrical circuit of the controller 42.

The heating element 286 preferably contains two heating zones: a load zone, which accounts for approximately a quarter of the heating element's area, and a test zone, which accounts for the other three-quarters. The load zone is situated in proximity to the slide loader 130 and insertion mechanism 51, and the test zone is situated in proximity to the rest of the slide track 284 about which the slides move. Providing for two heating zones means that the load zone can quickly compensate for colder slides without also affecting the temperature of slides (on the other side of the carousel) that have already been warmed. Furthermore, having separate heating zones allows the slide processing unit 44 to compensate for any heat loss that may occur via the consumable slides and sample drawer 32 (i.e., the drawer being opened or closed) or in the event that the side chassis panel door is opened.

The evaporation caps 54 on the slide carousel 48 remain covering each slide except when fluid is dispensed onto the slide, in which case the evaporation cap 54 is pushed aside by the cap open and close mechanism 52, activated by the robot of the fluid handler, as will be described in greater detail. The evaporation caps 54 are sequentially opened and closed when the carousel positions each cap directly beneath and in alignment with a fluid dispense window formed in the plastic incubator cover 282.

An important feature of the slide processing unit 44 is to position the film portion 170 of each slide at a specific distance from and directly over a window in the bottom surface of the slide track 284 which is in alignment with the optics module 56. As the optics detecting spot diameter is preferably 3.1 mm and the electrolyte slide read film is 5 mm, the position of the slides above the optics module 56 is fine-tuned by the slide processing unit 44. The tangential position of the slides is determined by firmware; in this sense, the slide carousel 48 is an open loop positional device. Radial positioning of the optics module 56 preferably happens once, during assembly; at that point, the optics module 56 is attached to a normalizer casting 292 defining a support plate with screws (the heated aluminum plate 288, defining the bottom wall of the slide track 284, is also mounted on the normalizer casting 292). Determination of tangential alignment of the relative position of the slide carousel 48 and optics module 56 also preferably happens once, during assembly, preferably after the radial alignment of the optics module 56 has been set, as the adjustment of radial position can result in slight side-to-side movement of the module in relation to the normalizer casting plate 292 on which it is mounted.

The combined optics module 56 (reflectometer/fluorometer) of the chemical analyzer 2 of the present invention makes use of LEDs to illuminate the film portion 170 (and, therefore, the sample deposited thereon) of each reagent test slide moved by the carousel over the slide window in the track 284. These LEDs are symmetrically arranged around their illumination target (the film portion 170 of the slide containing an analyte). Any of the module's twenty-four LEDs (three LEDs for each of six wavelengths, and six LEDs for a seventh wavelength) are energized to illuminate the slide, depending on the type of slide presented to the optics module 56 (as determined by the bar code on the slide). Two lenses within the combined optics module channel the reflected and fluorescent light that comes off the slide and present this light to a photodiode at the base of the module. Simultaneously, three other photodiodes (intensity sensors) within the module measure the intensity of the LEDs and provide reference measurements by way of signals to the controller 42 to normalize the measurement taken by the sensor (the photodiode) at the base of the module.

The optics module 56 is similar in structure and operation in many respects to that described in the aforementioned U.S. Patent Application Publication No. 2010/0254854, and reference should be had to this published application for a more detailed description of the optics module 56. Nevertheless, various views of the optics module 56 is shown in FIGS. 11-13 and 21 of the drawings. The optics module 56 preferably includes a housing or cover 348 which limits the influence of electrostatic discharge from affecting the operation of the optics and electronics of the module, and a primary printed circuit board 350, received by the cover 348, having circuitry and a photodiode sensor mounted thereon for measuring the light reflected from, or fluoresced by, a chemical reagent test slide positioned by the slide carousel 48 over the optics viewing window in the slide track 284. The optics module assembly is mounted on the normalizer casting plate 292 through an opening formed therein. There is also a top housing for the assembly 352, which is mounted to the primary printed circuit board 350 by a plurality of machine screws 354. As can be seen from the drawings, the top housing 352 includes a plate 356 extending outwardly from the side wall of the housing. The plate includes 356 two sets of parallel, spaced apart elongated ribs 358 which protrude outwardly from the top surface thereof. Between each set of ribs 358 is received a corresponding elongated projection 360 situated on the bottom side of the normalizer casting plate 292 to which the optics module 56 is affixed. The ribs 358 of the optics module plate 356, and the projections 360 on the normalizer casting plate 292, extend generally in a radial direction, and are used to align the optics module 56 in a proper position with the slide carousel 48 and slide track viewing window. The optics module 56 is adjusted in a radial direction until in proper alignment, and then hold down screws 362 are tightened so that the optics module 56 will not move radially on the normalizer casting plate 292.

Within the interior chamber defined by the optics module housing 352 are situated a number of components. These components include an optics chamber heating element 364, in the form of a cylindrical ring, which is used to maintain the optical elements, LEDs and other components at a predetermined temperature; a top optics attenuator piece 366 and a bottom optics attenuator piece 368, positioned in alignment with each other; a printed circuit board 370, having a frusto-conical shape, on which is mounted a plurality (preferably 24) of LEDs used to illuminate a reagent test slide positioned above the optics module 56; a holder or support 372 for the frusto-conically shaped LED printed circuit board 370; and a two piece, mating lens holder 374. At least some of the LEDs emit light at different wavelengths, including 470 nm for fluorescence excitation. Preferably, there are colored glass filters 375 mounted on the top of the 470 nm LEDs to aid with filtering the 470 nm excitation light.

The lens holder 374 houses and maintains in position therewithin several optical components, including upper and lower lenses 376, 378, a notch filter 380 interposed between the two lenses 376, 378, and an aperture filter 382 (i.e., an aperture and filter, as an assembly) below the lower lens 378. The notch filter 380 is included in the optics module 56 to permit detection of fluorescence by filtering out the light from the fluorescence excitation LEDs (at 470 nm).

The top housing 352 of the optics module 56 also includes an adjustable window assembly holder 384, having a window and encircled by an o-ring 386, which is situated in alignment with the slide viewing window in the slide track 284, an upper printed circuit board 388 containing further electrical components for measuring light intensity, and an upper printed circuit board cover 390.

After the slides have been cycled over the optics module 56 as many times as is necessary for the given analysis (and this number could range from approximately five to thirty-five), the slides are pushed out of their segments by the ejector mechanism 58, described previously, attached to the bottom of the chassis 40. This ejector mechanism 58 is engaged by an elongated arm 202 on the fluid handler robot. Slides leave the slide processing unit 44 through a slide eject window or slot 250 formed in the outer side wall 280 of the slide track 284, which is in turn situated above an opening to the waste drawer 26.

The top portion, or incubator cover 282, of the slide processing unit 44 pivots to open upwardly on two hinge pins 392. This cover 282 is held in the raised (open) position by magnetic attraction between a magnet embedded in a handle 394 joined to the cover 282 and an appropriately placed ferrous material situated on the fluid handler. Of course, it should be realized that the magnet could be situated on the fluid handler, and another magnet, or the ferrous piece, may be positioned on the incubator cover 282.

Figure 21:
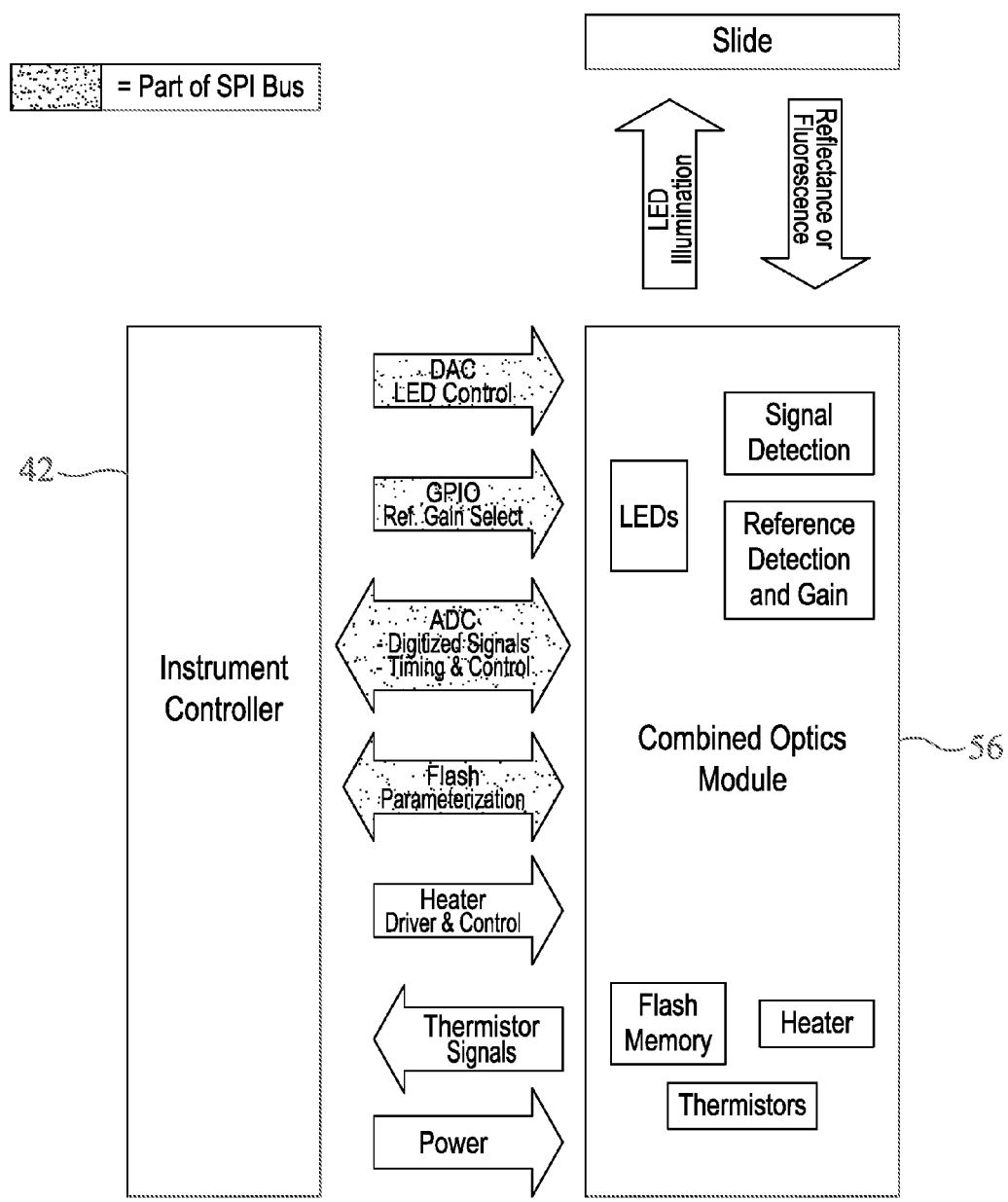
FIG. 21 is a functional mapping diagram of the optics module of the chemical analyzer of the present invention.

FIG. 21 illustrates a block diagram of how the optics module 56 interfaces with the controller 42. Each of the arrows in FIG. 21 represents an exchange of power, electrical signals, or light.

Digitized signals, using an analog-to-digital converter circuit on one or both of the optics module 56 and the controller 42 are sent from the optics module 56 to the controller 42, and timing and control signals are sent from the controller 42 to the optics module 56. The module includes one or more thermistors to monitor the temperature within the module housing 352, a flash memory and other circuits used for reference detection and gain control.

The optics module 56 receives commands, as well as its power supply, from the controller 42. Through these signals, the module controls the intensity and energization of the LEDs, gain selection, and flash memory parameterization, as shown in the arrows in FIG. 21. The other lower three arrows shown in this figure between the controller 42 and the combined optics module 56 represent preferred hardwire connections.

The arrows shown in FIG. 21 between the slide and the optics module 56 represent an exchange of light—the module emits light from LEDs and receives either reflectance or fluorescence optical signals from the slide.

Additional features of the slide processing unit 44 will now be described.

Proper slide positioning is important for accurate readings and analyses. The correct positioning of slides is the result not only of where the slide is, but where it is in relation to the optics module 56, and where it is located within the preferably plastic incubator housing 278. The size of the slides, and their preferred triangular shapes, make them specific to the shape of the carousel segments. The slide carousel 48 brings the slides over the slide read window (itself over the spot reader of the optics module 56) so that colorimetric changes in the slide may be properly and accurately measured by the optics module 56.

The slide processing unit 44 also positions the slides so that they are brought to one location for fluid dispense, another location for bar code reading, and still another location for being ejected.

Besides correct positioning, accurate slide read also depends on the reflectance or fluorescence stability of the optics module 56, and the control (that is, the barring) of light from entering the slide processing unit 44. The design of the normalizer casting 292 and incubator housing 278 together contribute to both positioning and thermal/light control.

For fluid dispense, the slide processing unit 44 presents the slides to the fluid handler and provides an ingress hole for the fluid dispense (this hole is on the top cover 282 of the plastic incubator housing 278). Fluid dispense (as far as the slide processing unit 44 is concerned) also relies on ingresses for the parts of the evaporation cap open and close mechanism 52 that move evaporation caps 54 into open (i.e., uncovered) and closed (i.e., covered) positions. Similarly, the reading of the slide bar codes is performed by the slide carousel 48 presenting slides, once loaded in the slide processing unit 44, to the one of the cameras 228, 230 of the vision system which functions as a slide bar code reader attached to the chassis 40. Both of these mechanisms are functions of the image plane provided by the heater ring and electrical connections to a home position sensor for the slide carousel 48 and to the drive motor for the carousel.

Inserting slides into the slide processing unit 44 is accomplished by the proper alignment of the slide entrance slot 206 in relation to the slide inserter mechanism 51, described previously, and the proper positioning of the slide carousel 48 to further align with the entrance slot 206 an empty segment of the carousel. Carousel movement (in concert with the actuation of the slide inserter mechanism 51, allows one slide to be loaded into each carousel segment at a time. Likewise, the slide eject function relies on carousel timing (in this case, timed with actuation of the slide eject mechanism 58). The slide eject function uses an ingress (in the slide processing unit 44) for the pusher pin 272 of the slide eject mechanism 58 to enter the slide processing unit 44 to push the slide in alignment with the pusher pin 272 out of the slide processing unit 44 through the slide eject slot 250.

The slide processing unit 44 also allows easy access to the slide carousel 48 and optics module 56 for cleaning. The slide processing unit 44 makes the glass surface at the site of optics module reading readily accessible to the user. The incubator cover 282 is lifted (and then held open by a magnet or ferrous piece on the fluid handler), and the slide carousel assembly may be lifted away from its coupling. After the glass surface is cleaned by the user, the carousel is replaced and the incubator cover 282 is unhitched from its magnetic attraction to the ferrous piece and lowered into place.

Thermal control of slides while they are being cycled through the slide processing unit 44 is effected by both quick warm-up of cold slides and maintenance of already-warmed slides. For the most part, slides are heated by the aluminum heater ring 288. Heat generated by the optics module 56 and the slide carousel drive may also contribute to overall slide temperature.

Another environmental consideration for the slide processing unit 44 is controlling the evaporation of the volume above the slide film portion 170 to promote assay development. As with thermal control, the heat produced by the optics module 56, by the heater element 286, and by the slide carousel drive are preferably taken into consideration. The slide evaporation caps 54 (part of the slide carousel 48) minimize evaporation, and the slide evaporation caps 54 are opened only at the time of fluid dispense.

The plastic incubator of the slide processing unit 44 preferably comprises two parts: the incubator housing 278 and the incubator cover 282. These two elements make up the outer sides and cover of the slide processing unit 44. They provide one window or a slot each for loading slides, reading slide bar codes, and dispensing fluid onto the slides. The incubator housing 278 also has structure which works in concert with the evaporation cap open and close mechanism 52 and the slide eject mechanism 58. More specifically, and as mentioned earlier, the incubator housing 278 provides openings for the shuttle arms 330 of the cap open and close mechanism 52 to access the slide evaporation caps 54 on the carousel. For the slide eject mechanism 58, the incubator housing 278 has a guide for the slide ejector pusher pin 272. The incubator housing 278 further provides precision location platforms and vertical keeper features to precisely locate the heater ring 288 in the Z-direction snugly. The incubator housing 278 also has a precise snap feature to lock the heater ring 288 in its proper precise tangential position and prevent inadvertent movement of the ring 288 during operation. Additionally, the incubator housing 278 provides a precisely Z-height located, low-friction (COF), low wear surface (i.e., the bottom surface of the slide track 284) that the slide carousel assembly rotates the slides upon during instrument operation. The incubator housing 278 preferably snaps onto the normalizer casting plate 292 by nine precisely located, center-double snap-features. The incubator housing 278 is also preferably located precisely to the normalizer casting plate 292 using two part-to-part datum-features pins that mate into mating hole/slot pair formed in the normalizer casting plate 292.

The incubator cover 282 provides the slide carousel 48 with a predetermined spring hold down force that, in turn, develops the carousel's capping force for each carousel segment. It also provides the user with a latch handle 394 to enable opening the incubator to gain access to the slide carousel 48 and slide track 284 for cleaning and/or maintenance. The incubator cover 282 develops a mostly light-tight barrier when closed for unwanted light entering the incubator during assay (slide) reads. This cover 282 has a magnet inside the latch area 394 that maintains the cover in an opened position by magnetically attracting to a ferrous material on the fluid handler robot when fully opened. The cover 282 also snaps onto and rotates on the incubator housing's precision, preferably stainless steel, pivot pins 392 that are mounted on the incubator housing 278.

Thus, the incubator serves not only to help maintain a fairly constant slide temperature, but also promotes accurate slide reading by blocking out any excess light inside the incubator housing 278.

The normalizer casting plate 292 is preferably made of thixotropic magnesium, a material chosen for its strength and stiffness. It is in many senses a positional unit, providing attachment for parts whose placement must be finely tuned, such as the optics module 56. The reliability of thixotropic magnesium, as a material for casting, means that all of the casting's snap holes, pin holes, slots, and optics module references are highly consistent from one casting to another and unlikely to warp in the way that another material might.

For attachment of the optics module 56, the normalizer casting plate 292 includes radially extending projections 360, or wings, which match with female mating parts 358 on the optics module 56, and help to maintain, and permit the adjustment of, the position of the optics module 56, as described previously.

Thixotropic magnesium for the nonnalizer casting plate 292 is also preferred for its ability to distribute heat. While the casting—and, indeed, much of the slide processing unit 44—is designed as an incubator for the slides, it should also be able to promote the dispersal of excess heat in order to keep slides at their optimal temperature. Also, there are carousel load assist guides along the inside of the plastic incubator housing 278, which provide an easy means of locating the slide carousel 48 onto its hub. These guides provide an easy means of accurately placing the slide carousel 48 on the mounting hub, in the event that the user has difficulty in viewing the positioning of the slide carousel 48 on the hub.

As previously described herein, the slide carousel 48 has preferably nineteen segments of equal sizes: eighteen segments are for slides and the nineteenth serves as the optics module's white reference tile. This tile patch is preferably read at every initialization of the analyzer 2 to provide a cleaning check of the optics module 56 (the window in the slide track 284 may become obscured through use; to check the condition of this window, the analyzer 2 preferably opens one or more of the evaporation caps 54 on the carousel, and uses the reference tile, to determine if the window needs to be cleaned).

Even more preferably, there are two types of cleaning checks. The first uses an empty carousel segment, for which the cap is opened. No slide is in place for this reading. This gives a good assessment if the low end of the reflectance dynamic range is compromised by a dirty window. The second check uses the white tile. No cap is preferably associated with segment 19 and, therefore, no cap needs to be opened. This checks the high end of the reflectance dynamic range.

Each of the other eighteen carousel segments has a small curved "cap" 54 which can, at the location of the cap open and close mechanism 52, be nudged radially outwardly to reveal the slide's chemistry chip (i.e., the film portion 170 of the slide, containing an analyte). Preferably, this function is performed only once, toward the beginning of a run cycle, when the sample is being distributed among the slides.

The slide carousel hold-down function is, essentially, the pressure placed on the axis of the carousel by the lid or cover 282 of the slide processing unit 44. The axis evenly distributes a preferred five pounds of lid pressure to the carousel "spokes" that not only retain each slide in its assigned window as the carousel rotates, but also maintains pressure of the slide evaporation caps 54 on the slides, thereby aiding their effectiveness in preventing sample evaporation.

There is a home flag sensor, which includes a small plastic protrusion on the bottom of the carousel and which is designed to interfere with a light transmissive sensor attached to the normalizer casting plate 292 but associated primarily with the carousel drive. This home sensor provides a reference for the position of the carousel's spokes.

The slide carousel drive assembly comprises a motor 290, a compound gear train, a coupling assembly, and the light transmissive home sensor.

The heater ring, which fits snugly into the incubator housing 278, preferably comprises two parts: (1) a precision CNC-machined (face-turned) aluminum black anodized ring 288 which defines the bottom surface of the slide track 284 on which the slides rest (and over which they slide), and (2) a heater element 286 bonded to the bottom of the aluminum ring 288. The heater ring's black anodized coating is a preferably a MIL (military) specified black hard-coat anodizing with Teflon™ coating.

The aluminum ring 288 of the heater provides a low-friction (COF), low consumable-slide wear surface on which the slides can be moved by the slide carousel 48 and the carousel drive assembly. This surface provides a reference for the "Z" coordinate for readings by the optics module 56.

The aluminum ring 288 preferably includes the following features: a circular opening (in the slide track 284) above the optics module 56 that provides unobstructed visual access to each slide as it is positioned over the optics module 56 by the carousel; an indented slot, situated radially on the aluminum ring 288 at the location of the slide eject mechanism 58, that provides a groove that guides the pusher pin 272 of the slide ejector's assembly that is used to eject the slides from the slide processing unit 44, and "keeper features" on the inner diameter and outer diameter portions of the ring 288 to help precisely locate the ring laterally and vertically in the incubator housing 278. The top of the window in the adjustable window assembly holder 384 of the optics module 56 preferably projects through the circular opening in the slide track aluminum ring 288 and is adjusted to be between about 0.001 inches and about 0.004 inches above the top surface of the ring 288.

As mentioned previously, the heater element 286 on the bottom of the aluminum ring 288 preferably has two heating zones, including a load zone which has an arc length of approximately 95 degrees. This zone is situated at the slide load and/or insert location and encompasses the location of the slide eject mechanism 58. This load zone preferably has a capacity of about 35 Watts. There is also a test zone, which preferably occupies the remaining 265 degrees of the aluminum ring 288. The test zone preferably has a capacity of about 22 Watts. Both of these zones are controlled by thermistors embedded into the heating element 286.

Figure 11:
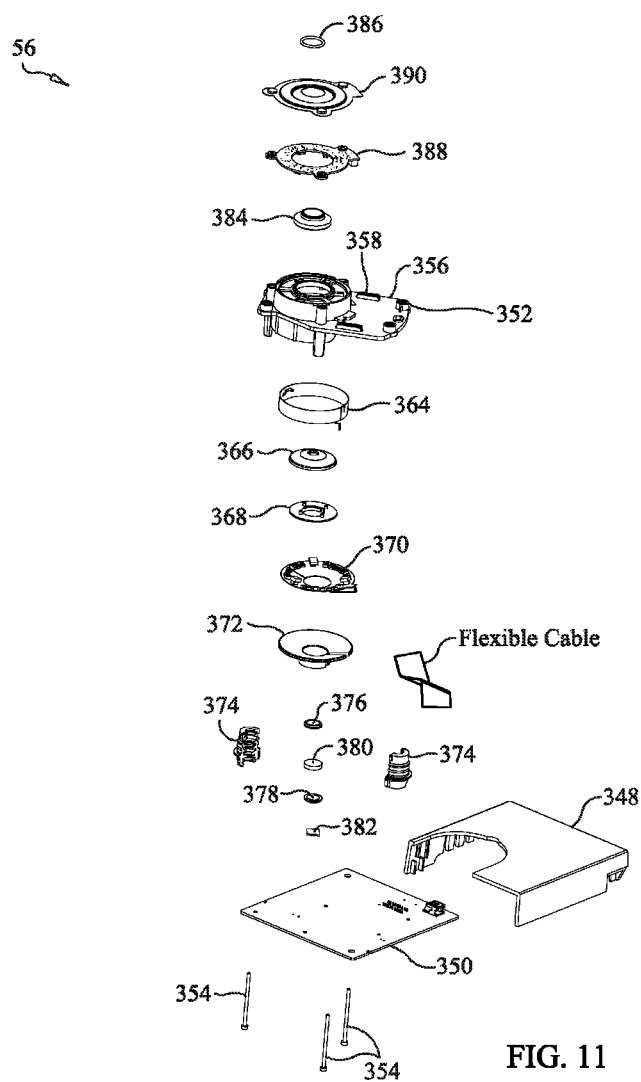
FIG. 11 is an exploded view of the optics module of the chemical analyzer of the present invention.
Figure 12:
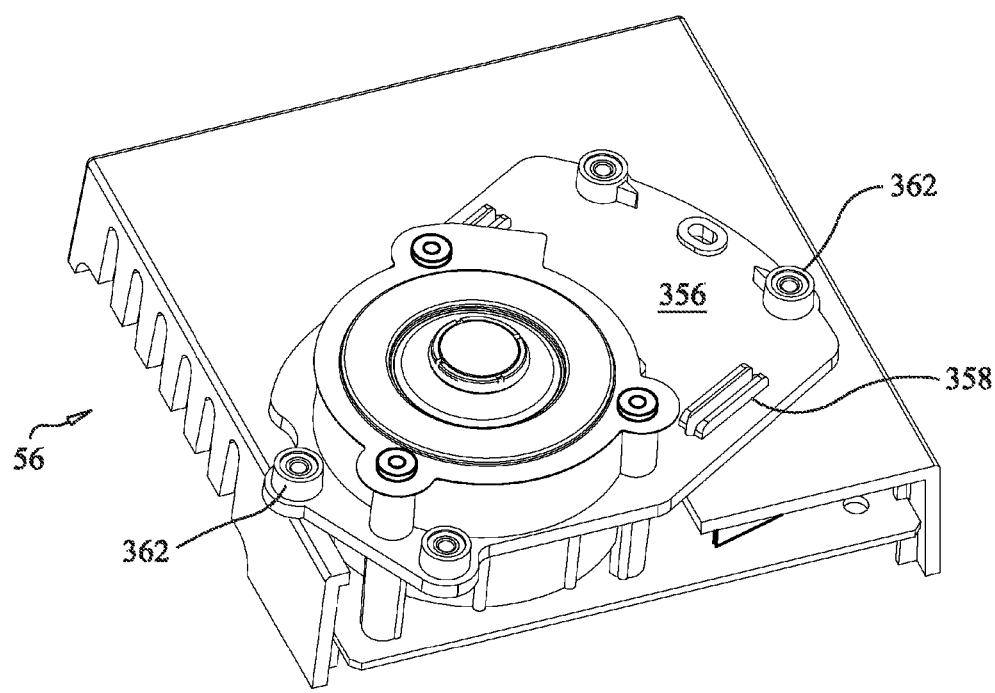
FIG. 12 is a perspective view of the assembled optics module of the chemical analyzer of the present invention shown in FIG. 11.
Figure 13:
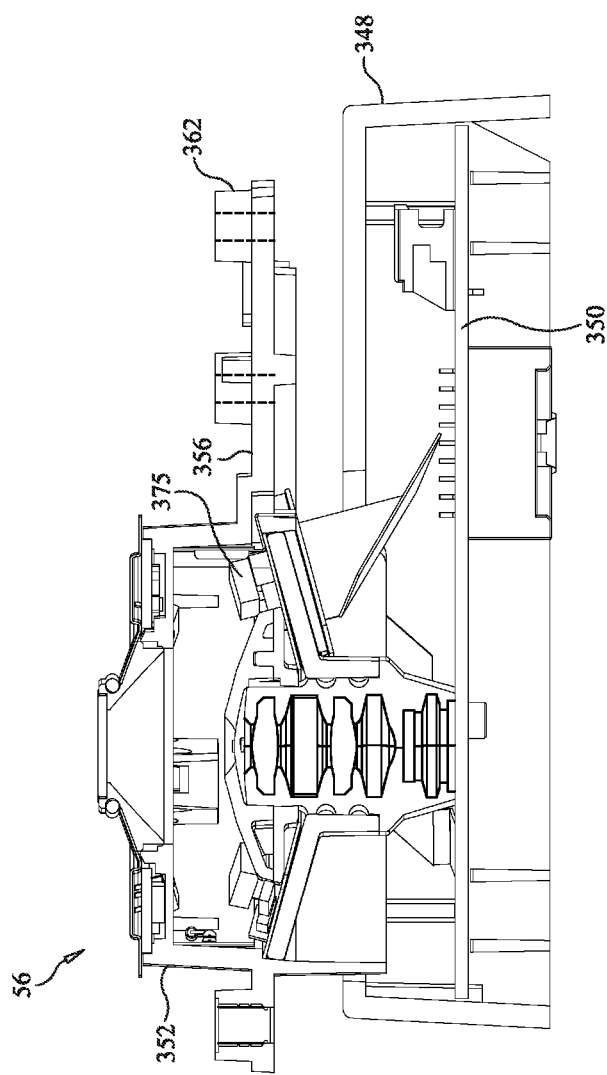
FIG. 13 is a longitudinal cross-sectional view of the assembled optics module of the chemical analyzer of the present invention shown in FIG. 12.

As described previously, the optics module 56 used in the analyzer 2 of the present invention combines reflectometer and fluorometer functions into one device, as shown in FIGS. 11-13 of the drawings. The optics module 56 is designed to be radially adjusted during assembly, as highly precise positioning of the optics module 56 in relation to the slide windows is important for accurate measurements.

A cavity heater inside the module 56 warms the components therein quickly. This feature ensures that the module is heated to a temperature conducive to the performance of the module. Although some heat from the heating ring 288 may reach the optics module 56, this collateral heat may not be enough to ensure a relatively rapid warm-up of the module; consequently, the optics module 56 is provided with its own heater, which may not be needed once the module is sufficiently warm.

A notch filter 380 between the two lenses 376, 378 filters out blue LED light used for exciting the fluorescence of electrolyte slides, allowing for the two modes of reading (i.e., reflectance and fluorescence) to exist in one module.

The illumination wavelengths for reflectance readings are preferably controlled by LED wavelength range specifications. In cases where the reflectance is significantly dependent on the illumination wavelength, a method called "wavelength compensation" can be employed to adjust the reflectance based on the measured wavelength emission characteristics of the ensemble of LEDs composing a given LED frequency band. This method is used to correct the $NH_3$ slide reflectances, although other chemistries, including $Ca^{2+}$, ALB (albumin), $Mg^{2+}$, lipase, and glucose, would also benefit from application of this method.

For fluorescence readings, the LED emissions of the 470 nm LEDs are shaped by colored glass filters mounted (by adhesive) directly to the LEDs.

It is possible to interrogate a reflectance sample slide with up to three different LED wavelength bands. Stated another way, with the chemical analyzer and optics module 56 of the present invention, it is possible to advance a slide to position it over the optics module 56; read the reflectance with the slide illuminated by one of seven wavelength bands; read the reflectance with the slide illuminated by a second of seven wavelength bands; read the reflectance with the slide illuminated by a third (or more) of seven wavelength bands; and advance the read slide and position the next slide over the optics module 56, and continue on in this fashion. This feature is used for obtaining the needed precision for ALT (alanine aminotransferase) by a "dual wavelength" read.

But, even more advantageously, with the combined optics module 56 of the present invention, and if so desired by the user, a fluorescence and a reflectance reading can be obtained from the same slide. In other words, with the combined optics module 56, it is also possible to advance a slide in the slide track 284 to position it over the optics module 56; read the reflectance with the slide illuminated by one of six (not blue at 470 nm) wavelength bands; read the fluorescence with the slide illuminated by the blue (470 nm) wavelength band; and advance the read slide and position the next slide over the optics module, and continue on in this fashion. The middle two steps may be performed in either order. Since the fluorescence readings take longer, it is preferred when measuring reflectance and fluorescence from one slide at a time to allow just one reflectance band reading with a fluorescence reading in order to maintain the carousel movement cadence.

The placement and board and viewing angle of the LEDs are designed to provide a maximally "flat"—consistent intensity—field of illumination. This illumination intensity is also self-referenced during every reading, in order to provide compensation for any shifts, sudden or gradual, of LED intensity.

The optics module 56 is designed to accommodate a number of self-tests, detecting and flagging noisy or malfunctioning photodiode sensors and "burned out" or dim LEDs. It also permits detection of the cleaning condition of the view window at the top of the module—providing readings of the white tile and the empty (no slide present) carousel segments, the latter with the evaporation caps 54 open. Because the optics module 56 detects the analyte concentration of a number of slides by a single "endpoint" reading, the exact reflectance detected should be consistent and stable from analyzer to analyzer—hence, it is preferred to conduct these window cleaning condition checks.

Also, the calibration of the optics module 56 is important for accurate readings. The optics module 56 can be calibrated by any user (with the addition of a white reference slide, and likely also a fluorescent reference slide) to accommodate changes in its sensitivity.

An advantageous feature of the chemical analyzer of the present invention is the combination of diffuse reflectance and front-surface fluorescence measurements in one module. The optics module 56 measures either reflectance or fluorescence along the same optical pathways and without the need for any moving parts. This combination of functions is achieved by four principal means:

1. Using a notch filter 380 to prevent diffuse reflectance of the selected excitation wavelength band (approximately 470 nm) from being detected to any significant extent by the photodiode sensor located on primary printed circuit board 350 of the optics module. The notch filter 380 filters out this band to greater than or equal to four optical density units, while passing at least about 95% of the diffusely reflected intensity of all other illumination wavelength bands (approximately 365, 405, 560, 588, 650, and 680 nm) provided by the optics module 56 through LEDs mounted on frustum printed circuit board 370. It also passes a sufficient fraction (preferably greater than about 50%) of the fluorescence emission intensity from the slides used for a fluorescence test;

2. Adding colored glass filters to further attenuate the higher wavelength emission of the 470 nm LEDs mounted on printed circuit board 370. Adhesive is used to adhere the rectangular box-shaped filters 375 to these LEDs;

3. Using relatively bright 470 nm LEDs. Generally, fluorescence detection requires a brighter light source than reflectance detection, due to various fluorescence quenching modes and the fluorescence quantum yields being less than 100% even in optimal conditions; and 4. Adding the functionality to adjust the sensitivity of the photodiode intensity detectors mounted on upper printed circuit board 388. This feature allows the illumination bands used for reflectance measurements to be detected at normal (high) gain. The gain setting in this case is the same as is used in the optics module described in U.S. Patent Application Publication No. 2010/0254854 and U.S. Pat. No. 7,616,317, the disclosures of which are incorporated herein by reference. But the added functionality allows the gains to be adjusted to preferably approximately ten times lower, allowing measurement of the higher intensity of the 470 nm LEDs used as the excitation source for the fluorescence measurements.

Thus, the same optical path is used, the same field of view, working distance and, as described in U.S. Pat. No. 7,616,317, a "substantially homogeneous irradiance", is provided by the optics module 56 for both reflectance and fluorescence readings. In addition, the control electronics allows for both reflectance and fluorescence measurements to be made, one after the other, of the same slide.

The electronic and software control method is also essentially identical for each type of measurement, reflectance and fluorescence. More specifically, the same data acquisition and processing of data from preferably four photodiode sensors is used in the optics module 56. The voltage output from a photodiode sensor transimpedance preamplifier on the primary printed circuit board 350 is divided by the weighted sum of the voltage outputs of photodiode sensor transimpedance preamplifiers on the upper printed circuit board 388. In this way, an intensity-corrected reflectance or fluorescence signal is obtained. The only difference between the two measurement types is that, as noted above, the gains on the transimpedance preamplifiers on the upper printed circuit board 388 are set to approximately ten times lower during fluorescence readings.

Also, the same calibration method for reflectance and fluorescence measurements is used. The drive current for each LED in a given wavelength band on printed circuit board 370 is optimized to provide, as described in U.S. Pat. No. 7,616,317, "substantially homogeneous irradiance" of a reflectance ("white reference") or fluorescence calibration slide. The weighting factors for the photodiode sensors ("intensity sensors") on printed circuit board 388 are also set according to U.S. Pat. No. 7,616,317. The only difference between the calibrations of the two measurement types (i.e., reflectance and fluorescence) comes at a higher data processing level, where a different arbitrary multiplier is applied to the fluorescence data.

Figure 22:
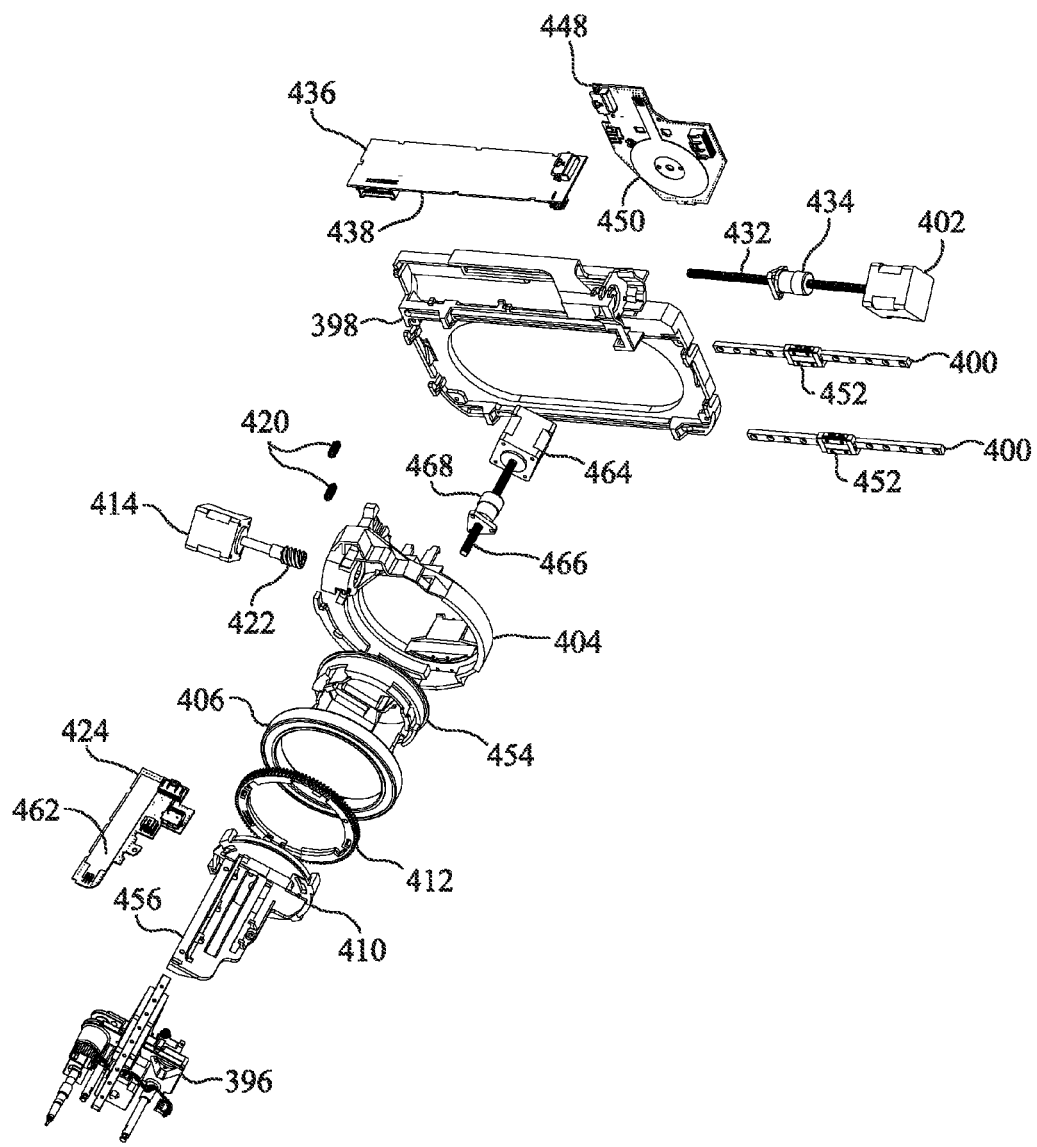
FIG. 22 is an exploded view of the robot assembly forming part of the fluid handler unit of the chemical analyzer of the present invention.

The fluid handler assembly 50, with its robot and pump assembly 396, will now be described. Reference should be had to FIGS. 22, 23 and 35-62 of the drawings, and especially FIG. 22, which shows an exploded view of the fluid handler robot assembly 50, with the pump assembly 396 shown complete and unexploded, to facilitate an understanding of the components comprising the robot portion of the fluid handler unit. Some of the features of the robot assembly of the fluid handler unit 50 will be summarily described first.

The robot "base" 398, which is actually the uppermost portion of the fluid handler unit 50, as the fluid handler unit is suspended within the interior cavity of the chemical analyzer 2, is preferably a molded plastic frame onto which linear rails 400 mount. These rails 400, along with their requisite motor 402, provide the basis of movement of the robot and the pump assembly 396 along the X-axis.

Mounted to each linear rail 400 is a molded plastic bearing holder 404, which holds preferably a 90 millimeter ball bearing ring assembly 406, and locking structure 454 for attaching the bearing holder 404 to the hub 410 of the robot, a worm wheel 412, and the central hub 410 of the robot. There is a second motor 414 which is attached to one side of the bearing holder 404 and which is used to effect movement of the robot assembly 50, and the pump assembly 396 mounted thereon, in the θ direction (that is, in the horizontal, X-Y plane).

Rotational movement in the θ direction is provided by an anti-backlash worm wheel 412. This wheel 412 comprises two smaller wheels 416, 418 co-axially arranged. One wheel 416 is fixed and the other wheel 418 is not. The movement of the wheel 418 that is not fixed is limited by a stiff spring. A warm gear 422 mounted on the shaft of the second motor 414 engages the fixed and movable portions 416, 418 of the worm wheel assembly 412 to effect rotational movement of the robot of the fluid handler, and the pump assembly 396 mounted thereon, in the θ direction. The anti-backlash quality of the worm wheel assembly 412 is based on the fact that the two wheels 416, 418 comprising the assembly will, because of the spring-loaded nature of the bottom wheel 418, pinch the ridges of the worm gear teeth such that there is not a gap between the points of the worm gear teeth and the teeth of the worm wheels 416, 418.

Also attached to the hub 410 is a printed circuit board 460 for Z-axis (upward and downward) movement. There are printed circuit boards on the fluid handler unit 50, and in particular the robot thereof, for each of the three axes of movement, and this reduces the overall number of electrical cables required, provides a mounting for linear and circular potentiometers which are used to determine the position of the robot and pump assembly 396 of the fluid handler 50 in the three planes of movement, also provides a mounting for hall effect sensors, and generally provides for easier cable routing. Ball plungers 420 are used as the wiper arm for these potentiometers. A more detailed explanation of the components of the robot assembly of the fluid handler unit 50 will now be provided. It should be noted that, on some of the figures, certain components have been omitted to facilitate an understanding of the operation and structure of the fluid handler unit 50.

The fluid handler unit 50, and in particular, the robot assembly thereof, includes a robot base 398 which is mounted to the upper portion of the chassis 40 of the analyzer 2. The robot base 398 includes a main body 426 which is generally planar and rectangular in form, and includes an oblong opening 428 formed through the thickness thereof. The center hub 410 for the robot and several other components of the robot assembly move through this oblong opening 428 in the robot base 298 in the X-direction. The robot base 398 includes a cantilevered bracket 430 extending therefrom for mounting a motor assembly to effect movement of the robot, and the pump assembly 396 attached thereto, in the X-direction. More specifically, on this bracket 430 is mounted a motor 402, whose shaft is connected to a lead screw 432. On the lead screw is mounted an anti-backlash coupling 434 which, as the lead screw 432 is turned in either direction by the motor 402, reciprocatingly moves axially on the lead screw 432.

There is also a printed circuit board 436 supported by the robot base 398 on its bottom side and above the lead screw 432 of the X-direction drive motor 402. This printed circuit board 436 includes electrical circuitry, but further has mounted thereon a linear potentiometer 438. The linear potentiometer 438 varies in resistance at its wiper arm in correspondence with the position of the robot, and the pump assembly 396 mounted thereon, in the X-direction. Signals from the printed circuit board 436, including resistance measurements of the linear potentiometer 438, are provided to the controller 42 of the analyzer 2 so that the controller 42 knows the precise position in the X-direction that the robot and the pump assembly 396 mounted thereon are in.

A bearing holder 404 forms the upper portion of the movable section of the robot assembly. It serves several purposes. First, it includes a bracket 440 that extends upwardly from the main circular portion 442 of the bearing holder 404, and this bracket 440 is affixed to the anti-backlash coupling 434 on the lead screw 432 used to move the robot of the fluid handler unit 50 in the X-direction within the oblong opening 428 formed in the robot base 398.

Second, there is a leg 444 which extends downwardly from the main cylindrical portion 442 of the bearing holder 404. A second motor 414, which is used to effect rotational movement of the robot in the θ direction, is held in place by this leg 444. Third, the bearing holder 404, as its name implies, holds a ring-shaped ball bearing assembly 406 to provide frictionless rotational movement to the robot.

Fourth, the bearing holder 404 includes upstanding resilient legs 446 extending from the cylindrical main portion 442 of the holder. These legs 446 hold in place a printed circuit board 448. The printed circuit board 448 includes electronic circuitry, as well as having mounted thereon a circular potentiometer 450 which is used to sense the rotational position of the robot. Signals from this printed circuit board 448 which correspond to the resistance measured by this potentiometer 450 are provided to the controller 42 of the analyzer 2 so that the controller 42 knows exactly what rotational position the robot of the fluid handler unit 50 is in.

There are a pair of linear rails 400 which are affixed to the bottom surface of the robot base 398, on opposite sides of the oblong opening 428 formed through the base and which extend laterally, in the X-direction, on the base. Each linear rail 400 includes a slide block 452 mounted on it, and the bearing holder 404 is affixed to these slide blocks 452. In this way, the bearing holder 404 and the other components of the robot assembly, and the pump assembly 396 mounted thereto, of the fluid handler unit 50 may move reciprocatingly in the X-direction within the oblong opening 428 of the robot base 398 on the linear rails 400 with uniformity and with no appreciable twisting when driven by the X-direction motor 402 and lead screw 432 mounted on one side of the robot base 398.

The robot assembly of the fluid handler unit 50 further includes a cylindrical center hub 410, a locking hub cap 454 which mates with the center hub 410 and is held in place by the bearing holder 404, the ring-shaped bearing 406, held in place within the bearing holder 404 and surrounding the locking hub cap 454, and a worm wheel assembly 412, comprised of two co-axially mounted upper and lower wheels 416, 418. A second motor 414 is held in place by the bearing holder 404. This second motor 414 is used to effect rotational movement of the rotor, and the pump assembly 396 mounted thereon, in the θ direction (that is, the X-Y, horizontal plane). This second motor 414 includes a shaft on which is mounted a worm gear 422, which worm gear 422 engages the worm wheels 416, 418 of the worm wheel assembly 412. The motor mounting leg 444 of the bearing holder 404 positions the θ-direction drive motor 414 at an angle such that the worm gear 422 engages the teeth of the worm wheels 416, 418 tangentially.

The center hub 410 of the robot of the fluid handler unit 50 includes a bracket 456 extending downwardly from the upper cylindrical portion 458 thereof. This bracket 456 is provided for mounting a third printed circuit board 460 as well as the pump assembly 396 of the fluid handler unit 50. This third printed circuit board 460 also includes electronic circuitry and another linear potentiometer 462 mounted on it. This linear potentiometer 462 is used to determine the position in the Z-axis (upward and downward) of certain components of the robot assembly and the pump assembly 396 mounted thereto. Such components include a pair of downwardly extending arms 202 which are used to actuate the slide inserter mechanism 51, the slide eject mechanism 58, and the evaporation cap open and close mechanism 52, each of which has been described previously. As will be explained in greater detail when the pump assembly 396 is described, these components, and the pump assembly, are moved in the Z-direction by a third motor 464. This third motor 464 is mounted within the center portion of the bearing holder 404, and its shaft is connected to a downwardly extending lead screw 466 on which an anti-backlash coupling 468 is driven axially as the shaft of the motor 464 turns. This coupling 468 is connected to the pump assembly 396 to effect movement of the pump assembly, and the elongated arms 202 of the robot, in the Z-direction.

Figure 23:
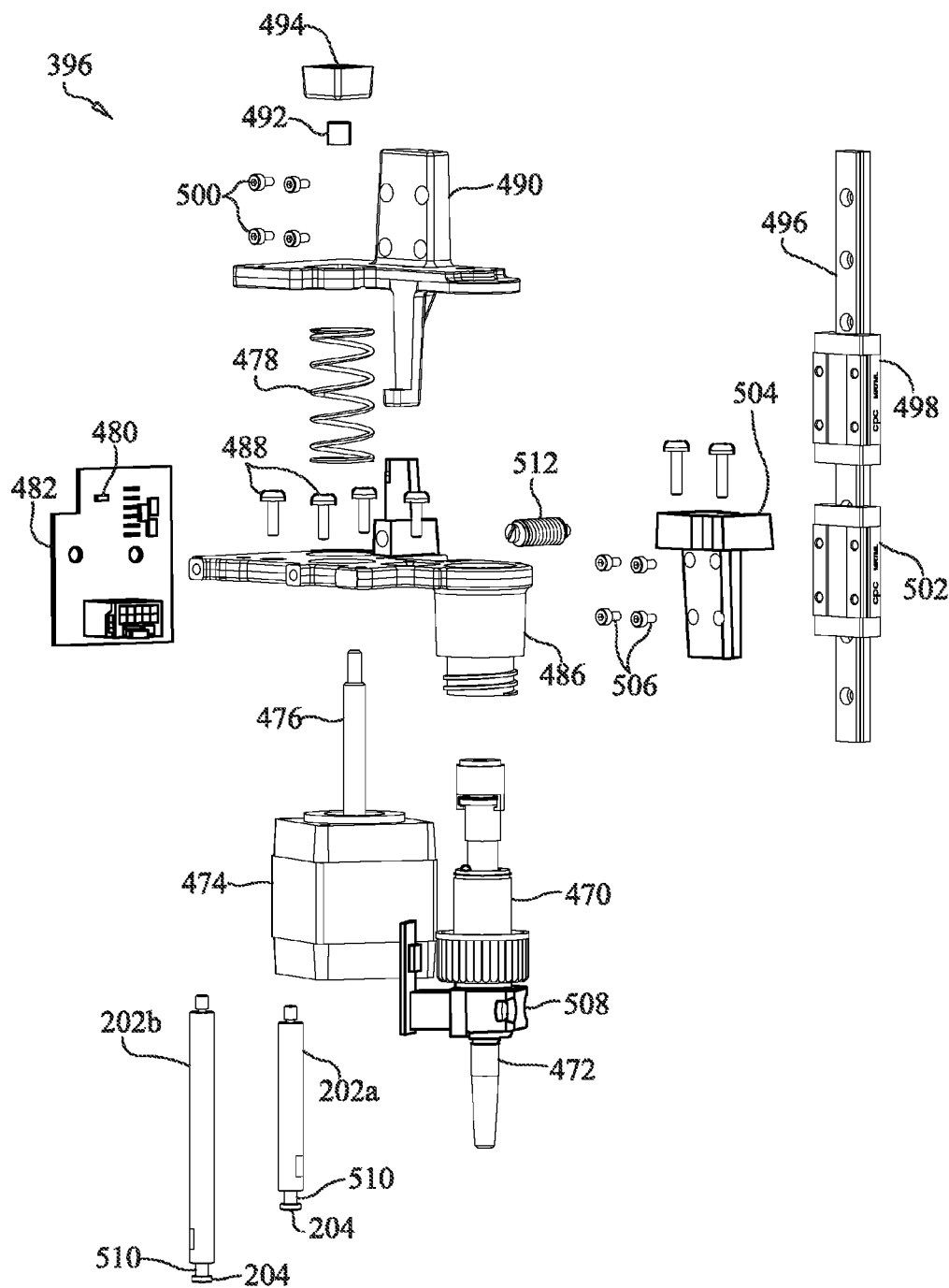
FIG. 23 is an exploded view of the pump assembly forming part of the fluid handler unit of the chemical analyzer of the present invention.

An exploded view of the pump assembly 396 is shown in FIG. 23 and will first be summarily described. Reference should also be had to FIGS. 56-62, which show portions of the pump assembly. The pump assembly 396 includes a liquid sample pump 470 having a cylinder and a piston movable within the cylinder connected to a proboscis 472 on which is removably mounted a disposable pipette tip. The piston and cylinder are precision ceramic components. Together, these two pieces provide an air tight connection without need for a seal. A stepper 474 motor on the pump assembly 396 engages a non-captive lead screw 476, which, during fluid dispense, pushes down on the piston (i.e., moves the piston in a vertically downward direction). During aspiration, the motor 474 moves the lead screw 476 so that the piston can be elevated by a spring 478 built into the pump 470.

There are two elongated arms 202a, 202b situated at the base of the pump 470, as mentioned previously. Each arm 202a, 202b has a different axial length. The shorter arm 202a is used for engaging and actuating the evaporation cap opening and closing mechanism 52, and the longer atm 202b is used for engaging and actuating the slide eject mechanism 58 and the slide insertion mechanism 51.

There is a hall effect sensor 480 mounted on a printed circuit board 482 affixed to the pump assembly 396, and a magnet 484 mounted on the pump 470 itself (or on a bracket supporting the pump). The hall effect sensor 480, and the magnet 484, are used to identify the pump's home position to the controller 42, and in particular, the control module, of the analyzer 2.

There is also a pressure sensor at the end of the pump's proboscis 472. This sensor uses a respiratory action to determine the fluid level within either a sample cup or the centrifuge rotor. This same pressure sensor, in concert with the control module of the analyzer controller 42, may be used to communicate the topography of the surface on which it finds itself. In other words, the pressure sensor may be used by the analyzer 2 to determine the location, absence or presence of various surfaces and components within the analyzer 2. For example, the controller 42 may direct the robot of the fluid handler 50 to move the pump 470 and its proboscis 472 towards the vertical actuators of the slide eject mechanism 58 and the slide inserter mechanism 51. As the disposable pipette tip on the end of the proboscis 472 approaches closely the top free ends of these actuators, the resistance caused by the surfaces to air aspirated through the orifice of the pipette tip will increase and be sensed by the pressure sensor. The sensor sends signals corresponding to the pressure detected to the controller 42 of the analyzer 2 and, from this, the analyzer 2 can determine and store in memory the coordinates of various components of the analyzer 2, including consumables loaded therein, and to verify or correct prior measurements and to calibrate the instrument.

In the same manner, the pressure sensor on the pump assembly may be used to determine if clots are present in a blood sample. For example, the pipette tip may be lowered into a sample of blood held by a sample cup or centrifuge rotor loaded onto the consumables manager drawer 32. By having the pump 470 continually conducting aspiration routines, the pressure sensor will detect an increase in pressure if the pipette tip orifice contacts a blood clot in the sample. This information is conveyed to the controller 42 of the analyzer 2, which will alert the user to the presence of clots in the blood sample (a fresh blood sample may then be required for proper testing).

As can be seen by the figures, the pump has a folded over design in that the pump motor 474 is not co-axially mounted over the pump cylinder as is described in U.S. Patent Application Publication No. 2010/0254854, but rather the pump cylinder and pump motor 474 are positioned side-by-side. This arrangement reduces the overall axial length of the pump assembly 396, as well as the height required by the analyzer 2.

The pump stepper motor 474 is affixed to a pump lower mounting plate 486 using four machine screws 488 which are fastened to the housing of the pump motor 474. The lead screw shaft 476 of the pump motor 474 passes through an opening formed through the thickness of the pump lower mounting plate 486 and into an opening in a pump upper mounting plate 490. The pump upper mounting plate 490 can move relative to the pump lower mounting plate 486, and is biased away from the pump lower mounting plate 486 by a compression spring 478 surrounding the motor lead screw 476. A brass insert 492 is fitted into the opening in the pump upper mounting plate 490 through which the lead screw 476 of the motor 474 passes. The top surface of the pump upper mounting plate 490 is formed with a square or rectangular recess in which is received a pump motor nut 494 having a similar shape as the recess so that it will not turn on the upper mounting plate 490. The pump motor nut 494 is internally threaded and receives therethrough the lead screw 476 of the pump motor 474.

When the pump motor 474 is energized to cause its lead screw 476 to rotate in a first direction, its cooperation with the pump motor nut 494 will cause the pump upper mounting plate 490 to move downwardly toward the lower mounting plate 486 against the bias of the compression spring 478. When the pump motor 474 turns its lead screw 476 in the opposite direction, the upper mounting plate 490, biased by the compression spring 478, will move away from the lower mounting plate 486.

There is a linear rail 496 that is mounted on the downwardly extending bracket 456 of the robot center hub 410. A first movable mount 498 is situated on this linear rail 496, and the pump upper mounting plate 490 is secured to this first movable mount 498 by a plurality of machine screws 500. There is also a second movable mount 502 situated on this rail 496 and disposed below the first movable mount 498. A long carriage 504 is used to secure the pump lower mounting plate 486 to this second movable mount 502, again by machine screws 506. Returning briefly to the exploded view of the robot assembly of the fluid handler 50 shown in FIG. 22, it will be seen that the anti-backlash coupling mounted 468 on the Z-axis lead screw 466 is secured to the top surface of the pump lower mounting plate 486. When the Z-direction drive motor 464 turns its associated lead screw 466 in either direction, this will cause the pump lower mounting plate 486 to move reciprocatingly on the linear rail 496 of the pump assembly 396 in an upward and downward direction, with the pump upper mounting plate 490 moving with it on the linear rail 496.

The pump assembly 396 is mounted on the underside of the pump lower mounting plate 486. It includes the cylinder, the piston movable within the cylinder, and a proboscis 472 extending downwardly from one axial end of the pump cylinder. The proboscis 472 is secured to the other components of the assembly by a mounting block 508.

The piston inside the cylinder of the pump 470 is connected by a pin to the upper mounting plate 490. Therefore, movement of the upper mounting plate 490 relative to the lower mounting plate 486 (on which the pump cylinder is secured) will move the piston axially within the cylinder. The internal bore of the cylinder in which the movable piston resides is in fluid communication with an axially extending bore through the proboscis 472, the free end of which a disposable pipette tip is mounted on. The pipette tip is tapered towards its distal end. There is an orifice located at this distal tip. Movement of the piston within the cylinder of the pump will cause fluid, either air or liquid, to be aspirated or expelled into or out of the disposable pipette tip affixed to the end of the proboscis 472.

Also affixed to the bottom surface of the pump lower mounting plate 486 and extending outwardly (downwardly) therefrom are two spaced apart robot arms 202a, 202b. As mentioned previously, these arms 202a, 202b are used to actuate other mechanisms in the analyzer 2, such as the slide eject mechanism 58, the slide inserter mechanism 51 and the evaporation cap open and close mechanism 52. Each arm 202a, 202b has a free end formed with a reduced diameter portion 510 which leads to a larger diameter end plate 204, and this end plate 204 is used to mechanically engage the actuators on the slide eject mechanism 58, the slide inserter mechanism 51 and the evaporation cap open and close mechanism 52.

The pump lower mounting bracket 486 also has affixed to it a printed circuit board 482 on which electronic circuitry and connectors are mounted. On one side of this printed circuit board 482 is also mounted a hall effect sensor 480. The hall effect sensor 480 works in conjunction with a magnet 484 situated on a facing edge on the pump upper mounting plate 490 so that the home position of the pump 470 may be determined by the controller 42 of the analyzer 2.

There is also a ball plunger 512 which is threaded into a receiving bore formed horizontally through a block 514 situated on the top surface of the pump lower mounting plate 486. This ball plunger 512 acts a wiper for the linear potentiometer 462 situated on the printed circuit board 460 of the robot assembly that is mounted to the bracket 456 of the robot center hub 410, and is used to determine the relative position of the pump lower mounting plate 486 and, indirectly, the robot arms 202a, 202b extending therefrom.

The preferred shape of the disposable pipette tips which are removably mounted on the end of the proboscis is shown in FIGS. 74 and 75 of the aforementioned U.S. Patent Application Publication No. 2010/0254854, the disclosure of which is incorporated herein by reference. As shown in these figures of the aforementioned published U.S. application, there is a "tip shucker" in the chemical analyzer disclosed therein which is used to remove tips after their use from the end of the proboscis. The proboscis, with the disposable tip mounted thereon, is moved between the prongs of a forked member, which forces the pipette tip to slip off the distal end of the proboscis and fall into a used pipette tip/slide drawer.

Although this structure for removing pipette tips from the proboscis works quite well, the analyzer 2 of the present invention includes an improved mechanism for removing the disposable pipette tips from the proboscis 472.

More specifically, and as shown in FIGS. 63-67 of the drawings, the mechanism for removing disposable tips from the end of the proboscis 472 is preferably formed as an integral part of the left side of the chassis 40, when the analyzer 2 is viewed from the front. The tip removal member 88 projects into the interior cavity defined by the housing from the inner surface of a vertical wall of the chassis 40. It is generally in the shape of a clevis, having two parallel, spaced apart legs 516 between which the disposable tip on the end of the proboscis 472 is positioned by the fluid handler unit 50. The sides of the legs 516 which face each other include a recessed area 518, the spacing between the recessed areas 518 of the two legs 516 being just slightly greater than the diameter of the cylindrical larger axial end of the pipette tip so that this portion of the pipette tip may be closely received and held between the legs 516 without falling when the pipette tip is loosened from the end of the proboscis 472.

When removing a disposable tip from the proboscis 472, the fluid handler 50 moves toward the side of the analyzer 2 where the tip removal structure 88 is located, and positions the pipette tip through the open end of the structure 88, with the upper cylindrical portion of the tip situated between the recessed areas 518 of the protruding legs 516. The fluid handler 50 then moves slightly upwardly in the Z-direction to gently dislodge, without removing, the pipette tip from the proboscis 472. After that, the fluid handler 50, with the loose tip still thereon, moves a predetermined distance away from the tip removal structure 88 so that the disposable pipette tip, loosely held between the parallel legs 516, is moved out from between them. The tip may then fall through the opening 520 formed in a raised portion 522 of the base of the chassis 40 below the tip removal structure 88 and into the waste drawer 26 located beneath the opening 520.

Removal of the tip from the proboscis 472 using such structure is relatively gentle and results in no spillage or splashing of any liquid sample adhering to the disposable tip.

As can be seen from the foregoing description, the chemical analyzer 2 of the present invention includes many improvements over convention analyzers, some of which are summarized below.

Optics Alignment—Method for Mechanical Adjustment to Align Optics Module

Radial alignment of the optics module 56 is an important feature for proper assay precision. In the chemical analyzer 2 of the present invention, this alignment is achieved through the use of a cam to position the optics module 56 along two dedicated rails in the system. Once alignment is achieved, the module is locked down through a series of four screws.

Carousel Drive

The slide carousel drive system in the chemical analyzer 2 of the present invention features a plastic gear box designed to minimize thermal transmission from the drive motor to the hub on which the slide carousel 48 is mounted and, therefore, the slide incubator. Additionally, this gear box is matched to the index ratio of the carousel. The gear box is preferably a 19:1 gear box to match the index segments or stop positions of the driven carousel.

Fluid Handler System

Folded Pump Design

In order to minimize vertical height in the system, the fluid pump is folded approximately in half such that the drive motor and piston are parallel to each other.

Motor Dampening in the Pump Design

Because the pump assembly is folded in half, it includes a cantilever drive system to actuate the piston pump. To minimize or avoid any transmission of irregularity (runout) from the drive into the piston movement and thus dispensed volume, the design of the pump assembly incorporates a balance between flexibility in the joints to a spring dampening of the motor motion.

Rotational Third Axis in a Robot System

The metering system allows for positioning along three axes of motion based on the size and layout of the consumables drawer. The robot of the fluid handler unit features a rotational axis of motion in addition to two linear axes. The rotational axis (theta) provides Y axis positioning front to back in the analyzer 2. This results in a reduction of space for the robot and short cantilevers for the operating parts subject to the highest forces.

Finger Actuators for Mechanical Operations

The chemical analyzer 2 of the present invention implements a strategy to reduce the number of motors in the system. This is accomplished by a using the Z-axis linear motion of the robot of the fluid handler in order to drive several of the required motions of the system. Two rods extending from the robot engage with mechanical actuators that translate the motion of the robot to achieve: slide loading, slide ejecting, evaporation cap opening, evaporation cap closing and consumable drawer locking.

Positional Sensors for Safe Travel of Fluid Handler System

Given the compact nature of the chemical analyzer 2 of the present invention, steps are taken to avoid collision caused by the robot not being driven in the right directions. Linear potentiometers are used to identify the absolute position of the end effectors (i.e., the robot arms) of the fluid handler robot. This data is fed into an algorithm that will identify the proper motions to drive the robot around potential collisions.

Reagent Consumables

Reagent Consumable Drawer Receivers

The consumables manager drawer 32 is constructed to receive the fluid packs from the reagent consumables used for TT4, PhBr, and other assays. The spacing of the receivers or wells in the drawer prevents misplacement of the consumables.

Consumables Incubation

Reagent consumables are incubated directly in the drawer. The consumable reagent packs fit into heated receptacles which act to incubate the fluid in the consumables to the proper temperature.

Actuation Mechanisms

Slide Inserter Mechanism

The slide inserter mechanism features a cam motion to load slides into the carousel. The down motion imparted through the robot is translated into a motion into the slide carousel 48 through a gear rack mechanism. A leaf spring with protruding forks or fins drives the slide into the carousel. The spring rides in a groove as the slide is driven into the carousel. As the slide is driven in, the leaf spring transitions out of the track such that the mechanism returns on a different path, preventing the forks or fins from protruding on the return stroke. In this manner, the stack of slides can be loaded from the bottom without disturbing the slides above the loaded slide.

Cap Open and Close Mechanism

The evaporation cap open and close mechanism achieves the opening and closing of the evaporation caps 54 within one up and down motion of the robot. Through a series of cams and springs, the downward motion is translated into motion to push the evaporation cap open. As the robot returns to the neutral position (back up), the same mechanism closes the evaporation cap. Additionally, motion of the robot arm approximately halfway down opens the cap without closing it on the return stroke.

Whole Blood Separator Drive

For the chemical analyzer 2 of the present invention, the whole blood separator drive features a zero insertion force, high speed chuck that interfaces with the whole blood separator consumable (i.e., the centrifuge rotor). The chuck is preferably a solid machined metal piece that is manufactured to be a close fit with the inner diameter of the centrifuge rotor on its bottom side. The user places the centrifuge rotor onto the chuck and gravity causes the centrifuge rotor to slide into place on the chuck. As the chuck rotates, friction between the chuck and the centrifuge rotor causes the rotor to remain in place and spin with the chuck. This feature is a simple design without any side actuations (spring fingers, etc.) targeted at holding the centrifuge rotor down. Since there are none of these extra forces, placement and removal of the centrifuge rotor from the chuck is facilitated for the user.

Engager

As described previously, the engager is a mechanical part in the analyzer 2 which serves as the drawer lock, separator splash cover, fluid pack hold down, slide cover, slide load weight, and in situ vision alignment check. The engager is a multi-featured part that spans the width of the consumables manager drawer 32. When the part is raised, the drawer is unlocked, but when lowered, it engages with the chassis 40, the drawer and the lift door to lock these three parts together and prevent the opening of the drawer and accessing the interior of the analyzer 2. Also, when the engager is lowered, its parts cover the separator rotor for splash protection, cover the fluid packs to hold them down, cover the slides to provide a top slide cover and provide a slide weight to aid in slide loading. Also, the engager is marked to provide a vision system reference for alignment purposes.

Gentle Release Tip Shucker

In the chemical analyzer 2 of the present invention, the improved design of the tip shucker eliminates any shock forces to the disposable pipette tip during removal thereof to avoid residual fluid in the tip splashing about and entering the pneumatic part of the system which could then subsequently lead to errors due to blockages and obstruction in the lines. The analyzer 2 of the present invention includes a gentle release tip shucker. In this design, the disposable pipette tip is positioned in a retaining part with a gap larger than the shoulder or larger diameter axial upper end of the pipette tip. The tip is then raised such that the proboscis disengages with the tip, but the tip is still retained by the shucker component. The proboscis is then moved out of the shucker and moves the tip with it, and allows the tip to drop into the waste receptacle.

Vision System

The vision system in the chemical analyzer 2 of the present invention includes a one or more cameras. One camera is placed on the robot so that it may be positioned for views of and around the consumables manager drawer 32.

The camera can be positioned in the X, Y and Z axes of the analyzer 2 to center and focus on different areas of the analyzer 2.

Primary Vision Functions

The primary functions of the vision system are to identify the consumable states for the consumables manager drawer 32. This includes the absence/presence detection of tips, separator rotor, sample cup, test slides, dilution cups and reagent consumables. Additionally, for the reagent consumables, the vision system identifies the type and lot of the reagent by reading the barcodes thereon. Detection is achieved by positioning the camera, capturing an image and then using feature recognition to identify the presence or absence of the consumable.

Sample Quality Detection

The vision system of the analyzer 2 can also be used to take an image of the sample, and the color or contrast of the sample can be used to detect sample quality such as hemolysis, lipemia or clotting.

Mechanism Positioning (Engager)

Lastly, the vision system used in the analyzer 2 of the present invention can be used for absolute positioning of the robot in the system. It can be used to capture pictures of the instrument and use patterns in the image to determine the robot position and calculate trajectories for the robot from those positions. The vision system can also be used for feedback for proper motion of the robot. The vision system is also used to identify if the engager mechanism has been placed properly on the consumables manager drawer 32 for error detection and calculation.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A medical apparatus for analyzing fluid samples comprising:
    a. an outer casing, the outer casing defining an interior cavity;
    b. a slide loading mechanism disposed within the interior cavity of the outer casing for loading fluid analysis slides;
    c. a slide ejecting mechanism disposed within the interior cavity of the outer casing for ejecting fluid analysis slides;
    d. an evaporation cap opening mechanism disposed within the interior cavity of the outer casing for opening an evaporation cap;
    e. an evaporation cap closing mechanism disposed within the interior cavity of the outer casing for closing an evaporation cap;
    f. a consumables manager drawer, the consumables manager drawer being received by an opening formed in the outer casing;
    g. at least one camera disposed within the interior cavity of the outer casing;
    h. a fluid handler unit disposed within the interior cavity of the outer casing, the fluid handler unit including a robot assembly having portions thereof which are movable within the interior cavity relative to the outer casing, the fluid handler unit further including a fluid pump assembly mounted on the robot assembly and at least one elongated robot arm coupled to the fluid pump assembly, the fluid pump assembly movable within the interior cavity of the outer casing, the movable portions of the robot assembly being movable in an X-Z plane and a Y-Z plane, and being arcuately movable in an angular direction theta within an X-Y plane, the at least one elongated robot arm moving at least arcuately with the fluid pump assembly and engaging at least two of:
        i. the slide loading mechanism to load fluid analysis slides;
        ii. the slide ejecting mechanism to eject fluid analysis slides;
        iii. the evaporation cap opening mechanism to open the evaporation caps; and
        iv. the evaporation cap closing mechanism to close the evaporation caps;
    i. an optics module, the optics module being in optical communication with at least one fluid analysis slide and conducting at least one of reflectance and fluorescence measurements on the at least one fluid analysis slide; and
    j. a controller, the controller including electronic circuitry, the electronic circuitry being in electrical communication with at least one of the optics module, the consumables manager drawer, the robot assembly and the fluid pump assembly.

2. The apparatus of claim 1, wherein the at least one camera is mounted on the robot assembly and movable therewith within the interior cavity of the outer casing to be positionable to view at least the consumables manager drawer and generating image signals thereof and providing the signals to the controller.

3. The apparatus of claim 1, wherein the at least one elongated robot arm engages at least one of the slide loading mechanism, the slide ejecting mechanism, the evaporation cap opening mechanism and the evaporation cap closing mechanism by moving in a linear, Z-axis motion.

4. The apparatus of claim 1,
    wherein the optics module is disposed within the interior cavity of the outer casing; and
    wherein the optics module is a combined reflectometer and fluorometer and includes:
    a housing, the housing defining an interior chamber;
    a first photodiode sensor situated within the interior chamber of the housing, the first photodiode sensor measuring light reflected from or fluoresced by a fluid analysis slide in optical communication with the optics module;
    a printed circuit board situated within the interior chamber of the housing, the printed circuit board having a frusto-conical shape and defining a central opening, the central opening being in axial alignment with the first photodiode sensor;
    a plurality of light emitting diodes mounted on the printed circuit board, the light emitting diodes being selectively energizable to emit light and illuminate the fluid analysis slide in optical communication with the optics module; and
    a notch filter, the notch filter being situated in optical alignment with the first photodiode sensor, the notch filter filtering out light emitted by at least one light emitting diode at a fluorescence excitation wavelength.

5. The apparatus of claim 4, wherein the notch filter filters out light at a fluorescence excitation wavelength of about 470 nanometers.

6. The apparatus of claim 4, wherein the optics module further includes:
    a heating element, the heating element being situated within the interior chamber of the housing.

7. The apparatus of claim 4, wherein the optics module further includes:
at least one second photodiode sensor situated within the interior chamber of the housing, the at least one second photodiode sensor measuring the intensity of light emitted by the selectively energized light emitting diodes.

8. The apparatus of claim 4, wherein the optics module further includes:
a lens holder situated within the interior chamber of the housing and in optical alignment with the first photodiode sensor; and
a lens/filter assembly mounted on the lens holder, the lens/filter assembly including an upper lens, a lower lens and the notch filter interposed between the upper lens and the lower lens.

9. The apparatus of claim 4, wherein at least one light emitting diode emits light at a fluorescence excitation wavelength of about 470 nanometers; and
wherein the optics module further includes a filter mounted directly on the at least one light emitting diode that emits light at the fluorescence excitation wavelength.

10. The apparatus of claim 9, wherein the filter which is mounted on the at least one light emitting diode is a colored glass filter; and
wherein the colored glass filter is mounted on the at least one light emitting diode with an adhesive.

11. The apparatus of claim 4, which further comprises:
a normalizer casting plate disposed within the interior cavity of the outer casing, the optics module being adjustably mounted on the normalizer casting plate; and
wherein the optics module further includes:
an optics module plate, the optics module plate extending radially outwardly from the housing of the optics module, the optics module plate having a surface and including at least one set of parallel, spaced apart, elongated ribs protruding outwardly from the surface thereof, the normalizer casting plate having a surface and including at least one elongated projection situated on the surface thereof, the ribs of the at least one set of ribs of the optics module plate of the optics module receiving therebetween the at least one elongated projection of the normalizer casting plate, the at least one elongated projection being received by the ribs of the at least one set of ribs permitting adjustment of the position of the optics module with respect to the normalizer casting plate.

12. The apparatus of claim 1, wherein the robot assembly of the fluid handler unit includes:
a base, the base being disposed in an upper portion of the interior cavity of the outer casing, the base having a main portion which is generally planar in shape;
a pair of spaced apart, parallelly disposed linear rails mounted on the base near opposite sides thereof;
a bearing holder assembly, the bearing holder assembly being movably mounted on the pair of linear rails of the base in the X-direction; and
an X-direction motor assembly mounted on the base and coupled to the bearing holder assembly, the X-direction motor assembly causing the bearing holder to move in the X-direction on the pair of linear rails of the base, the pump assembly of the fluid handler unit being operatively coupled to the bearing holder assembly and movable therewith on the base in the X-direction.

13. The apparatus of claim 12, wherein the robot assembly of the fluid handler unit further includes a first linear potentiometer, the first linear potentiometer being mounted on the base, the first linear potentiometer providing a signal to the controller of the apparatus corresponding to the position of the robot assembly and the pump assembly of the fluid handler unit in an X-axis.

14. The apparatus of claim 12, wherein the X-direction motor assembly includes a motor having a motor shaft, a lead screw operatively linked to the motor shaft, and an anti-backlash coupling mounted on the lead screw and reciprocatingly movable thereon, the anti-backlash coupling being coupled to the bearing holder assembly such that the X-direction motor assembly effects movement of the bearing holder assembly in the X-direction.

15. The apparatus of claim 12, wherein the bearing holder assembly of the robot assembly of the fluid handler unit includes a worm wheel, a theta-direction motor operatively linked to the worm wheel to cause the worm wheel to rotate, and a robot center hub, the robot center hub being coupled to the worm wheel and rotating with the worm wheel, the pump assembly being mounted on the robot center hub.

16. The apparatus of claim 15, wherein the theta-direction motor assembly includes a motor having a motor shaft, and a worm gear mounted on the motor shaft, the worm gear engaging the worm wheel, the motor causing the worm wheel to rotate in the theta-direction within the X-Y plane.

17. The apparatus of claim 16, wherein the robot assembly of the fluid handler unit further includes a circular potentiometer, the circular potentiometer being mounted on the base, the circular potentiometer sensing the position of the robot assembly and the pump assembly of the fluid handler unit in the theta-direction, the circular potentiometer providing a signal corresponding to the position of the robot assembly and the pump assembly in the theta-direction to the controller of the apparatus.

18. The apparatus of claim 12, wherein the robot assembly of the fluid handler unit further includes a Z-direction motor assembly, the Z-direction motor assembly being mounted on the bearing holder assembly and effecting movement of the pump assembly in the Z-direction.

19. The apparatus of claim 18, wherein the Z-direction motor assembly includes a motor having a motor shaft, a lead screw operatively linked to the motor shaft and rotatable by the motor, and an anti-backlash coupling mounted on the lead screw and movable axially thereon, the anti-backlash coupling of the Z-direction motor assembly being operatively linked to the pump assembly such that the pump assembly is moved in the Z-direction with movement of the coupling on the lead screw of the Z-direction motor assembly.

20. The apparatus of claim 15, wherein the robot center hub includes a main body, and a bracket extending outwardly from the main body, the pump assembly being mounted on the bracket of the robot center hub.

21. The apparatus of claim 20, wherein the bracket of the robot center hub includes a linear potentiometer, the linear potentiometer of the robot center hub detecting the position in the Z-axis of the pump assembly, the linear potentiometer of the robot center hub providing a signal to the controller corresponding to the position in the Z-axis of the pump assembly mounted on the bracket of the robot center hub.

22. The apparatus of claim 1, wherein the pump assembly of the fluid handler unit includes:
a pump motor assembly, the pump motor assembly including a stepper motor having a motor shaft, and a lead screw operatively linked to the motor shaft;

a pump lower mounting plate, the pump motor being affixed to the pump lower mounting plate, the at least one elongated robot arm being affixed to the pump lower mounting plate and extending outwardly therefrom in the Z-direction;

a pump upper mounting plate, the pump upper mounting plate being spaced apart from the pump lower mounting plate and being movable relative thereto;

a pump spring, the pump spring being mounted between the pump lower mounting plate and the pump upper mounting plate;

a pump motor nut, the pump motor nut being secured to the pump upper mounting plate and receiving a portion of the lead screw of the pump motor assembly therethrough, whereby rotational movement of the lead screw caused by the pump motor will effect movement of the pump upper mounting plate toward and away from the pump lower mounting plate;

a linear rail, the linear rail having a first movable rail mount and a second movable rail mount, the pump upper mounting plate being mounted on the first movable rail mount, the pump lower mounting plate being mounted on the second movable rail mount; and a pump sub-assembly, the pump sub-assembly including a cylinder and a movable piston within the cylinder, the pump sub-assembly being mounted on the pump lower mounting plate and being movable therewith on the linear rail, the pump sub-assembly including a proboscis on which may be removably mounted disposable pipette tips.

23. The apparatus of claim 1, wherein the at least one elongated robot arm of the robot assembly includes a first elongated robot arm and a second elongated robot arm, each of the first elongated robot arm and the second elongated robot arm being affixed to the fluid pump assembly, each of the first elongated robot arm and the second elongated robot arm having a free end, the free end of at least one of the first elongated robot arm and the second elongated robot arm being selectively engageable with at least one of the slide loading mechanism, the slide ejecting mechanism, the evaporation cap opening mechanism and the evaporation cap closing mechanism.

24. The apparatus of claim 1, wherein the at least one elongated robot arm of the robot assembly includes a free end, the free end having formed thereon a reduced diameter portion and an end plate mounted on the reduced diameter portion, the end plate of the at least one elongated robot arm being selectively engageable with at least one of the slide loading mechanism, the slide ejecting mechanism, the evaporation cap opening mechanism and the evaporation cap closing mechanism.

25. The apparatus of claim 1, wherein the at least one camera is mounted on the robot assembly and movable therewith.

26. The apparatus of claim 1, wherein the at least one camera includes a first camera and a second camera, the first camera being mounted on the robot assembly and being movable therewith within the interior cavity of the outer casing, the second camera being fixedly mounted within the interior cavity of the outer casing.

\* \* \* \* \*